United States Patent
Ziv et al.

(10) Patent No.: US 12,337,036 B2
(45) Date of Patent: Jun. 24, 2025

(54) COMPOUNDS AND METHODS FOR TRANS-MEMBRANE DELIVERY OF MOLECULES

(71) Applicant: Aposense Ltd, Petach-Tikva (IL)

(72) Inventors: Ilan Ziv, Kfar Saba (IL); Hagit Grimberg, Herzliya (IL); Joseph Dubrovsky, Tel Aviv (IL)

(73) Assignee: APOSENSE LTD, Petach-Tikva (IL)

(*) Notice: Subject to any disclaimer, the term of this patent is extended or adjusted under 35 U.S.C. 154(b) by 1252 days.

(21) Appl. No.: 16/959,494

(22) PCT Filed: Dec. 31, 2018

(86) PCT No.: PCT/IL2018/051416
§ 371 (c)(1),
(2) Date: Jul. 1, 2020

(87) PCT Pub. No.: WO2019/130319
PCT Pub. Date: Jul. 4, 2019

(65) Prior Publication Data
US 2021/0052736 A1 Feb. 25, 2021

Related U.S. Application Data

(60) Provisional application No. 62/612,648, filed on Jan. 1, 2018, provisional application No. 62/612,733, filed
(Continued)

(51) Int. Cl.
*A61K 47/54* (2017.01)
*A61K 31/713* (2006.01)
*C07J 41/00* (2006.01)

(52) U.S. Cl.
CPC ......... *A61K 47/554* (2017.08); *C07J 41/0033* (2013.01); *A61K 31/713* (2013.01)

(58) Field of Classification Search
CPC . A61K 31/713; A61K 47/554; C07J 41/0033; C12N 15/00
See application file for complete search history.

(56) References Cited

U.S. PATENT DOCUMENTS 6,028,066 A 2/2000 Unger
6,046,228 A 4/2000 Rice
(Continued)

FOREIGN PATENT DOCUMENTS

CN 101076538 A 11/2007
CN 111246855 A 6/2020
(Continued)

OTHER PUBLICATIONS

Bhatia D, Yue-Ming L, Ganesh KN. Steroid-DNA conjugates: improved triplex formation with 5-amido-(7-deoxycholic acid)-dU incorporated oligonucleotides. Bioorg Med Chem Lett. Jul. 5, 1999;9(13):1789-94. doi: 10.1016/s0960-894x (99)00274-7. PMID: 10406643.
(Continued)

*Primary Examiner* — Sarah Pihonak
*Assistant Examiner* — Padmaja S Rao
(74) *Attorney, Agent, or Firm* — The Roy Gross Law Firm, LLC; Roy D. Gross

(57) ABSTRACT

The Invention provides a novel delivery system for delivery of drugs across biological membranes. It provides novel chemical conjugates that comprise said delivery system, methods for synthesis of said compounds, and methods for utilization of said delivery system, among others, for delivery of genetic drugs into tissues and cells, in vitro, ex vivo, and in vivo, for the treatment of various medical disorders.

14 Claims, 10 Drawing Sheets

Figure 1A:
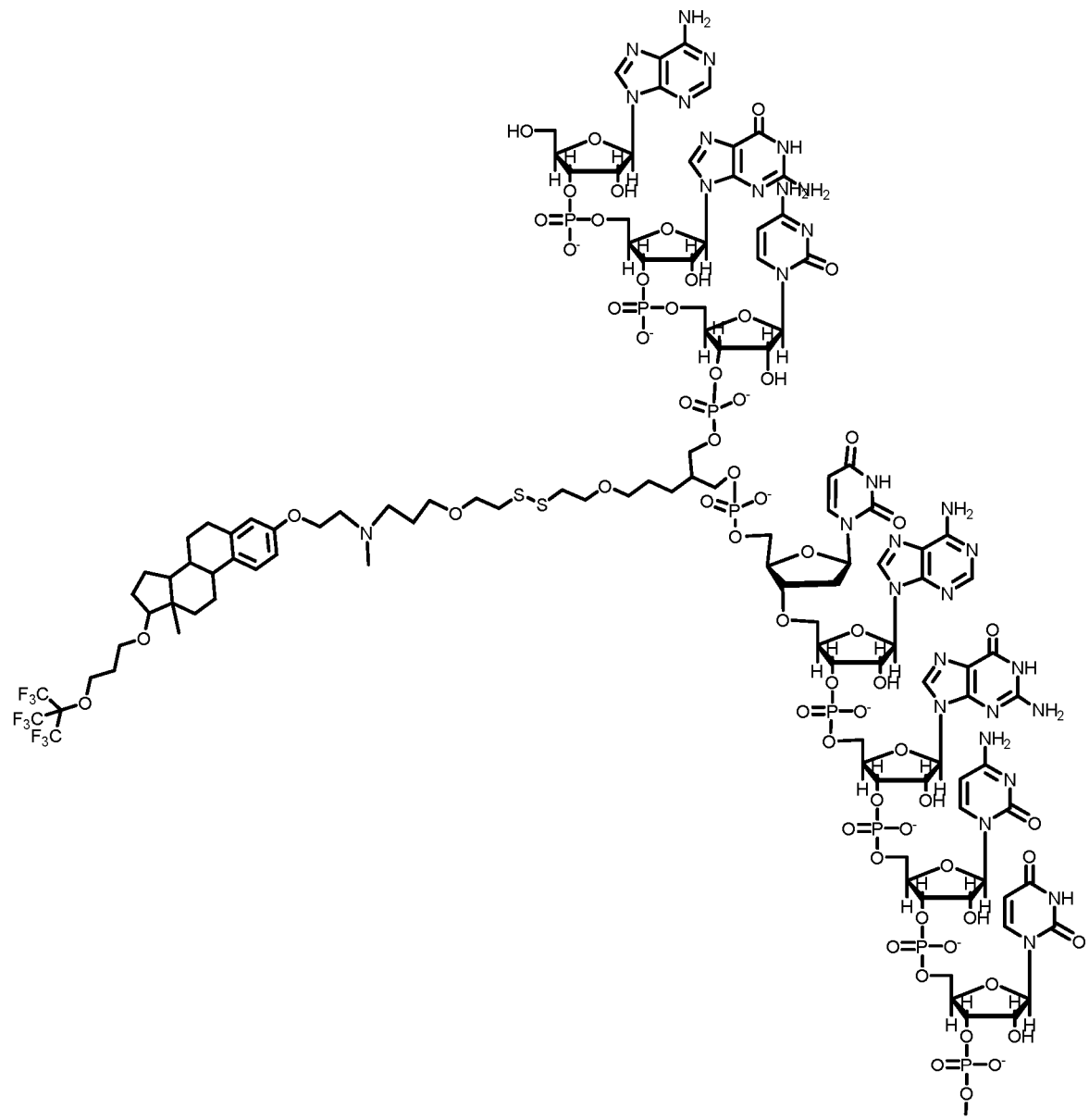

Related U.S. Application Data on Jan. 2, 2018, provisional application No. 62/624,815, filed on Feb. 1, 2018, provisional application No. 62/626,179, filed on Feb. 5, 2018, provisional application No. 62/629,731, filed on Feb. 13, 2018, provisional application No. 62/633,107, filed on Feb. 21, 2018, provisional application No. 62/648,974, filed on Mar. 28, 2018, provisional application No. 62/684,763, filed on Jun. 14, 2018, provisional application No. 62/693,922, filed on Jul. 4, 2018.

(56) References Cited

U.S. PATENT DOCUMENTS

| | | |
|---|---|---|
| 8,101,666 B2 | 1/2012 | Ziv et al. |
| 8,809,514 B2 | 8/2014 | Yamada et al. |
| 9,889,202 B2 | 2/2018 | Ziv |
| 2004/0110220 A1 | 6/2004 | Mirkin |
| 2006/0167223 A1 | 7/2006 | Pucci |
| 2007/0232702 A1 | 10/2007 | Ziv |
| 2011/0123457 A1 | 5/2011 | Yu |
| 2012/0035362 A1 | 2/2012 | Barta et al. |
| 2012/0270917 A1 | 10/2012 | DeGrado |
| 2013/0178512 A1 | 7/2013 | Manoharan et al. |
| 2013/0211055 A1 | 8/2013 | Raines |
| 2015/0141678 A1 | 5/2015 | Payne et al. |
| 2016/0106855 A1 | 4/2016 | Ziv |
| 2017/0100486 A1 | 4/2017 | Ziv |
| 2019/0008976 A1 | 1/2019 | Ziv et al. |

FOREIGN PATENT DOCUMENTS

| | | |
|---|---|---|
| EA | 201991661 A1 | 12/2019 |
| FR | 2846969 | 5/2004 |
| JP | 2001507207 A | 6/2001 |
| JP | 2011-521054 | 7/2011 |
| JP | 2012-502657 | 2/2012 |
| JP | 6669719 B2 | 4/2017 |
| JP | 2017-509710 A | 3/2020 |
| JP | 7191869 B2 | 12/2022 |
| JP | 7348064 B2 | 9/2023 |
| RU | 2007134566 A | 3/2009 |
| RU | 2408605 C2 | 1/2011 |
| RU | 2703416 C2 | 10/2019 |
| WO | WO 1997/40679 | 11/1997 |
| WO | WO 1998/50041 | 11/1998 |
| WO | WO 2005/041859 | 5/2005 |
| WO | WO 2005/077968 | 8/2005 |
| WO | WO 2006/027711 | 3/2006 |
| WO | 2006086871 A1 | 8/2006 |
| WO | 2009140427 A2 | 11/2009 |
| WO | 2009155335 A2 | 12/2009 |
| WO | 2010033247 A2 | 3/2010 |
| WO | WO 2013/098244 | 7/2013 |
| WO | WO 2013/176772 | 11/2013 |
| WO | WO 2013/181440 | 12/2013 |
| WO | WO 2014/062697 | 4/2014 |
| WO | 2014088923 A1 | 6/2014 |
| WO | WO 2014/127052 | 8/2014 |
| WO | WO 2015/145417 | 10/2015 |
| WO | 2017/029664 A1 | 2/2017 |
| WO | 2018127927 A1 | 7/2018 |
| WO | 2019008574 A1 | 1/2019 |

OTHER PUBLICATIONS

"Metabolite ." The Oxford Pocket Dictionary of Current English. Updated May 29, 2018. Retrieved Aug. 25, 2023 from Encyclopedia. com: https://www.encyclopedia.com/humanities/dictionaries-thesauruses-pictures-and-press-releases/metabolite.
International Search Report in respect of PCT/IL2018/051416—May 23, 2019.
IPRP in respect of PCT/IL2018/051416—Jul. 16, 2020.
Alconcel, S. N. et al. (2011). FDA-approved poly (ethylene glycol)-protein conjugate drugs. Polymer Chemistry, 2(7), 1442-1448.
Andersen, O. S. et al. (1976). Effect of phloretin on the permeability of thin lipid membranes. The Journal of general physiology, 67(6), 749-771.
Bellucci, M. C. et al. (2010). Multicomponent Synthesis of Peptide-Sugar Conjugates Incorporating Hexafluorovaline. Advanced Synthesis & Catalysis, 352(16), 2791-2798.
Blazejewski, J.C. et al. (2003). Synthesis, characterization and biological evaluation of 7α-perfluoroalkylestradiol derivatives. Bioorganic & medicinal chemistry 11.3: pp. 335-345.
Buer, B. C. et al. (2013). Perfluoro-tert-butyl-homoserine as a sensitive 19F NMR reporter for peptide-membrane interactions in solution. Journal of Peptide Science, 19(5), 308-314.
Cai, X. et al. (2012). Effective gene delivery using stimulus-responsive catiomer designed with redox-sensitive disulfide and acid-labile imine linkers. Biomacromolecules, 13(4), 1024-1034.
Extended European Search Report for EP Application No. 15770224 dated Sep. 22, 2017.
Grijalvo, S. et al. (2010). Synthesis of oligonucleotides carrying amino lipid groups at the 3'-end for RNA interference studies. The Journal of organic chemistry, 75(20), 6806-6813.
Hunt, J. A. et al. (2010). 2-Arylbenzoxazoles as CETP inhibitors: Substitution and modification of the α-alkoxyamide moiety. Bioorganic & medicinal chemistry letters, 20(3), 1019-1022.
Ikumi, Y. et al. (2008). Polymer-phloridzin conjugates as an anti-diabetic drug that Inhibits glucose absorption through the Na+/glucose cotranspor ter (SGLT1) in the small intestine. Journal of controlled release, 125(1), 42-49.
International Search Report for Application No. PCT/IL2015/000019, mailed on Jul. 28, 2015.
International Search Report for PCT Application No. PCT/IL2016/50893 dated Dec. 28, 2016.
International Search Report for PCT Application No. PCT/IL2018/050031 dated May 24, 2018.
International Search Report for PCT Application No. PCT/IL2018/50714 dated Nov. 20, 2018.
Janout, V. et al. (2014). Molecular umbrella conjugate for the ocular delivery of siRNA. Bioconjugate chemistry, 25(2), 197-201.
Jiang, Z. X. et al. (2007). The synthesis of a geminally perfluoro-tert-butylated β-amino acid and its protected forms as a potential pharmacokinetic modulator and reporter for peptide-based pharmaceuticals. The Journal of organic chemistry, 72(4), 1464-1467.
Jiang, Z. X. et al. (2008). The design and synthesis of highly branched and spherically symmetric fluorinated macrocyclic chelators. Synthesis, 2008(2), 215-220.
Krafft, M. P. (2001). Fluorocarbons and fluorinated amphiphiles in drug delivery and biomedical research. Advanced drug delivery reviews, 47(2-3), 209-228.
Office Action of U.S. Appl. No. 14/872,179 mailed Apr. 25, 2016.
Riess, J. G. (2002). Fluorous micro-and nanophases with a biomedical perspective. Tetrahedron, 58(20), 4113-4131.
Schiller, R. et al. (2004). DSC measurements on full thickness mice skin. Journal of thermal analysis and calorimetry, 77(2), 497-510.
Seibutsu Butsuri (Biophysics) 2010, vol. 50, No. 3, pp. 137-140.
Sun, S. et al. (2006). Fluorinated molecules as drugs and imaging agents in the CNS. Current topics in medicinal chemistry, 6(14), 1457-1464.
Üllen, A. et al. (2015). Covalent adduct formation between the plasmalogen-derived modification product 2-chlorohexadecanal and phloretin. Biochemical pharmacology, 93(4), 470-481.
Vierling, P. et al. (2001). Highly fluorinated amphiphiles as drug and gene carrier and delivery systems. Journal of Fluorine Chemistry, 107(2), 337-354.
Yue, X. et al. (2013). Synthesis and characterization of fluorinated conjugates of albumin. Journal of Fluorine Chemistry, 152, 173-181.
Yue-Ming, D. B. L. et al. (1999). Steroid—DNA conjugates: improved triplex formation with 5-amido-(7-deoxycholic acid)-dU incorporated oligonucleotides. Bioorganic & medicinal chemistry letters, 9(13), 1789-1794.

(56) References Cited

OTHER PUBLICATIONS

Wolfrum,C et al; Mechanisms And Optimization Of In Vivo Delivery Of Lipophilic Sirnas. Nature Biotechnology, Oct. 2007; 25 (10):1149-57. doi:10.1038/nbt1339.

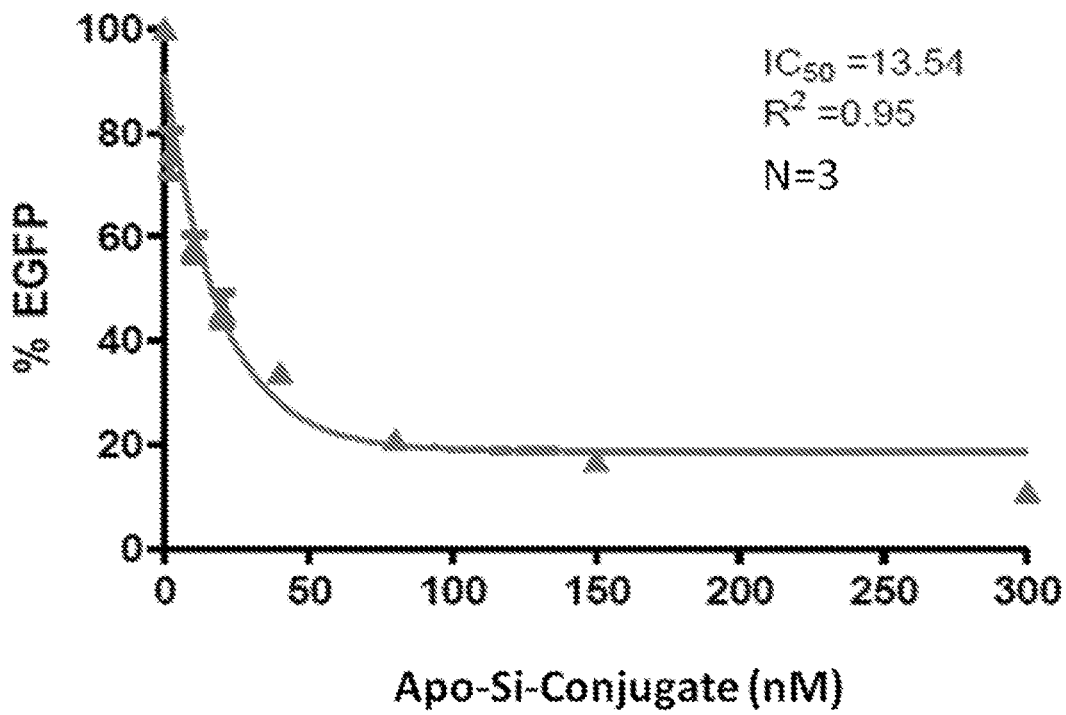
Figure 4A - Hela cells
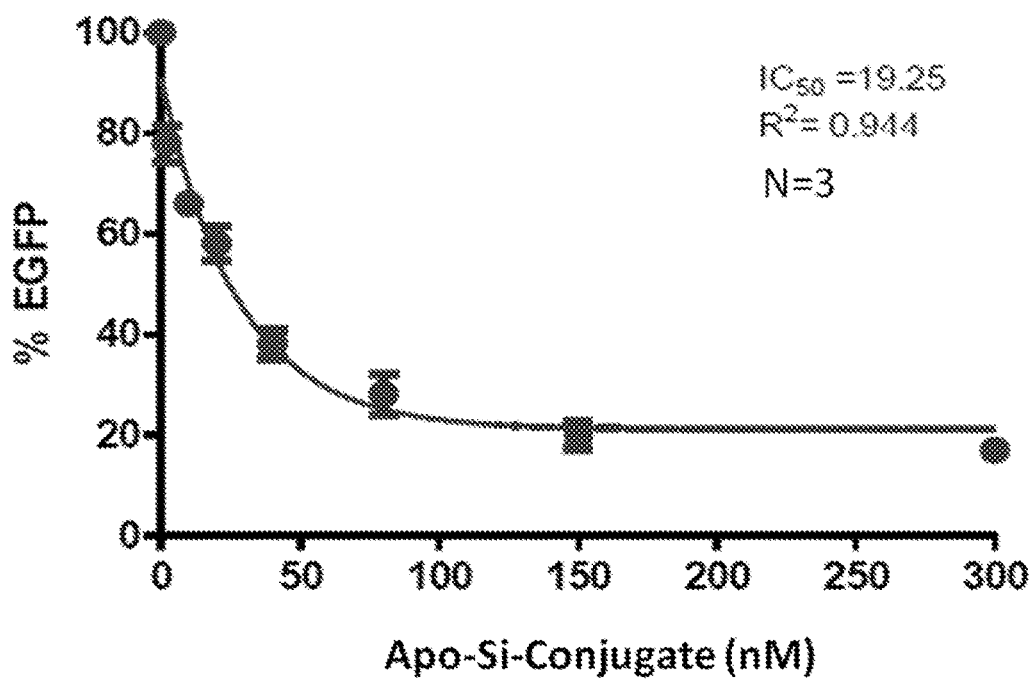
Figure 4B - 3T3 cells

COMPOUNDS AND METHODS FOR TRANS-MEMBRANE DELIVERY OF MOLECULES

CROSS-REFERENCE TO RELATED APPLICATIONS

This application is a National Phase Application of PCT International Application No. PCT/IL2018/051416, International Filing Date 31 Dec. 2018, claiming the benefit of U.S. Patent Applications Nos. 62/612,648 filed 1 Jan. 2018, U.S. 62/612,733 filed 2 Jan. 2018, U.S. 62/624,815 filed 1 Feb. 2018, U.S. 62/626,179 filed 5 Feb. 2018, U.S. 62/629,731 filed 13 Feb. 2018, U.S. 62/633,107 filed 21 Feb. 2018, U.S. 62/648,974 filed 28 Mar. 2018, U.S. 62/684,763 filed 14 Jun. 2018 which is/are hereby incorporated by reference.

FIELD OF THE INVENTION

The invention relates to compounds and conjugates that comprise a delivery system, cargo compounds and macromolecules, and methods for delivery of molecules and macromolecules across biological membranes into cells, destined for utilization for biological purposes in vitro and in vivo.

BACKGROUND

"Oligonucleotide drugs" (OD), are macromolecule drugs that comprise sequences of nucleosides or nucleotides. OD may hold the promise for revolutionary medical treatments for numerous medical disorders. OD are single-stranded or double-stranded, natural or modified RNA or DNA molecules, or combinations thereof, as known in the art. Examples for OD are, among others, siRNA (small interfering RNA), being substrates for the RNA-induced silencing complex (RISC); siRNA sequences that are substrates for the Dicer endonuclease (dsiRNA), microRNA (miRNA), messenger RNA (mRNA) drugs, or DNA sequences designed to serve as antisense oligonucleotides (ASO); all of which are active in down-regulation of expression of target genes.

Due to the large and heavily electrically-charged structures of OD, there is an unmet need for delivery systems that are capable of delivering OD across the hydrophobic phospholipid membranes into cells. For the purposes of utilization of OD in the clinical setting, several features of the conjugate of the OD linked to the delivery system can be advantageous, such as activity in both presence or absence of plasma proteins, or comprising red-ox-sensitive cleavable group, that is stable at the extracellular compartment, but undergoes efficient cleavage in the reductive conditions that prevail in the cytoplasm, thus enabling a cargo drug such as OD, to exert its activity on cytoplasmatic targets, such as Dicer or RISC.

SUMMARY OF THE INVENTION

The invention is based on a novel molecular delivery system (MDS), being chemical moieties that have the structure as set forth in Formula (II), and which upon conjugation to a cargo drug, such as macromolecular OD, thus creating a Conjugate according to Formula (I), entails delivery of the OD across phospholipid membranes into cells, where it exerts its respective biological activity, for example, gene silencing. The invention is based on the discovery and development of novel compounds by the Inventors, which enable to overcome the huge delivery barrier, for large and heavily charged macromolecular drugs, across lipophilic cell membranes. The Invention provides the MDS, Conjugates that comprise it, methods for synthesis of the MDS and its conjugates, and methods for utilization of the MDS, among others, for delivery of genetic drugs into tissues and cells, in vitro, ex vivo, and in vivo, for the treatment of various medical disorders.

In an embodiment of the invention, there are provided Conjugates, having the structure as set forth in Formula (I):

Formula (I)

including pharmaceutically acceptable salts, hydrates, solvates and metal chelates of the compound represented by the structure as set forth in Formula (I), and solvates and hydrates of the salts, wherein:

D is a drug to be delivered across biological membranes (i.e., a cargo drug), selected from a group consisting of a small-molecule drug, a peptide, a protein, and an OD (i.e., a native or modified, single-stranded or double-stranded, DNA or RNA, siRNA, dsiRNA, or ASO);

y, z and w are each an integer, independently selected from the group consisting of 0, 1, 2, 3 or 4, wherein if any of y, z or w is 0, it means that the respective E moiety (or moieties) is (are) null; at least one of y, z or w is different from 0;

E, E', or E" can be the same or different, each having independently a structure as set forth in general Formula (II):

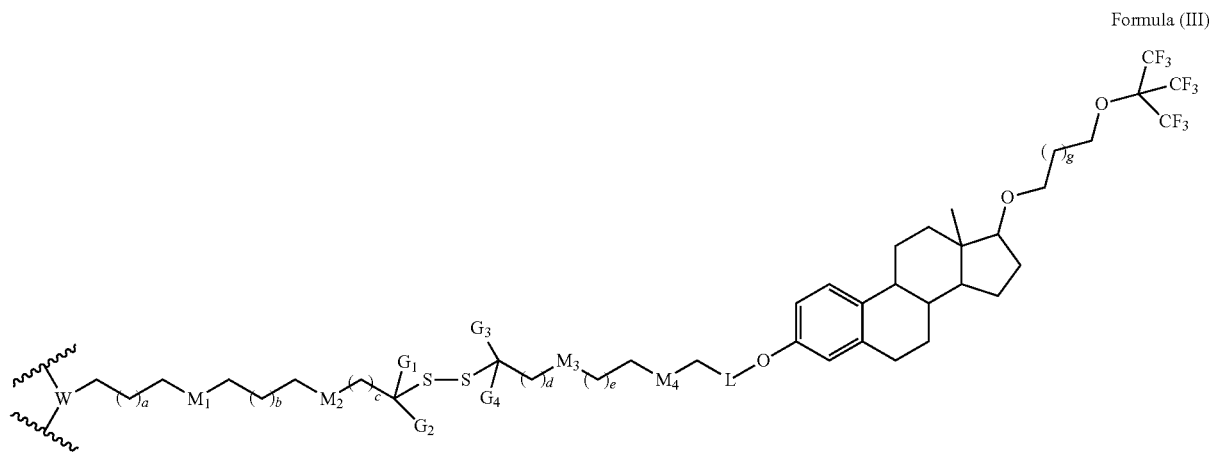

Formula (III)

including pharmaceutically acceptable salts, hydrates, solvates and metal chelates of the compound represented by the structure as set forth in Formula (II), and solvates and hydrates of the salts, wherein:

$M_1$, $M_2$, $M_3$, $M_4$ are each individually selected from the group consisting of N', N", null, ether, amide, ester, thioether and thioester; wherein N' and N" are each selected independently from the group consisting of —N(CH$_3$)—, —NH—, and —N(X)—; wherein X is a protecting group for amine; $M_1$, $M_2$, $M_3$, $M_4$ can be the same or different; N', N" can be the same or different.

L is a linker, selected from the group consisting of null, $C_1$, $C_2$, $C_3$, $C_4$, $C_5$, $C_6$ alkylene or heteroalkylene; $C_5$ or $C_6$ aryl or heteroaryl, optionally substituted by fluorine atom(s), or hydroxyl group(s); and combinations thereof;

$G_1$, $G_2$, $G_3$, $G_4$, each stands independently for a hydrogen atom or a methyl group; G groups can be the same or different; at least two of $G_1$, $G_2$, $G_3$ or $G_4$ groups are hydrogen atoms;

a, b, c, d, e are integers, each independently selected from the group consisting of 0, 1, 2, 3, 4, 5, or 6, wherein 0=null; a, b, c, d, e can be the same or different; g stands for an integer, selected from 0, 1, 2, 3, 4 or 5;

W is selected from the group consisting of null, a residue of hydroxyl, di-hydroxyl, amide, natural or modified nucleoside, any of the structures as set forth in Formulae (II$^1$), (II$^2$) and (II$^3$), and combinations thereof:

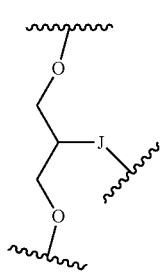

Formula (II$^1$)

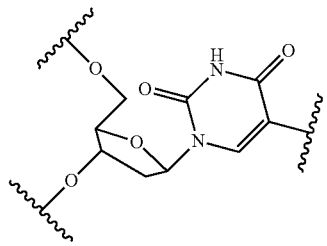

Formula (II$^2$)

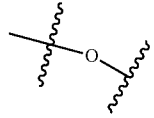

Formula (II$^3$)

wherein J is selected from the group consisting of null, —CH$_2$—, a secondary or tertiary amine, and oxygen;

E, E', or E" can be linked to any moiety of the group consisting of D; a protecting group, as defined herein (e.g., a protecting group for alcohol); R or R' group, selected from the group consisting of hydrogen, phosphate, sulfate and carboxyl group; and a solid support. In the context of the Invention, an E, E' or E" moiety may be linked to one D moiety via one or more points; and W can be linked concomitantly to both D and R or R'.

In one of the embodiments of the Invention g is an integer of 0, 1, or 2.

In an embodiment, c and d each stands independently for an integer of 1, 2 or 3; c and d can be the same or different.

In an embodiment of the Invention $G_1$, $G_2$, $G_3$, $G_4$ are all hydrogen atoms.

In an embodiment, L is difluorobenzylamine.

In another embodiment, X is the protecting groups for amines TEOC [2-(trimethylsilyl)ethyl carbamate], or Fmoc.

In an embodiment, the Invention provides a Conjugate according to Formula (I) and Formula (II), wherein E, E', or E" have the structure as set forth in Formula (V):

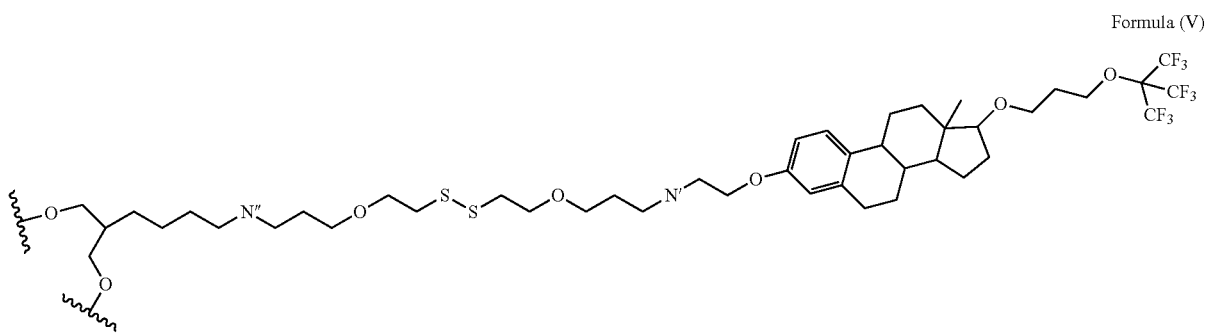

Formula (V)

including pharmaceutically acceptable salts, hydrates, solvates and metal chelates of the compound represented by the structure as set forth in Formula (V), and solvates and hydrates of the salts; wherein N' and N" each has independently the same meaning as defined in Formula (II).

In another embodiment, the Invention provides a Conjugate according to Formula (I) and Formula (II), wherein E, E', or E" have the structure as set forth in Formula (VII):

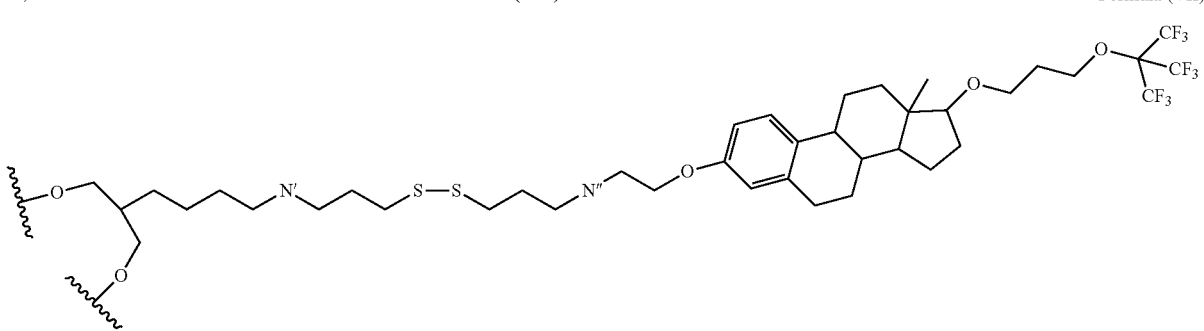

Formula (VII)

including pharmaceutically acceptable salts, hydrates, solvates and metal chelates of the compound represented by the structure as set forth in Formula (VII), and solvates and hydrates of the salts; wherein N' and N" each has independently the same meaning as defined in Formula (II).

In another embodiment, the Invention provides a Conjugate according to Formula (I) and Formula (II), wherein E, E', or E" have the structure as set forth in Formula (VIII):

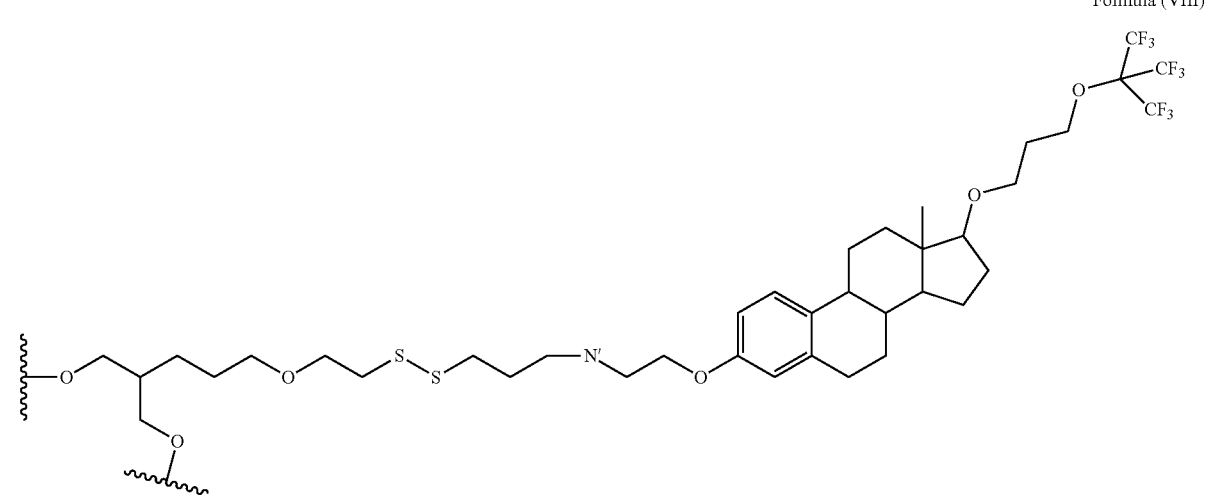

Formula (VIII)

including pharmaceutically acceptable salts, hydrates, solvates and metal chelates of the compound represented by the structure as set forth in Formula (VIII), and solvates and hydrates of the salts; wherein N' has the same meaning as in Formula (II).

In an embodiment, the Invention provides a Conjugate according to Formula (I) and Formula (II), wherein E, E', or E" have the structure as set forth in Formula (VIII-H):

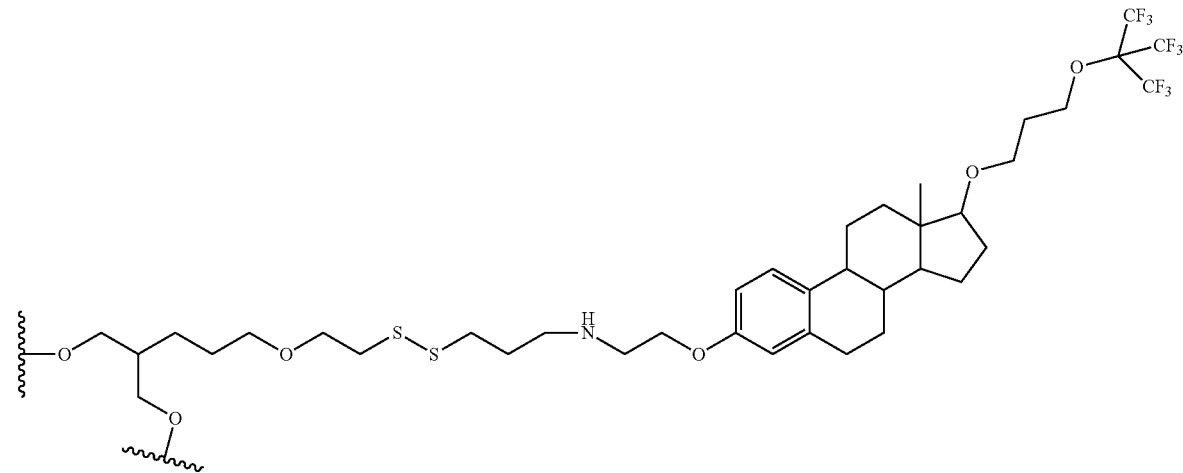

Formula (VIII-H)

including pharmaceutically acceptable salts, hydrates, solvates and metal chelates of the compound represented by the structure as set forth in Formula (VIII-H), and solvates and hydrates of the salts.

In a related embodiment, the Invention provides a Conjugate according to Formula (I) and Formula (II), wherein E, E', or E" have the structure as set forth in Formula (VIII-M):

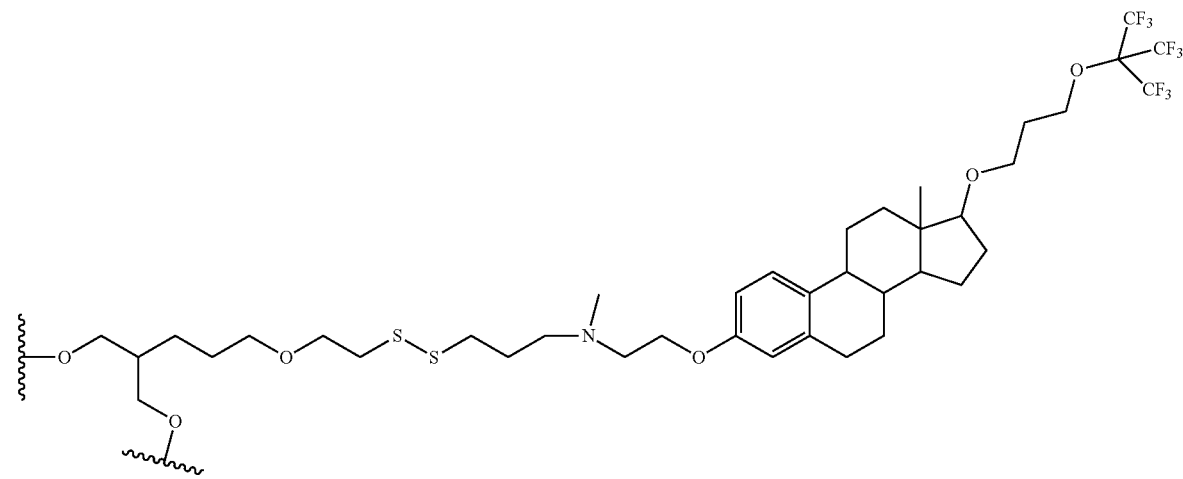

Formula (VIII-M)

including pharmaceutically acceptable salts, hydrates, solvates and metal chelates of the compound represented by the structure as set forth in Formula (VIII-M), and solvates and hydrates of the salts.

In another embodiment, the Invention provides a Conjugate according to Formula (I) and Formula (II), wherein E, E', or E" have the structure as set forth in Formula (VIII-F):

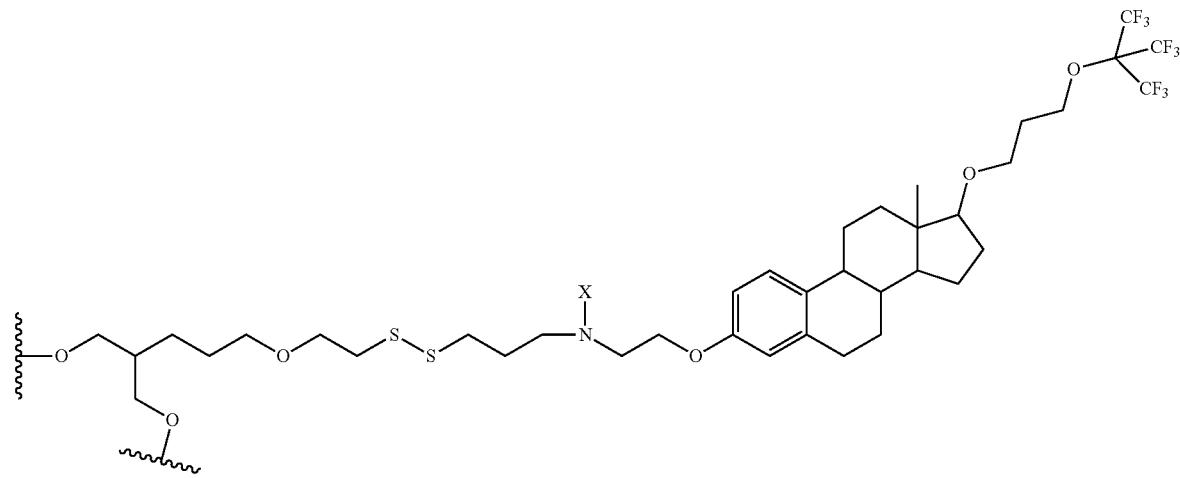

Formula (VIII-F)

including pharmaceutically acceptable salts, hydrates, solvates and metal chelates of the compound represented by the structure as set forth in Formula (VIII-F), and solvates and hydrates of the salts; wherein X is a protecting group for amine.

In an embodiment, the Invention provides a Conjugate according to Formula (I) and Formula (II), wherein E, E', or E'' have the structure as set forth in Formula (XIV):

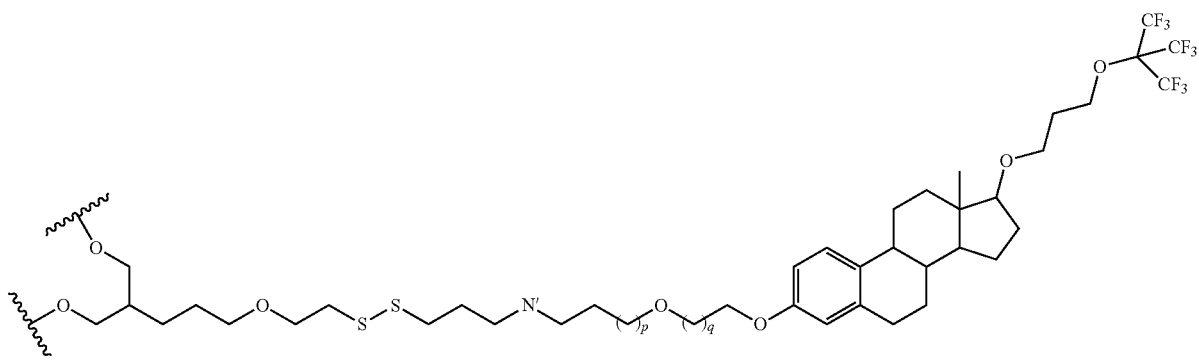

Formula (XIV)

including pharmaceutically acceptable salts, hydrates, solvates and metal chelates of the compound represented by the structure as set forth in Formula (XIV), and solvates and hydrates of the salts; wherein p and q are each independently an integer of 0, 1, 2, 3, 4, 5, or 6; N' has the same meaning as in Formula (II).

In an embodiment, the Invention provides a Conjugate according to Formula (I) and Formula (II), wherein E, E', or E'' have the structure as set forth in Formula (XIV-H):

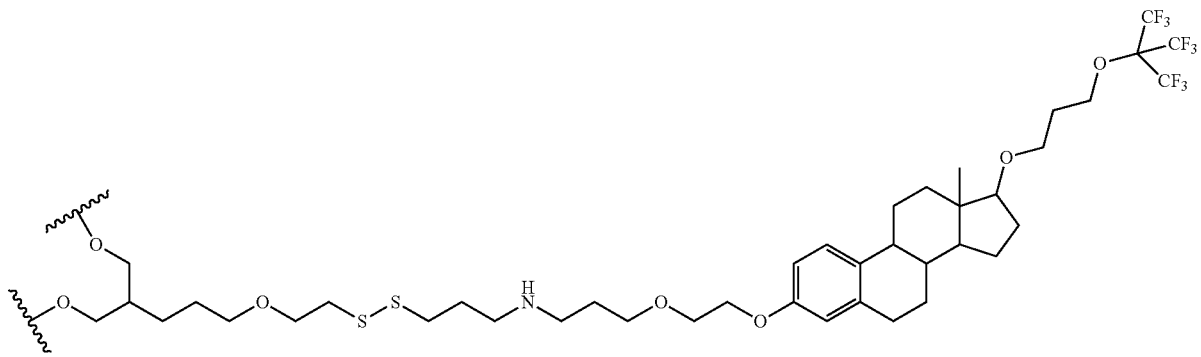

Formula (XIV-H)

including pharmaceutically acceptable salts, hydrates, solvates and metal chelates of the compound represented by the structure as set forth in Formula (XIV-H), and solvates and hydrates of the salts.

In an embodiment, the Invention provides a Conjugate according to Formula (I) and Formula (II), wherein E, E', or E" have the structure as set forth in Formula (XIV-M):

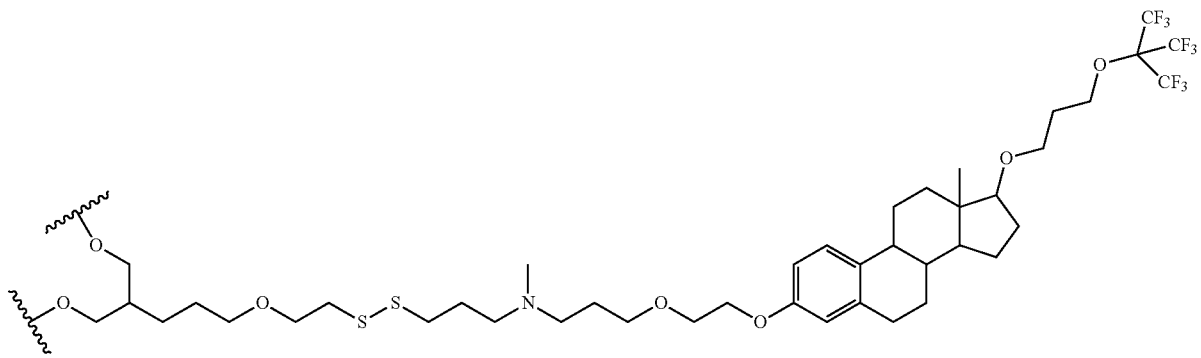

Formula (XIV-M)

including pharmaceutically acceptable salts, hydrates, solvates and metal chelates of the compound represented by the structure as set forth in Formula (XIV-M), and solvates and hydrates of the salts.

In an embodiment, the Invention provides a Conjugate according to Formula (I) and Formula (II), wherein E, E', or E" have the structure as set forth in Formula (XIV-F):

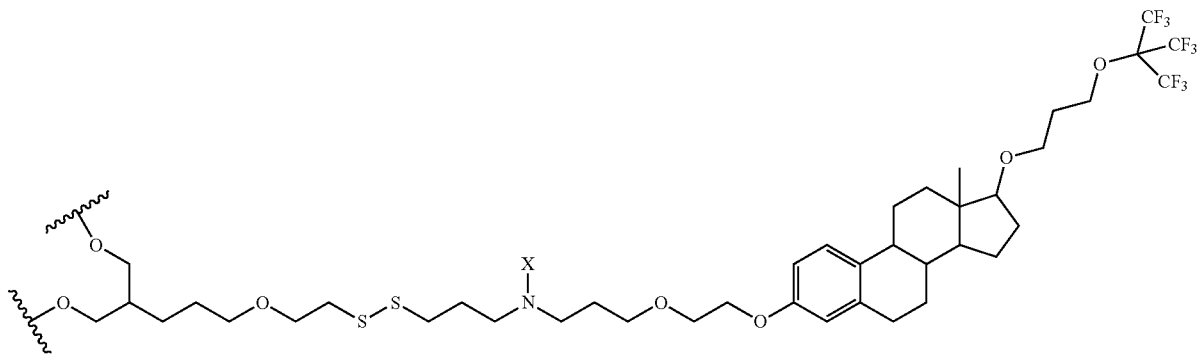

Formula (XIV-F)

including pharmaceutically acceptable salts, hydrates, solvates and metal chelates of the compound represented by the structure as set forth in Formula (XIV-F), and solvates and hydrates of the salts, wherein X is a protecting group for amine.

In an embodiment, the Invention provides a Conjugate according to Formula (I) and Formula (II), wherein the L moiety is diflurobenzylamine; and therefore E, E', or E" each having the structure as set forth in Formula (XV):

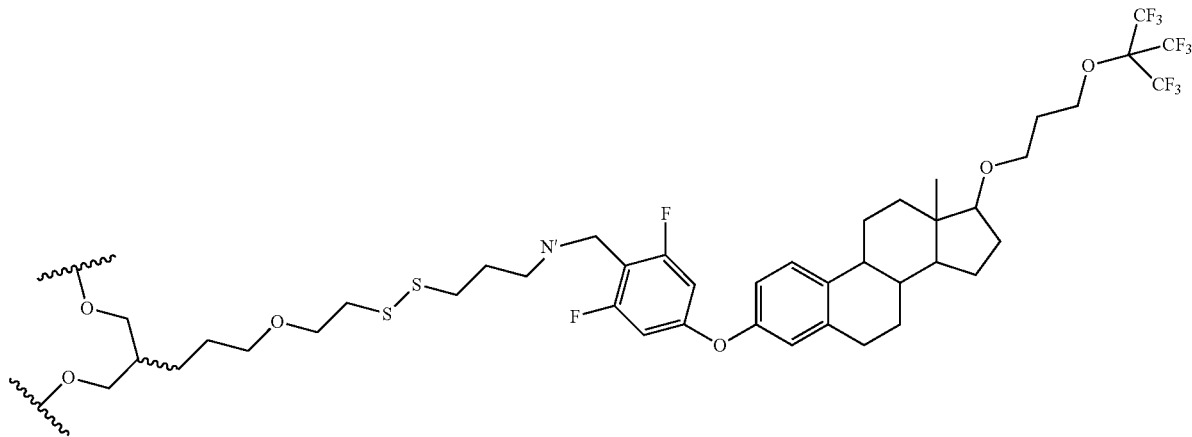

Formula (XV)

including pharmaceutically acceptable salts, hydrates, solvates and metal chelates of the compound represented by the structure as set forth in Formula (XV), and solvates and hydrates of the salts; wherein N' has the same meaning as in Formula (II).

In an embodiment, the Invention provides a Conjugate according to Formula (I) and Formula (II), wherein E, E', or E" have the structure as set forth in Formula (XV-H):

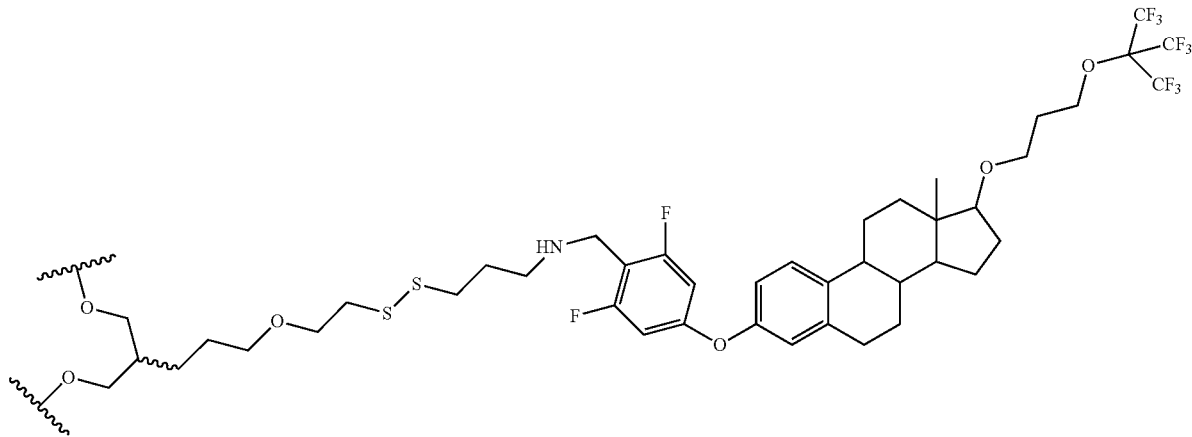

Formula (XV-H)

including pharmaceutically acceptable salts, hydrates, solvates and metal chelates of the compound represented by the structure as set forth in Formula (XV-H), and solvates and hydrates of the salts.

In an embodiment, the Invention provides a Conjugate according to Formula (I) and Formula (II), wherein E, E', or E" have the structure, as set forth in Formula (XV-M):

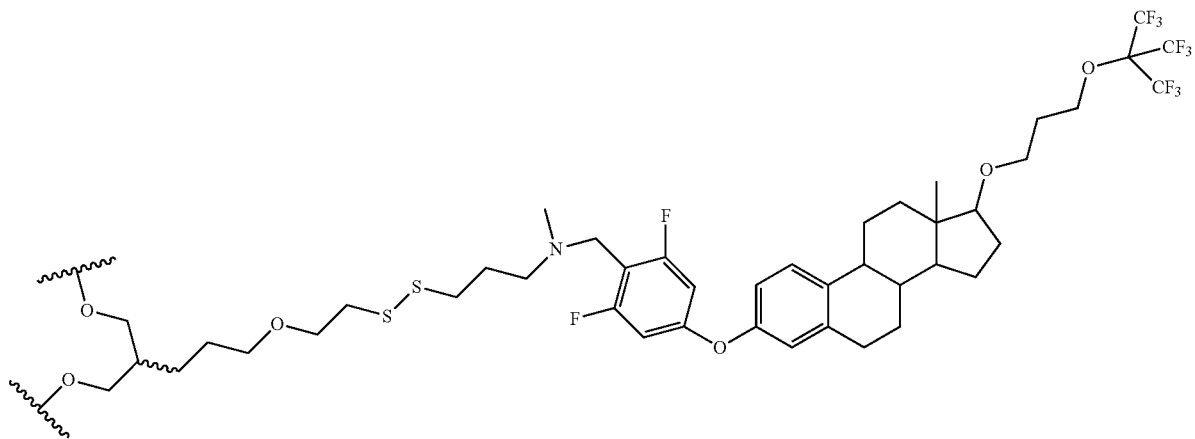

Formula (XV-M)

including pharmaceutically acceptable salts, hydrates, solvates and metal chelates of the compound represented by the structure as set forth in Formula (XV-M), and solvates and hydrates of the salts.

In an embodiment, the Invention provides a Conjugate according to Formula (I) and Formula (II), wherein E, E', or E" have the structure as set forth in Formula (XV-F):

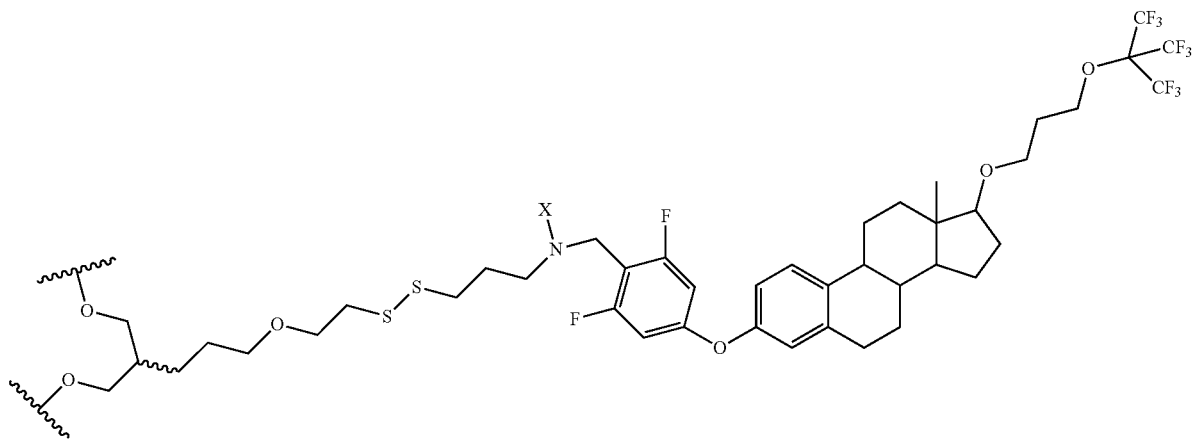

Formula (XV-F)

including pharmaceutically acceptable salts, hydrates, solvates and metal chelates of the compound represented by the structure as set forth in Formula (XV-F), and solvates and hydrates of the salts; wherein X is a protecting group for amine.

In another embodiment, the Invention provides a Conjugate according to Formula (I) and Formula (II), wherein the L moiety is tetra-fluoro-benzylamine; and therefore E, E', or E" each has the structure as set forth in Formula (XVI):

Formula (XVI)

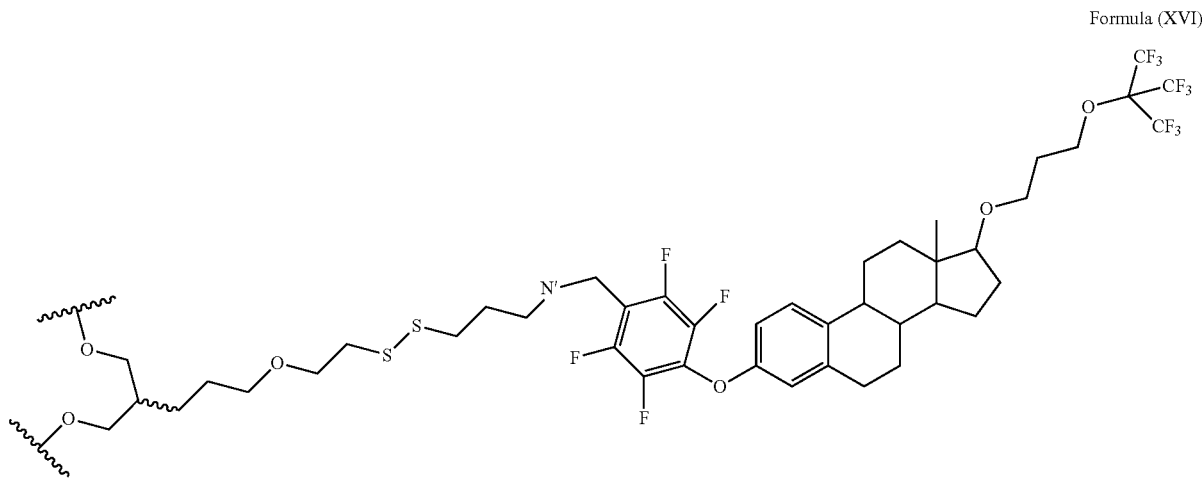

including pharmaceutically acceptable salts, hydrates, solvates and metal chelates of the compound represented by the structure as set forth in Formula (XVI), and solvates and hydrates of the salts; wherein N' has the same meaning as in Formula (II).

In an embodiment, the Invention provides a Conjugate according to Formula (I) and Formula (II), wherein E, E', or E" have the structure as set forth in Formula (XVI-H):

Formula (XVI-H)

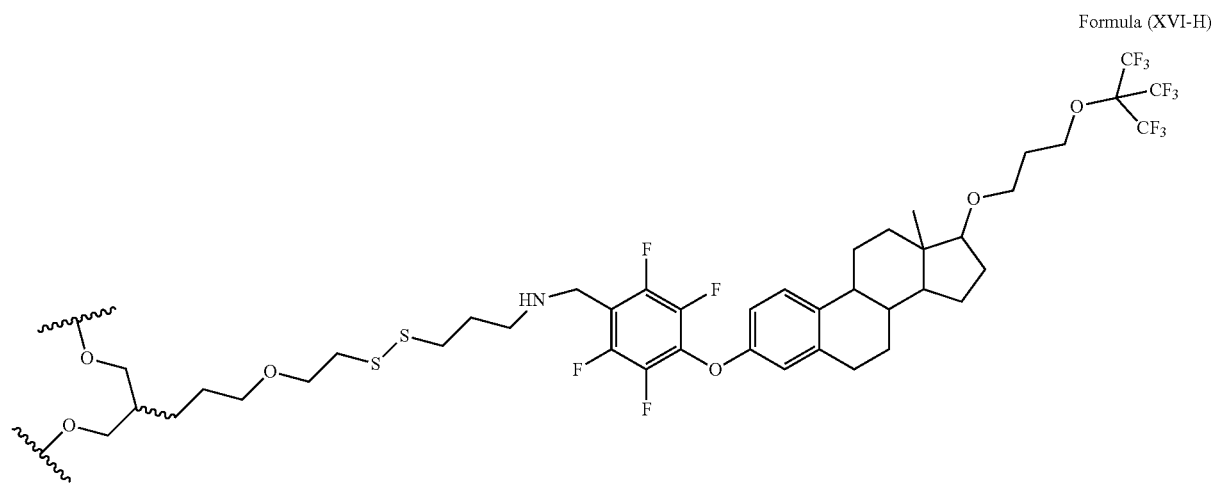 [SMILES: *OCC(CCCOCCSSCCCNCc1c(F)c(F)c(Oc2ccc3c(c2)CCC2C3CCC3(C)C(OCCCOC(C(F)(F)F)(C(F)(F)F)C(F)(F)F)CCC23)c(F)c1F)CO*]

including pharmaceutically acceptable salts, hydrates, solvates and metal chelates of the compound represented by the structure as set forth in Formula (XVI-H), and solvates and hydrates of the salts.

In an embodiment, the Invention provides a Conjugate according to Formula (I) and Formula (II), wherein E, E', or E" have the structure as set forth in Formula (XVI-M):

Formula (XVI-M)

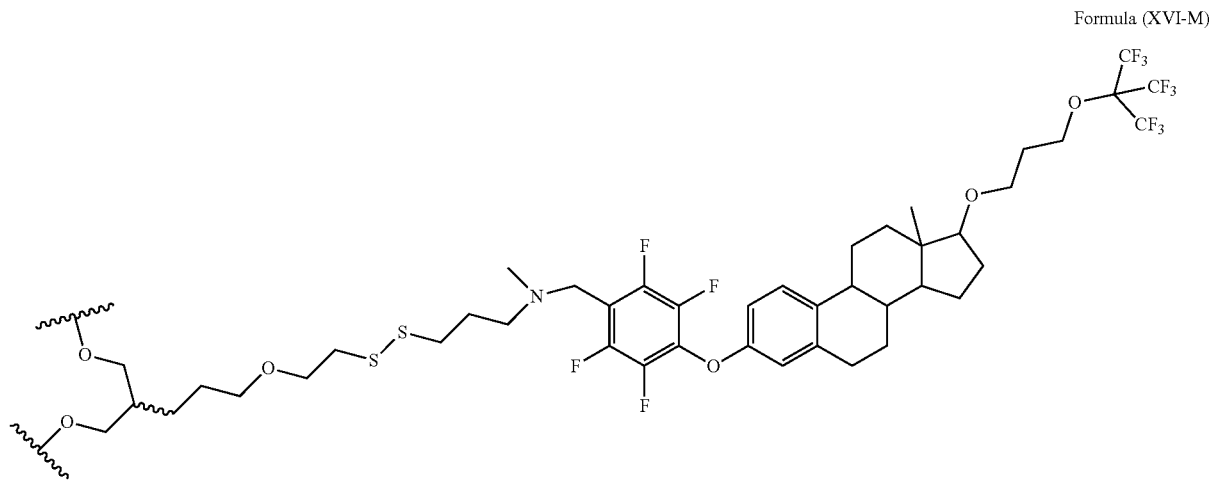 [SMILES: *OCC(CCCOCCSSCCCN(C)Cc1c(F)c(F)c(Oc2ccc3c(c2)CCC2C3CCC3(C)C(OCCCOC(C(F)(F)F)(C(F)(F)F)C(F)(F)F)CCC23)c(F)c1F)CO*]

including pharmaceutically acceptable salts, hydrates, solvates and metal chelates of the compound represented by the structure as set forth in Formula (XVI-M), and solvates and hydrates of the salts.

In an embodiment, the Invention provides a Conjugate according to Formula (I) and Formula (II), wherein E, E', or E" have the structure as set forth in Formula (XVI-F):

Formula (XVI-F)

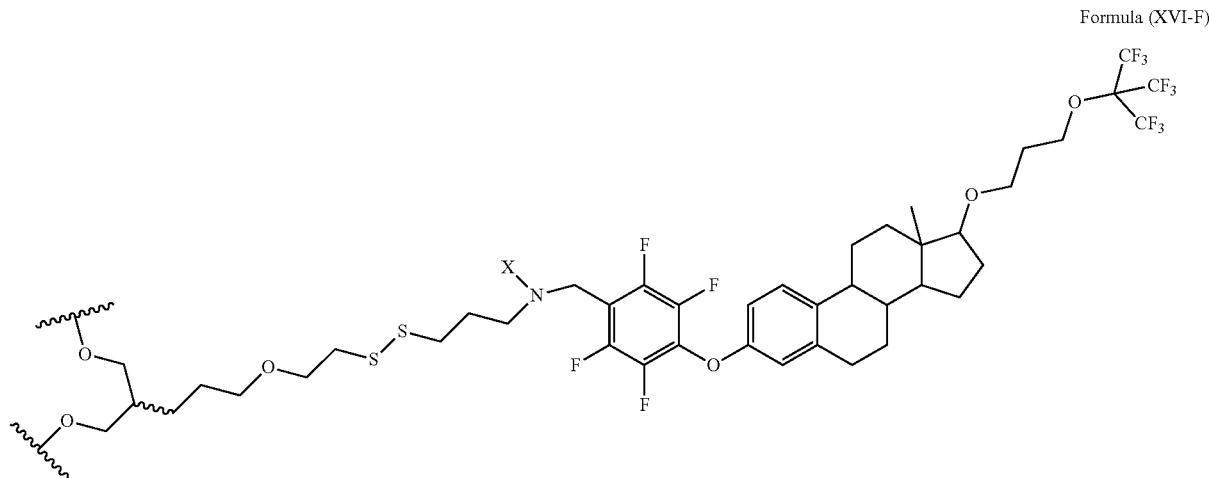

including pharmaceutically acceptable salts, hydrates, solvates and metal chelates of the compound represented by the structure as set forth in Formula (XVI-F), and solvates and hydrates of the salts; wherein X is a protecting group for amine.

The Invention also provides a Precursor Molecule, being any E, E' or E" moiety or moieties of the Invention, having the structure as set forth in any of Formulae (II), (III), (IV), (V), (VI), (VII), (VIII), (VIII-H), (VIII-M), (IX), (X), (XI), (XII), (XIIa), (XIII), (XIIIa), (XIV), (XIV-H), (XIV-M), (XV), (XV-H), (XV-M), (XVI), (XVI-H), (XVI-M), linked to protecting groups for alcohols and/or protecting groups for amines, wherein said protecting groups are destined to be removed during chemical processing of the molecule, e.g., during conjugation to oligonucleotide chain.

Some embodiments of the invention relate to a method for delivery of a drug across a biological membrane into cells, either in vitro or in vivo; said method comprising contacting the cells with a Conjugate as described herein.

Another embodiment of the Invention relates to a method for treating a medical disorder in a patient in need; the method comprising administering to the patient a therapeutically-effective amount of a pharmaceutical composition, that comprises a Conjugate of the Invention, that includes the drug D that is useful for the treatment of the disease of said patient, and a pharmaceutically-acceptable salt or carrier.

Described are also Examples, that illustrate the invention, in a non-limiting manner, in order to demonstrate how embodiments of the invention can be carried-out in practice. The Examples describe various Compounds and Conjugates of the Invention. All described Conjugates are according to Formulae (Cn-1) or (Cn-2), each comprising E, E' or E" moieties, having the structure according to general Formula (II). The Examples provide various E, E' or E" moieties, representing structures as set forth in Formulae (III), (IV), (V), (VI), (VII), (VIII), (VIII-H), (VIII-M), (IX), (X), (XI), (XII), (XIIa), (XIII), (XIIIa), (XIV), (XIV-H), (XIV-M), (XV), (XV-H), (XV-M), (XVI), (XVI-H), (XVI-M). All these Conjugates manifest biological performance in gene silencing, in contrast to Control compounds, that may share structural similarity to the above compounds, but which, however, do not fully comply with the structural motifs according to Formula (II), and respectively do not show the desired biological activity. The performance profile demonstrated by the Conjugates of the Invention according to Formulae (I) and (II), therefore represents a general and unique structural framework, which enables its related compounds to be useful in the delivery of macromolecular ODs across phospholipid membranes into cells, with consequent performance of a useful biological activity, both in vitro and in vivo.

In addition, the Examples describe methods for chemical synthesis of the E moieties of the Invention, their precursors, and their assembly into useful Conjugates.

BRIEF DESCRIPTION OF THE FIGURES AND DRAWINGS

Figure 1B:
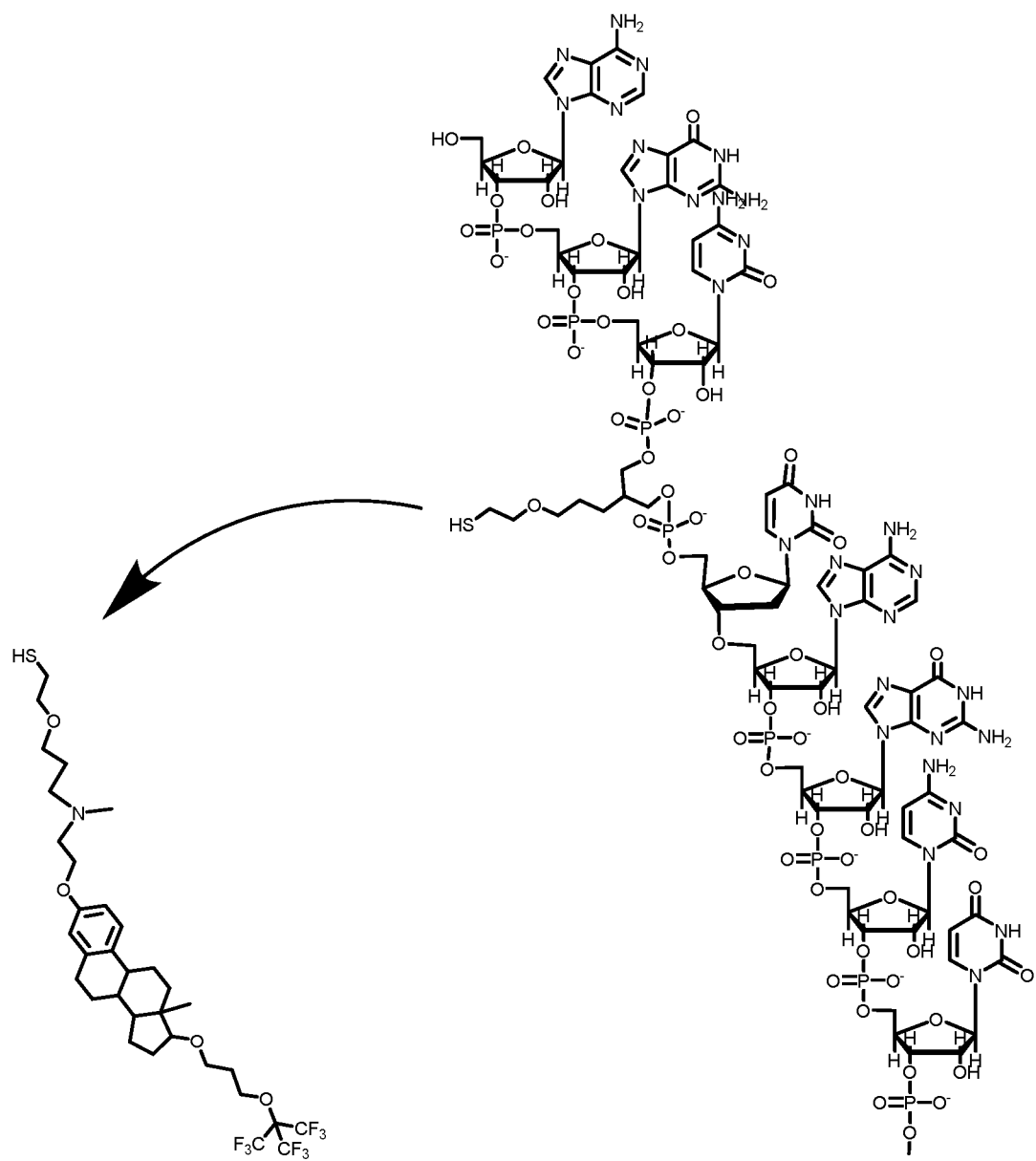

FIGS. 1A and 1B exemplify the mode of linkage of an E moiety of the Invention, according to Formula (III) to an oligonucleotide chain, and respective red-ox-mediated cleavage of an E moiety. FIG. 1A shows an RNA strand, wherein an E moiety according to Formula (III) is linked at an internal position; FIG. 1B exemplifies red-ox-mediated cleavage of the disulfide group of this E moiety according to Formula (III) in reductive conditions, such as those prevailing within the cytoplasm, with consequent release of an RNA drug.

Figure 2A:
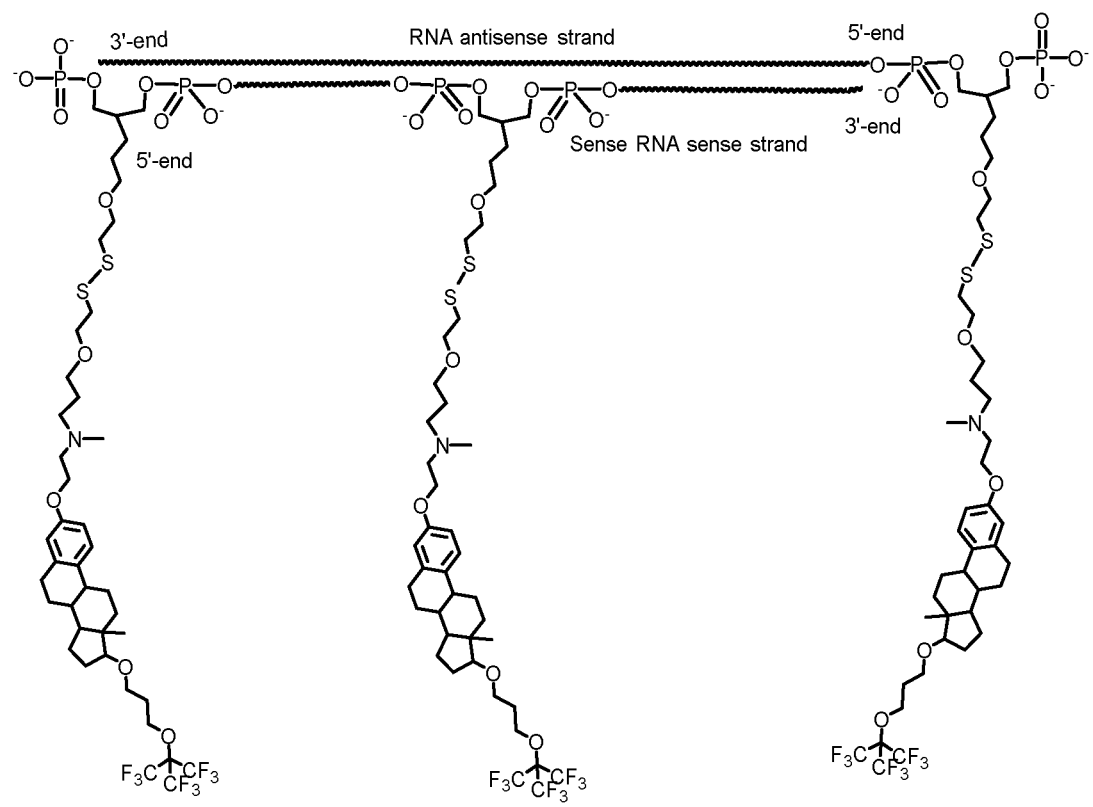
Figure 2B:
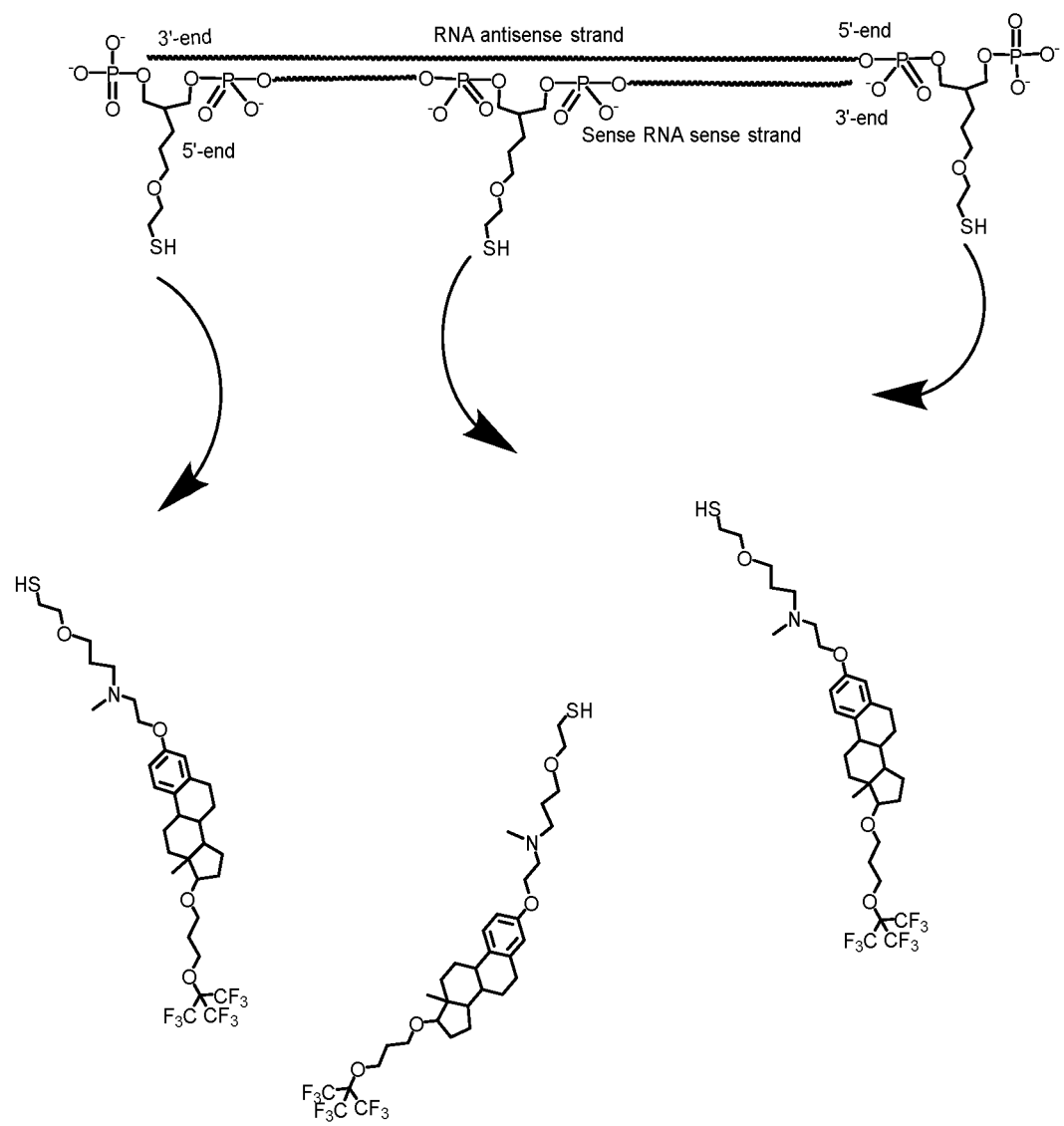
Figure 2C:
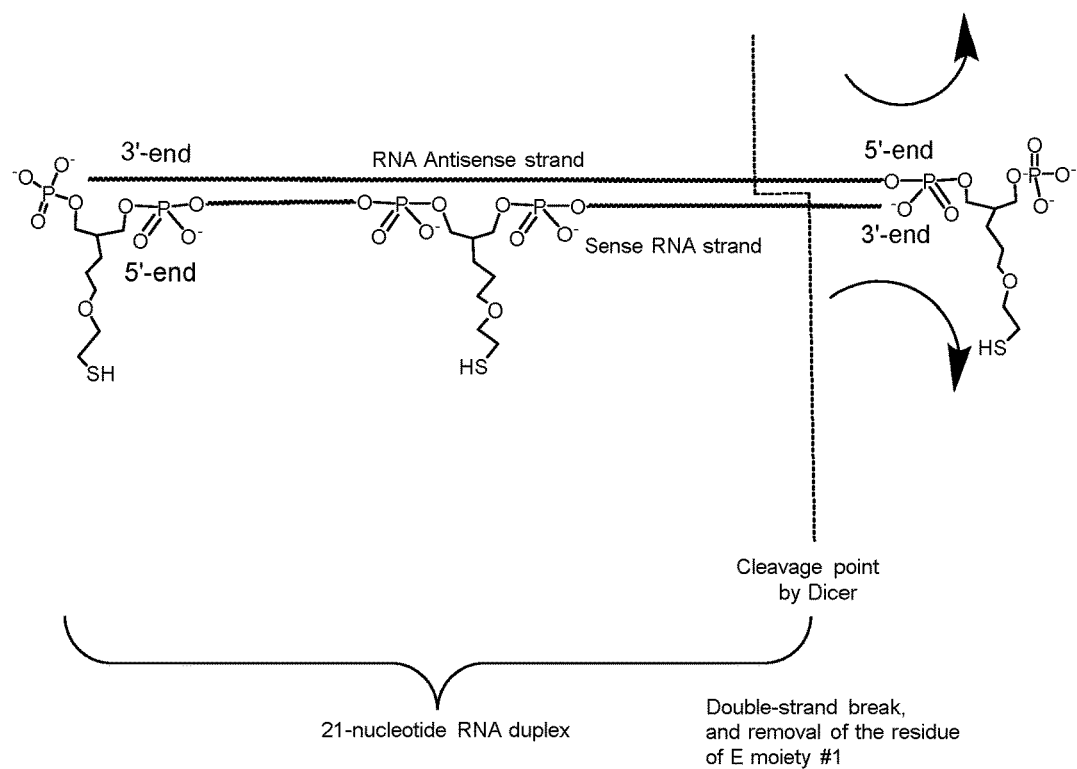
Figure 2D:
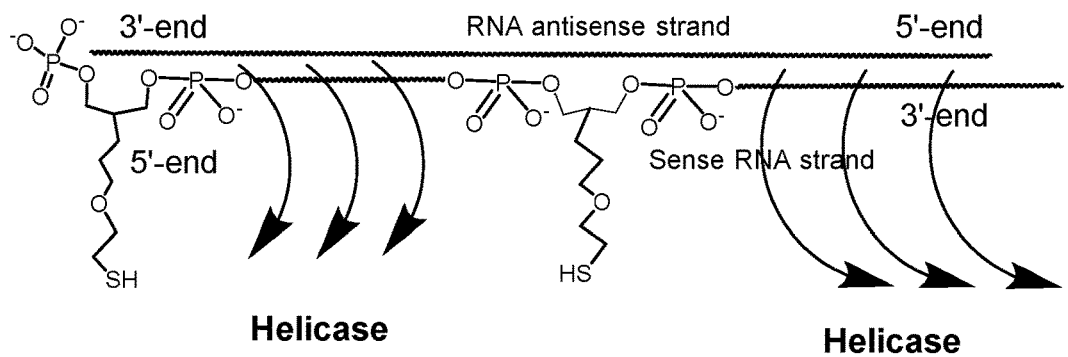

FIGS. 2A, 2B, 2C, 2D and 2E exemplify the Mechanism of Action (MOA) of a Conjugate of the Invention, wherein the Conjugate is according to Formula [Cn-2-(III)]. The RNA Duplex is a Dicer substrate of 25/27-nucleotide long, with a phosphate group linked at the 5'-end of each strand, and wherein W group of the internally positioned E moiety is according to Formula (II$^1$), with J being —CH$_2$—; FIG. 2A demonstrates the intact Conjugate; FIG. 2B demonstrates the cleavage and removal of the E, E' and E" moieties in the reductive conditions that prevail in the cytoplasm, leaving for each E, E' or E" moiety a short residual stump; FIG. 2C demonstrates interaction of the RNA Duplex with the Dicer endonuclease, that results in a double-strand break, leaving a 21/21 RNA Duplex, and removal of the stump of the E" moiety, leaving two remaining stumps of E and E', linked at the 5'-end and at an internal position of the passenger strand; FIG. 2D demonstrates the removal of the sense (passenger) strand by the enzyme helicase (i.e., a cytoplasmatic enzyme, capable of separating RNA strands), with concomitant removal of the remaining stumps of the E and E' moieties, which are linked to the passenger strand. Consequently, there is release of the intact antisense strand, to enter the RNA-induced silencing complex (RISC), in order to induce the desired gene silencing [FIG. 2E].

Figure 3A:
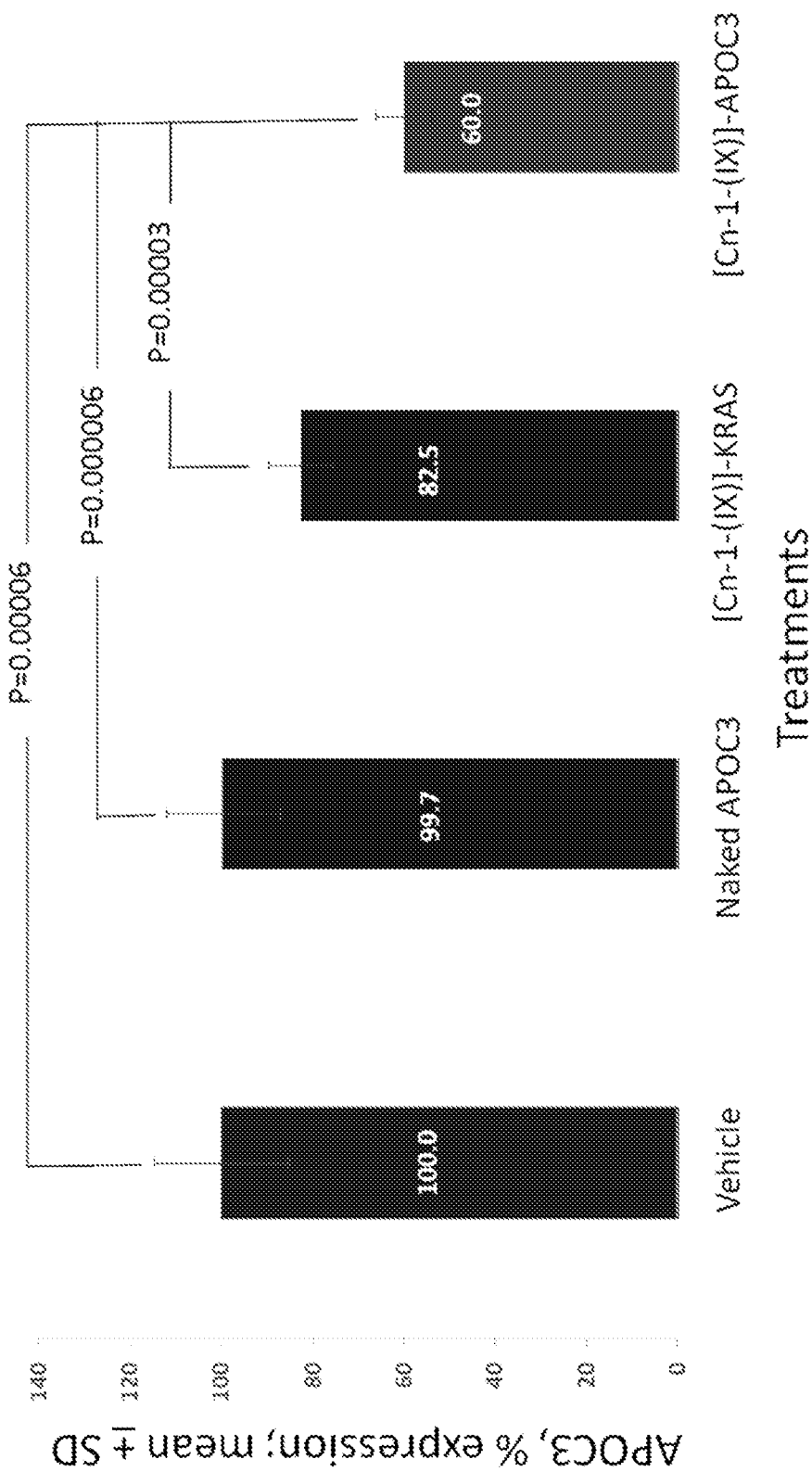
Figure 3B:
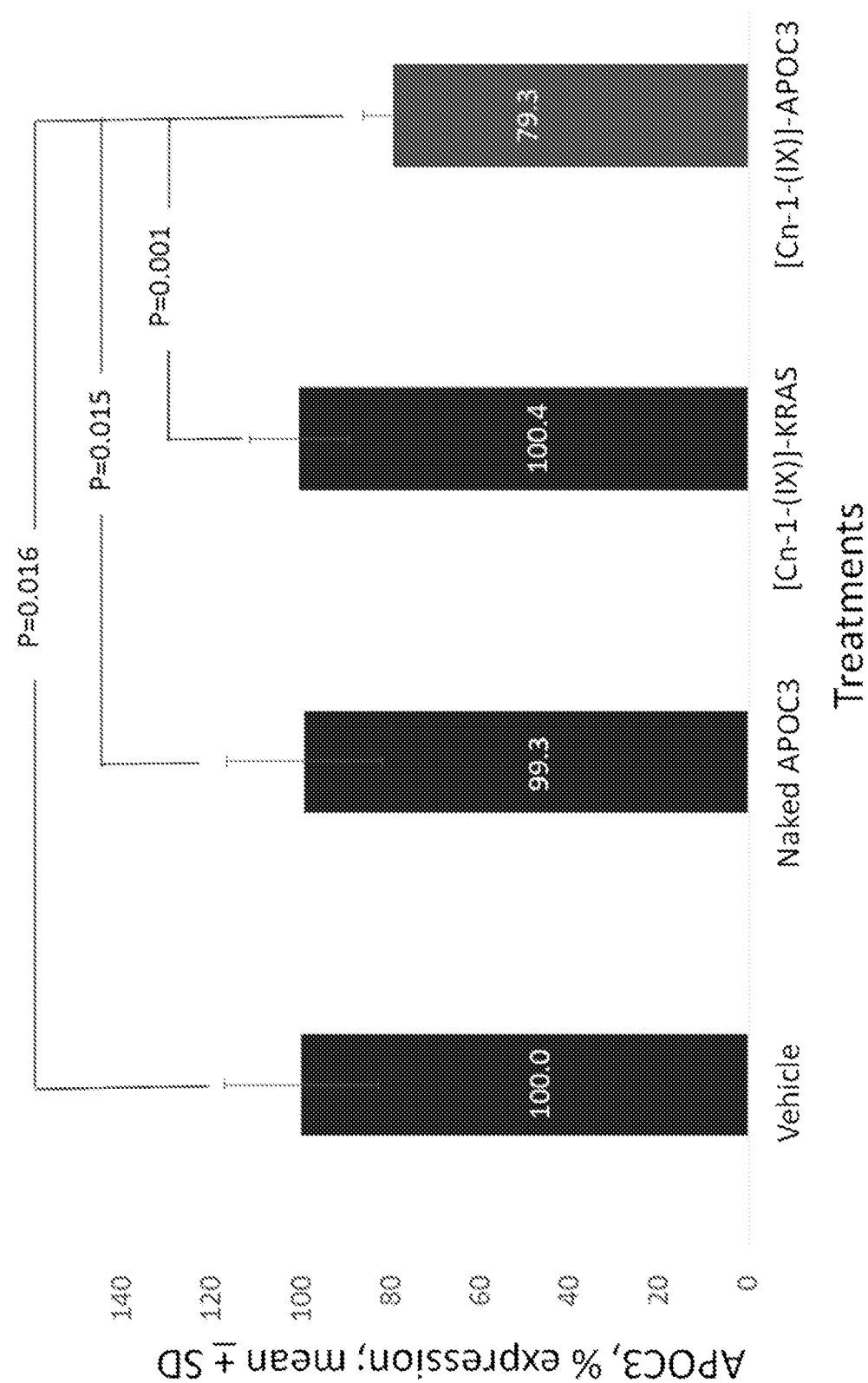

FIGS. 3A and 3B describe the performance of a Conjugate of the Invention Formula [Cn-1-(IX)], namely, harboring E and E' moieties, each being according to Formula (IX) in silencing the expression of the ApoC3 gene upon intravenous administration in a murine model, in vivo; (FIG. 3A). Gene silencing in the liver; (FIG. 3B). Gene silencing in the kidney. Experimental groups were: (i). Vehicle: 5% glucose in water for injection; (ii). "Naked" dsiRNA for ApoC3 (without attachment of Molecular Nanomotor moieties); (iii). [Cn-1-(IX)]-Kras dsiRNA Conjugate (non-related RNA sequence, conjugated to the Apo-Si Molecular Nanomotor delivery system); (iv). The target [Cn-1-(IX)]-ApoC3 dsiRNA Conjugate.

FIGS. 4A and 4B [Cn-2-(VIII)], namely, harboring E, E', and E" moieties, each being according to Formula (VIII), in silencing the expression of the EGFP gene, in vitro: (FIG. 4A): Cultured Hela cells; (FIG. 4B): Cultured 3T3 cells. Presented are dose-response curves, in the concentration range of 0-300 nM.

Figure 5:
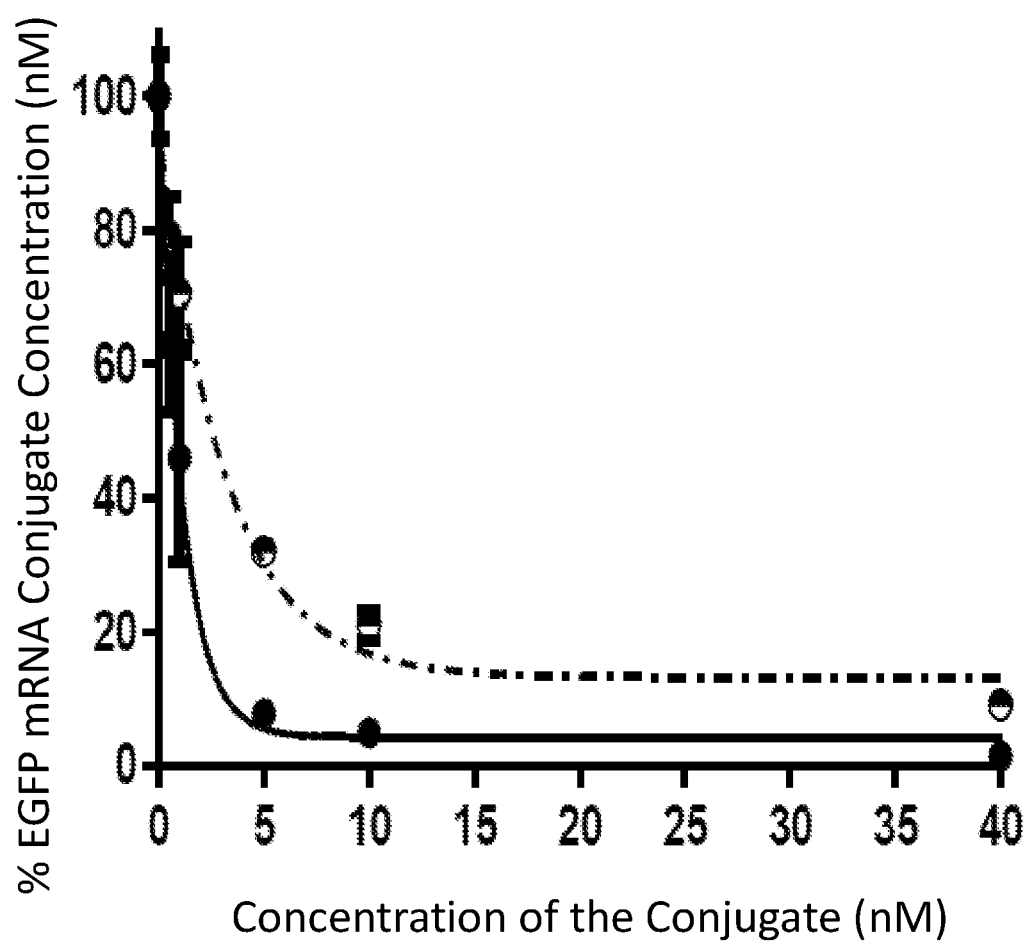

FIG. 5 describes the biological performance of two Conjugates of the Invention: Conjugate [Cn-1-(VIII-M)] and Conjugate [Cn-2-(VIII-M)], in silencing the expression of the EGFP gene in 3T3 cells, in vitro. A clear dose/response was observed, with a highly-significant logarithmic decay, with a curve fit of $R^2 \approx 0.97$ for both cell lines. For Conjugate [Cn-1-(VIII-M)] (dotted line), having 2 E moieties, IC$_{50}$ was found to be 2.2 nM, while for Conjugate [Cn-2-(VIII-M)] (solid line), having 3 E moieties, IC$_{50}$ was found to be 0.8 nM.

DETAILED DESCRIPTION OF THE INVENTION

The invention relates to Conjugates and Precursors thereof, comprising macromolecule drugs such as OD, linked to a novel molecular delivery system (MDS) that can deliver the cargo drug across phospholipid biological membranes into cells, to exert biological activity, such as silencing the expression of a target gene. This delivery system enables the trans-membrane delivery of macromolecule drugs, such as genetic drugs, for example, siRNA or dsiRNA, antisense oligonucleotides (ASO), or therapeutic proteins. The invention is based on the discovery and development of novel compounds by the Inventors that manifest advantageous performance in gene silencing, by combining efficacious trans-membrane delivery across phospholipid membranes, with subsequent robust reduction-based liberation of the cargo OD into the cytoplasm, to exert its biological effect.

In an embodiment of the invention, there are provided Conjugates, having the structure as set forth in Formula (I):

Formula (I)

including pharmaceutically acceptable salts, hydrates, solvates and metal chelates of the compound represented by the structure as set forth in Formula (I), and solvates and hydrates of the salts, wherein:

D is a drug to be delivered across biological membranes (i.e., a cargo drug), selected from a group consisting of a small-molecule drug, a peptide, a protein, and an OD (i.e., a native or modified, single-stranded or double-stranded, DNA or RNA, siRNA, dsiRNA, or ASO);

y, z and w are each an integer, independently selected from 0, 1, 2, 3 or 4, wherein if any of y, z or w is 0, it means that the respective E moiety (or moieties) is (are) null; at least one of y, z or w is different from 0;

E, E', or E" can be the same or different, each having independently a structure as set forth in general Formula (II):

Formula (II)

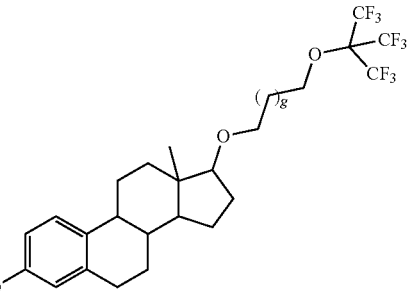
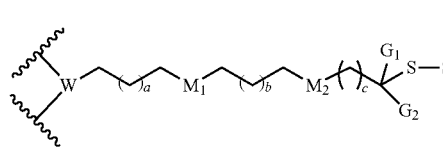

including pharmaceutically acceptable salts, hydrates, solvates and metal chelates of the compound represented by the structure as set forth in Formula (II), and solvates and hydrates of the salts, wherein:

- $M_1$, $M_2$, $M_3$, $M_4$ are each individually selected from the group consisting of N', N", null, ether, amide, ester, thioether and thioester; wherein N' and N" are each selected independently from the group consisting of —N(CH$_3$)—, —NH—, and —N(X)—; wherein X is a protecting group for amine; $M_1$, $M_2$, $M_3$, $M_4$ can be the same or different; N', N" can be the same or different.

- L is a linker, selected from the group consisting of null, $C_1$, $C_2$, $C_3$, $C_4$, $C_5$, $C_6$ alkylene or heteroalkylene; $C_5$ or $C_6$ aryl or heteroaryl, optionally substituted by fluorine atom(s), or hydroxyl group(s); and combinations thereof;

- $G_1$, $G_2$, $G_3$, $G_4$, each stands independently for a hydrogen atom or a methyl group; G groups can be the same or different; at least two of $G_1$, $G_2$, $G_3$ or $G_4$ groups are hydrogen atoms;

- a, b, c, d, e are integers, each independently selected from the group consisting of 0, 1, 2, 3, 4, 5, or 6, wherein 0=null; a, b, c, d, e can be the same or different; g stands for an integer, selected from 0, 1, 2, 3, 4 or 5;

- W is selected from the group consisting of null, a residue of hydroxyl, di-hydroxyl, amide, natural or modified nucleoside, and any of the structures as set forth in Formulae (II$^1$), (II$^2$) and (II$^3$), and combinations thereof:

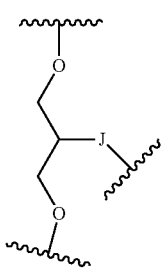

Formula (II$^1$)

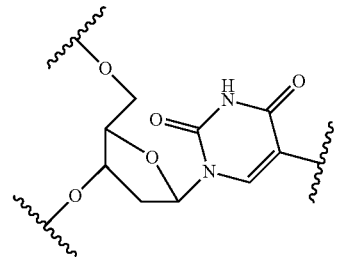

Formula (II$^2$)

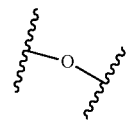

Formula (II$^3$)

wherein J is selected from the group consisting of null, —CH$_2$—, a secondary or tertiary amine, and oxygen;

E, E', or E" can be linked to any moiety of the group consisting of D; a protecting group, as defined herein (e.g., a protecting group for alcohol); R or R' group, selected from the group consisting of hydrogen, phosphate, sulfate and carboxyl group; and a solid support. In the context of the Invention, an E, E' or E" moiety may be linked to one D moiety via one or more points; and W can be linked concomitantly to both D and R or R'.

In one of the embodiments of the Invention g is an integer of 0, 1, or 2.

In an embodiment, c and d each stands independently for an integer of 1, 2 or 3; c and d can be the same or different.

In an embodiment of the Invention $G_1$, $G_2$, $G_3$, $G_4$ are all hydrogen atoms.

In an embodiment, L is difluorobenzylamine.

In another embodiment, X is TEOC [2-(trimethylsilyl) ethyl carbamate], or Fmoc.

Accordingly, in an embodiment, the Invention provides Conjugates according to Formula (I) and Formula (II), wherein E, E', or E" have the structure as set forth in Formula (III):

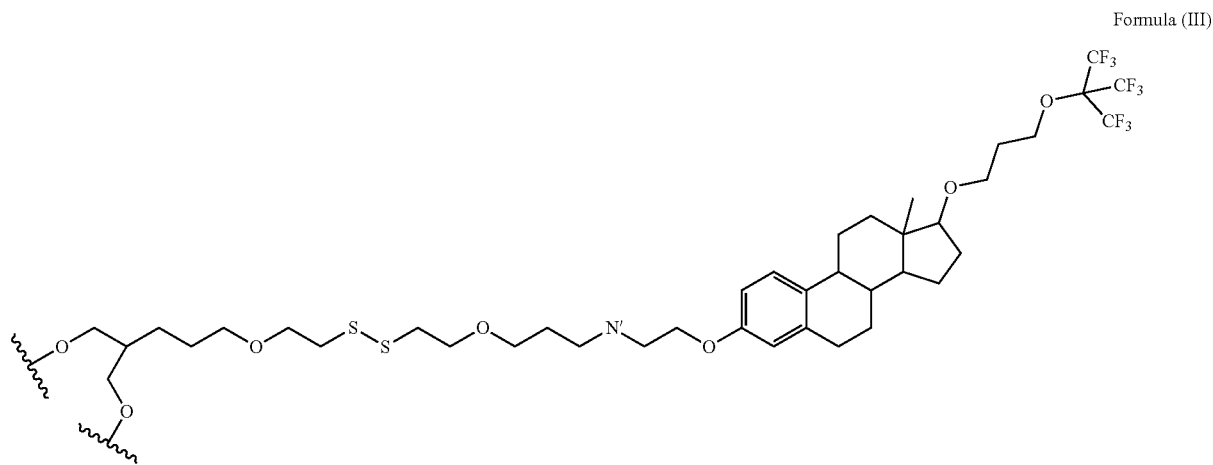

Formula (III)

including pharmaceutically acceptable salts, hydrates, solvates and metal chelates of the compound represented by the structure as set forth in Formula (III), and solvates and hydrates of the salts; wherein N' has the same meaning as defined in Formula (II).

In another embodiment, the Invention provides a Conjugate according to Formula (I) and Formula (II), wherein E, E', or E" have the structure as set forth in Formula (IV):

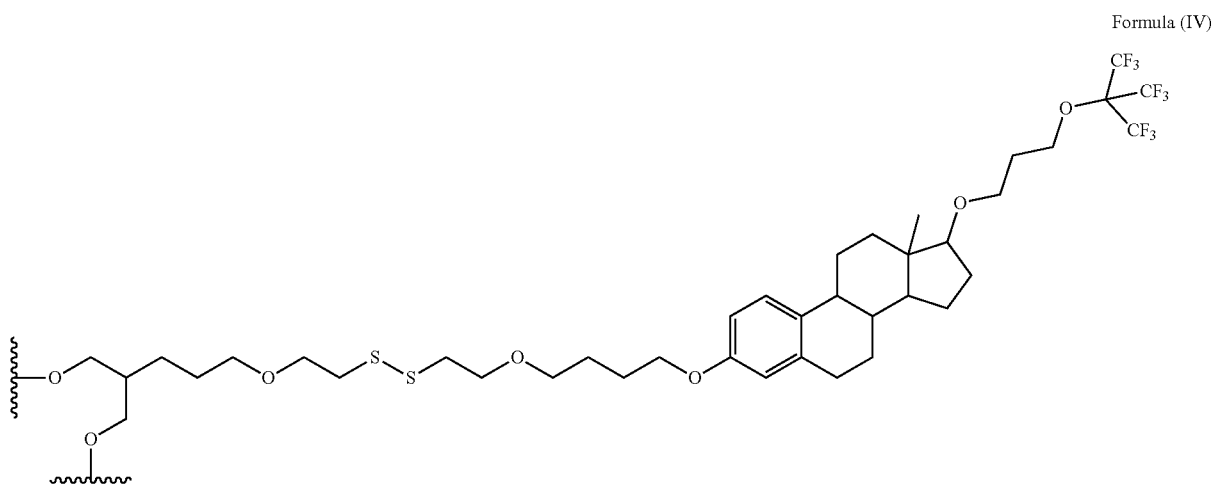 [SMILES: *OCC(CCCOCCSSCCOCCCCOc1ccc2c(c1)CCC1C2CCC2(C)C(OCCCOC(C(F)(F)F)(C(F)(F)F)C(F)(F)F)CCC12)CO*]

Formula (IV)

including pharmaceutically acceptable salts, hydrates, solvates and metal chelates of the compound represented by the structure as set forth in Formula (IV), and solvates and hydrates of the salts.

In another embodiment, the Invention provides a Conjugate according to Formula (I) and Formula (II), wherein E, E', or E" have the structure as set forth in Formula (V):

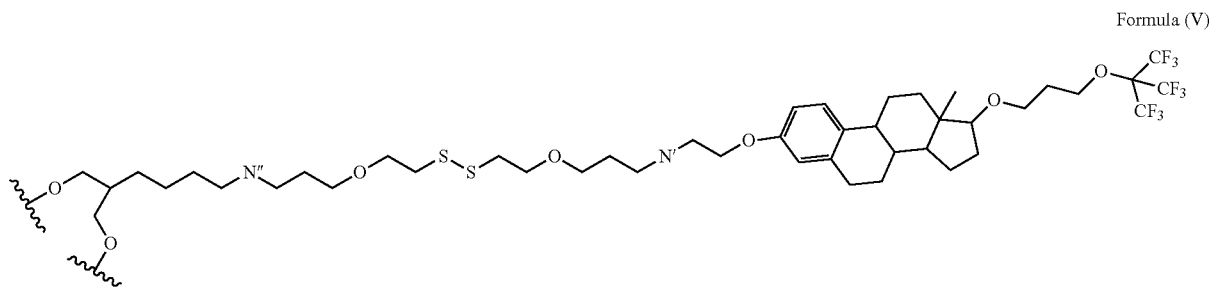

Formula (V)

including pharmaceutically acceptable salts, hydrates, solvates and metal chelates of the compound represented by the structure as set forth in Formula (V), and solvates and hydrates of the salts; wherein N' and N" each has independently the same meaning as defined in Formula (II).

In another embodiment, the Invention provides a Conjugate according to Formula (I) and Formula (II), wherein E, E', or E" have the structure as set forth in Formula (VI):

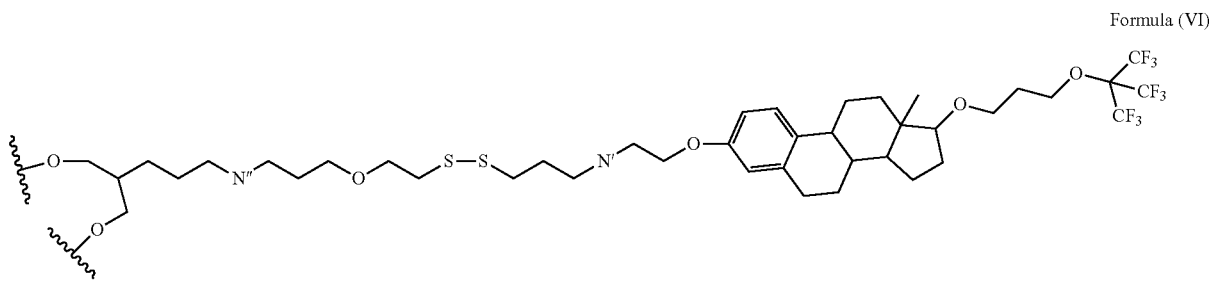

Formula (VI)

including pharmaceutically acceptable salts, hydrates, solvates and metal chelates of the compound represented by the structure as set forth in Formula (VI), and solvates and hydrates of the salts; wherein N' and N" each has independently the same meaning as defined in Formula (II).

In another embodiment, the Invention provides a Conjugate according to Formula (I) and Formula (II), wherein E, E', or E" have the structure as set forth in Formula (VII):

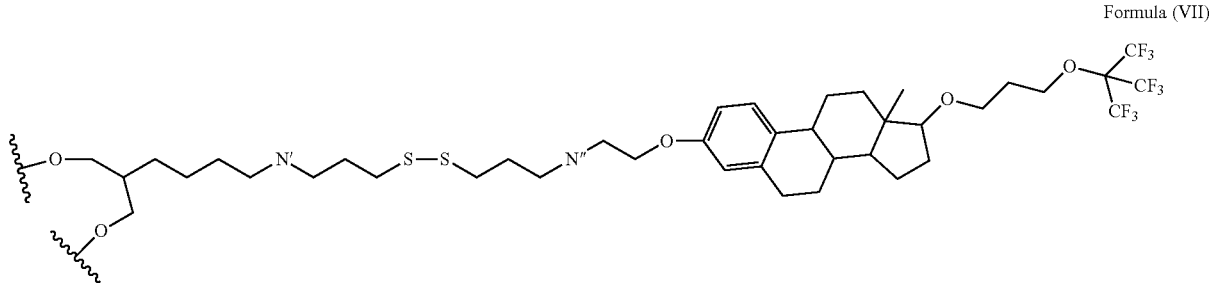

Formula (VII)

including pharmaceutically acceptable salts, hydrates, solvates and metal chelates of the compound represented by the structure as set forth in Formula (VII), and solvates and hydrates of the salts; wherein N' and N" each has independently the same meaning as defined in Formula (II).

In another embodiment, the Invention provides a Conjugate according to Formula (I) and Formula (II), wherein E, E', or E" have the structure as set forth in Formula (VIII):

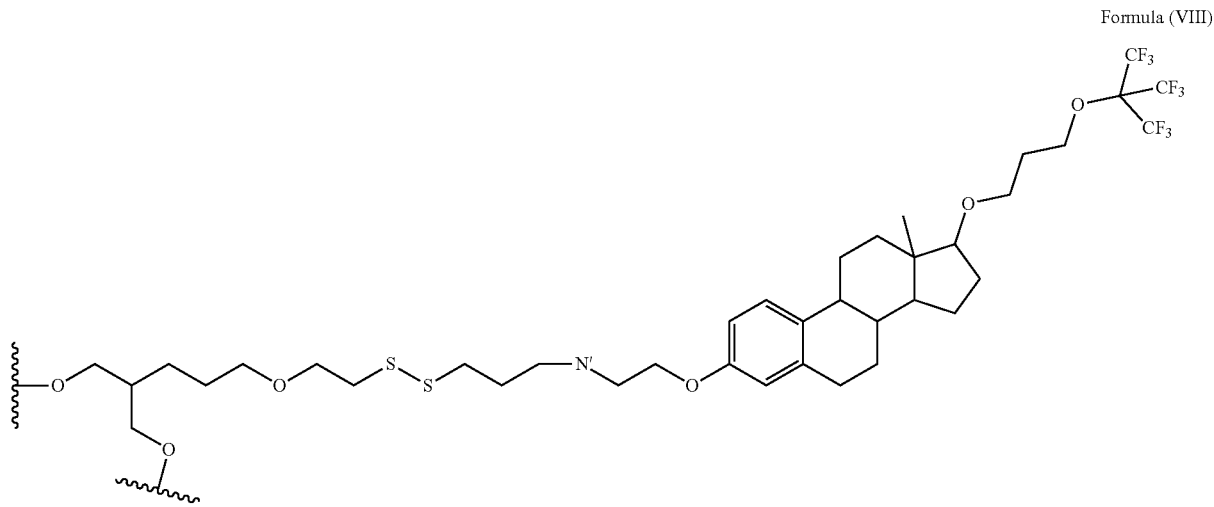

Formula (VIII)

including pharmaceutically acceptable salts, hydrates, solvates and metal chelates of the compound represented by the structure as set forth in Formula (VIII), and solvates and hydrates of the salts; wherein N' has the same meaning as in Formula (II).

In an embodiment, the Invention provides a Conjugate according to Formula (I) and Formula (II), wherein E, E', or E" have the structure as set forth in Formula (VIII-H):

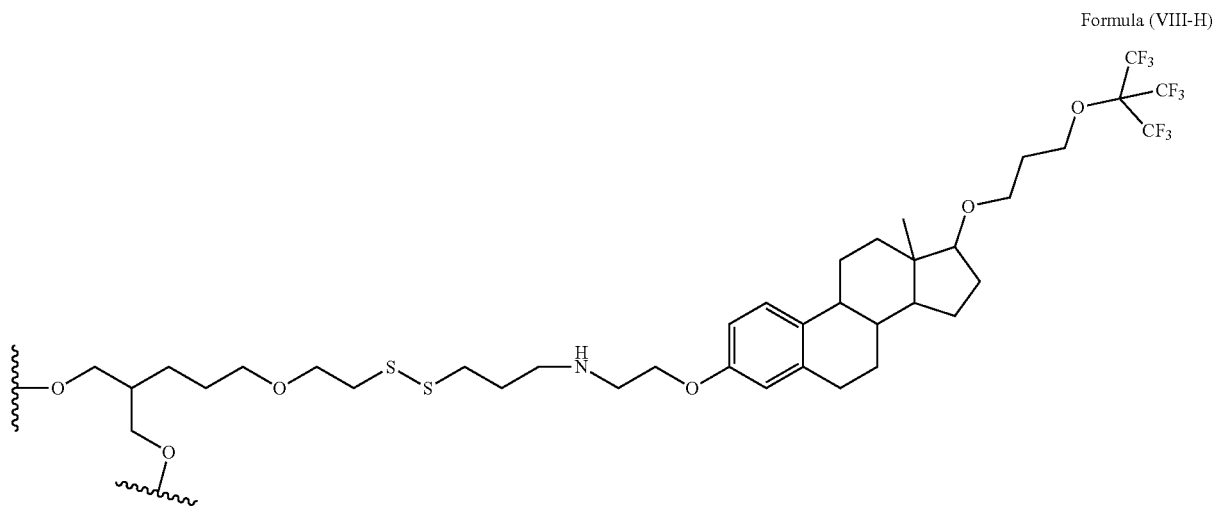 [SMILES: *OCC(CCCOCCSSCCCNCCOc1ccc2c(c1)CCC1C2CCC2(C)C(OCCCOC(C(F)(F)F)(C(F)(F)F)C(F)(F)F)CCC12)CO*]

Formula (VIII-H)

including pharmaceutically acceptable salts, hydrates, solvates and metal chelates of the compound represented by the structure as set forth in Formula (VIII-H), and solvates and hydrates of the salts.

In a related embodiment, the Invention provides a Conjugate according to Formula (I) and Formula (II), wherein E, E', or E" have the structure as set forth in Formula (VIII-M):

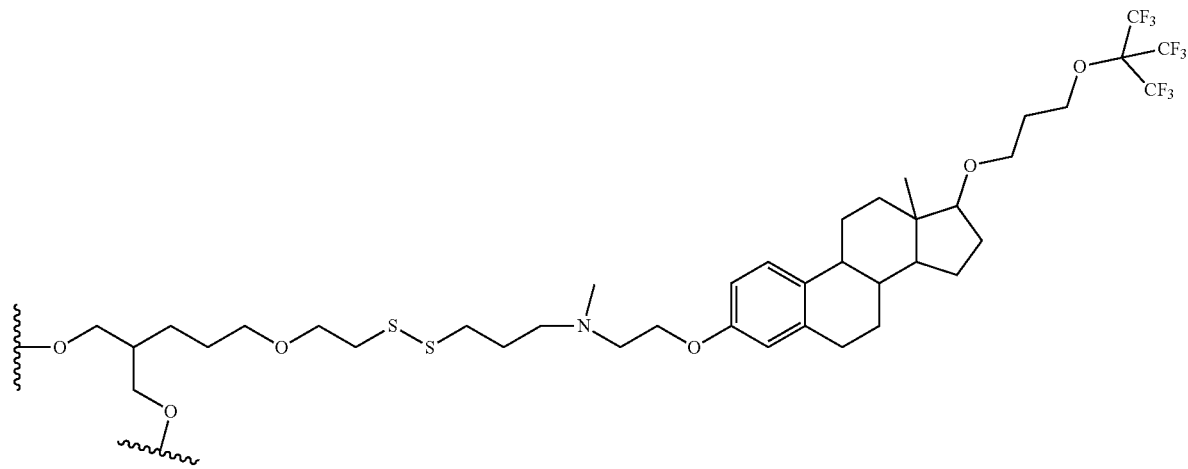

Formula (VIII-M)

including pharmaceutically acceptable salts, hydrates, solvates and metal chelates of the compound represented by the structure as set forth in Formula (VIII-M), and solvates and hydrates of the salts.

In another embodiment, the Invention provides a Conjugate according to Formula (I) and Formula (II), wherein E, E', or E" have the structure as set forth in Formula (VIII-F):

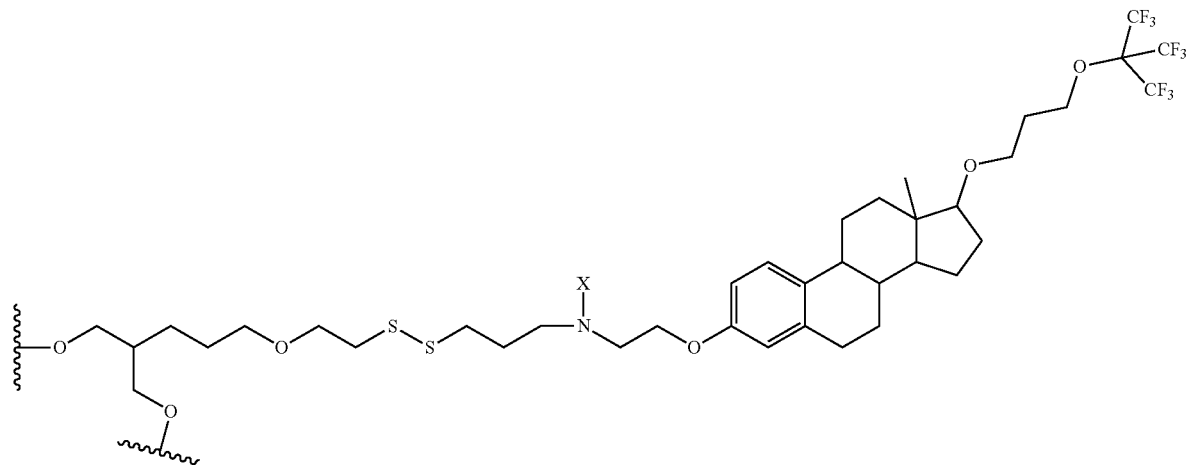

Formula (VIII-F)

including pharmaceutically acceptable salts, hydrates, solvates and metal chelates of the compound represented by the structure as set forth in Formula (VIII-F), and solvates and hydrates of the salts; wherein X is a protecting group for amine.

In another embodiment, the Invention provides a Conjugate according to Formula (I) and Formula (II), wherein E, E', or E" have the structure as set forth in Formula (IX):

Formula (IX)

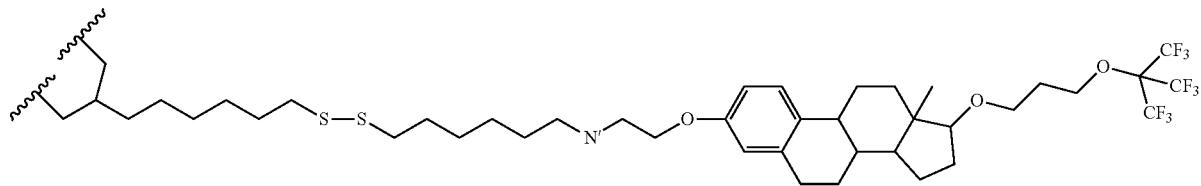

including pharmaceutically acceptable salts, hydrates, solvates and metal chelates of the compound represented by the structure as set forth in Formula (IX), and solvates and hydrates of the salts; wherein N' has the same meaning as in Formula (II).

In yet another embodiment, the Invention provides a Conjugate according to Formula (I) and Formula (II), wherein E, E', or E" have the structure as set forth in Formula (X):

Formula (X)

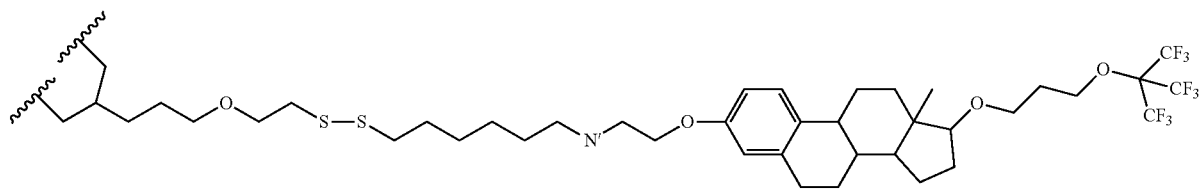

including pharmaceutically acceptable salts, hydrates, solvates and metal chelates of the compound represented by the structure as set forth in Formula (X), and solvates and hydrates of the salts; wherein N' has the same meaning as in Formula (II).

In yet another embodiment, the Invention provides a Conjugate according to Formula (I) and Formula (II), wherein E, E', or E" have the structure as set forth in Formula (XI):

Formula (XI)

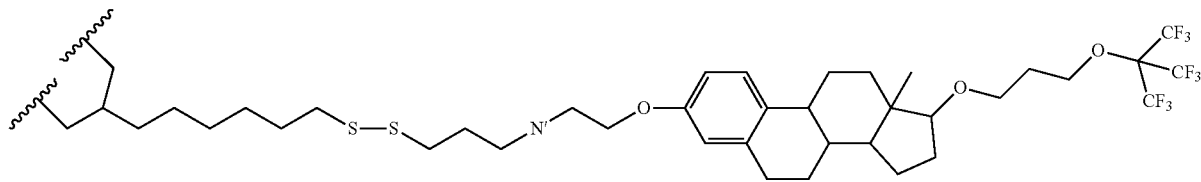

including pharmaceutically acceptable salts, hydrates, solvates and metal chelates of the compound represented by the structure as set forth in Formula (XI), and solvates and hydrates of the salts; wherein N' has the same meaning as in Formula (II).

In another embodiment, the Invention provides a Conjugate according to Formula (I) and Formula (II), wherein E, E', or E" have the structure as set forth in Formula (XII):

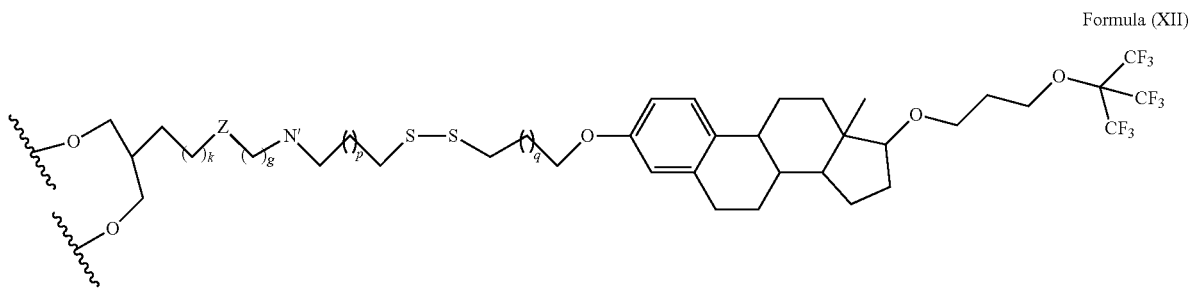

Formula (XII)

including pharmaceutically acceptable salts, hydrates, solvates and metal chelates of the compound represented by the structure as set forth in Formula (XII), and solvates and hydrates of the salts; wherein p and q each stands independently for an integer of 0, 1, 2, 3, 4, 5, or 6, wherein 0 means null; p and q can be the same or different; k and g each stands independently for an integer of 0, 1, 2, 3, 4, 5, 6, wherein 0 means null; k and g can be the same or different; Z is selected from the group consisting of null, —O—, and N"; wherein N' and N" have the same meaning as in Formula (II).

In an embodiment, the Invention provides a Conjugate according to Formula (I) and Formula (XII), wherein E, E', or E" have the structure as set forth in Formula (XIIa):

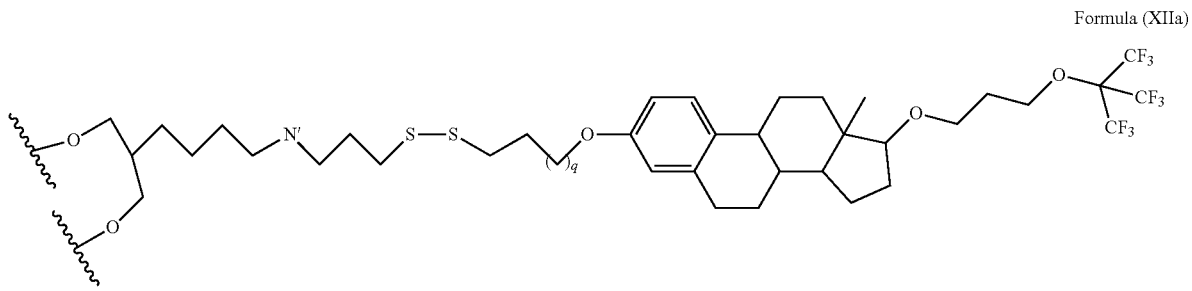

Formula (XIIa)

including pharmaceutically acceptable salts, hydrates, solvates and metal chelates of the compound represented by the structure as set forth in Formula (XIIa), and solvates and hydrates of the salts; wherein q is an integer of 0 or 1; and N' has the same meaning as in Formula (II).

The invention also provides a Conjugate according to Formula (I) and Formula (II), wherein E, E', or E" have the structure as set forth in Formula (XIII):

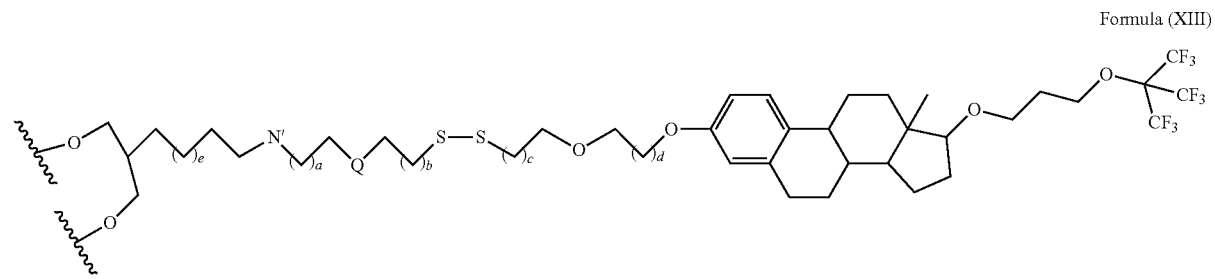

Formula (XIII)

including pharmaceutically acceptable salts, hydrates, solvates and metal chelates of the compound represented by the structure as set forth in Formula (XIII), and solvates and hydrates of the salts; wherein a, b, c, d, e, each stands independently for an integer of 0, 1, 2, or 3, wherein 0 means null; a, b, c, d, and e can be the same or different; Q is selected from the group consisting of null and —O—; N' has the same meaning as in Formula (II).

In another embodiment, the Invention provides a Conjugate according to Formula (I) and Formula (XIII), wherein E, E', or E" have the structure as set forth in Formula (XIIIa):

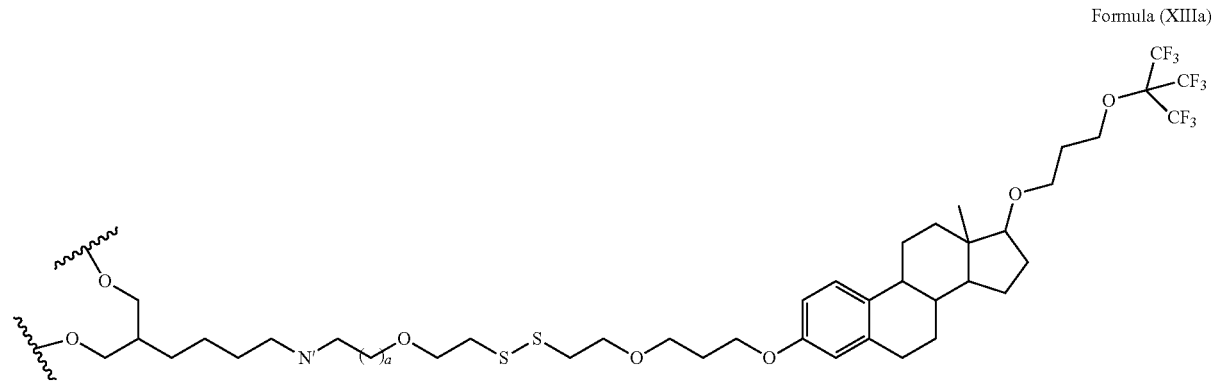

Formula (XIIIa)

including pharmaceutically acceptable salts, hydrates, solvates and metal chelates of the compound represented by the structure as set forth in Formula (XIIIa), and solvates and hydrates of the salts; wherein a is an integer of 1 or 2; N' has the same meaning as in Formula (II).

In an embodiment, the Invention provides a Conjugate according to Formula (I) and Formula (II), wherein E, E', or E" have the structure as set forth in Formula (XIV):

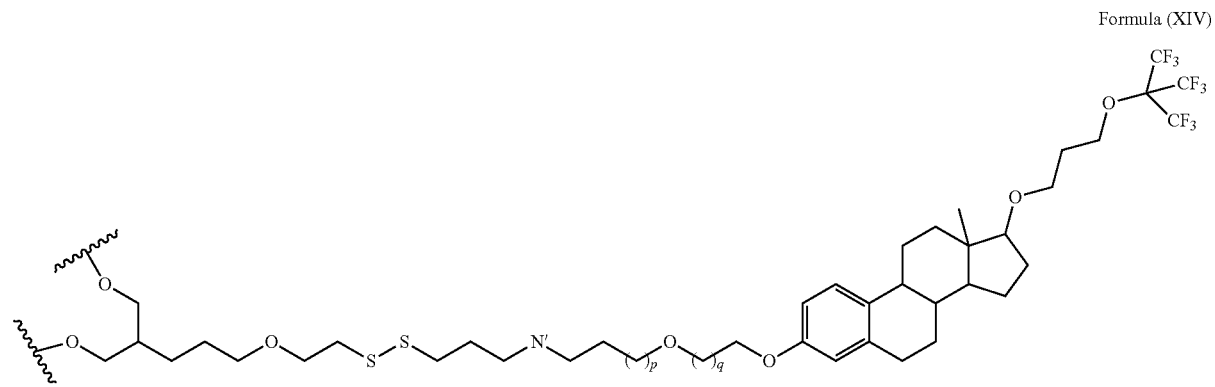

Formula (XIV)

including pharmaceutically acceptable salts, hydrates, solvates and metal chelates of the compound represented by the structure as set forth in Formula (XIV), and solvates and hydrates of the salts; wherein p and q are each independently an integer of 0, 1, 2, 3, 4, 5, or 6; N' has the same meaning as in Formula (II).

In an embodiment, the Invention provides a Conjugate according to Formula (I) and Formula (II), wherein E, E', or E" have the structure as set forth in Formula (XIV-H):

Formula (XIV-H)

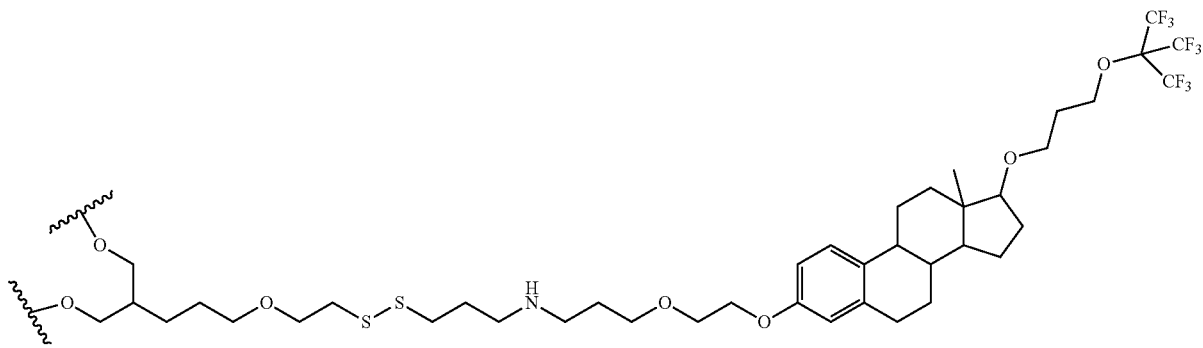

including pharmaceutically acceptable salts, hydrates, solvates and metal chelates of the compound represented by the structure as set forth in Formula (XIV-H), and solvates and hydrates of the salts.

In an embodiment, the Invention provides a Conjugate according to Formula (I) and Formula (II), wherein E, E', or E" have the structure as set forth in Formula (XIV-M):

Formula (XIV-M)

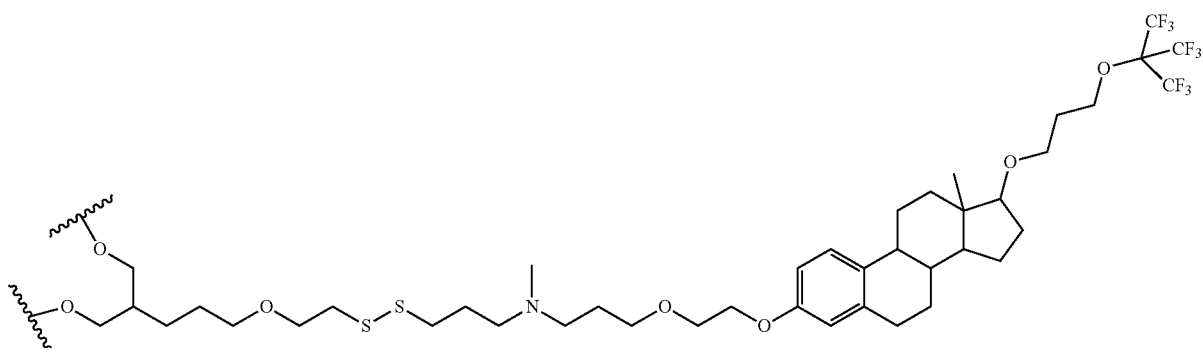

including pharmaceutically acceptable salts, hydrates, solvates and metal chelates of the compound represented by the structure as set forth in Formula (XIV-M), and solvates and hydrates of the salts.

In an embodiment, the Invention provides a Conjugate according to Formula (I) and Formula (II), wherein E, E', or E" have the structure as set forth in Formula (XIV-F):

Formula (XIV-F)

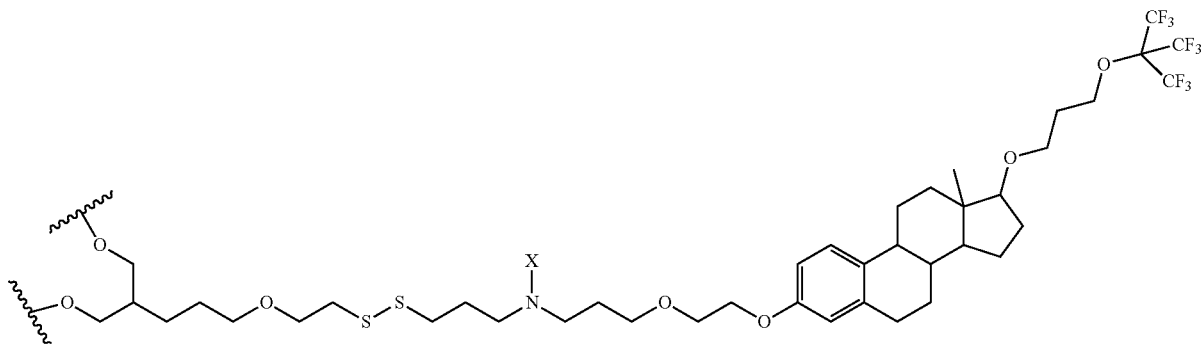

including pharmaceutically acceptable salts, hydrates, solvates and metal chelates of the compound represented by the structure as set forth in Formula (XIV-F), and solvates and hydrates of the salts, wherein X is a protecting group for amine.

In an embodiment, the Invention provides a Conjugate according to Formula (I) and Formula (II), wherein the L moiety is diflurobenzylamine; and therefore E, E', or E" each having the structure as set forth in Formula (XV):

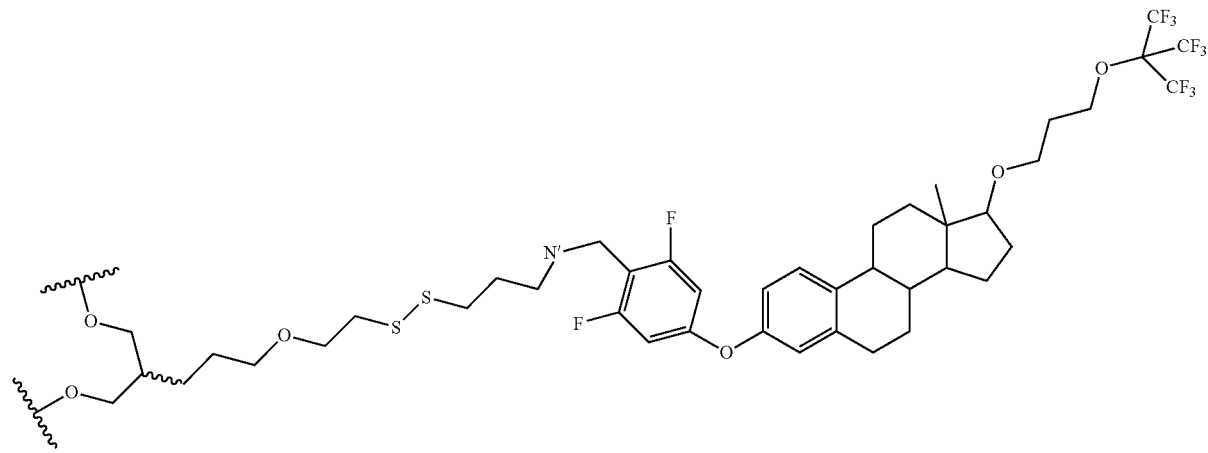

Formula (XV)

including pharmaceutically acceptable salts, hydrates, solvates and metal chelates of the compound represented by the structure as set forth in Formula (XV), and solvates and hydrates of the salts; wherein p and q are each independently an integer of 0, 1, 2, 3, 4, 5, or 6; N' has the same meaning as in Formula (II).

In an embodiment, the Invention provides a Conjugate according to Formula (I) and Formula (II), wherein E, E', or E" have the structure as set forth in Formula

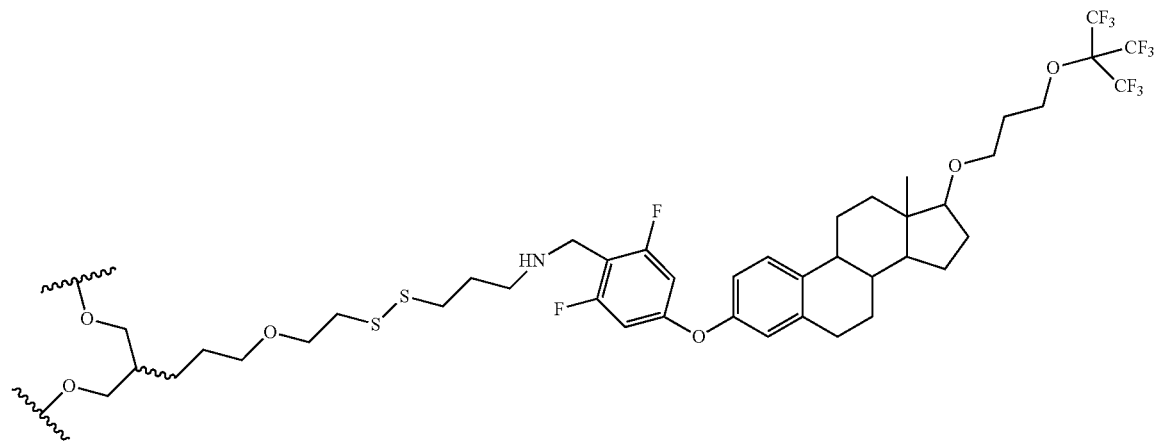

Formula (XV-H)

including pharmaceutically acceptable salts, hydrates, solvates and metal chelates of the compound represented by the structure as set forth in Formula (XV-H), and solvates and hydrates of the salts.

In an embodiment, the Invention provides a Conjugate according to Formula (I) and Formula (II), wherein E, E', or E" have the structure as set forth in Formula (XV-M):

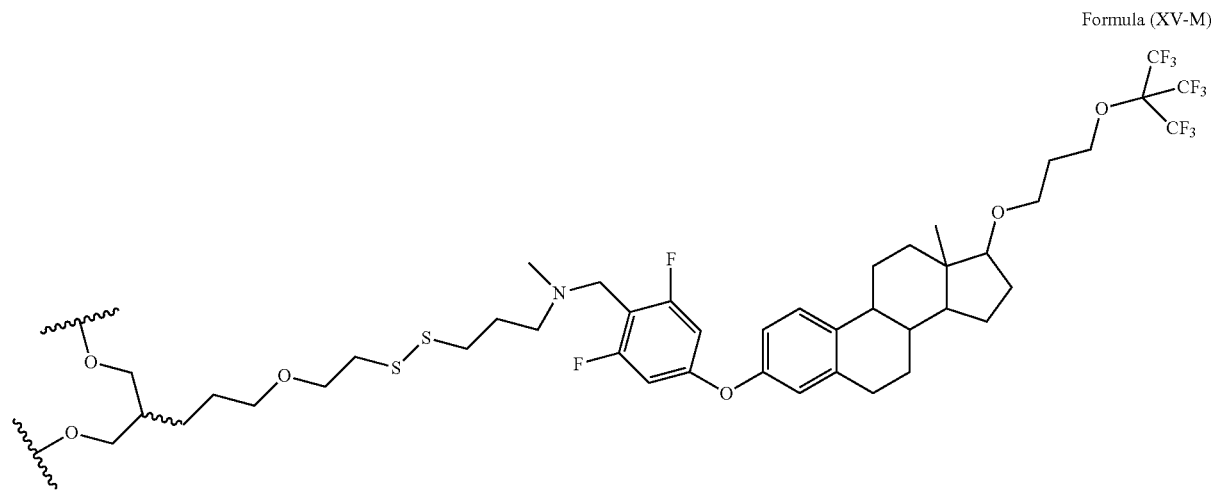 [SMILES: *OCC(CCCOCCSSCCCN(C)Cc1c(F)cc(Oc2ccc3c(c2)CCC2C3CCC3(C)C(OCCCOC(C(F)(F)F)(C(F)(F)F)C(F)(F)F)CCC23)cc1F)CO*]

Formula (XV-M)

including pharmaceutically acceptable salts, hydrates, solvates and metal chelates of the compound represented by the structure as set forth in Formula (XV-M), and solvates and hydrates of the salts.

In an embodiment, the Invention provides a Conjugate according to Formula (I) and Formula (II), wherein E, E', or E" have the structure as set forth in Formula (XV-F):

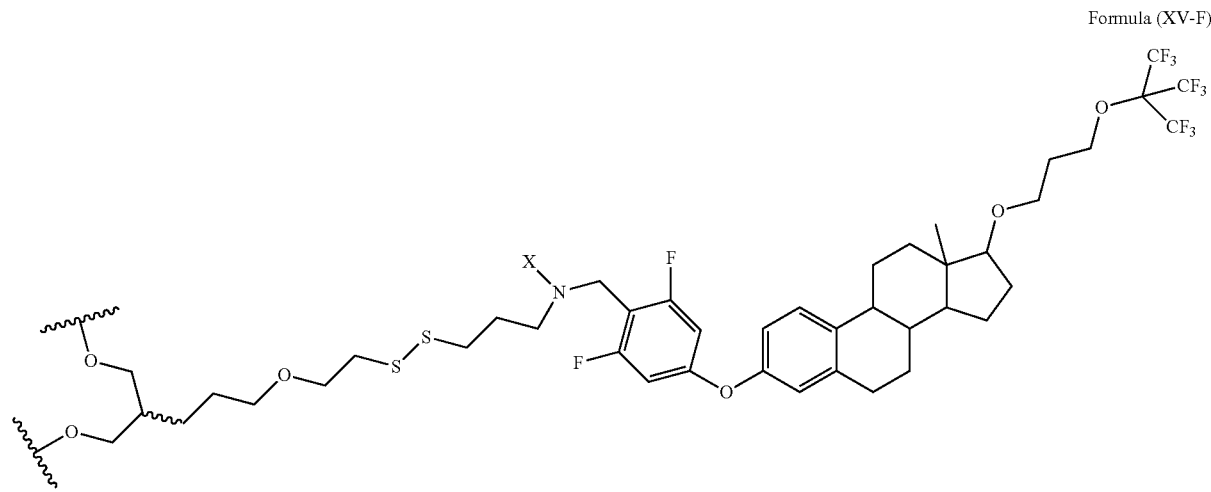

Formula (XV-F)

including pharmaceutically acceptable salts, hydrates, solvates and metal chelates of the compound represented by the structure as set forth in Formula (XV-F), and solvates and hydrates of the salts; wherein X is a protecting group for amine.

In another embodiment, the Invention provides a Conjugate according to Formula (I) and Formula (II), wherein the L moiety is tetra-fluoro-benzylamine; and therefore E, E', or E" each has the structure as set forth in Formula (XVI):

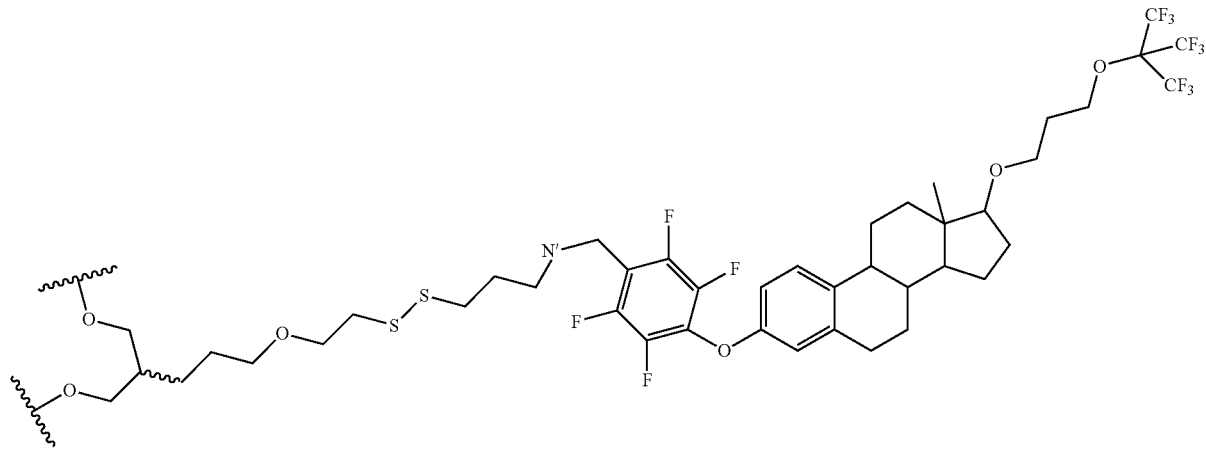

Formula (XVI)

including pharmaceutically acceptable salts, hydrates, solvates and metal chelates of the compound represented by the structure as set forth in Formula (XVI), and solvates and hydrates of the salts; wherein N' has the same meaning as in Formula (II).

In an embodiment, the Invention provides a Conjugate according to Formula (I) and Formula (II), wherein E, E', or E" have the structure as set forth in Formula (XVI-H):

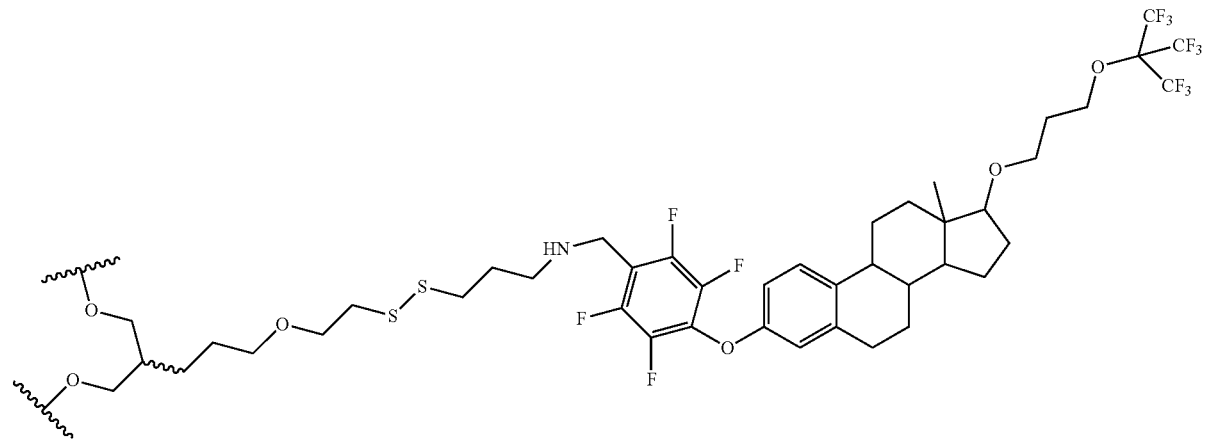

Formula (XVI-H)

including pharmaceutically acceptable salts, hydrates, solvates and metal chelates of the compound represented by the structure as set forth in Formula (XVI-H), and solvates and hydrates of the salts.

In an embodiment, the Invention provides a Conjugate according to Formula (I) and Formula (II), wherein E, E', or E" have the structure as set forth in Formula (XVI-M):

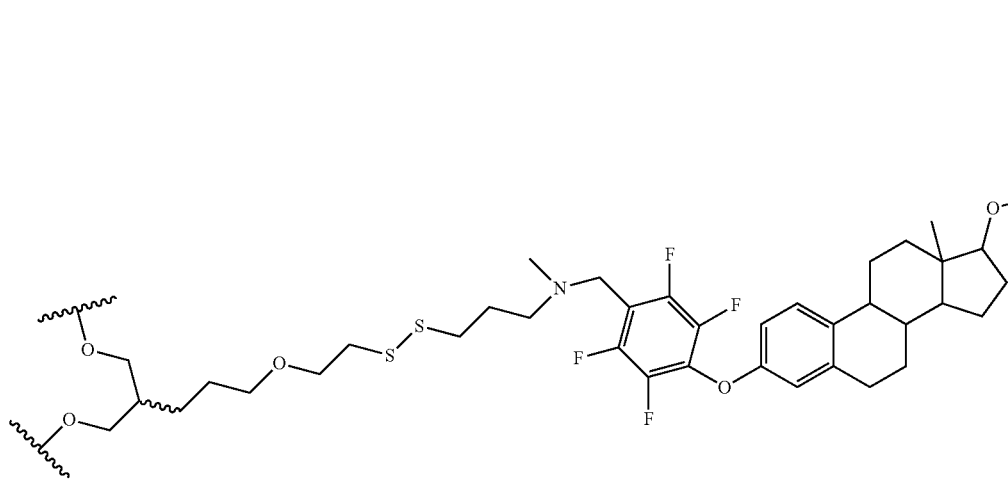

Formula (XVI-M)

including pharmaceutically acceptable salts, hydrates, solvates and metal chelates of the compound represented by the structure as set forth in Formula (XVI-M), and solvates and hydrates of the salts.

In an embodiment, the Invention provides a Conjugate according to Formula (I) and Formula (II), wherein E, E', or E" have the structure as set forth in Formula (XVI-F):

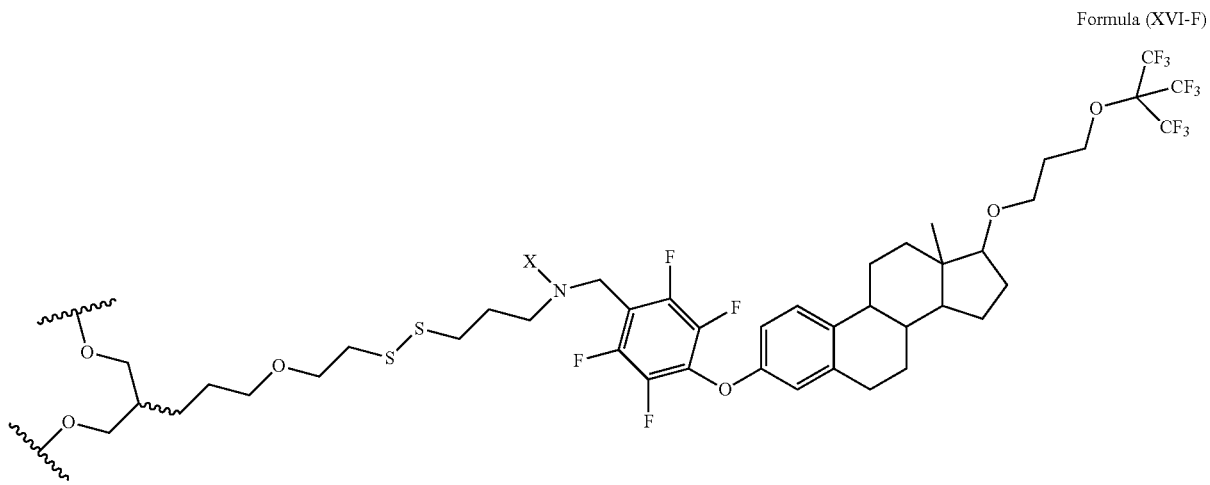

Formula (XVI-F)

including pharmaceutically acceptable salts, hydrates, solvates and metal chelates of the compound represented by the structure as set forth in Formula (XVI-F), and solvates and hydrates of the salts; wherein X is a protecting group for amine.

In the case that E, E' or E" has the structure as set forth in any of Formulae (II), (III), (IV), (V), (VI), (VII), (VIII), (VIII-H), (VIII-M), (IX), (X), (XI), (XII), (XIIa), (XIII), (XIIIa), (XIV), (XIV-H), (XIV-M), (XV), (XV-H), (XV-M), (XVI), (XVI-H), (XVI-M), it can be linked to protecting groups for alcohols or amines, wherein the protecting groups for alcohol are often, without limitation, Dimethoxytrityl [bis-(4-methoxyphenyl) phenylmethyl] (DMT) and phosphoramidite. These moieties are useful, among others, for the conjugation process of an E, E' or E" moiety of the Invention to an oligonucleotide chain, during the construction process of an oligonucleotide drug (OD).

In addition, frequently-used protecting groups for amine are Fmoc and TEOC [2-(trimethylsilyl)ethyl carbamate], which can be used to protect various functional groups attached to the E, E' or E" during synthesis of an OD. Being removed in basic conditions, such protecting groups can therefore be effectively removed during the steps of removal of the protecting groups, at the end of the OD synthesis, thus exposing a desired functional group on the final OD Conjugate, which has been previously masked by the protecting moiety(ies).

A Precursor Molecule in the context of the present Invention is any E, E' or E" moiety or moieties, having the structure as set forth in any of Formulae (II), (III), (IV), (V), (VI), (VII), (VIII), (VIII-H), (VIII-M), (IX), (X), (XI), (XII), (XIIa), (XIII), (XIIIa), (XIV), (XIV-H), (XIV-M), (XV), (XV-H), (XV-M), (XVI), (XVI-H), (XVI-M), linked to protecting groups for alcohols and/or amines, wherein said protecting groups are destined to be removed during chemical processing of the molecule, e.g., during conjugation to oligonucleotide chain; including respective pharmaceutically acceptable salts, hydrates, solvates and metal chelates, solvates and hydrates of the salts.

An example of a Precursor Molecule of the Invention, provided in a non-limiting manner, is based on the structure of Formula (VIII), and has the structure as set forth in the following Formula (VIII-F)-Precursor:

Formula (VIII-F)-Precursor

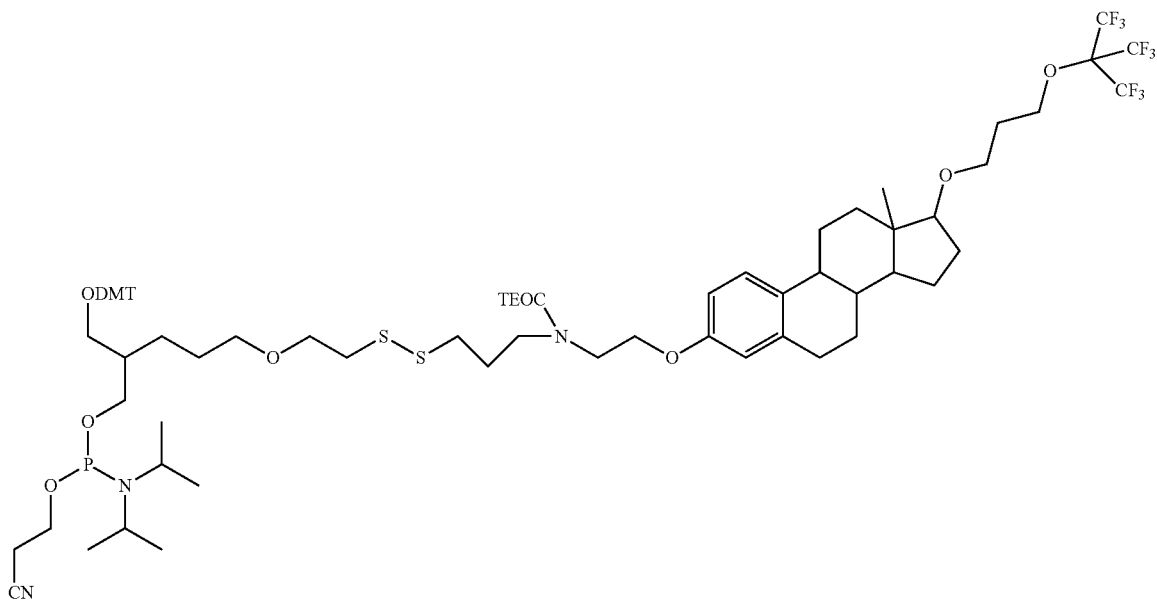

including pharmaceutically acceptable salts, hydrates, solvates and metal chelates of the compound represented by the structure as set forth in Formula (VIII-F)-Precursor, and solvates and hydrates of the salts.

Another example of a Precursor Molecule of the Invention, still based on the structure of Formula (VIII), is the following Formula (VIII-M)-Precursor:

Formula (VIII-M)-Precursor

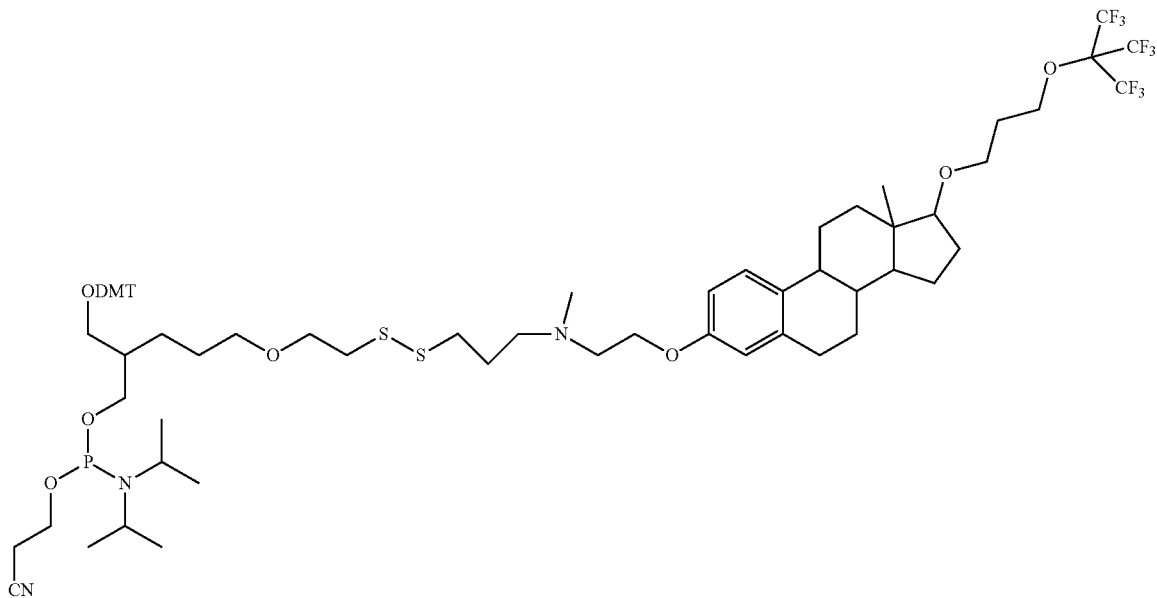

including pharmaceutically acceptable salts, hydrates, solvates and metal chelates of the compound represented by the structure, and solvates and hydrates of the salts.

Another example of a Precursor Molecule of the Invention, is based on the structure of Formula (XIV), and is the following Formula (XIV-F)-Precursor:

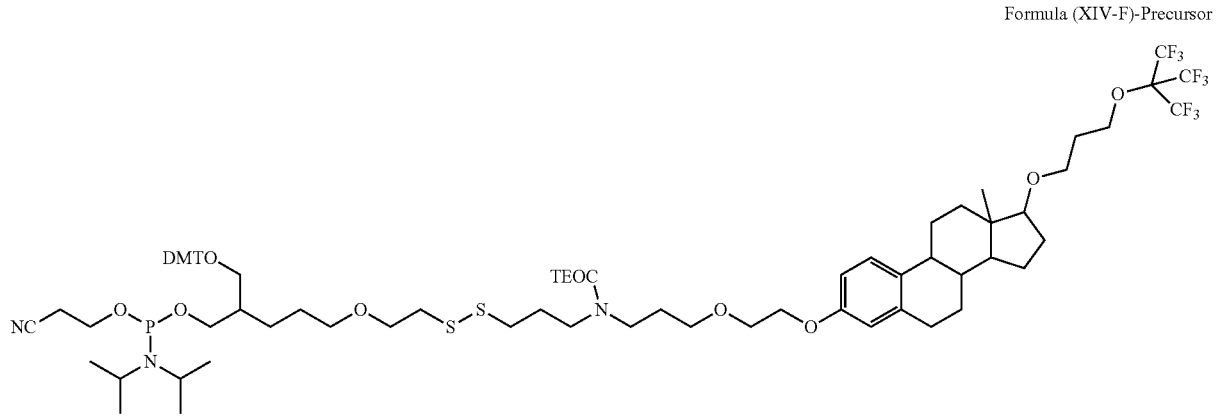

Formula (XIV-F)-Precursor including pharmaceutically acceptable salts, hydrates, solvates and metal chelates of the compound represented by the structure as set forth in Formula (XIV-F)-Precursor, and solvates and hydrates of the salts.

Another example of a Precursor Molecule of the Invention still based on the structure of Formula (XIV), having the following Formula (XIV-M)-Precursor:

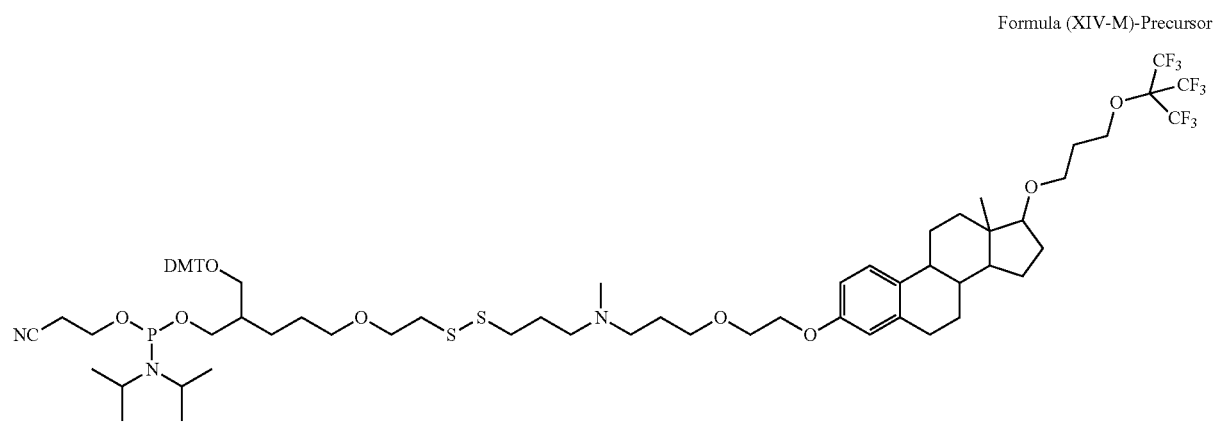

Formula (XIV-M)-Precursor including pharmaceutically acceptable salts, hydrates, solvates and metal chelates of the compound represented by the structure, and solvates and hydrates of the salts.

Yet another example of a Precursor Molecule of the Invention, is based on the structure of Formula (XV), having the following Formula (XV-F)-Precursor:

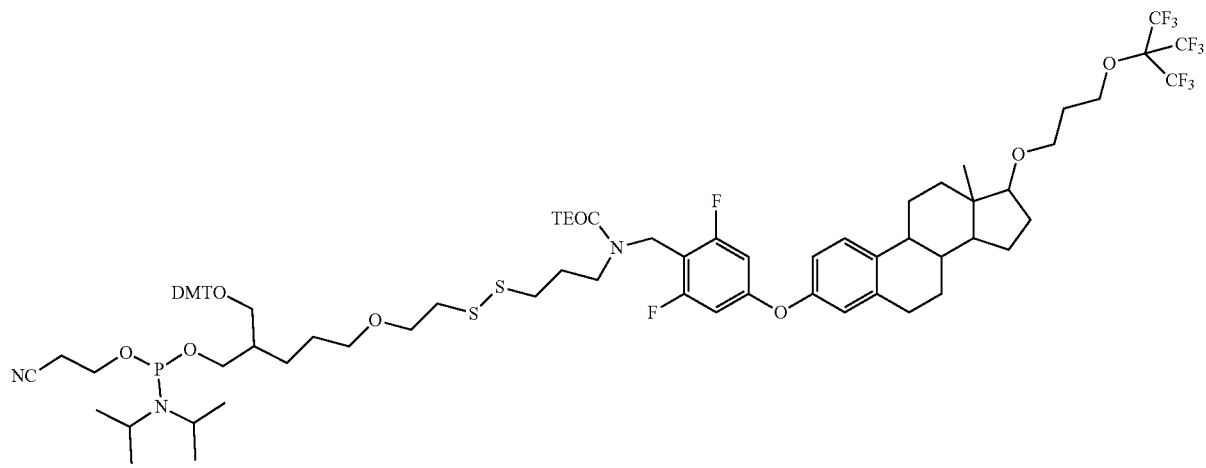

Formula (XV-F)-Precursor including pharmaceutically acceptable salts, hydrates, solvates and metal chelates of the compound represented by the structure as set forth in Formula (XV-F)-Precursor, and solvates and hydrates of the salts.

Another example of a Precursor Molecule of the Invention is still based on the structure of Formula (XV), having the following Formula (XV-M)-Precursor:

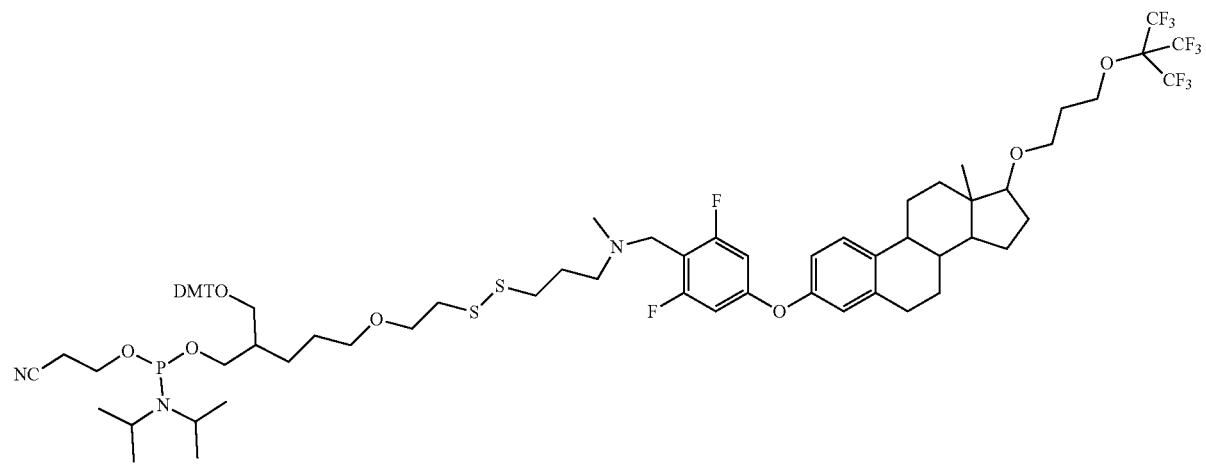

Formula (XV-M)-Precursor including pharmaceutically acceptable salts, hydrates, solvates and metal chelates of the compound represented by the structure, and solvates and hydrates of the salts.

Another example of a Precursor Molecule of the Invention, is based on the structure of Formula (XVI), having the following Formula (XVI-F)-Precursor:

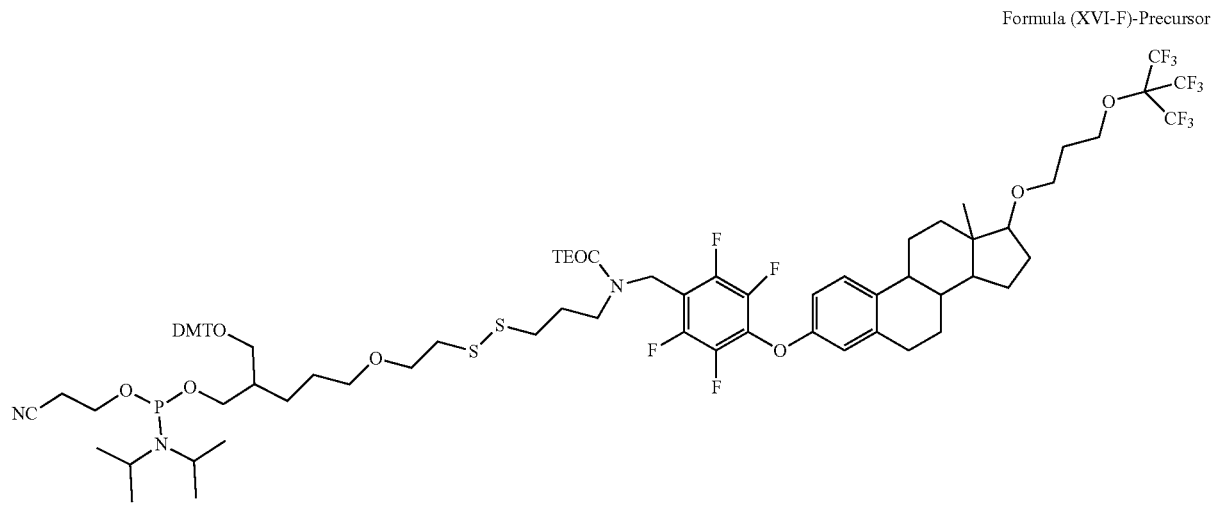

Formula (XVI-F)-Precursor including pharmaceutically acceptable salts, hydrates, solvates and metal chelates of the compound represented by the structure as set forth in Formula (XVI-F)-Precursor, and solvates and hydrates of the salts.

Another example of a Precursor Molecule of the Invention is still based on the structure of Formula (XVI), having the following Formula (XVI-M)-Precursor:

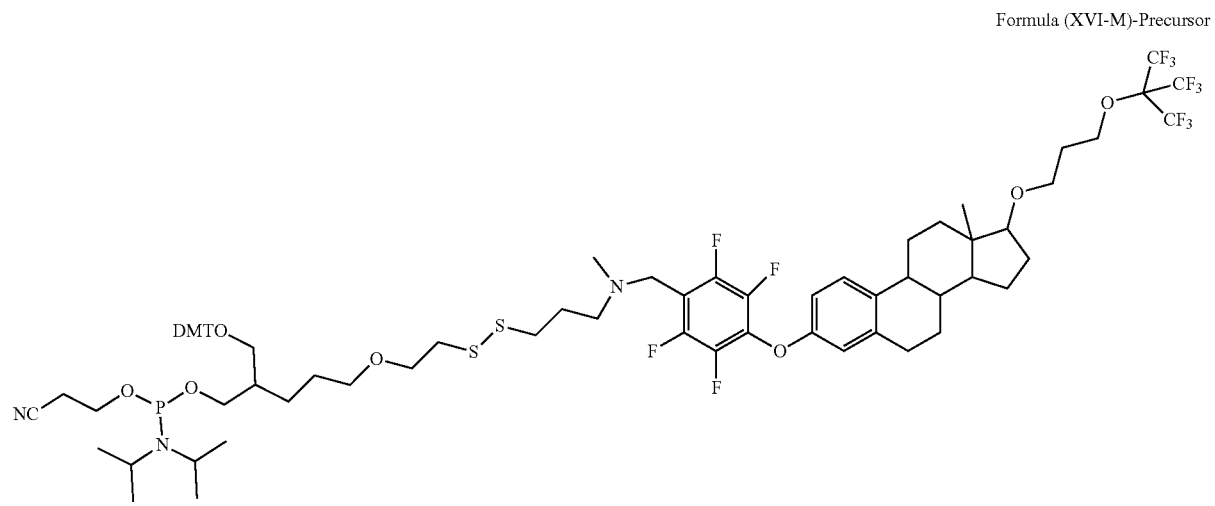

Formula (XVI-M)-Precursor including pharmaceutically acceptable salts, hydrates, solvates and metal chelates of the compound represented by the structure, and solvates and hydrates of the salts.

Compound(s) according to any of Formulae (II), (III), (IV), (V), (VI), (VII), (VIII), (VIII-H), (VIII-M), (IX), (X), (XI), (XII), (XIIa), (XIII), (XIIIa), (XIV), (XIV-H), (XIV-M), (XV), (XV-H), (XV-M), (XVI), (XVI-H), (XVI-M), can serve as E, E', or E" moieties, for linkage to a drug, D, thus forming a desired Conjugate of the Invention, aimed at biological performance in the trans-membrane delivery of D into cells.

In an embodiment of the Invention, it provides Conjugates, wherein D is an OD, such as siRNA or a Dicer's substrate, linked to E, E' or E" moieties, each being according to any of Formulae (II), (III), (IV), (V), (VI), (VII), (VIII), (VIII-H), (VIII-M), (IX), (X), (XI), (XII), (XIIa), (XIII), (XIIIa), (XIV), (XIV-H), (XIV-M), (XV), (XV-H), (XV-M), (XVI), (XVI-H), (XVI-M), including pharmaceutically-acceptable salts, hydrates, solvates and metal chelates of the respective Conjugates.

In the case, that D is an Oligonucleotide Drug (OD), Conjugates can be, among others, according to any one of the following options:
(i). The OD is linked to a single E, E', or E" moiety.
(ii). The OD is linked to two E moieties, being the same or different; each being optionally linked at one end (e.g., the 5'-end) of each oligonucleotide chain.
(iii). The OD is linked to three E moieties, being the same or different; E and E' moieties being linked at the end (e.g., at the 5'-end) of each oligonucleotide chain, while E" is linked at an internal position within the oligonucleotide chain.
(iv). The OD is linked to several (n>3) E moieties, being the same or different; E moieties are linked at the end (e.g., at the 5'-end) of each oligonucleotide chain, while several other E moieties are linked at several internal positions along the oligonucleotide chain.

In case that an E moiety is inserted at an internal position along the oligonucleotide chain, it can be at positioned at any point as desired. In the case that D is an OD, being a siRNA RNA Duplex, it is preferable to insert the internal E moiety on the passenger strand. Potentially beneficial positions along the passenger strand that would not interfere with the activity of the construct in gene silencing can be positions #12 or #14. The E moiety can either replace a nucleotide along the chain, or be an addition to the sequence, thus creating, following the annealing process that generates the siRNA Duplex, a "bulge" in the structure of the RNA Duplex.

For each Conjugate, E, E' or E" can be linked also to R or R' moieties, each being as defined in Formula (II) (a phosphate, sulfate or a carboxyl group). E, E', E" moieties can be the same or different, and also R and R' moieties can be same or different.

For example, Conjugates of the Invention may have the structures, as set forth in the following Formulae (Cn-1), (Cn-2), (Cn-3), comprising E, E' or E" moieties, each having the structure according to any of Formulae (II), (III), (IV), (V), (VI), (VII), (VIII), (VIII-H), (VIII-M), (IX), (X), (XI), (XII), (XIIa), (XIII), (XIIIa), (XIV), (XIV-H), (XIV-M), (XV), (XV-H), (XV-M), (XVI), (XVI-H), (XVI-M), while R and R' are each as defined in Formula (II):

Formula (Cn-1)

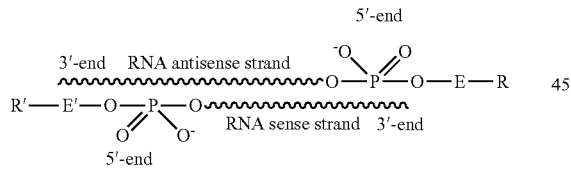

Formula (Cn-2)

3'-end　　　　RNA antisense strand　　　5'-end
~~~~~~~~~~~~~~~~~~~~~~~~~~~~~~~~~~~~~~O—P—O—E"—R'
R—E—O—P—O~O—P—O　　　O—P—O~~ ‑O⁄　\\O
　　　　O⁄　\O-　　O⁄　\O- E'　O⁄　\O-　3'-end
　5'-end　　　　　　　　　　　　　Sense RNA strand including pharmaceutically-acceptable salts, hydrates, solvates and metal chelates of the respective Conjugates.

In an embodiment of the Invention, it provides a Conjugate that comprises D that is an antisense oligonucleotide (ASO) as defined above, comprising a single-stranded oligonucleotide of 15-25 nucleotides long. This ASO is selected from the group consisting of natural or modified DNA, RNA, locked nucleic acid nucleotides (LNA), with the nucleotides being linked via phosphotriester groups, phosphorothioate groups, other nucleic acid linkage strategy, as known in the art, or combinations thereof. This Conjugate comprises linkage to E, E' moieties, as set forth in Formula (Cn-3):

Formula (Cn-3)

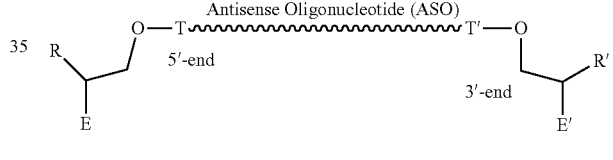

wherein T and T' are each selected independently from null, and the group consisting of 1',2'-Dideoxyribose, nucleotide, or combinations thereof; T and T' can be the same or different; and R and R' moieties are as defined in Formula (II); including pharmaceutically acceptable salts, hydrates, solvates and metal chelates of the compound represented by the structure as set forth in Formula (Cn-3), and solvates and hydrates of the salts.

In one of its embodiments, the Invention provides a Conjugate according to Formula (Cn-1) wherein R and R' are each a phosphate group; and E and E' are each according to Formula (VIII-H); said Conjugate therefore having the structure as set forth in the following Formula [Cn-1-(VIII-H)]:

Formula [Cn-1-(VIII-H)]

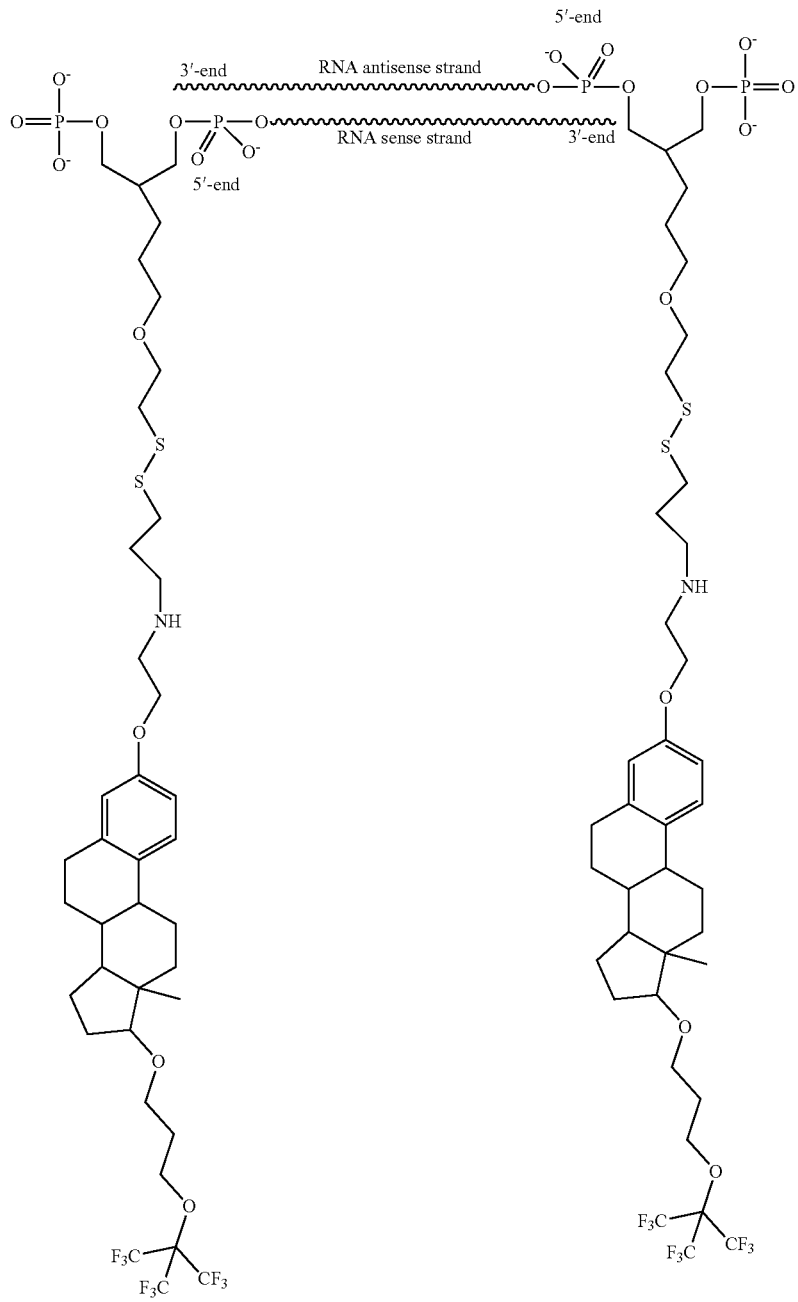

including pharmaceutically-acceptable salts, hydrates, solvates and metal chelates of the compound represented by the structure as set forth in Formula [Cn-1-(VIII-H)], and solvates and hydrates of the salts.

In another embodiment, the Invention provides a Conjugate according to Formula (Cn-1) wherein R and R' are each a phosphate group; and E and E' are each according to Formula (VIII-M), having the structure as set forth in the following Formula [Cn-1-(VIII-M)]:

Formula [Cn-1-(VIII-M)]

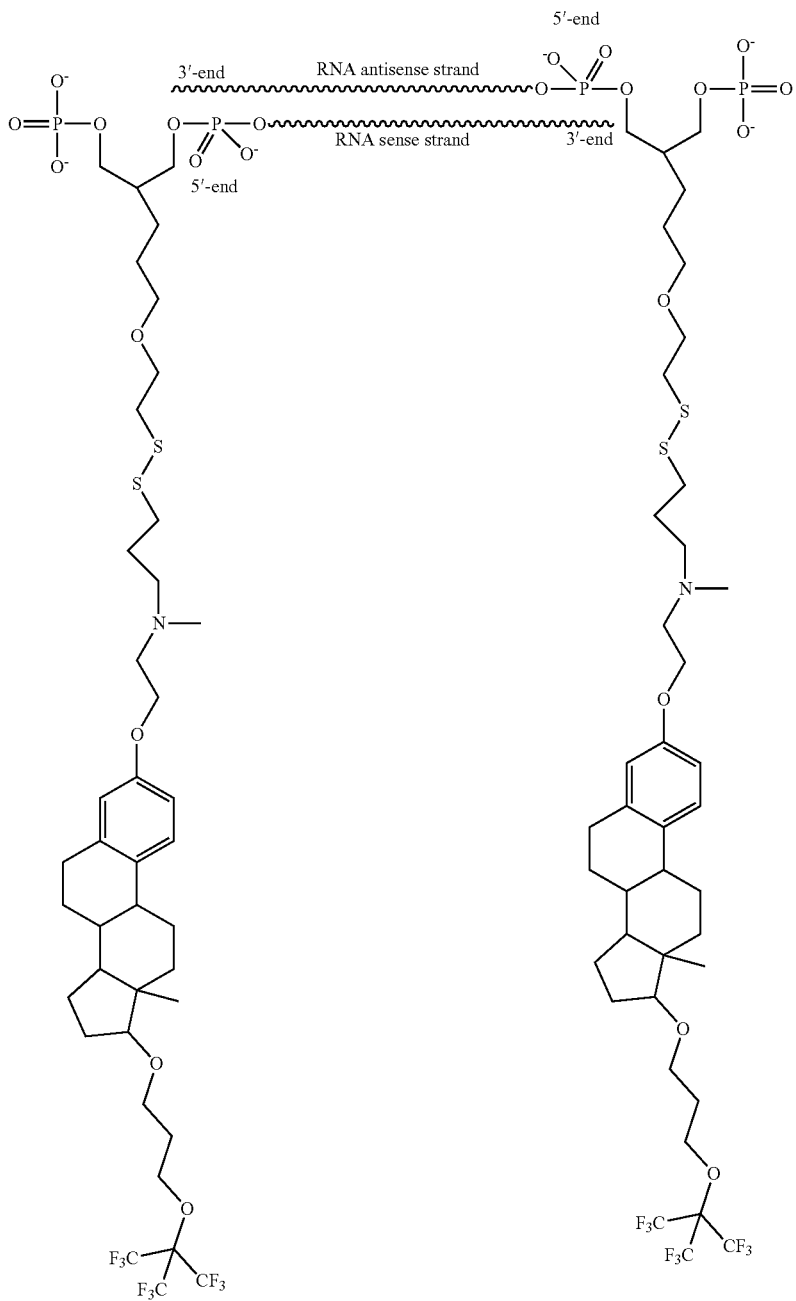

including pharmaceutically-acceptable salts, hydrates, solvates and metal chelates of the compound represented by the structure as set forth in Formula [Cn-1-(VIII-M)], and solvates and hydrates of the salts.

In another embodiment, the Invention provides a Conjugate according to Formula (Cn-2), wherein R and R' are each a phosphate group; and E and E' are each according to Formula (VIII-H), having the structure as set forth in the following Formula [Cn-2-(VIII-H)]:

Formula [Cn-2-(VIII-H)]

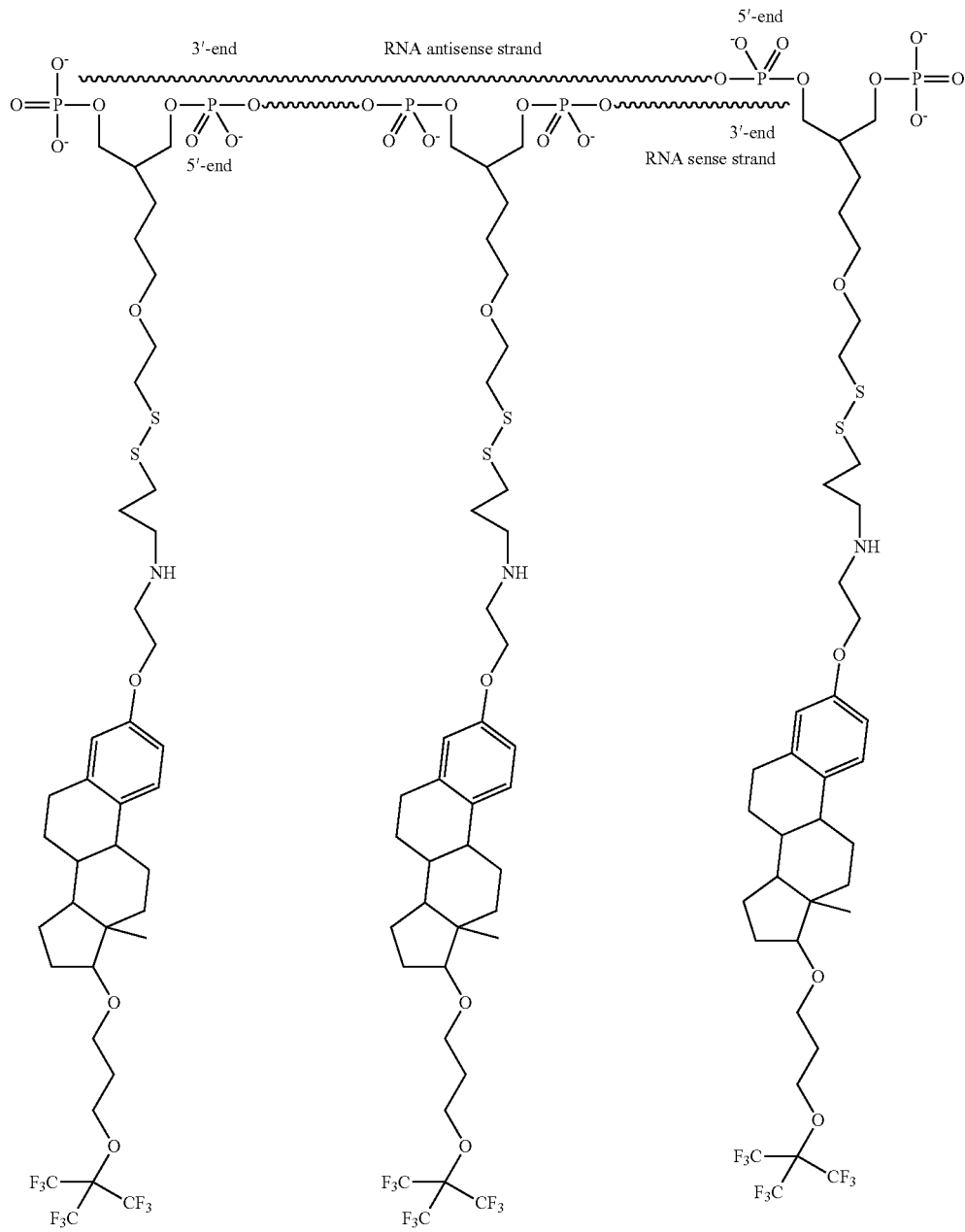

including pharmaceutically acceptable salts, hydrates, solvates and metal chelates of the compound represented by the structure as set forth in Formula [Cn-2-(VIII-H)], and solvates and hydrates of the salts.

In still another embodiment, the Invention provides a Conjugate according to Formula (Cn-2), wherein R and R' are each a phosphate group; and E and E' are each according to Formula (VIII-M), having the structure as set forth in the following Formula [Cn-2-(VIII-M)]:

Formula [Cn-2-(VIII-M)]

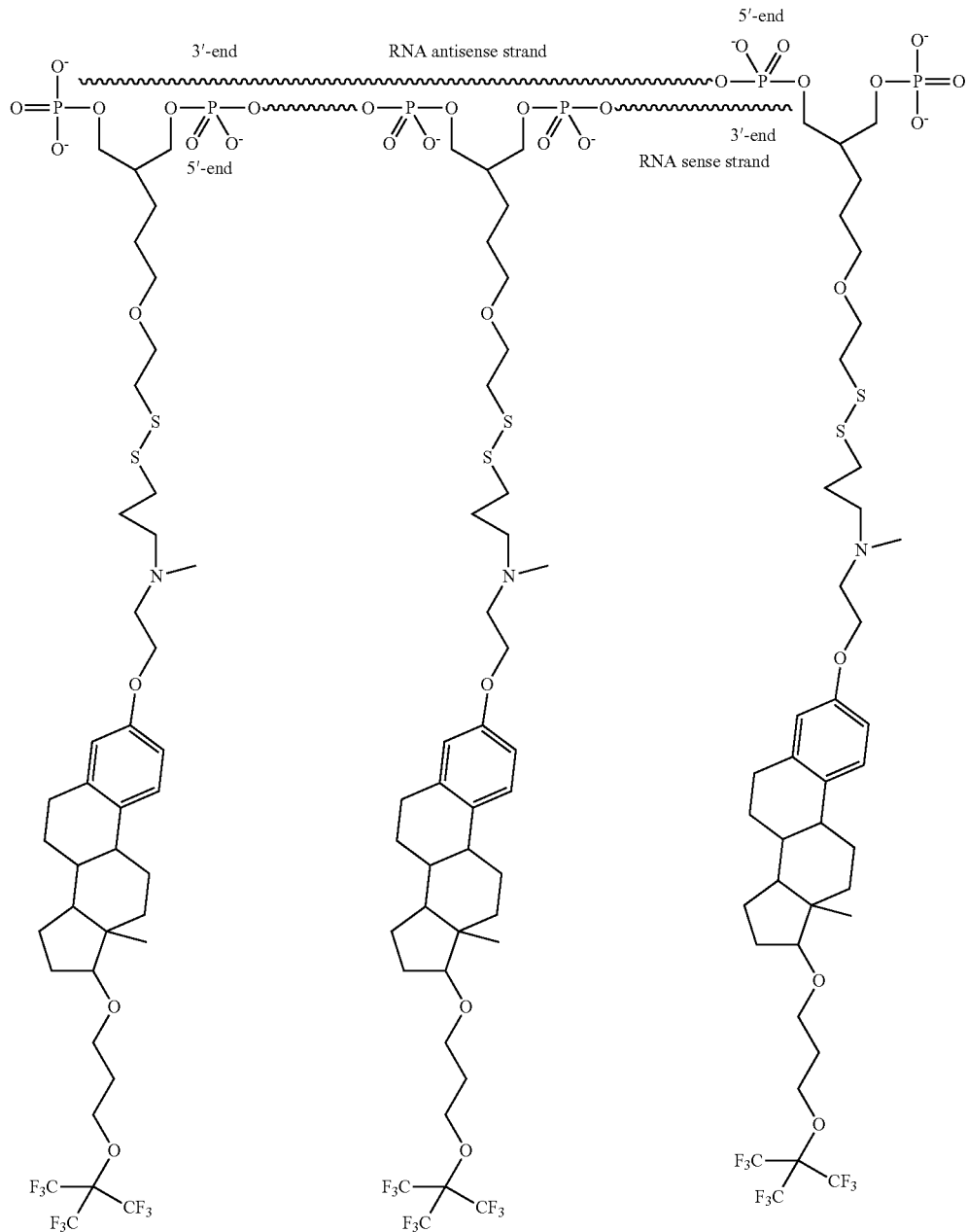

including pharmaceutically acceptable salts, hydrates, solvates and metal chelates of the compound represented by the structure as set forth in Formula [Cn-2-(VIII-M)], and solvates and hydrates of the salts.

In another embodiment, the Invention provides a Conjugate according to Formula (Cn-1), wherein R and R' are each a phosphate group; and E and E' are each according to Formula (XV-H), having the structure as set forth in the following Formula [Cn-1-(XV-H)]:

Formula [Cn-1-(XV-H)]

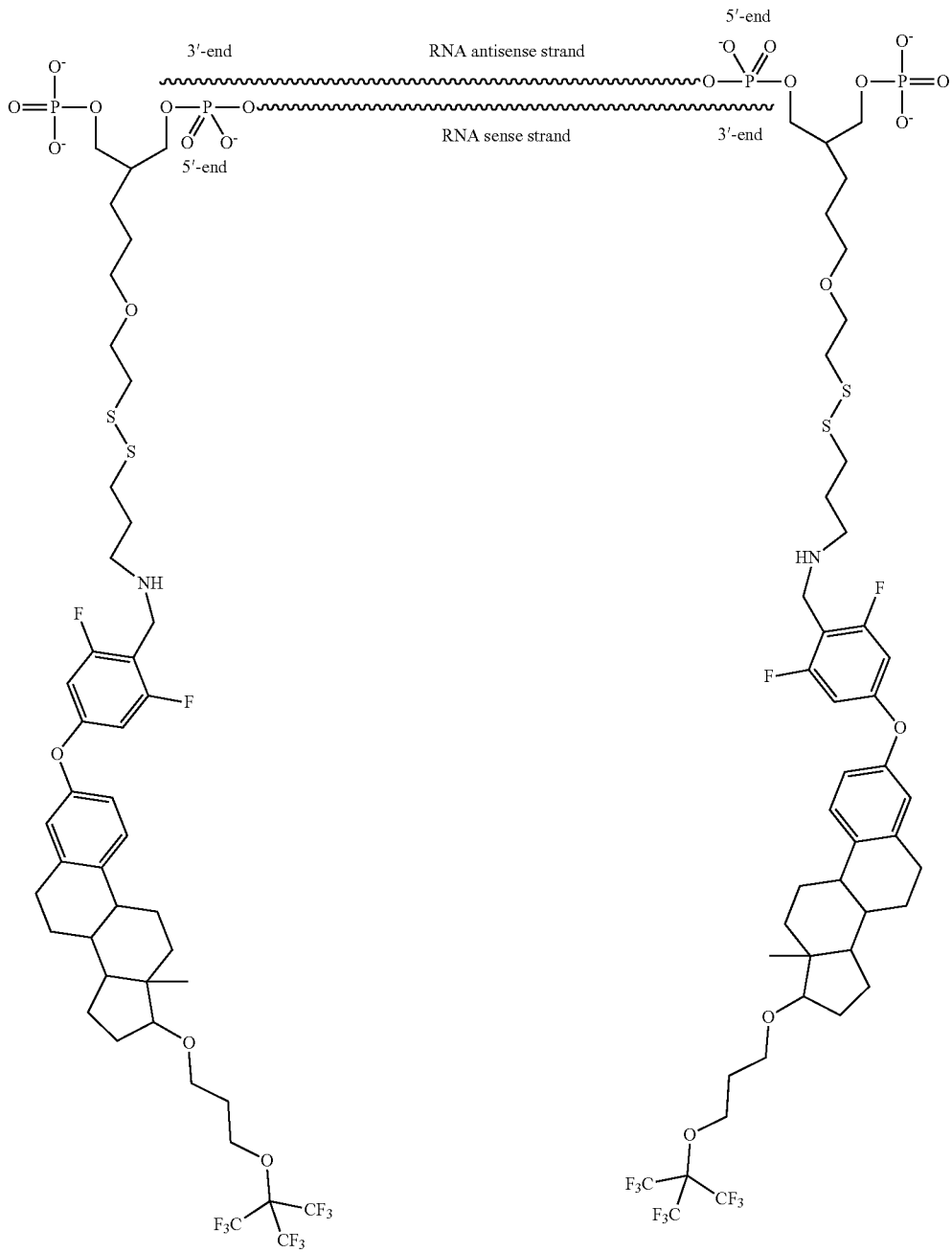

including pharmaceutically-acceptable salts, hydrates, solvates and metal chelates of the compound represented by the structure as set forth in Formula [Cn-1-(XV-H)], and solvates and hydrates of the salts.

In another embodiment, the Invention provides a Conjugate according to Formula (Cn-1), wherein R and R' are each a phosphate group; and E and E' are each according to Formula (XV-M), having the structure as set forth in the following Formula [Cn-1-(XV-M)]:

Formula [Cn-1-(XV-M)]

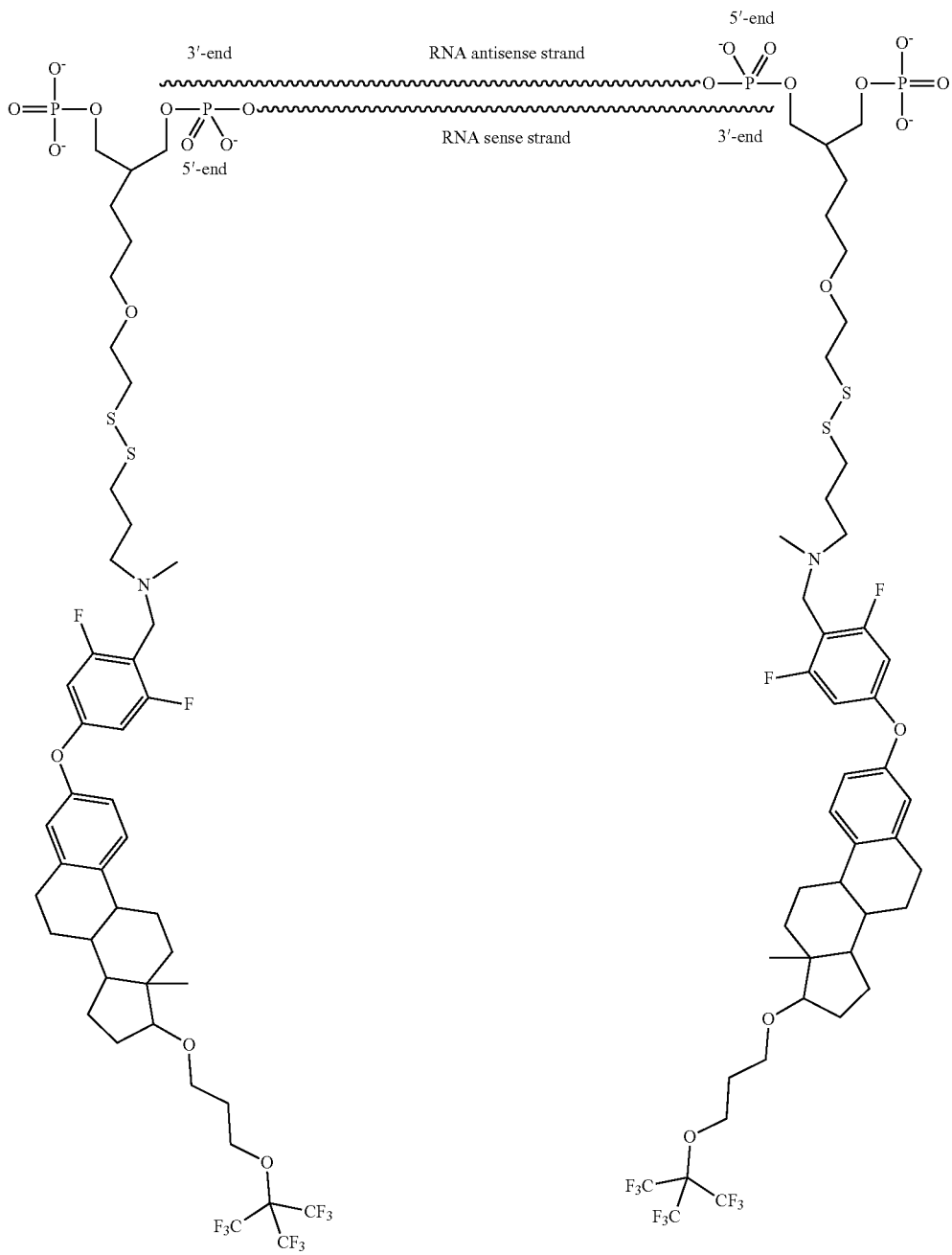

including pharmaceutically-acceptable salts, hydrates, solvates and metal chelates of the compound represented by the structure as set forth in Formula [Cn-1-(XV-M)], and solvates and hydrates of the salts.

In another embodiment, the Invention provides a Conjugate according to Formula (Cn-2), wherein R and R' are each a phosphate group; and E and E' are each according to Formula (XV-H), having the structure as set forth in the following Formula [Cn-2-(XV-H)]:

Formula [Cn-2-(XV-H)]

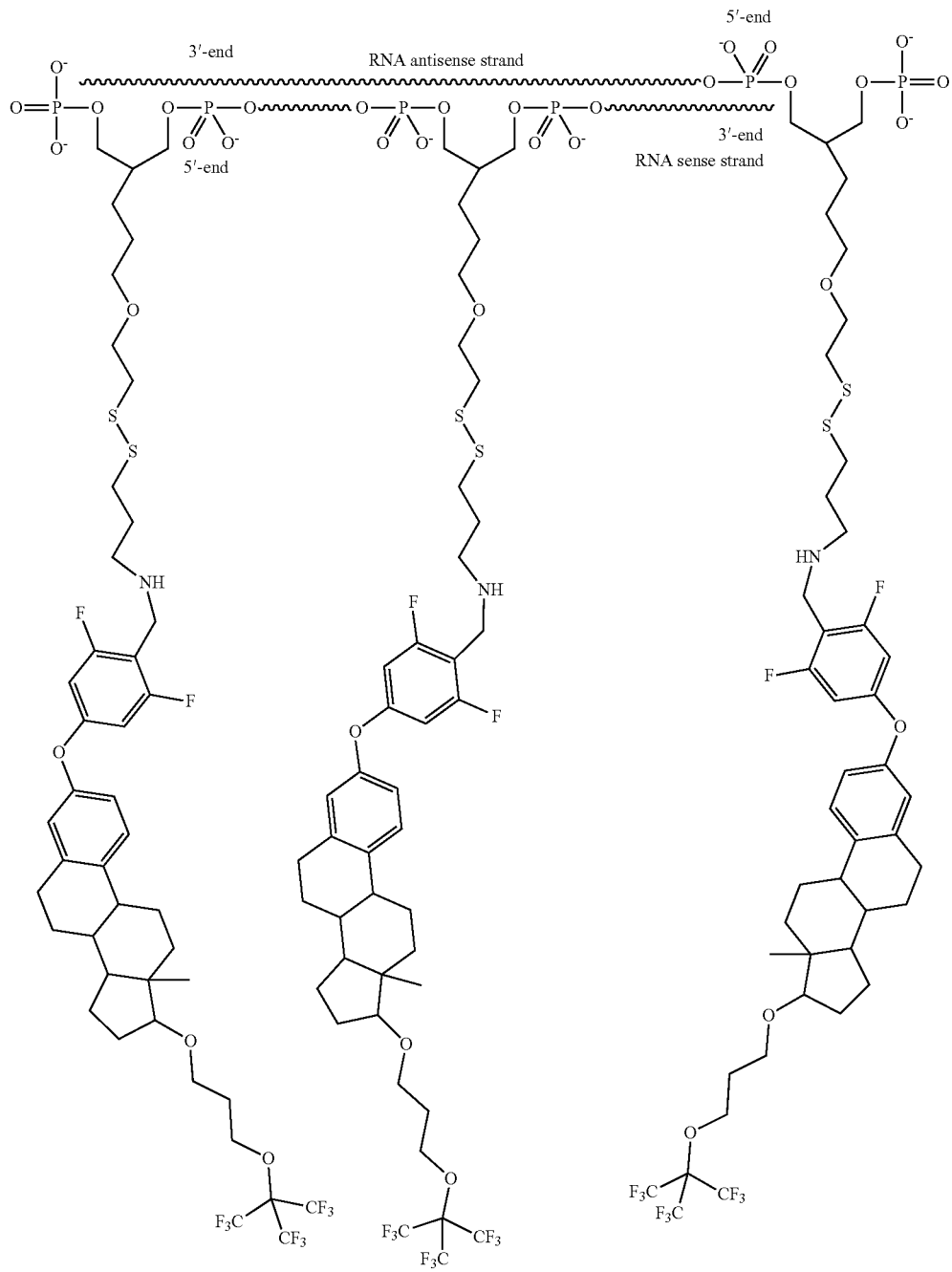

including pharmaceutically acceptable salts, hydrates, solvates and metal chelates of the compound represented by the structure as set forth in Formula [Cn-2-(XV-H)], and solvates and hydrates of the salts.

In another embodiment, the Invention provides a Conjugate according to Formula (Cn-2), wherein R and R' are each a phosphate group; and E and E' are each according to Formula (XV-M), having the structure as set forth in the following Formula [Cn-2-(XV-M)]:

Formula [Cn-2-(XV-M)]

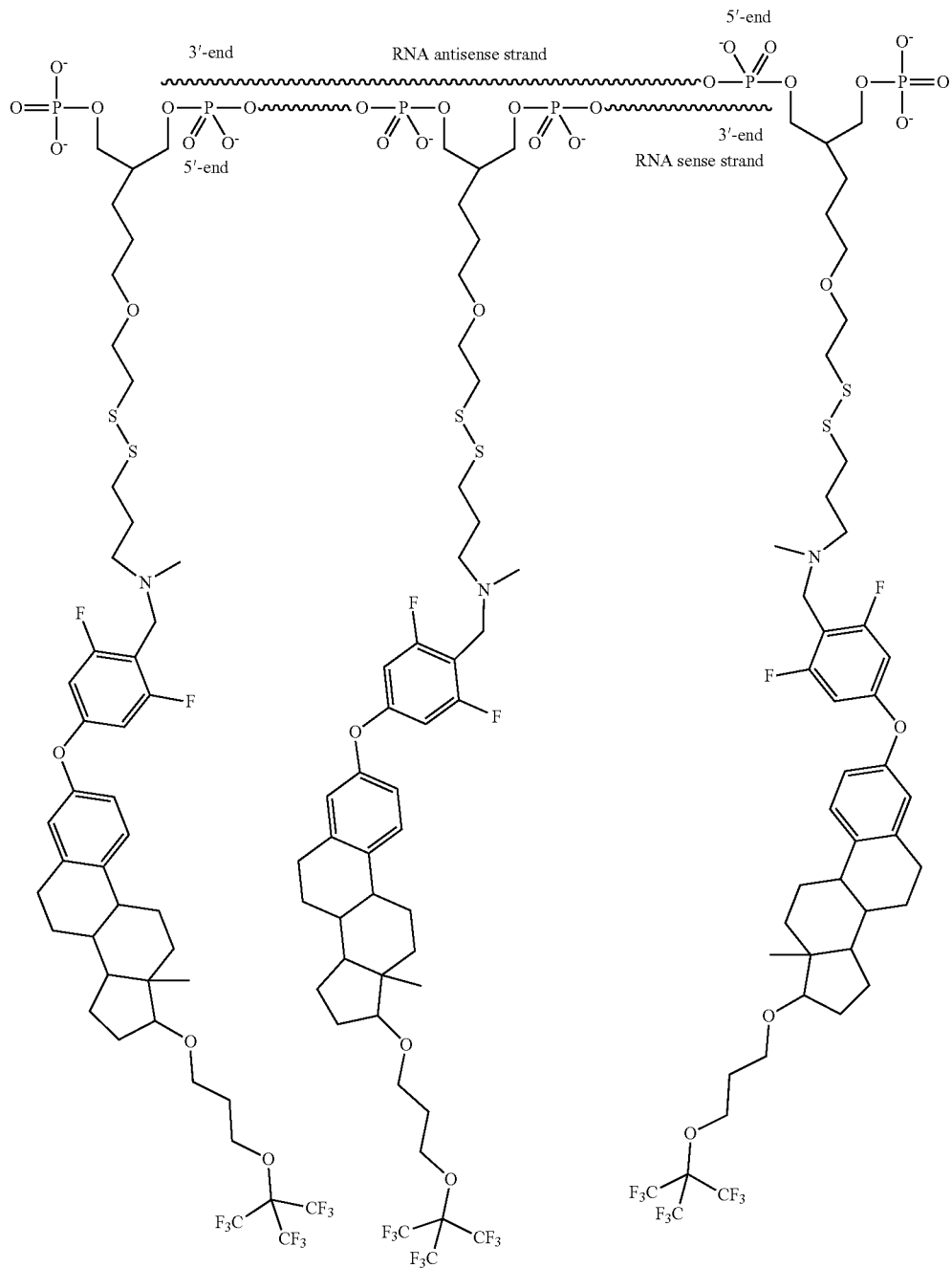

including pharmaceutically acceptable salts, hydrates, solvates and metal chelates of the compound represented by the structure as set forth in Formula [Cn-2-(XIV-M)], and solvates and hydrates of the salts.

In an embodiment, the Invention provides a Conjugate according to Formula (Cn-1), wherein R and R' are each a phosphate group; and E and E' are each according to Formula (XVI-H), having the structure as set forth in the following Formula [Cn-1-(XVI-H)]:

Formula [Cn-1-(XVI-H)]

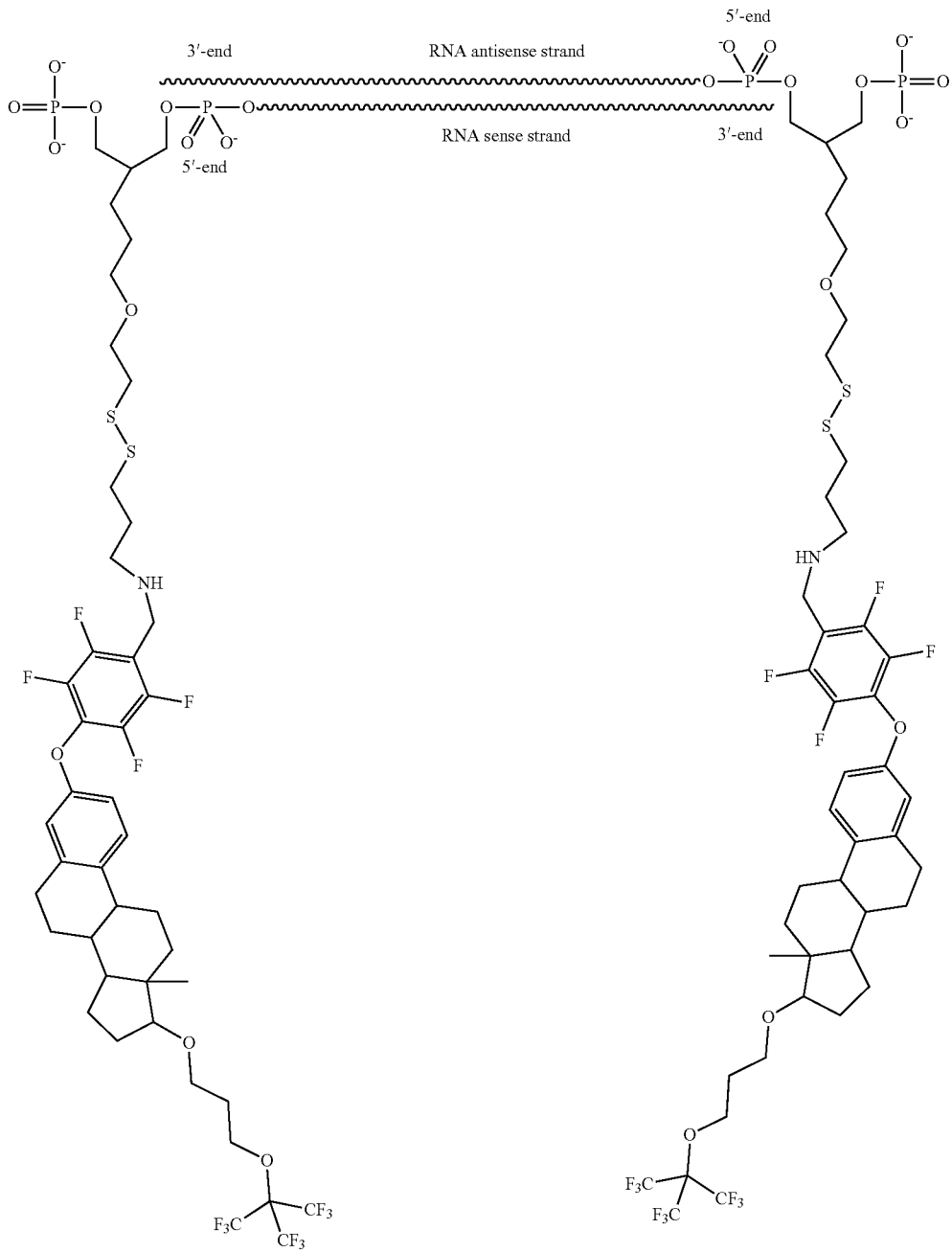

including pharmaceutically-acceptable salts, hydrates, solvates and metal chelates of the compound represented by the structure as set forth in Formula [Cn-1-(XVI-H)], and solvates and hydrates of the salts.

In another embodiment, the Invention provides a Conjugate according to Formula (Cn-1), wherein R and R' are each a phosphate group; and E and E' are each according to Formula (XVI-M), having the structure as set forth in the following Formula[Cn-1-(XVI-M)]:

Formula [Cn-1-(XVI-M)]

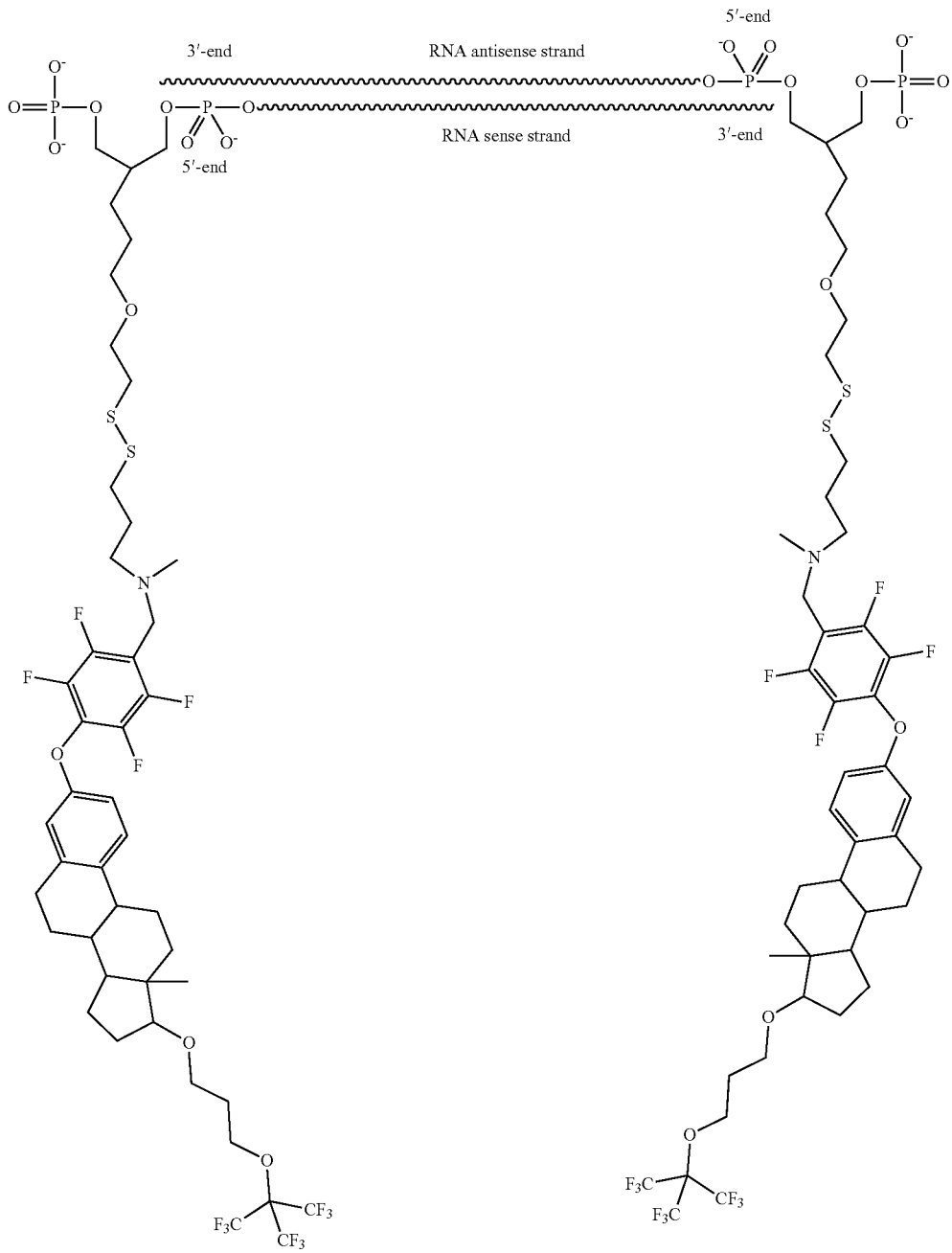

including pharmaceutically-acceptable salts, hydrates, solvates and metal chelates of the compound represented by the structure as set forth in Formula [Cn-1-(XVI-M)], and solvates and hydrates of the salts.

In another embodiment, the Invention provides a Conjugate according to Formula (Cn-2), wherein R and R' are each a phosphate group; and E and E' are each according to Formula (XVI-H), having the structure as set forth in the following Formula [Cn-2-(XVI-H)]:

Formula [Cn-2-(XVI-H)]

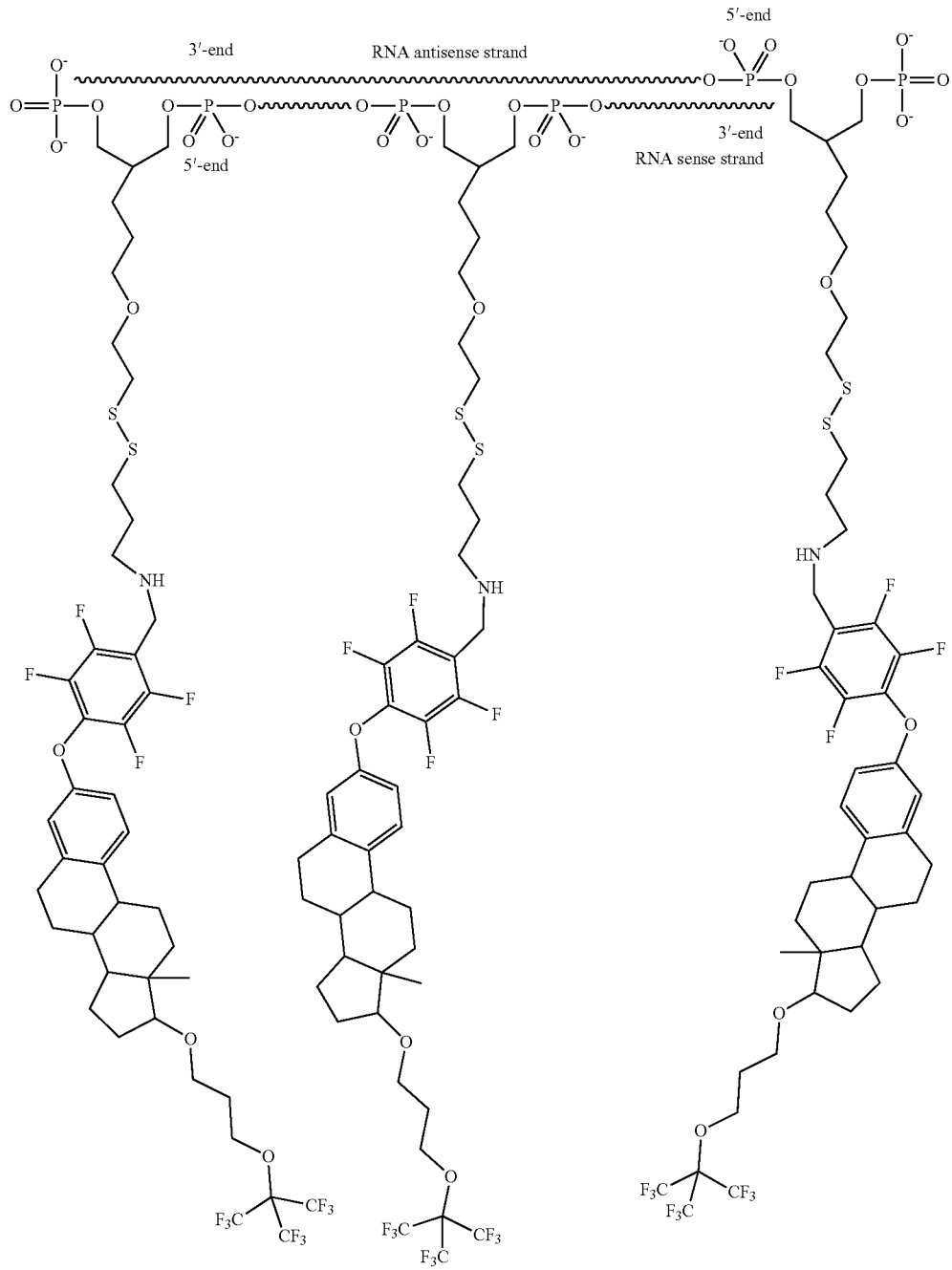

including pharmaceutically acceptable salts, hydrates, solvates and metal chelates of the compound represented by the structure as set forth in Formula [Cn-2-(XVI-H)], and solvates and hydrates of the salts.

In another embodiment, the Invention provides a Conjugate according to Formula (Cn-2), wherein R and R' are each a phosphate group; and E and E' are each according to Formula (XVI-M), having the structure as set forth in the following Formula[Cn-2-(XVI-M)]:

Formula [Cn-2-(XVI-M)]

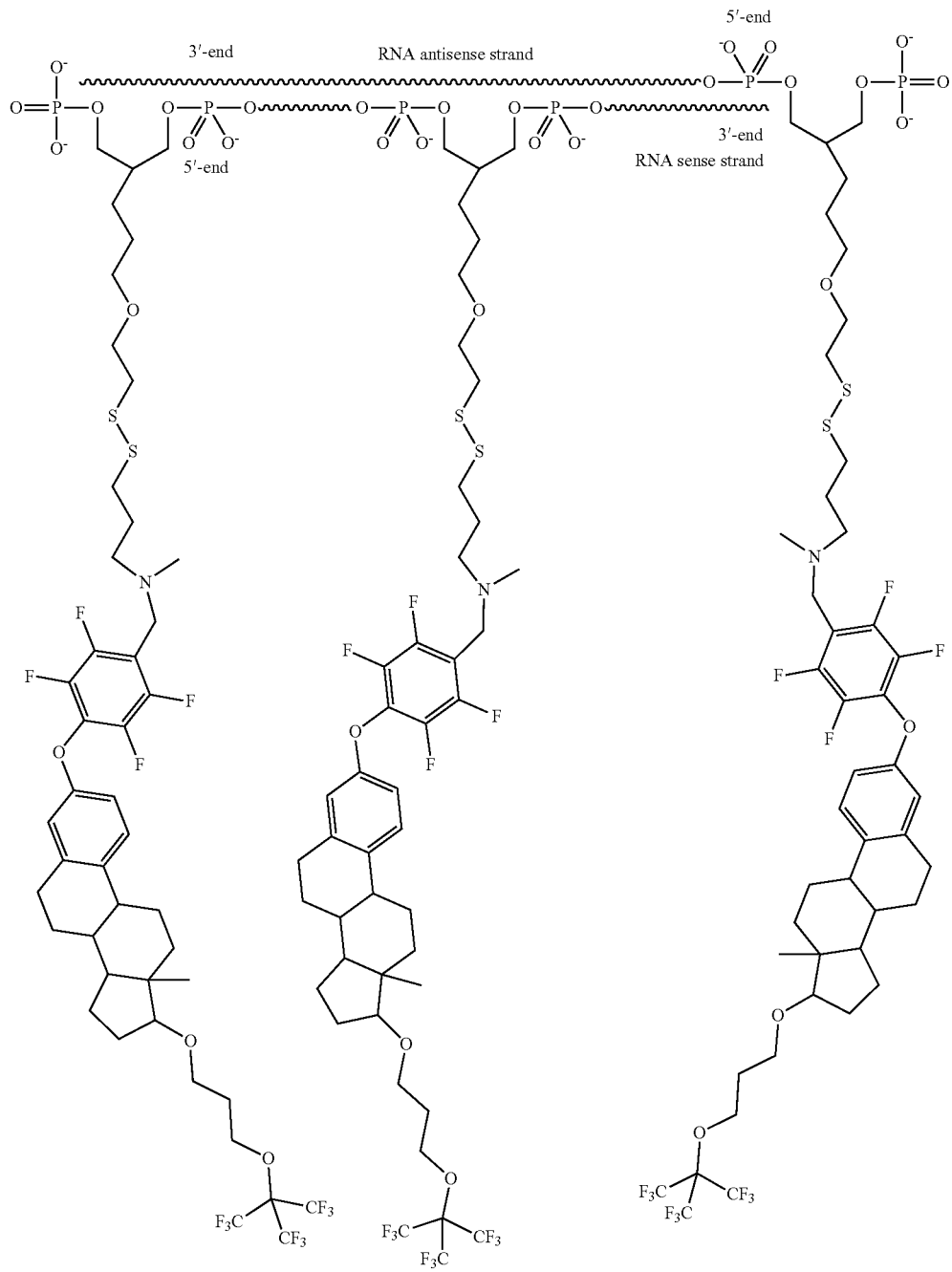

including pharmaceutically acceptable salts, hydrates, solvates and metal chelates of the compound represented by the structure as set forth in Formula [Cn-2-(XVI-M)], and solvates and hydrates of the salts.

"Drug" or "Cargo Drug" (i.e., moiety D) in the context of the present Invention, refers to a molecule that is aimed to be delivered by the Conjugates of the Invention across phospholipid membranes into cells, wherein D is either a small-molecule drug, or a macromolecule, such as peptide, protein or oligonucleotide drug (OD).

The term "drug" or "medicament" in the context of the present invention, relates to a chemical substance, that when administered to a patient suffering from a disease, is capable of exerting beneficial effects on the patient. The beneficial effects can range from amelioration of symptoms, to counteracting the effects of an agent or substance (e.g., proteins), that play(s) a role in the disease process. The drug may comprise a small molecule, or be a macromolecule such as a protein, or single- or double-stranded RNA or DNA, administered to inhibit gene expression. Among others, the drug may comprise siRNA, dsiRNA or ASO. In some embodiments, the drug is aimed at treating degenerative disorders, cancer, ischemic, infectious, toxic or traumatic insults, an inherited or acquired metabolic disease, or immune-mediated disorders.

The term "Oligonucleotide drug", also designated hereinafter "OD", refers in the context of the Invention, to a drug that comprises nucleosides or nucleotides. Examples for Oligonucleotide drugs (OD) are single-stranded or double-stranded, natural or modified RNA or DNA. OD can be siRNA (small interfering RNA), a substrate for the Dicer enzyme (dsiRNA), microRNA (miRNA), messenger RNA (mRNA), or DNA sequences, which are designed to serve as antisense oligonucleotides (ASO). Linkage between the nucleotide building blocks of the OD can be, among others, via phosphate-triester bridges, via phosphorothioate bonds, or via any other method known in the art. The nucleotides which serve as the building blocks of the OD can be either natural or modified nucleotides, such as locked nucleic acids (LNA).

More specific OD, which are embodiments of the Invention are: "siRNA", being an RNA duplex, wherein each RNA strand is 19-21-nucleotide long, aimed at silencing gene expression via the RISC (RNA-induced silencing complex) cytoplasmatic protein complex;

siRNA substrate for Dicer, ("dsiRNA"), being an RNA duplex, wherein each RNA strand is 24-30-nucleotide long. In an embodiment, the dsiRNA Duplex consists of one strand of 25 nucleotides, while the second strand consists of 27 nucleotides. In another embodiment, the dsiRNA Duplex consists of one strand of 24 nucleotides, while the second strand consists of 27 nucleotides. In yet another embodiment, the dsiRNA Duplex comprises RNA strands of equal length, each consisting of 27 nucleotides.

"Antisense Oligonucleotide" (ASO), being a synthetic, single stranded, natural or modified DNA or RNA oligonucleotide, usually 15-20 nucleotide long. The sequence of the ASO is antisense, i.e., it is complementary to the sense sequence of a specific mRNA that encodes for a protein, which synthesis is sought to be inhibited. Binding of the ASO to said complementary sequence blocks the ability of ribosomes to move along the mRNA, thus preventing synthesis of the protein, or alternatively, hastens the rate of degradation of the mRNA.

A "nucleoside" in the context of the present invention, is defined as a chemical moiety, that comprises a nitrogenous base (nucleobase), and a sugar of five- or six-carbon atoms (e.g., ribose or deoxyribose). The nucleobases are selected from natural or modified purines (e.g., adenine, guanine) and natural or modified pyrimidines (e.g., thymine, cytosine, uracil). The nucleobase can be modified by various modifications, as known in the art (e.g., methylation, acetylation). In addition, the sugar moiety of the nucleoside can also be modified, as known in the art [e.g., 2'-deoxy derivative, methylation at the 2' position of the ribose, installment of a 2'-fluoro atom or 2'-O-methoxyethyl, or having a bridge connecting the 2' oxygen and 4' carbon atoms, thus generating locked nucleic acid (LNA)]. The use of such modified nucleosides, conjugated to the E moieties of the Invention is therefore also within the scope of the invention. In an embodiment, the nucleoside comprises a pyrimidine derivative, selected from natural or modified cytosine, thymine and uracil, and the sugar moiety is either ribose or deoxyribose.

A "nucleotide", in the context of the Invention, is a nucleoside as defined above, linked to a phosphate group. Nucleotides are the building blocks of the oligonucleotides.

A "Precursor molecule" in the context of the invention, is defined as an E, E' or E" moiety, having the structure as set forth in any of Formulae (II), (III), (IV), (V), (VI), (VII), (VIII), (VIII-H), (VIII-M), (IX), (X), (XI), (XII), (XIIa), (XIII), (XIIIa), (XIV), (XIV-H), (XIV-M), (XV), (XV-H), (XV-M), (XVI), (XVI-H), (XVI-M), that is attached to a protecting group for alcohol o amine, as defined below.

A "protecting group" in the context of the invention, is defined as a chemical group that is destined to be removed or modified during the synthesis of the Conjugate of the Invention. Such removal or modification may occur at various stages of the synthesis; for example, without limitation, during the attachment of E, E' or E" moieties to D, in the case that D is a macromolecule drug, such as an oligonucleotide drug (OD). In a preferred embodiment of the Invention, the protecting group is a protecting group for alcohol, as defined below.

A "protecting group for alcohol" in the context of the Invention, refers to a chemical group attached to a hydroxyl group, in order to "mask" it during certain chemical reactions, and which is potentially removed thereafter, as known in the art. Examples for such protecting groups are Acetyl (Ac), Benzoyl (Bz), Benzyl (Bn), β-Methoxyethoxymethyl ether (MEM), Dimethoxytrityl [bis-(4-methoxyphenyl) phenylmethyl] (DMT), Methoxymethyl ether (MOM), Methoxytrityl [(4-methoxyphenyl)diphenylmethyl] (MMT), p-Methoxy-benzyl ether (PMB), Pivaloyl (Piv), Tetrahydropyranyl (THP), Tetrahydrofuran (THF), Trityl (triphenylmethyl, Tr), Silyl ether [e.g., trimethylsilyl (TMS), tert-butyldimethylsilyl (TBDMS), tri-iso-propylsilyloxymethyl (TOM), and triisopropylsilyl (TIPS) ethers], Ethoxyethyl ethers (EE), phosphoramidite, N-hydroxysuccinimide (NHS). Frequently used protecting groups for alcohol for conjugation of moieties to macromolecule drugs such as OD are Dimethoxytrityl [bis-(4-methoxyphenyl) phenylmethyl] (DMT), and phosphoramidite.

The term a "protecting group for amine" [X moiety, according to Formula (H)] in the context of the Invention, refers to a chemical group attached to an amine group, in order to "mask" it during certain chemical reactions, and which is potentially removed thereafter, as known in the art. Examples for protecting groups for amine, within the scope of the Invention, provided in a non-limiting manner are: Carbobenzyloxy (Cbz) group; p-Methoxybenzyl carbonyl (Moz or MeOZ) group; tert-Butyloxycarbonyl (BOC) group; 9-Fluorenylmethyloxycarbonyl (FMOC) group; Phenoxyacetyl (PAC) group; 4-tertbutylphenoxyacetyl (t-PAC) group; Acetyl (Ac) group; Benzoyl (Bz) group, Benzyl (Bn) group; Carbamate group; p-Methoxybenzyl (PMB); 3,4-Dimethoxybenzyl (DMPM); p-methoxyphenyl (PMP) group; Tosyl (Ts) group; Troc (trichloroethyl chloroformate) group, 2-(trimethylsilyl) ethyl carbamate (TEOC).

The term "linkage point to a solid support" in the context of the Invention, means a point of attachment of an E, E' or E" moiety to a solid support during chemical synthesis. For example, Controlled Pore Glass (CPG) may be used as a solid support, for attachment of the 3'-end of the oligonucleotide during the synthesis of the oligonucleotide chains of the invention.

The term "biological membrane" according to the invention, refers to any phospholipid membrane that is related to a biological system. Examples for such phospholipid membranes are plasma membranes of cells, intracellular membranes, or phospholipid membranes associated with biological barriers, such as the blood-brain-barrier (BBB), the blood-ocular-barrier (BOB), or the blood-placenta barrier.

The term "flip-flop" according to the invention, refers to movement of an amphipatic compound, (namely, a molecule that possesses both hydrophobic and hydrophilic elements) form one leaflet of a phospholipid membrane bilayer into the other leaflet.

The term "endocytosis" according to the invention, refers to the process by which a living cell takes up molecules bound to its surface; said process comprising folding of the plasma membrane inward, thus bringing said molecules into the cell.

Embodiments of the invention further relate to the use of Conjugates according to the invention, comprising therapeutically-useful drugs, such as proteins or OD (e.g., siRNA, dsiRNA or ASO), for the treatment of medical disorders, in a subject in need thereof. The medical disorders may be, without limitation, degenerative disorders, cancer, vascular disorders, metabolic disorders, traumatic, toxic or ischemic insults, infections (e.g., viral or bacterial) or immune-mediated disorders, in which specific protein(s) play(s) a role in either disease etiology or pathogenesis. For such medical disorders, modulation of expression of the gene(s) that encode for these disease-related proteins, through siRNA or antisense mechanisms, or modulation of the activity of the respective disease-related protein by a therapeutic protein, such as by an antibody, or by a protein that functions in signal transduction, or by protein replacement therapy, may have beneficial effects in inhibiting disease-related processes, or in treating an underlying cause of the disease.

For example, Conjugates according to embodiments of the invention, may be used as antisense, siRNA or dsiRNA therapy, which is a form of medical treatment, that comprises the administration of a single-stranded or a double-stranded nucleic acid sequences (DNA, RNA or chemical analogues thereof), that bind either to a DNA sequence that encodes for a specific protein, or to a messenger RNA (mRNA) that translates into a protein. This treatment may act to inhibit the expression of disease-related genes, thereby preventing the production of disease-related proteins, which may play a role in the etiology or pathogenesis of disease. Alternatively, the Conjugates of the invention may comprise therapeutic proteins, or protein/nucleic acid complexes, such as a Cas9-RNA complex, capable of performing gene editing.

Embodiments of the invention also provide pharmaceutical compositions, comprising the Conjugates described herein, and pharmaceutically-acceptable carrier(s) or salt(s). According to some embodiments, the Conjugates and pharmaceutical compositions of the invention, may be used in vitro (e.g., in cell culture), ex vivo, or in vivo, in a living subject, including in the clinical setting.

Other embodiments of the Invention include Conjugates of the invention, or pharmaceutical compositions comprising Conjugates of the invention, for use in the treatment of medical disorders, in a patient in need thereof. Further embodiments of the invention include the use of Conjugates of the invention, in the preparation of pharmaceutical compositions for the treatment of medical disorders, in a patient in need thereof. In some embodiments, the medical disorder is cancer, metabolic disease, infectious disease, degenerative disease, vascular disease, trauma, or an immune-mediated disease. Said pharmaceutical compositions can comprise pharmaceutically-acceptable ingredients as known in the art, included to enable beneficial properties to said composition, in aspects such as slow-release, prolongation of residence time, dispersion or safety.

A Conjugate according to embodiments of the invention may be advantageous in improving the efficacy of the delivery of siRNA, dsiRNA, ASO, or a therapeutic protein such as an antibody, through cell membranes, or through additional biological barriers, such as the Blood-Brain-Barrier (BBB), in comparison to the efficacy of delivery of the same therapeutic agents, which are devoid of E, E' or E" moieties of the Invention. Thus, Conjugates of the Invention may improve the performance of a macromolecule drug in one or more aspects, in addition to efficacy, for example, safety or pharmacokinetics. The Conjugates of the Invention may be administered via any mode of administration known in the art, including, among others, per os, intravenously, intramuscular, subcutaneous, intra-tracheal, intra-bronchial, intra-peritoneal or intra-thecal.

Conjugates of the Invention, wherein D is an OD can be synthesized, in a non-limiting manner, according to the following method: initially, a gene to be silenced is chosen, based on its role in disease etiology or pathogenesis. Then, based on bioinformatic methodologies, as known in the art, the nucleotide sequences to be incorporated in the Conjugate are designed and determined [typically 19-21 base-pairs double-stranded siRNA for a RISC substrate; or 24-29 base-pairs double-stranded RNA for a Dicer substrate (dsiRNA)]. Synthesis is carried-out in the 3' to 5' direction of the oligonucleotide. Solid phase synthesis is applied, using protected building blocks, such as protected 2'-deoxy-nucleosides (dA, dC, dG, and dT), ribonucleosides (A, C, G, and U), or chemically modified nucleosides, e.g. [LNA (locked nucleic acids), or BNA (bridged-nucleic-acids)]. The building blocks are provided as nucleoside precursors, wherein the 5'- and the 3'-hydroxyl groups are protected by DMT and phosphoramidite, respectively. These groups are sequentially removed during the reactions of coupling the nucleotide to the growing oligonucleotide chain during synthesis, in the order determined by the desired nucleotide sequence.

For the purpose of synthesis of the Conjugates of the Invention, the E groups are provided as Precursor molecules, each being an E, E' or E" moiety of the Invention, linked to protecting group(s), as described above. While the protecting group can be any protecting group for hydroxyl known in the art, phosphoramidite and DMT [Dimethoxytrityl bis-(4-methoxyphenyl) phenyl methyl] are customarily often used in oligonucleotide synthesis. A major advantage of Conjugates of the current Invention, is that they provide, as exemplified for Conjugates (Cn-1) and (Cn-2) above, an option to link E, E', or E" moieties to either the 5'-end of an oligonucleotide strand, the 3'-end of an oligonucleotide strand, or also at internal position(s) along the oligonucleotide chain. Thereby, the E moieties of the Invention can become integrated within the oligonucleotide chain, similar to any inherent, natural oligonucleotide building block. The linkage between the nucleotides can be via standard phosphotriester bonds, or through synthetic phosphorothioate bonds, which may provide advantages such as stability in the blood, or favorable binding to blood proteins, or via any other nucleotide linkage strategy as known in the art. Upon completion of the assembly of the chain, the product is released from the solid support into solution, de-protected, and collected. The desired Conjugate is then isolated by high-performance liquid chromatography (HPLC), in order to obtain the desired Conjugate of the Invention in high purity. In the case of siRNA or dsiRNA, each of the complementary RNA strand is synthesized separately, and then annealing of the two strands is performed, as known in the art, to yield the desired double-stranded siRNA or dsiRNA, which is then subjected to purification and aliquoting.

In an embodiment of the invention, it provides a method for delivery of drugs across phospholipid biological membranes, selected from a group consisting of cell membranes and biological barriers, wherein said biological barriers are selected from the blood-brain-barrier, the blood-ocular-barrier or the blood-fetal-barrier; the method comprising contacting the cells or respective biological barriers with a Conjugate of the invention.

In an embodiment of the invention, it provides a method for delivery of a drug into biological cells, wherein said cells are in culture, or in a living animal, or in a human subject; the method comprising contacting the cells with a Conjugate or with a pharmaceutical composition that comprises the Conjugate of the Invention. In the case of administration in vivo, the contact with the cell can be achieved through any route of drug administration known in the art, such as per-os, intravenously, subcutaneously, or by intramuscular administration.

In an embodiment of the invention, it provides a Conjugate of the Invention, or a pharmaceutical composition that includes a Conjugate according to Formula (I), wherein each of E, E' or E" has independently the structure as set forth in any of Formulae (II), (III), (IV), (V), (VI), (VII), (VIII), (VIII-H), (VIII-M), (IX), (X), (XI), (XII), (XIIa), (XIII), (XIIIa), (XIV), (XIV-H), (XIV-M), (XV), (XV-H), (XV-M), (XVI), (XVI-H), (XVI-M). The invention also comprises methods for specific inhibition of gene expression, in vitro or in vivo. In one embodiment of the Invention, the method may include utilization of a Conjugate according to any of Formulae (I), (II), (III), (IV), (V), (VI), (VII), (VIII), (VIII-H), (VIII-M), (IX), (X), (XI), (XII), (XIIa), (XIII), (XIIIa), (XIV), (XIV-H), (XIV-M), (XV), (XV-H), (XV-M), (XVI), (XVI-H), (XVI-M), (Cn-1), (Cn-2), (Cn-3), or a pharmaceutical composition that includes said Conjugate, wherein D is siRNA, dsiRNA or an ASO, designed to silence the expression of a specific gene. In some embodiments, the gene encodes for a pathogenic protein that has a role in the etiology or pathogenesis of a disease. In some embodiments, D is a therapeutic protein.

In yet another embodiment of the Invention, it provides, in a non-limiting manner, a method for induction of endocytosis and/or flip-flop within a biological membrane; Said method comprising contacting the biological membrane with a Conjugate of the Invention, or with a pharmaceutical composition that includes said Conjugate, wherein said Conjugate comprises an OD and E, E' or E" moiety(ies), each having the structure as set forth in any of Formulae (II), (III), (IV), (V), (VI), (VII), (VIII), (VIII-H), (VIII-M), (IX), (X), (XI), (XII), (XIIa), (XIII), (XIIIa), (XIV), (XIV-H), (XIV-M), (XV), (XV-H), (XV-M), (XVI), (XVI-H), (XVI-M), thus achieving endocytosis and/or flip-flop of said Conjugate, at the biological membrane.

In a non-limiting hypothesis, the basis for said induction of endocytosis or flip-flop relates to the structure of the Conjugate of the Invention. In the case that the OD is siRNA or dsiRNA, linked to E moieties, the Conjugate approaches the outer leaflet of the membrane, with its cylindrical RNA duplex being parallel to the membrane surface, and its E moieties being are oriented towards the membrane core, perpendicular to the membrane surface. This orientation thus anchors the RNA Duplex to the membrane's outer leaflet. The resultant forced proximity of the highly negatively-charged RNA to the outer membrane leaflet, causes energetically-unfavorable focal strain, with extension of the surface area of the outer phospholipid leaflet, disturbance of the hydration shells around the phospholipid headgroups, and focal bending of the membrane. Relaxation of this bending energy can then take place through either endocytosis, and/or flip-flop. Both processes support the initiation and/or propagation of trans-membrane delivery of the Conjugate of the Invention into the cell, including its macromolecule cargo drug. Accordingly, a method for induction of endocytosis or flip-flop in a phospholipid membrane is within the scope of the Invention; said method comprising contacting the membrane with the Conjugates of the Invention.

Conjugates according to embodiments of the invention, may be used for the treatment of a medical disorder. Embodiments of the invention include methods for medical treatment, comprising the administration to a patient in need, therapeutically effective amounts of a pharmaceutical composition, comprising a Conjugate according to any of Formulae (I), (II), (III), (IV), (V), (VI), (VII), (VIII), (VIII-H), (VIII-M), (IX), (X), (XI), (XII), (XIIa), (XIII), (XIIIa), (XIV), (XIV-H), (XIV-M), (XV), (XV-H), (XV-M), (XVI), (XVI-H), (XVI-M), (Cn-1), (Cn-2), (Cn-3), wherein D is a drug useful for treatment of the respective medical disorder.

In one embodiment, the method is for genetic medical treatment with siRNA, dsiRNA or ASO as therapeutic agents. Said method comprises the administration to a patient in need, therapeutically effective amounts of a pharmaceutical composition, comprising a Conjugate of the invention, according to any of Formulae (I), (II), (III), (IV), (V), (VI), (VII), (VIII), (VIII-H), (VIII-M), (IX), (X), (XI), (XII), (XIIa), (XIII), (XIIIa), (XIV), (XIV-H), (XIV-M), (XV), (XV-H), (XV-M), (XVI), (XVI-H), (XVI-M), (Cn-1), (Cn-2), (Cn-3), wherein D is siRNA, dsiRNA, mRNA, miRNA, ASO or a therapeutic protein, useful in inhibition of expression of a gene, or in blocking activity of a respective protein, that plays a role in the etiology or pathogenesis of a disease in the specific patient.

Said treatment may involve delivery of the drug into cells in either culture in vitro, ex vivo (i.e., cells taken out of a living tissue, to optionally be returned to the patient after a therapeutic manipulation), or into cells in a living animal or a human subject in vivo. In some embodiments, the cell is a neoplastic cell. In some embodiments, the neoplastic cell is a tumor cell. In some embodiments, the neoplastic cell is a cell within a metastasis. The cell may be a eukaryotic cell, an eukaryotic cell transfected by an oncogenic agent, a human cell, a cell-line, a cell that is a pre-cancerous cell, or any combination thereof.

In yet another embodiment of the invention, D is a protein, administered as a replacement therapy, i.e., to replace a mutated, malfunctioning protein, thus addressing a physiological need. In another embodiment, D is a protein that has as role in gene regulation, including, among others, proteins that have a role in DNA or RNA editing (adding, disrupting or changing the sequence of specific genes). In one embodiment, said protein may be a member of the CRISPRs (clustered regularly interspaced short palindromic repeats)-related proteins. Specifically, said protein can be the Cas9 protein (CRISPR associated protein 9), an RNA-guided DNA nuclease enzyme, or an analogue thereof, potentially loaded with its guide oligonucleotide sequence.

In one of the embodiments of the invention, it describes a method for genetic treatment of a medical disorder, wherein said method comprises administration to a patient in need, therapeutically effective amounts of a pharmaceutical composition, comprising a Conjugate according to any of Formulae (I), (II), (III), (IV), (V), (VI), (VII), (VIII), (VIII-H), (VIII-M), (IX), (X), (XI), (XII), (XIIa), (XIII), (XIIIa), (XIV), (XIV-H), (XIV-M), (XV), (XV-H), (XV-M), (XVI), (XVI-H), (XVI-M), (Cn-1), (Cn-2), (Cn-3), wherein D is a CRISPR protein, such as Cas9, administered together with an appropriate guide oligonucleotide, thus achieving delivery of the protein, loaded with a respective guide oligonucleotide into the cells, where the CRISPR protein can exert its genome editing activity. A guide oligonucleotide in this context is a sequence of RNA or DNA that guides the Cas9 protein to a specific locus (place) on the genomic DNA, in order to induce a double-strand DNA cleavage at that site, thus enabling repair of the local defect in the genome. In the case of Cas9, the guide oligonucleotide is a short segment of RNA, the sequence of which is complementary to the sequence of the target DNA locus.

Therefore, Conjugates according to embodiments of the invention and the respective pharmaceutical compositions, as well as the respective methods, may be beneficial, among others, in the treatment of medical disorders, selected, among others, from cancer, toxic insults, metabolic disease, ischemic disease, infectious disease, vascular disorders, protein storage disease, trauma, immune-mediated disease, degenerative diseases, inherited or acquired medical disorders.

Therefore, in an embodiment of the Invention, it provides a method for treatment of a medical disorder, said method comprising administration to a patient in need, therapeutically effective amounts of a pharmaceutical composition, that comprises a Conjugate according to any of any of Formulae (I), (II), (III), (IV), (V), (VI), (VII), (VIII), (VIII-H), (VIII-M), (IX), (X), (XI), (XII), (XIIa), (XIII), (XIIIa), (XIV), (XIV-H), (XIV-M), (XV), (XV-H), (XV-M), (XVI), (XVI-H), (XVI-M), (Cn-1), (Cn-2), (Cn-3), wherein D is drug useful for the treatment of this medical disorder.

According to some embodiments, the medical disorder is cancer. As used herein, the term "cancer" refers to the presence of cells that manifest characteristics that are typical of cancer-causing cells, such as uncontrolled proliferation, loss of specialized functions, immortality, significant metastatic potential, significant increase in anti-apoptotic activity, rapid growth and proliferation rate, or certain characteristic morphology and cellular markers known to be associated with cancer. Typically, cancer cells are in the form of a tumor, existing either locally within an animal, or circulating in the bloodstream as independent cells, as are, for example, leukemic cells.

In the field of neurological disorders, Conjugates according to embodiments of the invention may be useful, among others, in the treatment of neurodegenerative disorders, such as Alzheimer's disease, Motor Neuron Disease, Parkinson's disease, Huntington's disease, multiple sclerosis and Creutzfeldt-Jacob disease.

In the field of infectious disorders, Conjugates according to embodiments of the invention may be useful, among others, for the delivery of antibiotics to combat bacterial, fungal, or other parasitic infections; or delivery of antiviral agents to combat viral infractions. Accordingly, D of the Conjugates of the invention may have anti-infective properties, thus being useful for the treatment of infectious diseases, such as bacterial or viral infections. Examples of viral infections, for which the Conjugates of the invention may be useful, are, without limitation, human immunodeficiency virus (HIV); hepatotropic viruses, such as hepatitis C virus (HCV) or hepatitis B virus (HBV); infection by orthomyxoviridae, such as influenza virus A, influenza virus B, influenza virus C, or infections by parainfluenza viruses. Accordingly, an embodiment of the Invention, is a Conjugate of E, E' or E" moiety (or moieties), linked to an antiviral or antibacterial drug. Such drug can be, among others, an OD, which sequence is aimed at interacting with the genetic material of the infective agent, thus interfering with genetic processes that have a role in replication, metabolism, infectiveness, or survival of said pathogen. Such genetic sequences can be siRNA or dsiRNA, specifically-designed to silence the expression of gene(s) of the infective agent (e.g., a virus).

The utility of the Conjugates of the Invention in combating infection can be in at least one of the following utilizations: either in the delivery of therapeutically-useful agents across biological membranes into cells of the host (e.g., a human patient); or across biological membranes into cells of the pathogen (e.g., bacteria or virus).

In the field of metabolic disorders, Conjugates according to embodiments of the invention may be useful, among others, for the delivery of genetic treatments, aimed at down-regulating the expression of a gene or genes responsible for said metabolic disorder, or for administration of a protein, to replace a defective mutated protein, that has a role in the disease etiology or pathogenesis.

In other embodiments, the Invention relates to the potential utilization of the Compounds of the Invention to enhance delivery of chemical compounds across phospholipid membranes into cells of plants, thus being potentially beneficial for utilizations in agriculture. Depending on the attached chemical compound, and the desired indication, such delivery can have various useful utilizations in agriculture. For example, such delivery in plants can assist in improving crop quality and quantity, among others, by improving plant's genetics, or by eradication of various pathogens: insects, bacteria or fungi.

EXAMPLES

The following Examples illustrate the invention, in a non-limiting manner, in order to demonstrate how embodiments of the invention can be carried-out in practice. The Examples describe various Compounds and Conjugates of the Invention. All described Conjugates are according to Formulae (Cn-1) or (Cn-2), with each comprising E, E' or E" moieties, having the structure according to general Formula (II). The Examples provide various E, E' or E" moieties, selected among the structures set forth in Formulae (III), (IV), (V), (VI), (VII), (VIII), (VIII-H), (VIII-M), (IX), (X), (XI), (XII), (XIIa), (XIII), (XIIIa), (XIV), (XIV-H) or (XIV-M). These Conjugates manifest biological activity in gene silencing. This performance supports the notion, that Conjugates that comprise Formulae (I) and (II), present a general and unifying structural motif, that enables a useful delivery of macromolecular ODs across phospholipid membranes into cells, with consequent useful biological performance (in this case, gene silencing). In addition, the Examples describe methods for chemical synthesis of the E moieties of the Invention, their precursors, and their assembly into useful Conjugates.

Example 1: A General Method for Synthesis of Conjugates According to Embodiments of the Invention, Wherein D Moieties are Oligonucleotides Initially, a gene to be silenced is chosen, based on its role in disease etiology or pathogenesis. Then, based on bioinformatic methodologies known in the art, the nucleotide sequences to be incorporated in the Conjugate are designed and determined [typically 19-21 base-pairs double-stranded siRNA for a RISC substrate, or 24-29 base-pairs double-stranded RNA for a Dicer substrate (dsiRNA)].

Synthesis is carried-out in the 3' to 5' direction of the oligonucleotide. Solid phase synthesis is applied, using protected building blocks, derived from protected 2'-deoxy-nucleosides (dA, dC, dG, and dT), ribonucleosides (A, C, G, and U), or chemically modified nucleosides, e.g. [LNA (locked nucleic acids), or BNA (bridged-nucleic-acids)]. The building blocks are provided as nucleoside precursors, wherein the 5'- and the 3'-hydroxyl groups are protected by DMT and phosphoramidite, respectively. These groups are sequentially removed during the reactions of coupling the nucleotide to the growing oligonucleotide chain, in an order as determined by the desired nucleotide sequence.

For the purpose of synthesis of the Conjugates of the Invention, the E groups are provided as Precursor molecules, each being an E, E' or E" moiety of the Invention, linked to protecting group, as described above. While the protecting group can be any protecting group for hydroxyl known in the art, phosphoramidite and DMT [Dimethoxytrityl bis-(4-methoxyphenyl) phenyl methyl] are customarily often used in oligonucleotide synthesis. A major advantage of Conjugates of the current Invention, is that they provide, as exemplified for Conjugates (Cn-1) and (Cn-2), the option of linking E, E', or E" moieties to either the 5'-end of an oligonucleotide strand, the 3'-end of an oligonucleotide strand, or also at an internal position along the oligonucleotide chain. Thereby, the E moieties of the Invention can become integrated within the oligonucleotide chain, similar to any inherent, natural oligonucleotide building block. The linkage between the nucleotides can be via standard phosphotriester bonds, or through synthetic phosphorothioate bonds, which may provide advantages such as stability in the blood, or binding to blood proteins, or via any other nucleotide linkage methodology known in the art. Upon completion of the assembly of the chain, the product is released from the solid support into solution, de-protected, and collected. The desired Conjugate is then isolated by high-performance liquid chromatography (HPLC), to obtain the desired Conjugate of the Invention in high purity. In the case of siRNA or dsiRNA, each complementary RNA strand is synthesized separately, and then annealing of the two strands is performed in standard conditions, as known in the art, yielding the desired double-stranded siRNA or dsiRNA, which is then subjected to purification and aliquoting.

Examples 2: Methods for Chemical Synthesis of Precursor Molecules, Comprising E, E' or E" Moiety of the Invention Example 2A: Synthesis of Key Intermediate Phenol 1

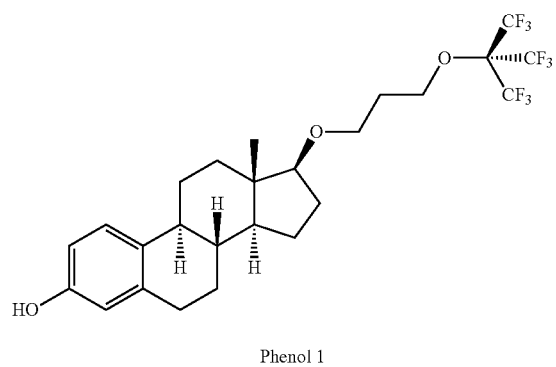

Phenol 1

Scheme 1. Synthesis of phenol 1.

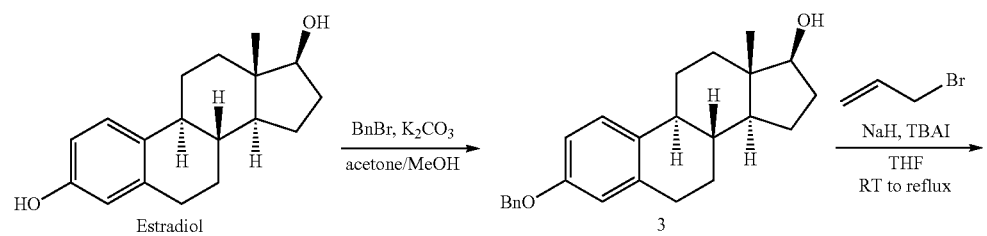

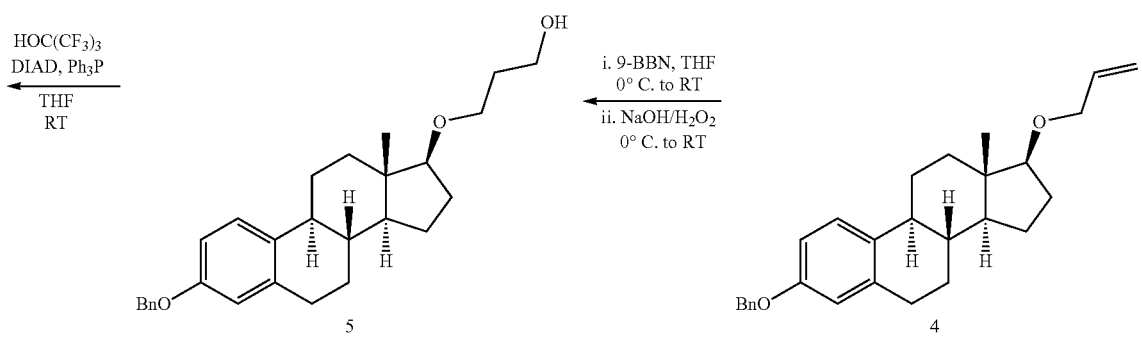

-continued

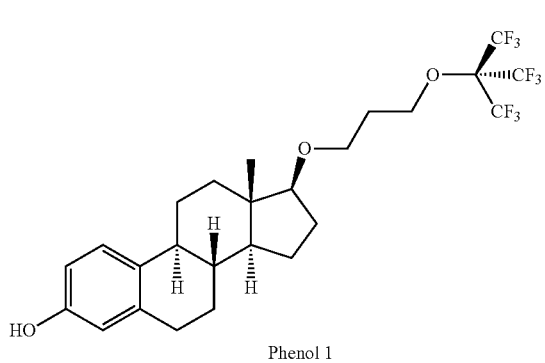

Phenol 1

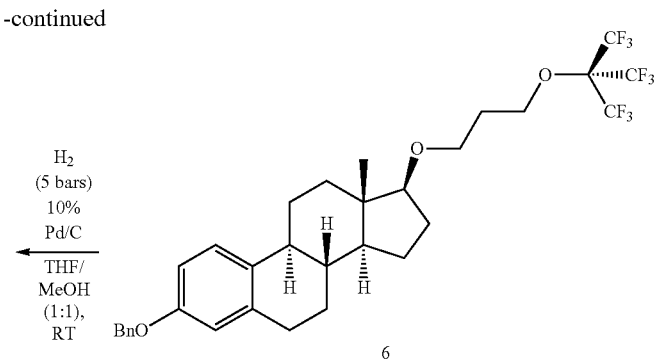

6

Estradiol was treated with excess of sodium hydride, followed by addition of allylbromide, which resulted in clean conversion towards compound 3. Subsequent hydroboration with 1.5 equivalents of 9-BBN solely resulted in the terminal hydroxy group, while hydroboration with $BH_3$ is much less selective and provided a mixture of adducts. Alcohol 5 was submitted to Mitsunobu-reaction conditions, to couple it with perfluorinated tert-butanol to receive compound 6. Hydrogenolysis of the benzyl group of compound 8 furnished phenol 1. In conclusion, phenol 1 was prepared from estradiol via 5 synthetic steps in 45% overall yield:

2bA1. (8R,9S,13S,14S,17S)-3-Benzyloxy-17-hydroxyestra-1,3,5(10)-triene (2)

The synthesis of (8R,9S,13S,14S,17S)-3-Benzyloxy-17-hydroxyestra-1,3,5(10)-triene (2) is disclosed herein above in section 2aA1.

2bA2. (8R,9S,13S,14S,17S)-17-Allyloxy-3-benzyloxyestra-1,3,5(10)-triene (3)

The synthesis of (8R,9S,13S,14S,17S)-17-Allyloxy-3-benzyloxyestra-1,3,5(10)-triene (3) is disclosed herein above in section 2aA2.

2bA3. (8R,9S,13S,14S,17S)-3-Benzyloxy-17-(3-hydroxypropoxy)estra-1,3,5(10)-triene (7)

9-Borabicyclo[3.3.1]nonane (800 mL, 0.5 M solution in THF, stabilized, 400 mmol) was added dropwise to a solution of the crude alkene 3 (101.2 g, 251 mmol) in THF (1 L) at 0° C. and upon complete addition the mixture was stirred at room temperature overnight. The solution was cooled to 0° C. and slowly aqueous 30% NaOH (150 mL, 1.3 mol) and 35% aqueous (120 mL, 1.3 mol) were added dropwise simultaneously and the resulting heterogeneous mixture was vigorously stirred at room temperature for ca. 1 h. The reaction mixture was then partitioned between EtOAc (2 L) and brine (500 mL). The organic phase was washed with an additional 500 mL brine, dried over $Na_2SO_4$ and concentrated in vacuo. This procedure was repeated in a similar fashion and both portions were combined. Further purification of the concentrate by flash chromatography (silica gel, gradient 25% to 35% EtOAc in heptanes) afforded the alcohol 5 (130 g, 310 mmol) as a white solid in 61% yield (3 steps).

2bA4. (8R,9S,13S,14S,17S)-3-Benzyloxy-17-[3-(perfluoro-tert-butyloxy) propoxy]estra-1,3,5(10)-triene (8)

Diisopropyl azodicarboxylate (80 mL, 407 mmol) was added dropwise to a stirred mixture of alcohol 7 (130 g, 301 mmol), triphenylphosphine (162 g, 618 mmol), perfluorotert-butanol (70 mL, 497 mmol) and in dry THF (2 L) under a nitrogen atmosphere. The mixture was stirred at room temperature for ca. 18 h. The reaction mixture partially concentrated and heptane (1 L) was added. After full removal of the THF, precipitation started. The solids were removed using filtration and the filtrate was concentrated. Acetonitrile (1.5 L) was added and the mixture was stirred for 30 minutes while precipitation started. The solids were collected via filtration and dried in vacuo. Compound 8 (160 g, 251 mmol) was isolated as a white solid in 81% yield.

2bA5. (8R,9S,13S,14S,17S)-3-Hydroxy-17-[3-(perfluoro-tert-butyloxy) propoxy]estra-1,3,5(10)-triene (Phenol 1)

A Parr vessel was charged with benzyl ether 8 (160 g, 251 mmol) in EtOAc (1 L) to which 10% Palladium on carbon (4 g) was added. The mixture was stirred under hydrogen pressure (5 bars) at room temperature. The reaction was monitored with $^1H$ NMR. After ca. 72 h, the reaction mixture was filtered through a pad of Celite (flushed with EtOAc) and resubmitted with fresh 10% Palladium on charcoal (4 g) to a hydrogen atmosphere (5 bars). After ca. 16 h, the reaction mixture was filtered through a pad of Celite (flushed with EtOAc) and concentrated to provide phenol 1 (125 g, 228 mmol) as a greyish solid in 91% yield.

Example 2b: Synthesis of Key Building Block K-93-A-1

Synthesis is performed according to the following synthetic scheme:

Scheme 2. Synthesis of building block K-93-A-1

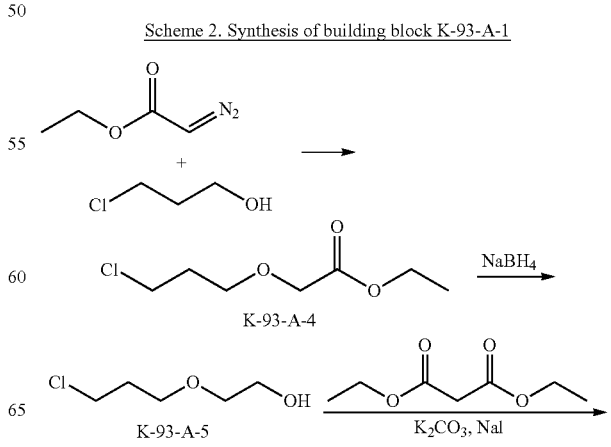

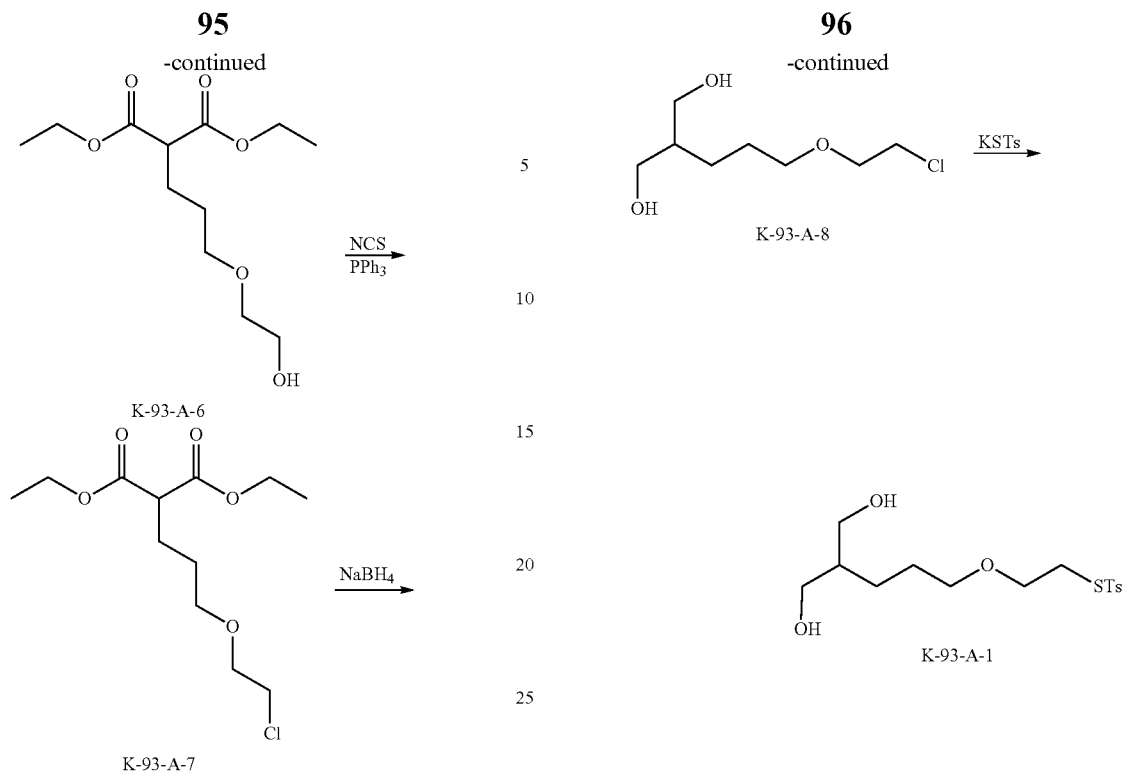
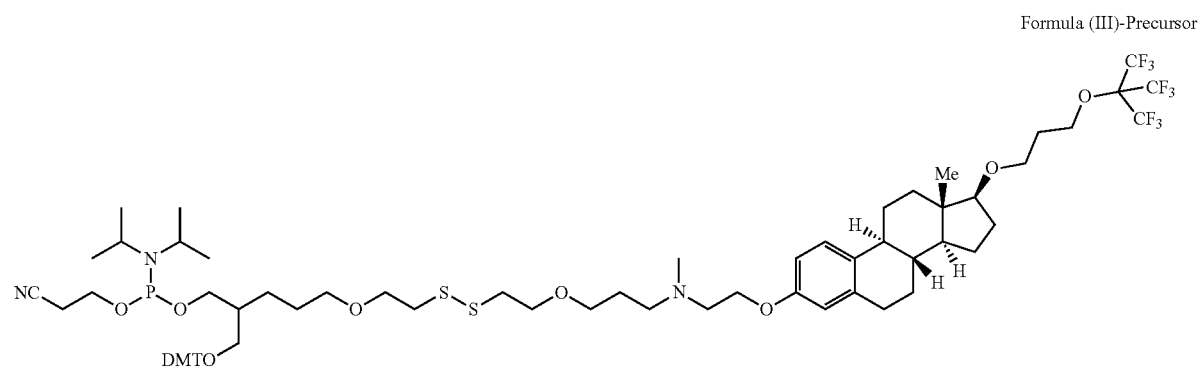
Example 2c: Synthesis of Formula (III)-Precursor
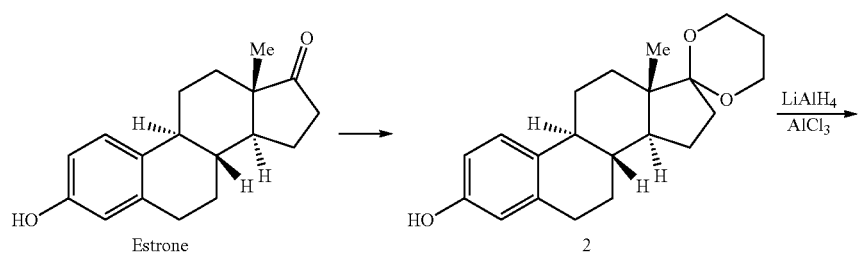
Scheme 3. Synthesis of Formula (III)-Precursor -continued
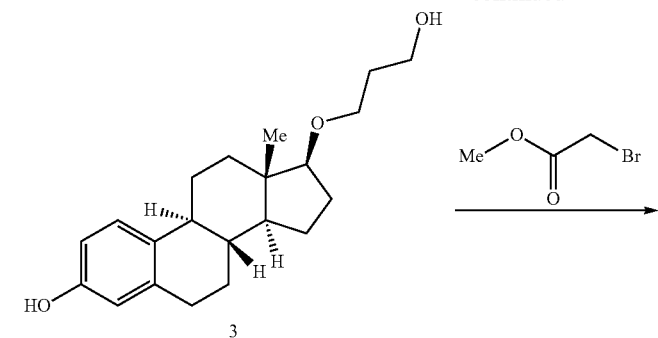
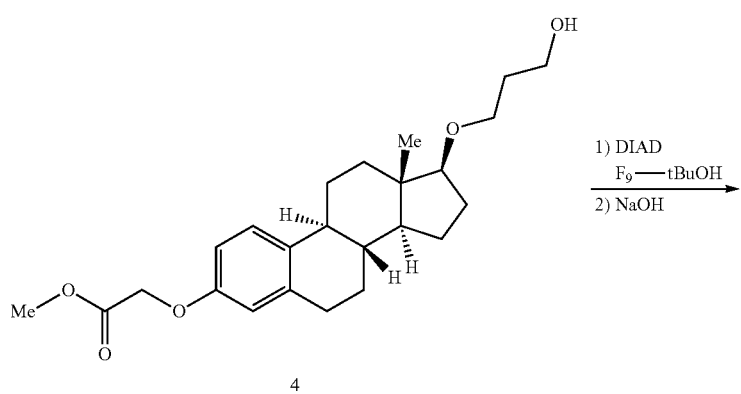
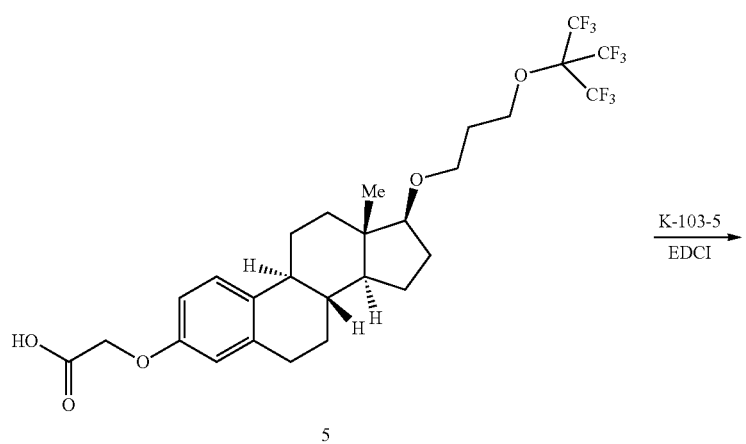
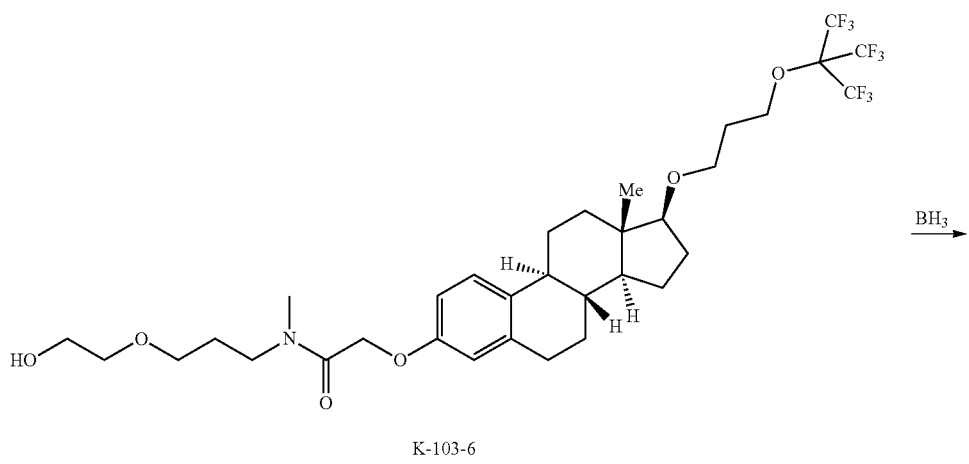

-continued
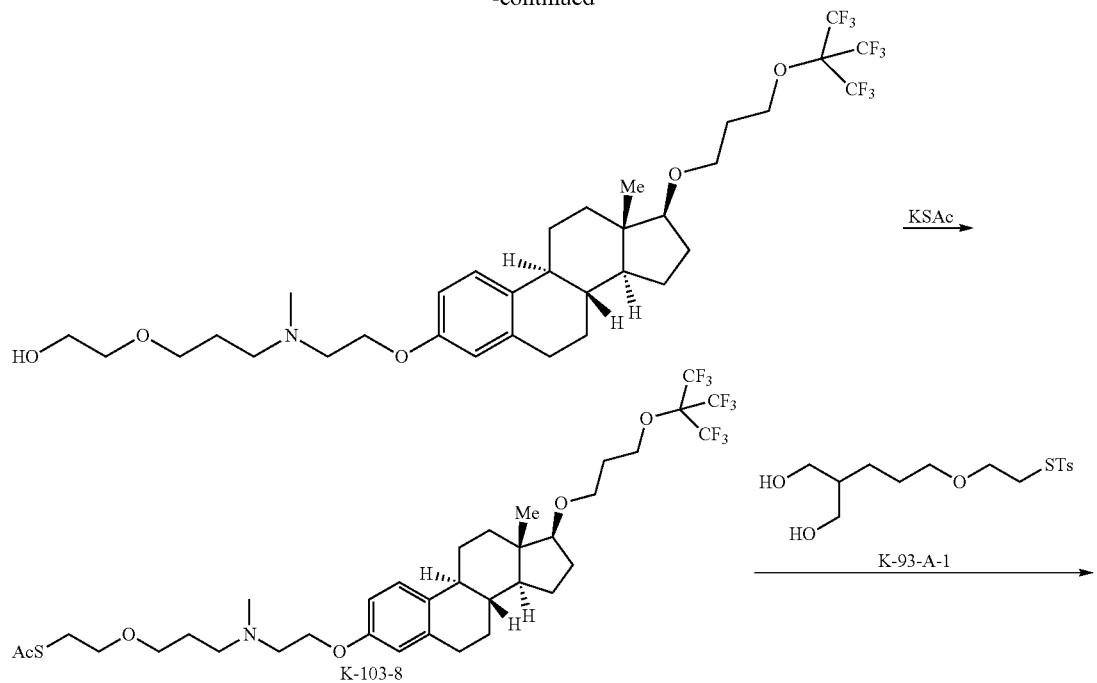
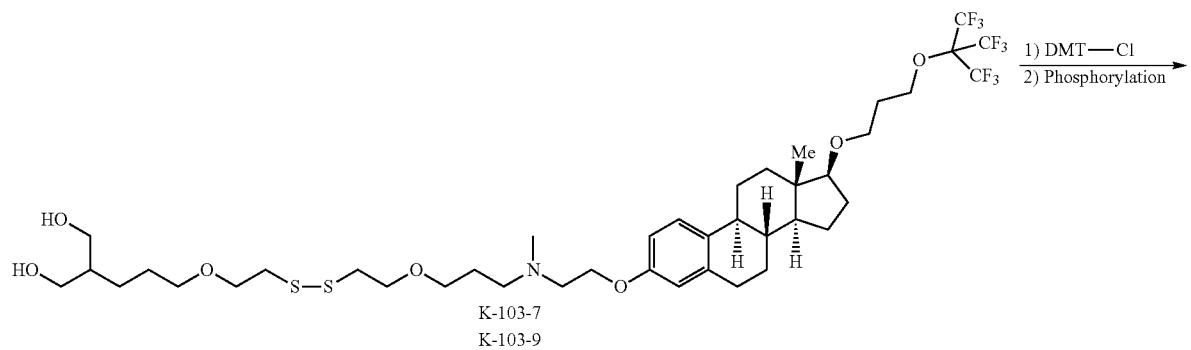
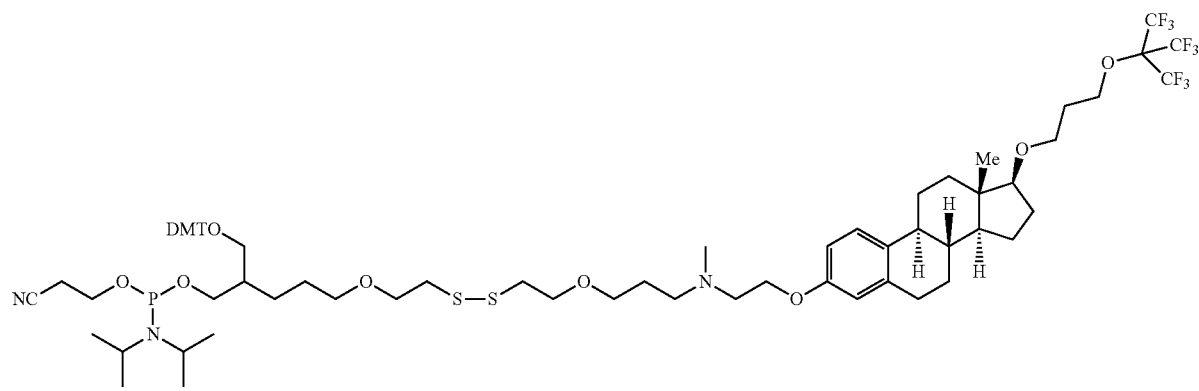
Formula (III)-Precursor

While intermediate K-93-A-1 is synthesized as described above, synthesis of intermediate K-103-5 is performed according to the following Synthetic Scheme:

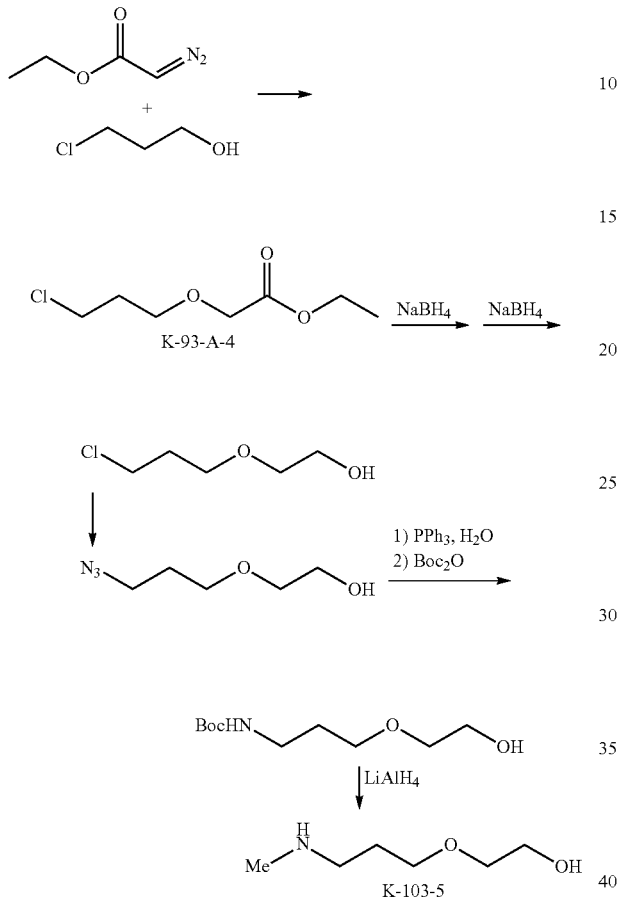

Example 2d: Synthesis of Formula (IV)-Precursor

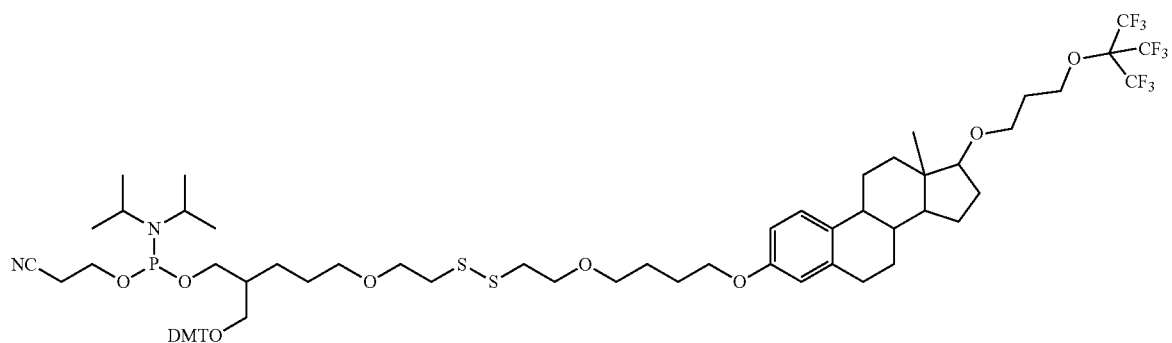

Formula (IV)-Precursor

Synthesis of Formula (IV)-Precursor is performed by conjugation of K-103A-2, which is a derivative of Phenol, 1 with key building block K-93-A-1. Synthesis is performed according to the following synthetic scheme:

Scheme 5. Synthesis of Formula (IV)-Precursor
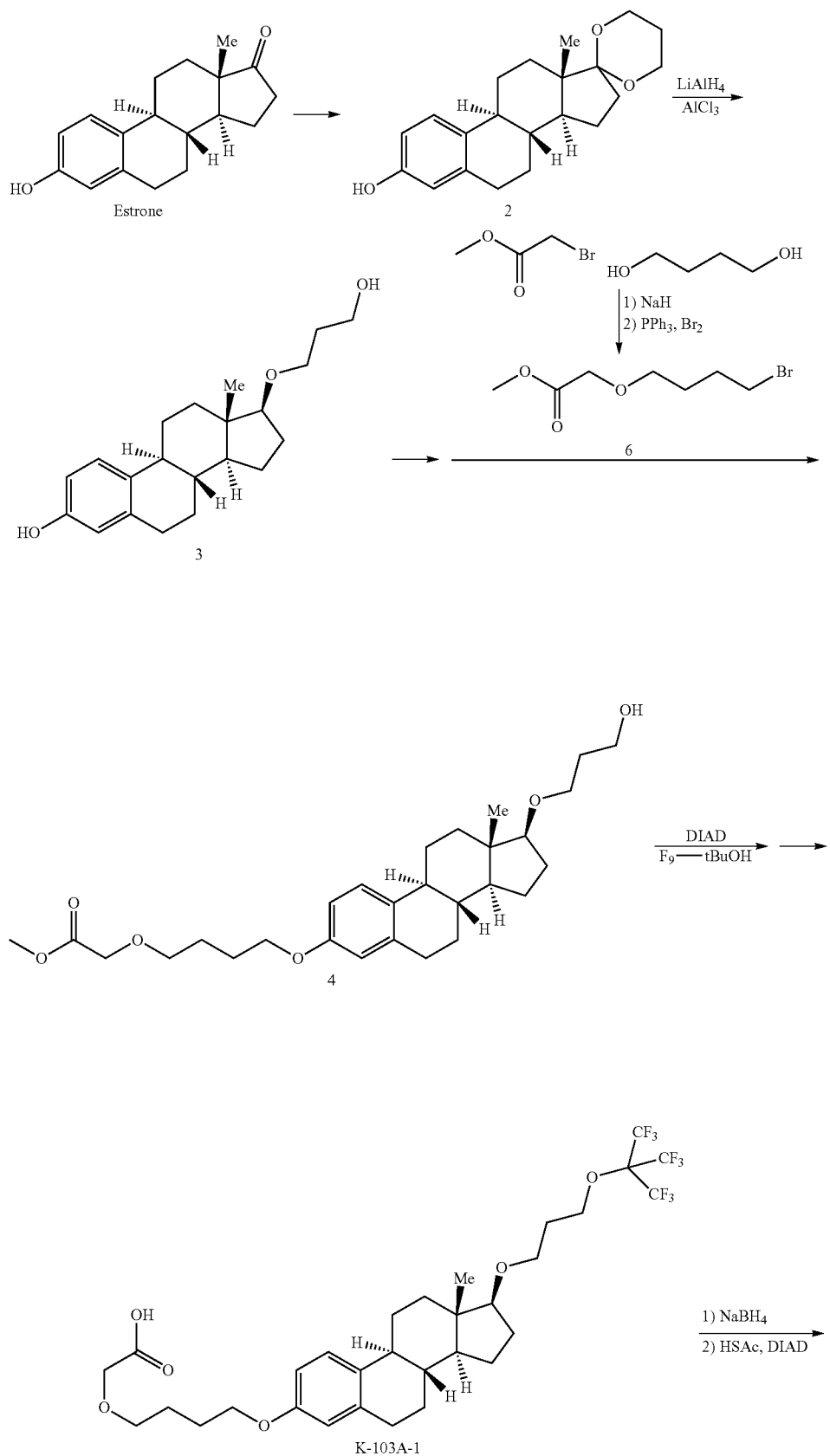

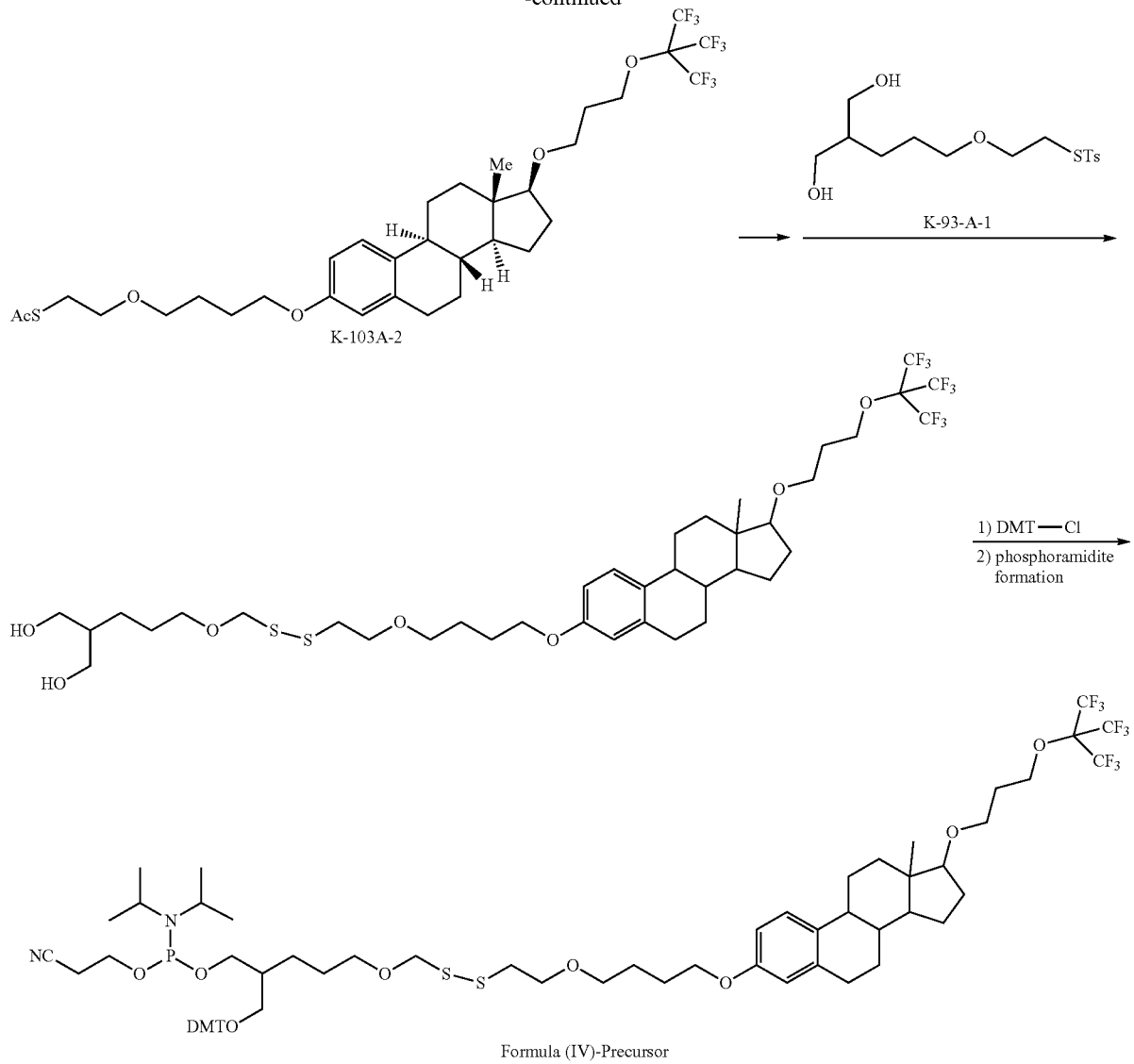
Example 2e: A Method for Synthesis of Formula (V)-Precursor
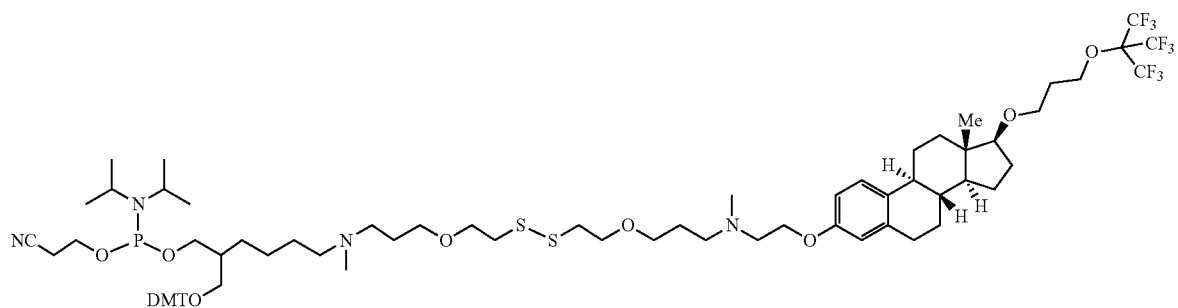

Synthesis of Thioacetate 11:
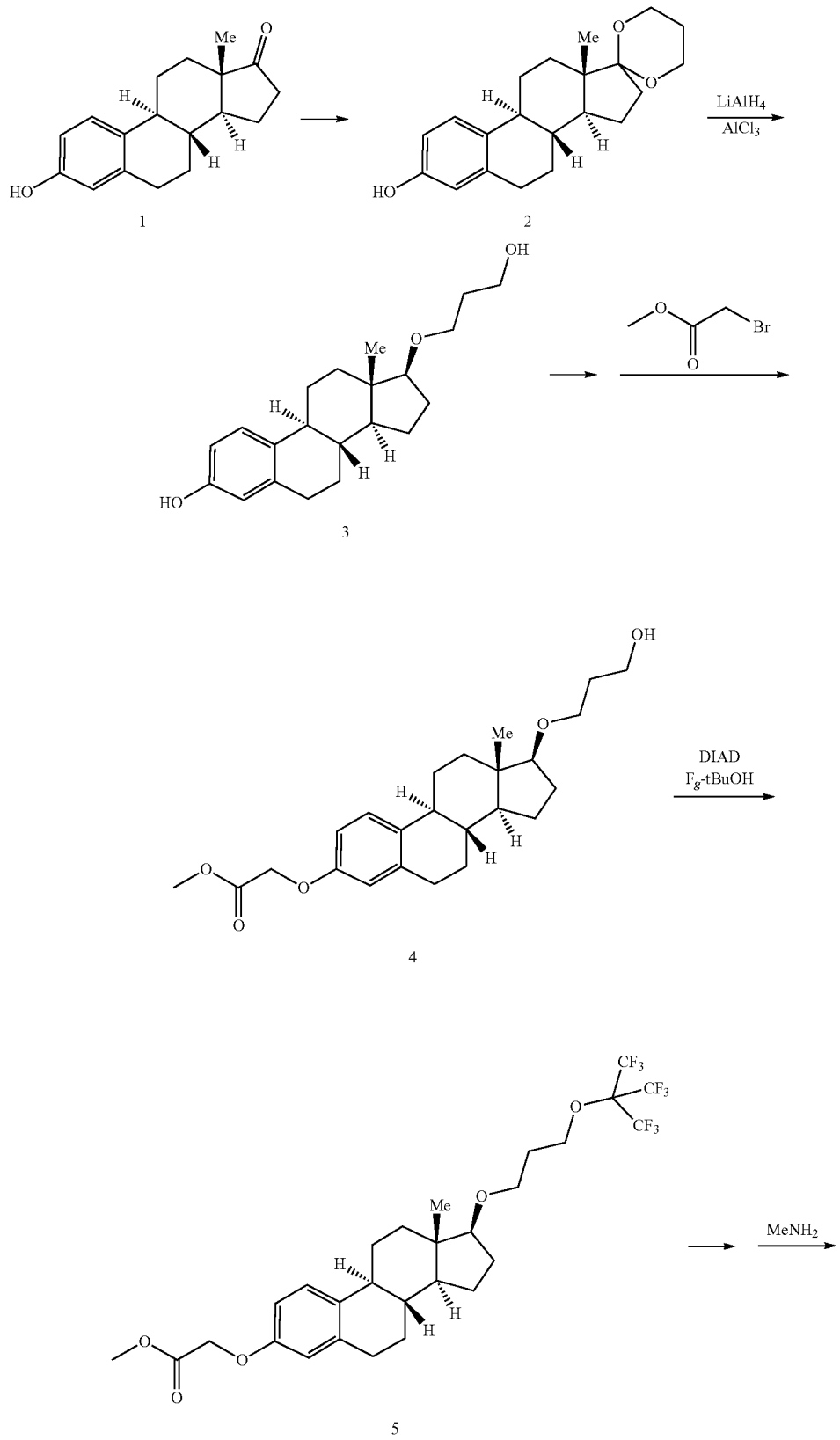

-continued
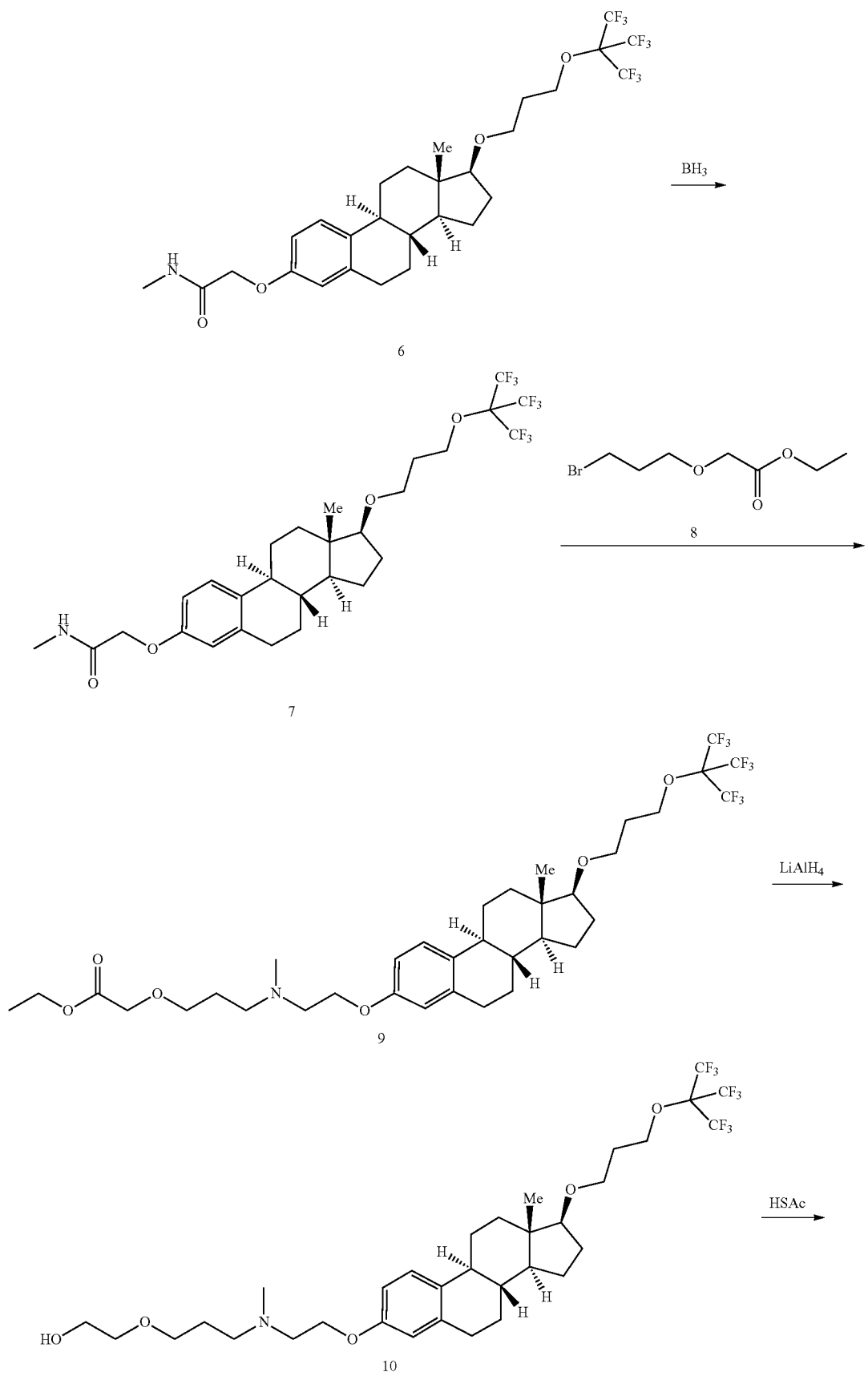

-continued

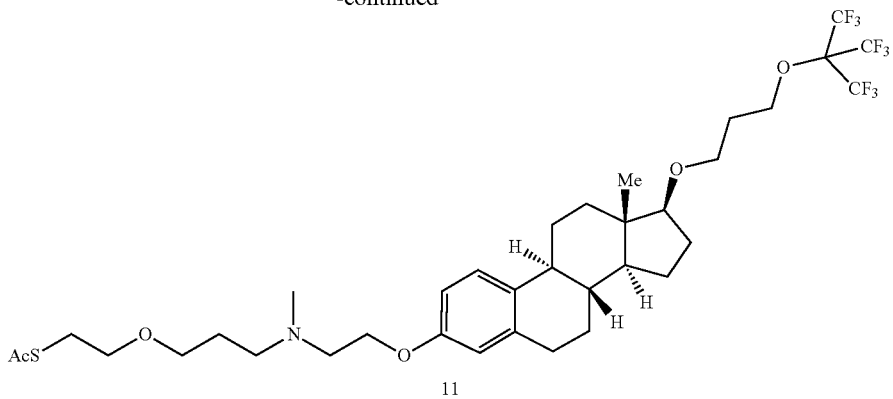
11

The synthesis commenced by protection of the ketone with 1,3-propanediol to provide compound 2 in good purity. LiAlH$_4$ and AlCl$_3$-ring opening of the acetal gave a mixture of compound 3 and estradiol in a ratio of ca 85:15, the latter being less reactive and will be removed in the next-steps.

The phenol was alkylated with methyl bromoacetate and compound 4 was obtained. The perfluoro-tert-butanol moiety was introduced using Mitsunobu conditions (compound 5). Compound 5 was treated with methylamine to provide amide 6. Reduction of the amide using BH$_3$·DMS provided amine 7. The amine was alkylated with bromide 8 to provide ester 9. The ester was reduced with LiAlH$_4$ to the corresponding alcohol (10). Finally, the thioacetate was introduced using Mitsunobu conditions to provide the desired building block 11.

Alkylation of amine 7 seems less straightforward than expected. At room temperature no conversion is achieved and the presence of base (such as Et$_3$N or K$_2$CO$_3$) seems to be a necessity. However, the resulting yields were usually in the range of 40%. The subsequent reduction of the ester to alcohol 10 with LiAlH$_4$ gave good conversion and an easy workup. The alumina-salts are usually destroyed by addition of aqueous 20% KOH (160 mL per mole), which after an easy filtration gives the desired material in THF. The transformation of the alcohol to the thioacetate is achieved via Mitsunobu-conditions. It must be noted that for the order of addition thioacetic acid should be added as the last component. After workup and careful purification thioester 11 could be obtained.

Synthesis of Thiotosylate 18:

Scheme 7. Synthesis of thiotosylate 18

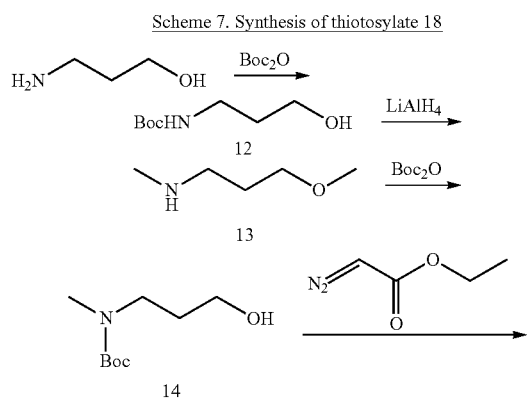

During the syntheses of a previous compound it was observed that the presence of an amine in the thiotosylate building block was the cause of very low yields. Therefore, Boc-protected thiotosylate 18 was needed. The Boc-group will be removed after disulfide formation and the amine will then be alkylated. Aminopropanol was protected with the Boc group, which was subsequently reduced by LiAlH$_4$ to the corresponding methylamine 13. The now secondary amine was then protected with a new Boc group to provide compound 14. The alcohol was reacted with ethyldiazoacetate to introduce the ether functionality (15). The ester was reduced using LiAlH$_4$ to provide alcohol 16. Bromination with NBS provided bromide 17. Substitution of the bromide with potassium thiotosylate afforded the desired thiotosylate building block 18.

Synthesis of Iodide 22:

Scheme 8. Synthesis of iodide 22

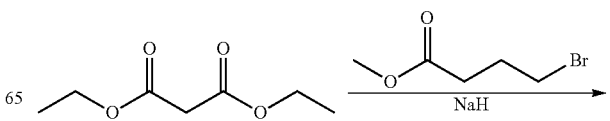

113

114

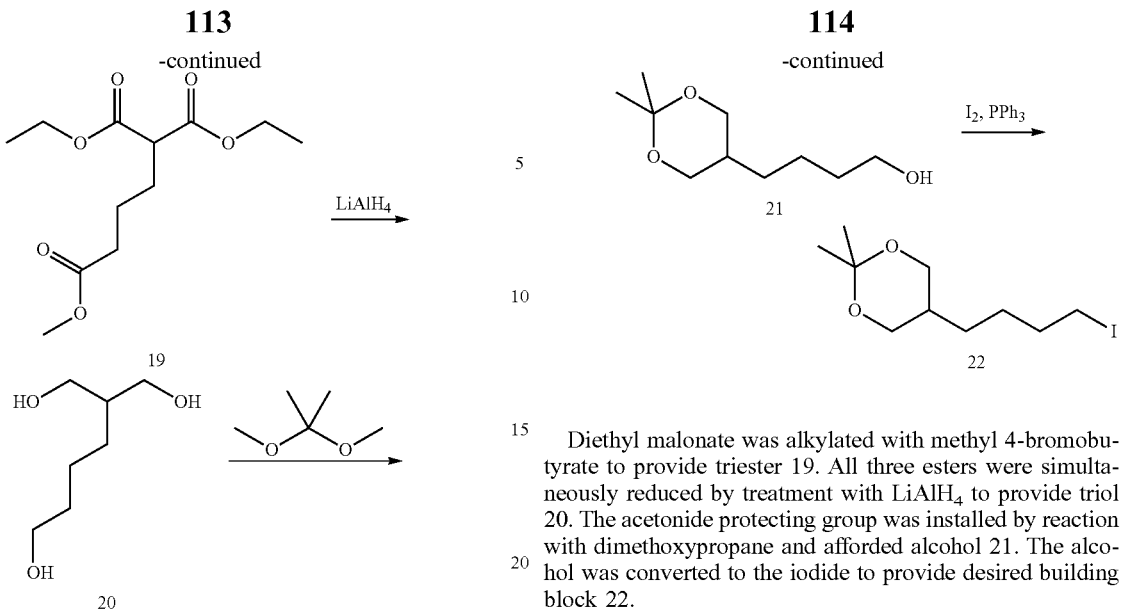

Diethyl malonate was alkylated with methyl 4-bromobutyrate to provide triester 19. All three esters were simultaneously reduced by treatment with LiAlH$_4$ to provide triol 20. The acetonide protecting group was installed by reaction with dimethoxypropane and afforded alcohol 21. The alcohol was converted to the iodide to provide desired building block 22.

Integration of the Synthesis of Formula (V)-Precursor:

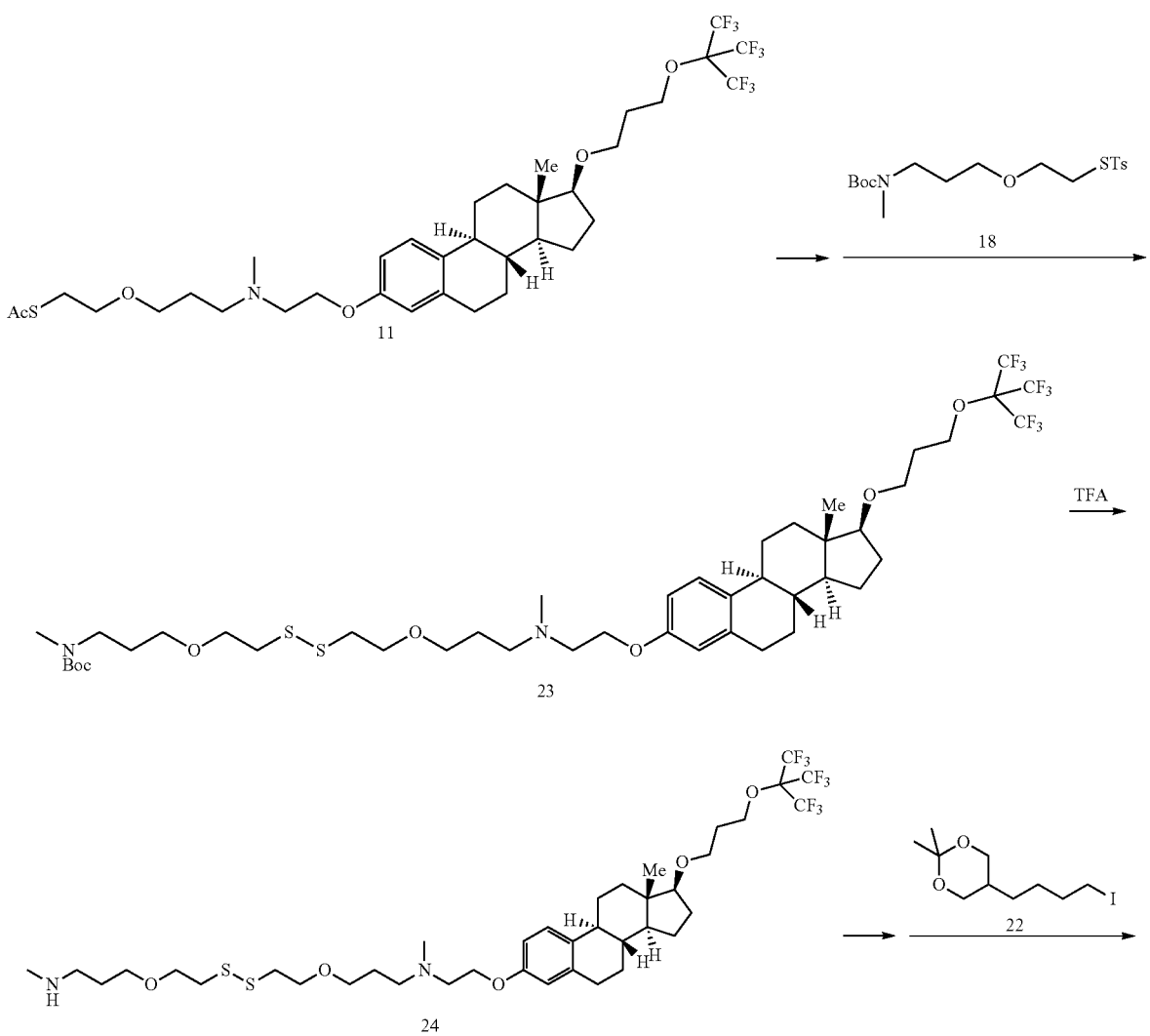

-continued
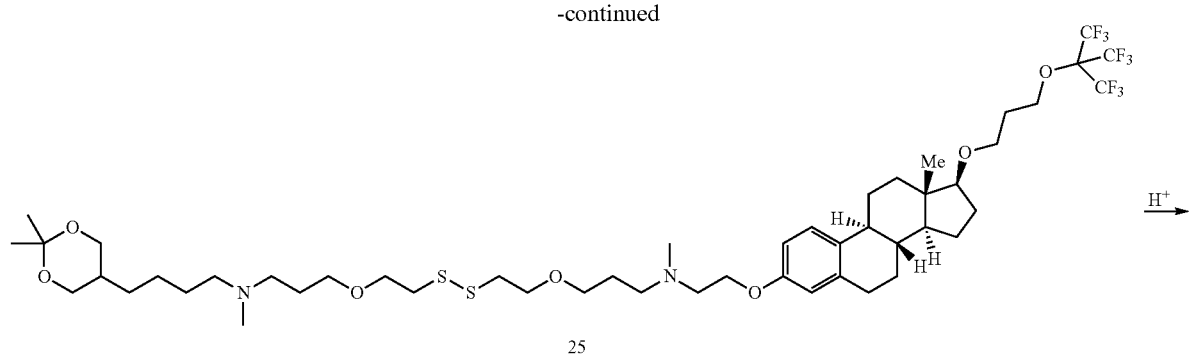
25
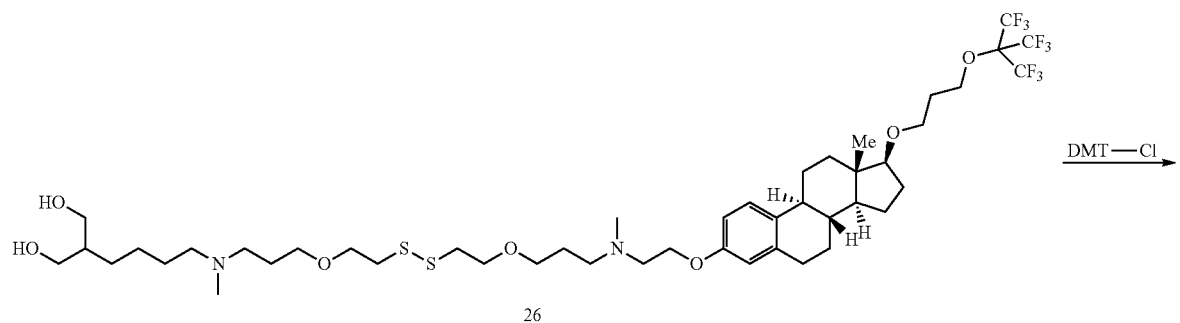
26
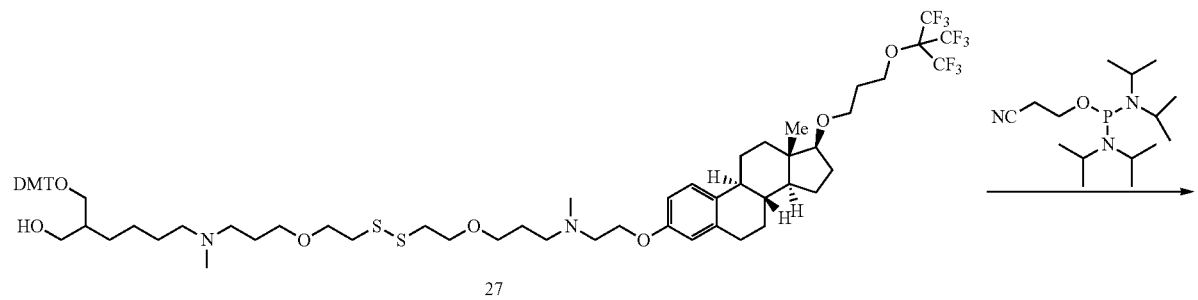
27
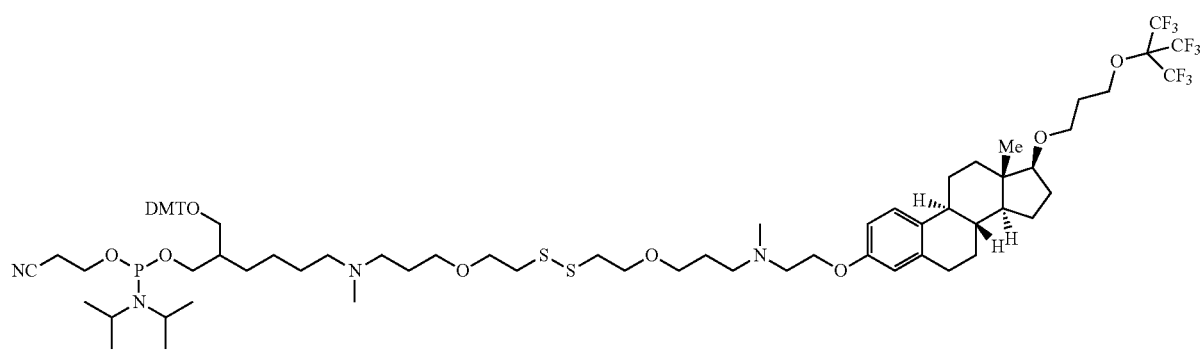
Apo-Si-K-105-B Disulfide formation between thioacetate 11 and thiotosylate 18 provided disulfide 23 in good yields. Treatment with TFA to remove the Boc group provided amine 24. The amine was alkylated with iodide 22 to provide 25 in 40% yield. The acetonide was removed by treatment with acid to provide diol 26. The DMT-group was installed to afford compound 27. Final phosphoramidite formation provided Formula (V)-Precursor.

Experimental Section:
Synthesis of Thioacetate 11:

(8R,9S,13S,14S)-13-Methyl-6,7,8,9,11,12,13,14,15, 16-decahydrospiro[cyclopenta[a]phenanthrene-17,2'-[1,3]dioxan]-3-ol (2)

To a suspension of estrone (252 gram, 0.93 mol) in toluene (1.5 L) were added trimethoxymethane (297 g, 350 mL, 2.80 mol), propane-1,3-diol (213 g, 250 mL, 2.80 mol) and pTsOH (2 g, 10 mmol). Warmed to 60° 0C and stirred for 16 h. Added triethylamine (6 mL) and water (600 mL) and continued stirring for 1 more hour. Separated phases and washed the organic layer with water (3×400 ml) and brine. Dried over $Na_2SO_4$ and partially concentrated to ca 1 L. Poured into heptane (4 L) and filtered the white solids of. Washed with heptane, dried in vacuo. Compound 2 (271 gram, 825 mmol) was isolated as a white solid in 88.5% yield (8R,9S,13S,14S,17S)-17-(3-Hydroxypropoxy)-13-methyl-7,8,9,11,12,13,14,15,16,17-decahydro-6H-cyclopenta[a]phenanthren-3-ol (3)

To a solution of (13S)-13-methyl-6,7,8,9,11,12,13,14,15, 16-decahydrospiro [cyclopenta[a]phenanthrene-17,2'-[1,3] dioxan]-3-ol (2, 60.7 g, 185 mmol) in THF at 0° C. was added carefully lithium aluminum hydride (8.42 g, 222 mmol) followed by portion wise addition of aluminum chloride (98.6 g, 739 mmol) (very exothermic!). Stirred 15 in at 0° C., then warmed to 50° C. Stirred 2 h at 50° C. (due to clogging on a rotary evaporator), then cooled to 0° C. and started quenching dropwise with $NH_4Cl$ (aq) (500 mL). Stirred 1 h at room temperature. The phases were separated and the organic layer was washed with brine, concentrated. White solid (65 gram) obtained, contaminated with estradiol (ca 15%)

Methyl 2-(((8R,9S,13S,14S,17S)-17-(3-hydroxypropoxy)-13-methyl-7,8,9,11,12,13,14,15,16,17-decahydro-6H-cyclopenta[a]phenanthren-3-yl)oxy) acetate (4)

The crude material 3 (89.4 gram) was dissolved in acetone (1.25 L) and MeOH (0.2 L) and treated with potassium carbonate (60 gram, 435 mmol) and methyl bromoacetate (50 mL, 435 mmol). The suspension was warmed to 60° C. and stirring continued for 16 h. Based on TLC, all phenolic moieties had been alkylated. The mixture was cooled to room temperature and filtered. The filtrate was concentrated and further purified using flash chromatography (eluent 20% to 30% EtOAc in heptane, removing all impurities, 100% EtOAc to obtain the desired material).

Compound 4 (56.7 gram, 140.3 mmol) was isolated as a yellow oil in 65% yield.

Methyl 2-(((8R,9S,13S,14S,17S)-17-(3-((1,1,1,3,3, 3-hexafluoro-2-(trifluoromethyl) propan-2-yl)oxy) propoxy)-13-methyl-7,8,9,11,12,13,14,15,16,17-decahydro-6H-cyclopenta[a]phenanthren-3-yl)oxy) acetate (5)

To a solution of compound 4 (56.7 gram, 140.3 mmol) in THF (1 L) were added triphenylphosphine (55.4 gram, 211 mmol), nonafluoro-tert-butyl alcohol (30 mL) and di-tert-butyl azodicarboxylate (38.5 gram, 167 mmol). The mixture was stirred for 30 min when TLC showed full conversion. Heptane (500 mL) was added and the mixture was partially concentrated to ~500 mL. More heptane (1 L) was added and the mixture was stirred overnight at room temperature. Precipitates had formed and were filtered off, the filtrate was concentrated to provide compound 5 as yellow syrup, albeit contaminated with traces of DBAD and triphenylphosphine.

2-(((8R,9S,13S,14S,17S)-17-(3-((1,1,1,3,3,3-Hexafluoro-2-(trifluoromethyl) propan-2-yl)oxy) propoxy)-13-methyl-7,8,9,11,12,13,14,15,16,17-decahydro-6H-cyclopenta[a]phenanthren-3-yl)oxy)-N-methylacetamide (6)

The crude syrup of compound 5 was diluted with MeOH (250 mL) and 40% aqueous methylamine (350 mL) was added. The white precipitate was stirred for 1 h when TLC showed full conversion. Water (1 L) was added and the solids were filtered off. The residue was washed with water and taken up in dichloromethane (1 L). The organic layer was washed with brine, dried over $Na_2SO_4$ and concentrated. Further purification was performed using ca 7 cm of silica and initial elution with 15% EtOAc in heptane. When all impurities were removed from the column, compound 6 was eluted with 100% EtOAc. Compound 6 (82.0 gram, 132 mmol) was isolated as a white solid in 94% yield, albeit traces of triphenylphosphoxide remained present.

2-(((8R,9S,13S,14S,17S)-17-(3-((1,1,1,3,3,3-Hexafluoro-2-(trifluoromethyl)propan-2-yl)oxy) propoxy)-13-methyl-7,8,9,11,12,13,14,15,16,17-decahydro-6H-cyclopenta[a]phenanthren-3-yl)oxy)-N-methylethan-1-amine (7)

To a solution of compound 6 (56.0 gram, 90.5 mmol) in THF (500 mL) at 65° C. was added dropwise $BH_3 \cdot DMS$ (56 mL, 590 mmol). Refluxing continued for an additional 5 h, then the mixture was cooled to room temperature. The mixture was carefully dissolved in MeOH (300 mL) and 4 M dioxane in HCl (50 mL) was added. The solution was refluxed for 30 min, then cooled to room temperature and concentrated. The mixture was dissolved in MeOH (300 mL) and refluxed for 30 min. After cooling and concentration, the syrup was taken up in $CH_2Cl_2$ (1 L) and washed with aqueous saturated sodium bicarbonate (2×). The organic layer was dried over $Na_2SO_4$ and concentrated. Compound 7 (50.0 gram, 82.6 mmol) was isolated as a clear oil which slowly solidified in 91% yield. The impurity-profile with traces of triphenylphosphoxide was similar to compound 6.

Ethyl 2-(3-bromopropoxy)acetate (8)

To a solution of ethyl 2-diazoacetate (100 g, 0.74 mol) and 3-bromopropan-1-ol (0.10 kg, 74 mL, 0.74 mol) in DCM (100 mL) was added at 0° C. $BF_3 \cdot OEt_2$ (1.1 g, 0.94 mL, 7.4 mmol) was added. The reaction was stirred at 0° C. for 15 min and at room temperature for 3 hours until no more gas development was observed. The mixture was diluted with DCM (500 mL) and the mixture was washed with $H_2O$ (500 mL) and brine (500 mL) and dried over $Na_2SO_4$. The solvents were removed in vacuo to provide ethyl 2-(3-bromopropoxy)acetate (8, 180 g, 0.80 mol, 110%) as a clear yellow oil.

Ethyl 2-(3-((2-(((8R,9S,13S,14S,17S)-17-(3-((1,1,1,3,3,3-hexafluoro-2-(trifluoro-methyl)propan-2-yl)oxy)propoxy)-13-methyl-7,8,9,11,12,13,14,15,16,17-deca-hydro-6H-cyclopenta[a]phenanthren-3-yl)oxy)ethyl)(methyl)amino)propoxy) acetate (9)

A suspension of ethyl 2-(3-bromopropoxy)acetate (11 g, 50 mmol) compound 7 (25 g, 41 mmol), potassium carbonate (11 g, 83 mmol) and potassium iodide (0.69 g, 4.1 mmol) in Acetonitrile (300 mL) warmed to 70 C for 16 h. The mixture was cooled to room temperature, diluted with EtOAc (100 mL), filtered and concentrated. Further purification using flash chromatography (gradient 20% to 30% acetone+1% $Et_3N$ in heptane) provided compound 8 (12.0 gram, 16 mmol) in 39% as a clear oil which slowly solidified.

2-(3-((2-(((8R,9S,13S,14S,17S)-17-(3-((1,1,1,3,3,3-Hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)ethyl)(methyl) amino) propoxy)ethan-1-ol (10)

To a solution of compound 9 (12 g, 16 mmol) in THF (200 mL) at 0° C. was added aluminum lithium hydride (0.91 g, 24 mmol). Reaction mixture warmed to room temperature and stirred 1 h30. TLC gave full consumption. The reaction mixture was quenched with KOH 20% (160 mL/mol, V=4.2 mL), stirred 1 h, filtered, and concentrated in vacuo. Compound 10 (10.2 gram, 14.4 mmol) was isolated as a clear S-(2-(3-((2-(((8R,9S,13S,14S,17S)-17-(3-((1,1,1,3,3,3-Hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)ethyl)(methyl)amino)propoxy)ethyl) ethanethioate (11)

To a solution of compound 10 (20.2 g, 28.5 mmol) in THF were added triphenylphosphine (9.73 g, 37.1 mmol) and DIAD (6.93 g, 6.66 mL, 34.3 mmol), then after 5 min thioacetic acid (3.26 g, 3.07 mL, 42.8 mmol) was added. Continued stirring for 3 h, added heptane (20 mL) and concentrated.
Purified using flash chromatography (10% acetone+1% $Et_3N$ in heptane). Compound 11(15.4 gram, 20.1 mmol) was isolated as a clear sticky oil in 71% yield.
Synthesis of Thiotosylate 18:

tert-butyl(3-hydroxypropyl)carbamate (12)

To a solution of 3-aminopropan-1-ol (28.5 g, 379 mmol) and triethylamine (38.4 g, 53 mL, 379 mmol) in DCM (500 mL) was slowly added di-tert-butyl dicarbonate (91.1 g, 417 mmol) and the resulting mixture was stirred at room temperature for 2 hours. The mixture was quenched with imidazole (a scoop) and stirred for 5 min. The mixture was washed with 1M HCl (300 mL), dried over $Na_2SO_4$, and concentrated to provide compound 12 (55 g, 0.31 mol, 83%) as a clear oil.

3-(methylamino)propan-1-ol (13)

To an ice-cooled suspension of lithium aluminum hydride (26 g, 0.67 mol) in THF (500 mL) was added at 0° C. a solution of ethyl tert-butyl (3-hydroxypropyl)carbamate (12, 88 g, 0.34 mol) in THF (250 mL) dropwise. After complete addition the mixture was stirred at room temperature for 30 minutes and 16 hours at 70° C. The mixture was cooled to room temperature and then quenched by the dropwise addition at 0° C. of KOH (20%, 107 mL). The resulting mixture was stirred at room temperature for 2 hours. The mixture was filtered over Celite and the filtrate was dried over $Na_2SO_4$ and concentrated. NMR showed still some Boc intact. The material was dissolved in THF (500 mL) and $LiAlH_4$ (13 g, 0.34 1 eq.) was added. The mixture was stirred at 80° C. for 16 hours. The mixture was cooled to room temperature. At 0° C. the reaction was quenched by the slow addition of KOH (20%, 54 mL) and the resulting mixture was stirred for 2 hours at room temperature. The mixture was filtered over Celite and the filtrate was dried over $Na_2SO_4$ and concentrated to provide Boc-methylaminopropanol (22.6 g, 170 mmol, 50%) as a clear oil.

tert-butyl (3-hydroxypropyl)(methyl)carbamate (14)

To a solution of 3-(methylamino)propan-1-ol (13, 22.6 g, 254 mmol) and triethylamine (25.7 g, 35 mL, 254 mmol) in DCM (500 mL) was added di-tert-butyl dicarbonate (55.3 g, 254 mmol) portionwise. The resulting mixture was stirred at room temperature for 1 hour until no more gas development was observed. The mixture was washed with 1M HCl, dried over $Na_2SO_4$, and concentrated to provide Boc-protected amine 14 (43 g, 230 mmol, 90%) as a clear oil.

Ethyl 2-(3-((tert-butoxycarbonyl)(methyl)amino)propoxy)acetate (15)

To a solution of alcohol 14 (36 g, 0.19 mol) in DCM (500 mL) was added ethyl 2-diazoacetate (25 g, 23 mL, 0.19 mol) and boron trifluoride etherate (2.7 g, 2.4 mL, 19 mmol) and the resulting mixture was stirred for 16 hours. The mixture was washed with water and brine, dried over $Na_2SO_4$, and concentrated. The crude material was purified using column chromatography (20% EtOAc in heptane) to provide eater 15 (11 g, 40 mmol, 21%) as a clear oil.

tert-butyl (3-(2-hydroxyethoxy)propyl)(methyl)carbamate (16)

To an ice-cooled suspension of lithium aluminum hydride (2.7 g, 71 mmol) in THF was added a solution of ester 15 (13 g, 47 mmol) in THF (50 mL) dropwise at 0° C. The mixture was stirred at room temperature for 1 hour. The reaction was quenched by dropwise addition of KOH (20%, 11 mL) at 0° C. The resulting mixture was stirred at room temperature for 30 minutes. The mixture was filtered over celite, dried over $Na_2SO$, and concentrated to provide alcohol 16 (8.5 g, 36 mmol, 77%) as a clear oil.

tert-butyl (3-(2-bromoethoxy)propyl)(methyl)carbamate (17)

To a solution of alcohol 16 (8.5 g, 36 mmol) in DCM (300 mL) were added triphenylphosphine (13 g, 51 mmol) and NBS (7.8 g, 44 mmol) and the resulting mixture was stirred at room temperature for 16 hours. The mixture was washed with $NaHCO_3$ and brine, dried over $Na_2SO_4$, and filtered. Heptane was added and the DCM was removed by evaporation. The formed solids were filtered off and the filtrate was concentrated. The crude material was purified using column chromatography (20% EtOAc/heptane) to provide tert-butyl bromide 17 (7.6 g, 26 mmol, 70%) as a clear oil.

S-(2-(3-((tert-butoxycarbonyl)(methyl)amino) propoxy)ethyl) 4-methylbenzene sulfonothioate (18)

A solution of bromide 17 (7.6 g, 26 mmol) and potassium 4-methylbenzenesulfonothioate (8.7 g, 38 mmol) in DMF (200 mL) was stirred at 50° C. for 16 hours. The mixture was cooled to room temperature and diluted with water (1 L). The mixture was extracted with EtOAc/heptane (3×200 mL 1:1) and the combined organic layers was washed with brine, dried over $Na_2SO_4$, and concentrated. The crude material was purified by column chromatography (20% EtOAc/heptane) to provide thiotosylate 18 (9.1 g, 23 mmol) 88%) as a clear oil.

Synthesis of Iodide 22:

1,1-diethyl 4-methyl butane-1,1,4-tricarboxylate (19)

To an ice-cooled suspension of sodium hydride (10 g, 0.26 mol) in DMF (500 mL) was added diethyl malonate (42 g, 40 mL, 0.26 mol) slowly and the reaction mixture was stirred at room temperature for 1 h until the mixture had clarified. Methyl 4-bromobutanoate (47 g, 0.26 mol) was added at 0° C. and the resulting mixture was stirred for 18 hours at room temperature. The mixture was partially concentrated and the residue was quenched with 1 N HCl (300 mL) and water (1.3 L). The mixture was extracted with Hept/EtOAc (1/1; 2×250 mL). The combined organic layers washed brine (500 mL), dried over $Na_2SO_4$, filtered and concentrate. The crude material was purified by column chromatography (20% EtOAc/heptane) to provide triester 19 (63 g, 0.24 mol, 92%) as a clear oil.

2-(hydroxymethyl)hexane-1,6-diol (20)

To an ice-cooled suspension of lithium aluminum hydride (25 g, 0.66 mol) in THF (500 mL) was added slowly at 0° C. a solution of triester 19 (63 g, 0.24 mol) in THF (100 mL) and the resulting mixture was stirred at room temperature for 16 hours. The reaction was quenched by the slow addition of KOH (20% aq. 106 mL) at 0° C. The resulting mixture was stirred for 1 hour at room temperature. The mixture was filtered over celite, dried over $Na_2SO_4$, and concentrated to provide triol 20 (16 g, 0.11 mol, 45%) as a clear yellow oil.

4-(2,2-dimethyl-1,3-dioxan-5-yl)butan-1-ol (21)

To a solution of triol 20 (16 g, 0.11 mol) in THF (200 mL) were added p-toluenesulfonic acid (5.1 g, 27 mmol) and 2,2-dimethoxypropane (34 g, 40 mL, 0.32 mol) and the resulting mixture was stirred at room temperature for 1 hour. The mixture was concentrated and the residue was dissolved in DCM (200 mL). The mixture was washed with $NaHCO_3$ (aq. sat. 200 mL) and brine (200 mL), dried over $Na_2SO_4$, and concentrated to acetonide 21 (9.0 g, 48 mmol, 44%) as a brown oil.

5-(4-iodobutyl)-2,2-dimethyl-1,3-dioxane (22)

To a solution of alcohol 21 (3.7 g, 20 mmol), triphenylphosphine (6.2 g, 24 mmol) and imidazole (1.6 g, 24 mmol) in DCM (250 mL) was added iodine (5.5 g, 22 mmol) and the resulting mixture was stirred at room temperature for 1 hour. The mixture was washed with sodium thiosulfate (sat. aq. 2×100 mL) and brine, dried over $Na_2SO_4$, and concentrated. The crude material was purified using column chromatography (15% EtOAc in heptane) to provide iodide 22 (3.7 g, 12 mmol, 63%) as a clear yellow oil.

Synthesis of Formula (V)-Precursor:

tert-butyl (1-(((8R,9S,13S,14S,17S)-17-(3-((1,1,1,3, 3,3-hexafluoro-2-(trifluoro methyl)propan-2-yl)oxy) propoxy)-13-methyl-7,8,9,11,12,13,14,15,16,17-decahydro-6H-cyclopenta[a]phenanthren-3-yl)oxy)-3-methyl-7,14-dioxa-10,11-dithia-3-azaheptadecan-17-yl)(methyl)carbamate (23)

To a solution of thiotosylate 18 (3.4 g, 8.5 mmol) and thioacetate 11 (5.0 g, 6.5 mmol) in DCM (200 mL) and MeOH (20 mL) was added a solution of sodium methoxide (1.1 g, 3.6 mL, 20 mmol) in MeOH (5.4 M) and the resulting mixture was stirred at room temperature for 1 hour. The mixture was diluted with 200 mL DCM, washed with $NaHCO_3$ and brine, dried over $Na_2SO_4$, and concentrated. The crude material was purified by column chromatography (10% Acetone in heptane+1% $NEt_3$) to provide disulfide 23 (6.5 g, 6.7 mmol, quant.) as a clear oil.

N-(2-(((8R,9S,13S,14S,17S)-17-(3-((1,1,1,3,3,3-hexafluoro-2-(trifluoromethyl)propan-2-yl)oxy) propoxy)-13-methyl-7,8,9,11,12,13,14,15,16,17-decahydro-6H-cyclopenta[a]phenanthren-3-yl)oxy) ethyl)-N-methyl-3-(2-((2-(3-(methylamino)propoxy) ethyl)disulfaneyl)ethoxy)propan-1-amine (24)

To a solution of tert-butyl disulfide 23 (6.5 g, 6.7 mmol) in DCM (200 mL) was added TFA (15 g, 10 mL, 0.13 mol) and the resulting mixture was stirred for 1 hour at room temperature. Extra TFA (5 mL) added and stirred for 30 minutes. The mixture was concentrated and the residue was dissolved in DCM (250 mL). The mixture was washed with $NaHCO_3$ and brine, dried over $Na_2SO_4$, and concentrated to provide amine 24 (5.3 g, 6.1 mmol, 91%) as a slightly yellow clear oil.

4-(2,2-dimethyl-1,3-dioxan-5-yl)-N-(1-(((8R,9S,13S, 14S,17S)-17-(3-((1,1,1,3,3,3-hexafluoro-2-(trifluoromethyl)propan-2-yl)oxy)propoxy)-13-methyl-7,8, 9,11,12,13,14,15,16,17-decahydro-6H-cyclopenta[a] phenanthren-3-yl)oxy)-3-methyl-7,14-dioxa-10,11-dithia-3-azaheptadecan-17-yl)-N-methylbutan-1-amine (25)

To a solution of amine 24 (5.3 g, 6.1 mmol) in acetonitrile (200 mL) were added potassium carbonate (0.84 g, 6.1 mmol) and iodide 22 (1.8 g, 6.1 mmol) and the resulting mixture was stirred at 50° C. for 16 hours. The mixture was concentrated and the residue was dissolved in DCM (300 mL). The mixture was washed with $NaHCO_3$ (half sat. aqueous. 250 mL) and brine, dried over $Na_2SO_4$, and concentrated. The crude material was purified using column chromatography (25% Acetone in heptane+1% $NEt_3$) to provide acetonide 25 (2.5 g, 39%) as a clear oil.

2-(1-(((8R,9S,13S,14S,17S)-17-(3-((1,1,1,3,3,3-hexafluoro-2-(trifluoromethyl) propan-2-yl)oxy) propoxy)-13-methyl-7,8,9,11,12,13,14,15,16,17-decahydro-6H-cyclopenta[a]phenanthren-3-yl)oxy)-3,18-dimethyl-7,14-dioxa-10,11-dithia-3,18-diazadocosan-22-yl)propane-1,3-diol (26)

To a solution of acetonide 25 in MeOH (100 mL) was added p-toluenesulfonic acid (1.1 g, 6.0 mmol) and the mixture was stirred for 1 hour at room temperature. The mixture was concentrated and the residue was dissolved in DCM (200 mL). The mixture was washed with NaHCO$_3$ and brine, dried over Na$_2$SO$_4$, and concentrated to provide diol 26 (2.1 g, 2.1 mmol, 87%) as a clear oil.

23-((bis(4-methoxyphenyl)(phenyl)methoxy)
methyl)-1-(((8R,9S,13S,14S,17S)-17-(3-((1,1,1,3,3,
3-hexafluoro-2-(trifluoromethyl)propan-2-yl)oxy)
propoxy)-13-methyl-7,8,9,11,12,13,14,15,16,17-
decahydro-6H-cyclopenta[a]phenanthren-3-yl)oxy)-
3,18-dimethyl-7,14-dioxa-10,11-dithia-3,18-
diazatetracosan-24-ol (27)

To a solution of diol 26 (2.1 g, 2.1 mmol) in DCM (200 mL) were added triethylamine (0.42 g, 0.58 mL, 4.2 mmol), DMAP (26 mg, 0.21 mmol), and 4,4'-(chloro(phenyl)methylene)bis(methoxybenzene) (0.71 g, 2.1 mmol) and the resulting mixture was stirred at room temperature for 16 hours. The mixture was washed with NaHCO$_3$ and brine, dried over Na$_2$SO$_4$, and concentrated. The crude material was purified using column chromatography (25-40% Acetone in heptane+1% NEt$_3$, silica pretreated with NEt$_3$) to provide DMT-protected compound 27 (2.3 g, 1.8 mmol, 84%) as a yellowish oil.

23-((bis(4-methoxyphenyl)(phenyl)methoxy)
methyl)-1-(((8R,9S,13S,14S,17S)-17-(3-((1,1,1,3,3,
3-hexafluoro-2-(trifluoromethyl)propan-2-yl)oxy)
propoxy)-13-methyl-7,8,9,11,12,13,14,15,16,17-
decahydro-6H-cyclopenta[a]phenanthren-3-yl)oxy)-
3,18-dimethyl-7,14-dioxa-10,11-dithia-3,18-
diazatetracosan-24-yl (2-cyanoethyl)
diisopropylphosphoramidite (Apo-Si—K-105-B)

To a solution of compound 27 (2.3 g, 1.8 mmol) in DCM (100 mL) were added 3-((bis(diisopropylamino)phosphaneyl)oxy)propanenitrile (0.69 g, 0.72 mL, 2.3 mmol) and a solution of NMM and TFA (4.6 mL, 0.5 M NMM and 0.25 M TFA, 1.3 eq. NMM) in DCM. The resulting mixture was stirred at room temperature for 3 hours. The mixture was washed with NaHCO$_3$ and brine, dried over Na$_2$SO$_4$, and concentrated. The crude material was purified using column chromatography (30% acetone in heptane+1% NEt$_3$, silica pretreated with heptane/NEt$_3$ to deactivate) to provide Formula (V)-Precursor (2.2 g, 83%) as a clear oil.

Example 2f: A Method for Synthesis of Formula (VII)-Precursor

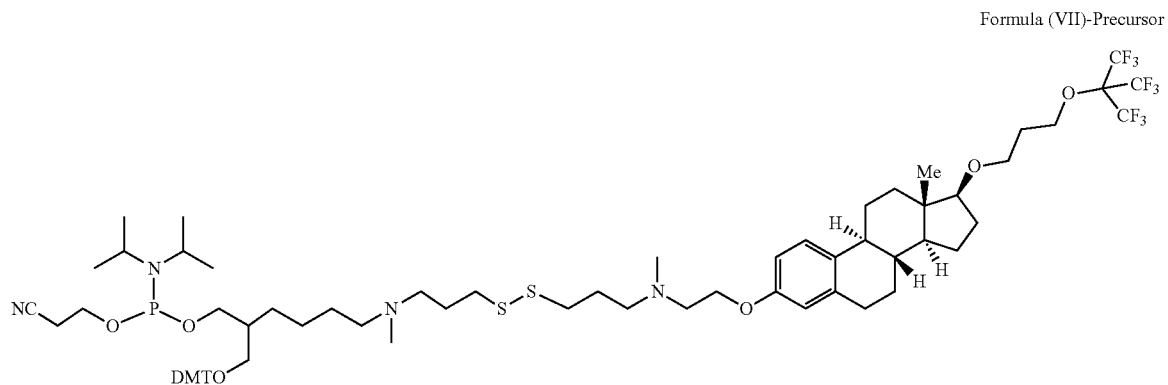

Formula (VII)-Precursor

Synthesis of Formula (VII)-Precursor is performed according to the following synthetic schemes. Synthesis is focused on three main building blocks:

Building Block K-105-6:

Scheme 10. Synthesis of K-105-6

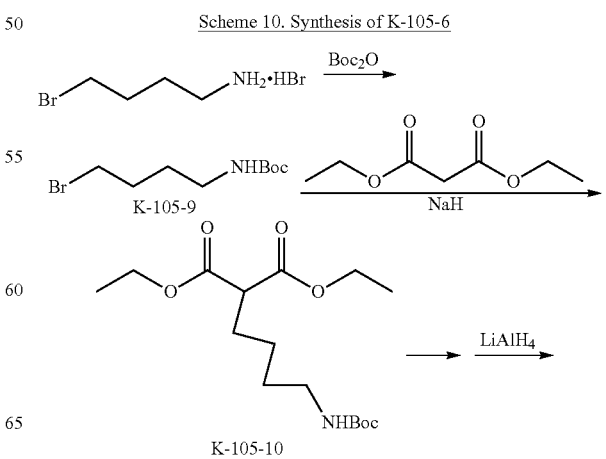

125
-continued
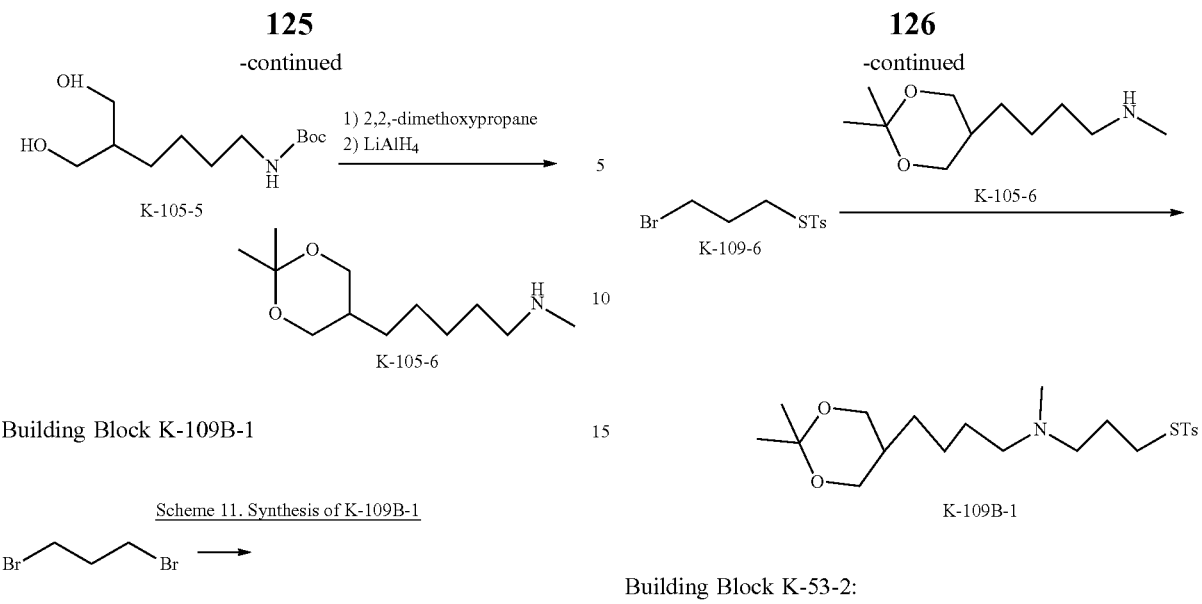
Building Block K-109B-1
Scheme 11. Synthesis of K-109B-1
126
-continued
Building Block K-53-2:
Scheme 12. Synthesis of K-53-2
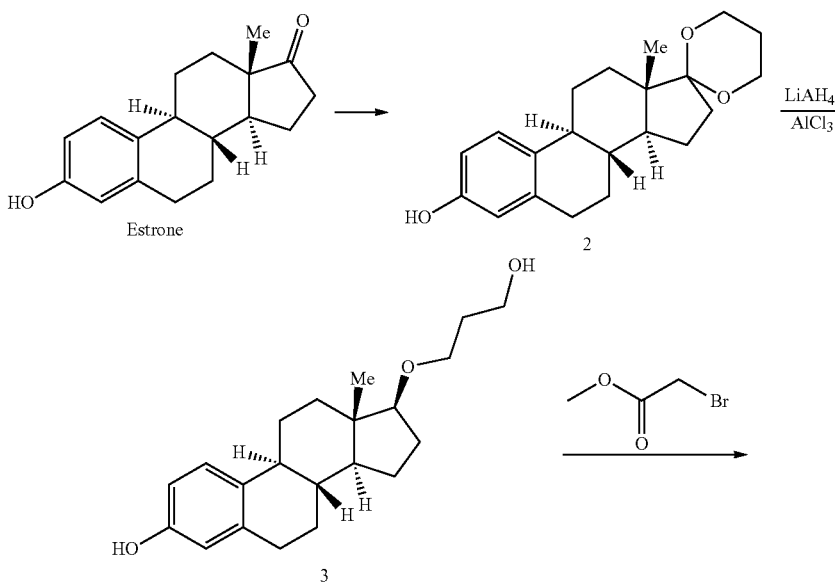
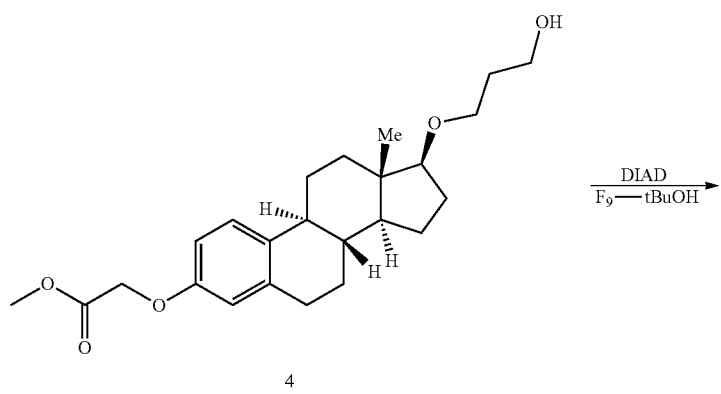

-continued
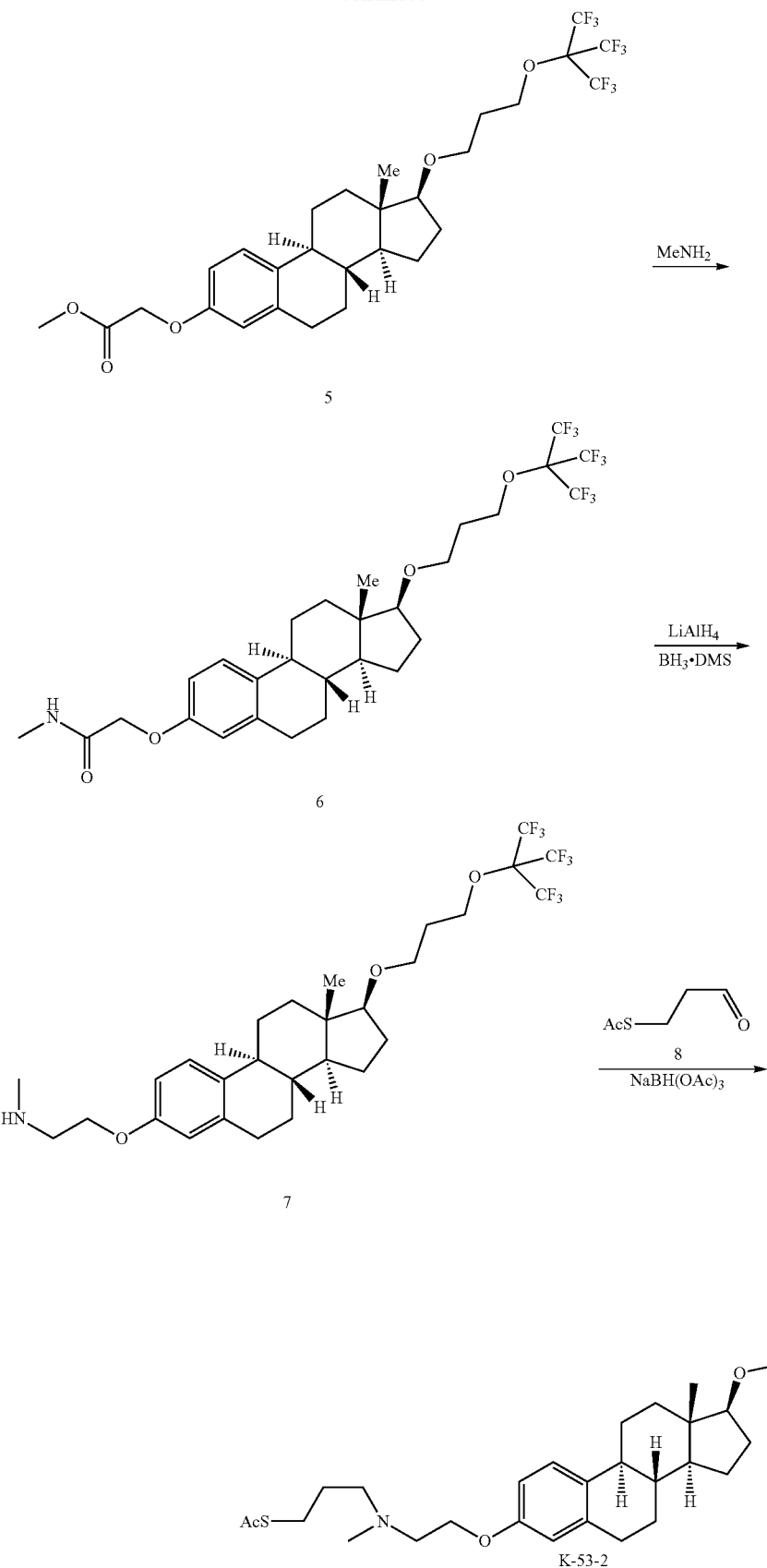

Then all Building Blocks are integrated into the final compound Formula (VII)-Precursor:
Scheme 13. Synthesis of Formula (VII)-Precursor
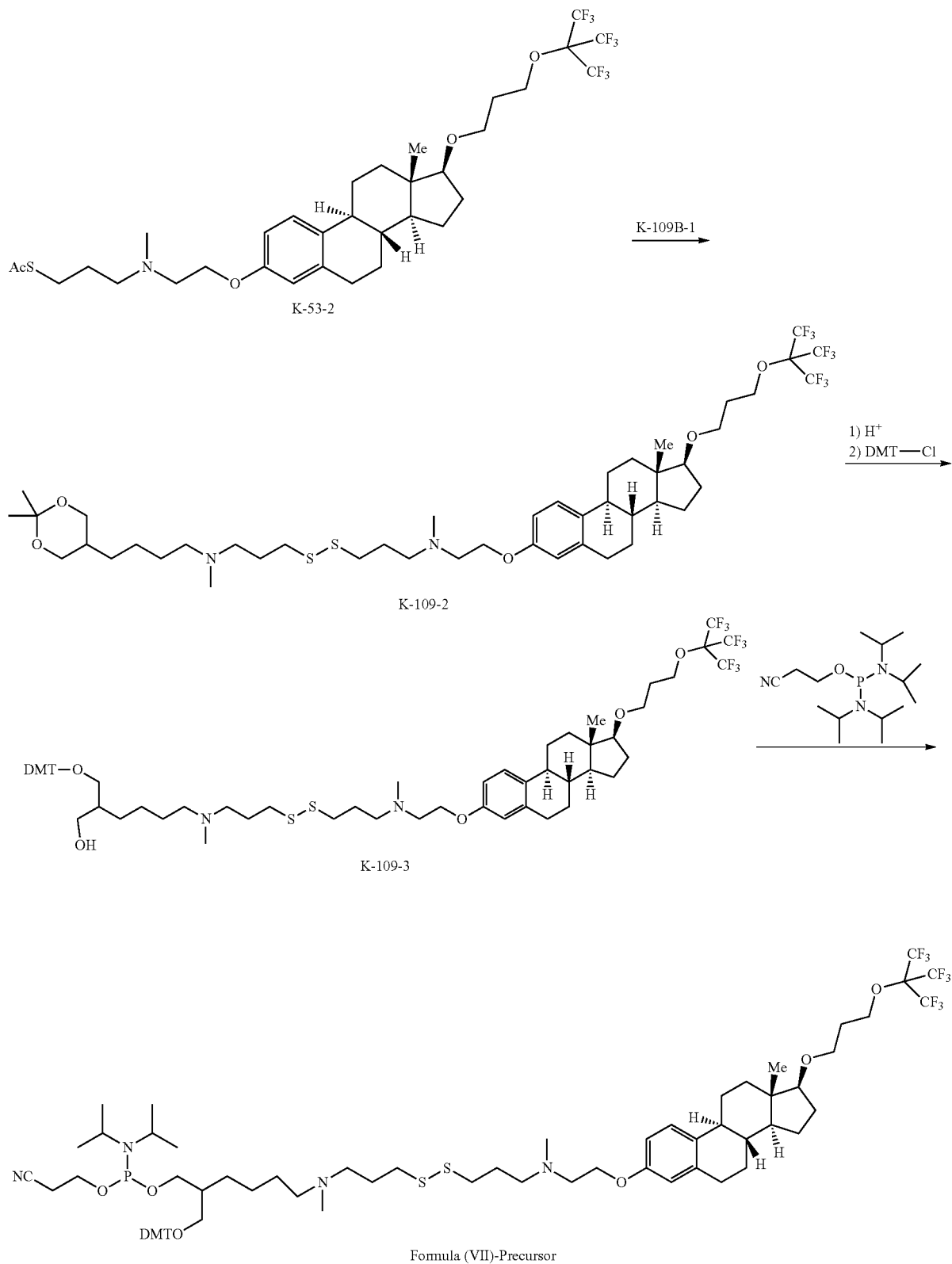

Example 2m: A Method for Synthesis of Formula (VIII-F)-Precursor

Starting from estrone, known chemistry can be employed to make methyl ester 5, a known intermediate. The nitrogen can then be introduced by reaction with aminopropanol. This might be possible directly like previously done for methyl-amine. Otherwise the methyl ester can be hydrolyzed and the nitrogen can be introduced using a standard peptide coupling protocol. The amide can then be reduced to afford the desired secondary amine K-93-F-2. Subsequent introduction of the Boc-group and Mitsunobu facilitated introduction of the thioacetate functionality will provide desired building block K-93-F-4.

Scheme 14: Synthesis of thioacetate K-93-F-4

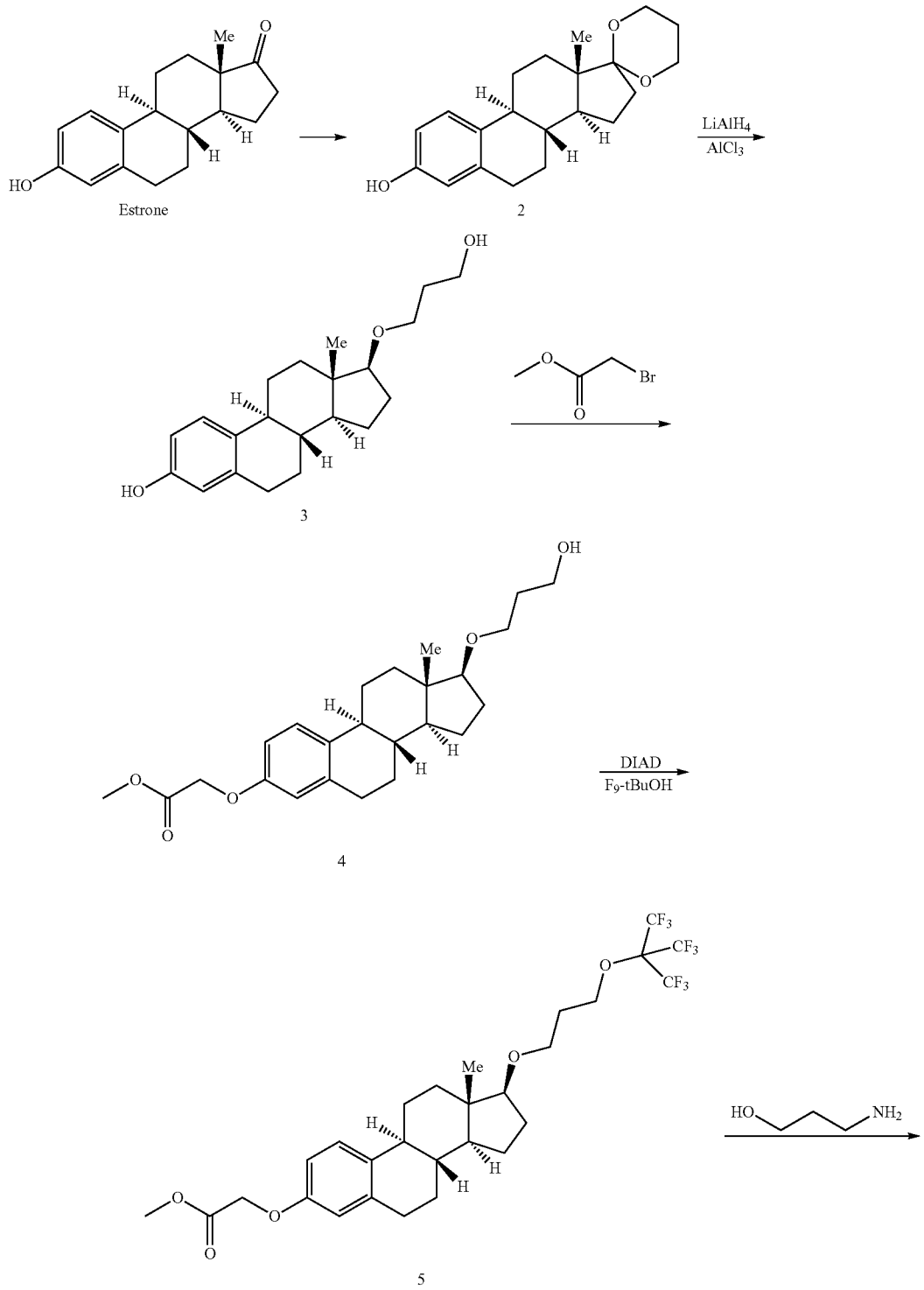

-continued
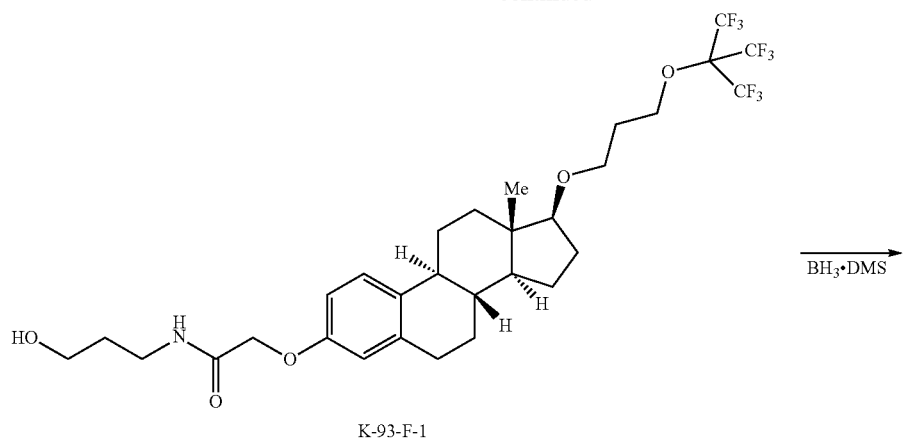
K-93-F-1
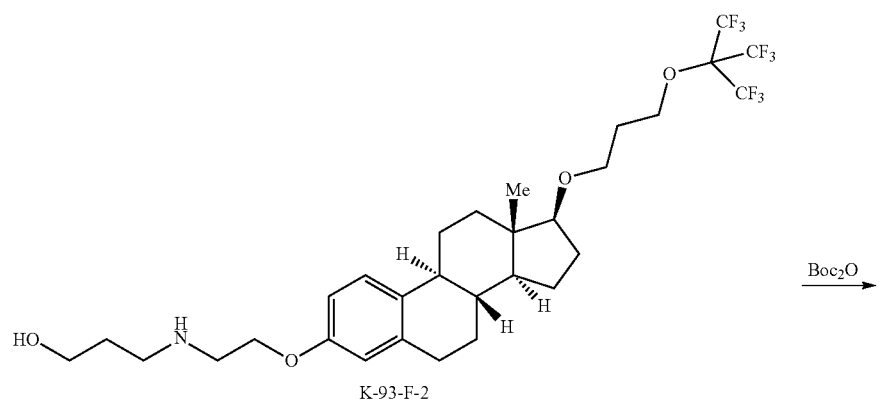
K-93-F-2
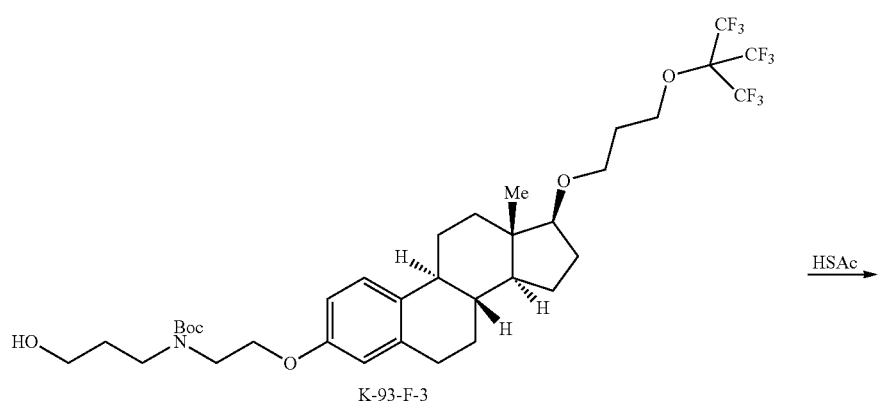
K-93-F-3
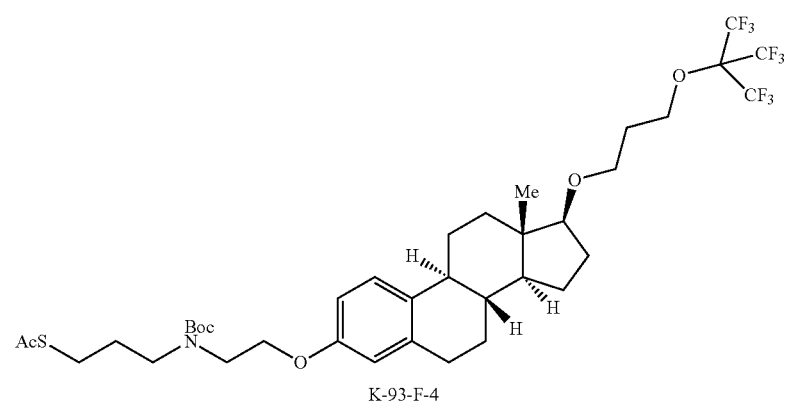
K-93-F-4

Scheme 15: Synthesis of thiotosylate 6

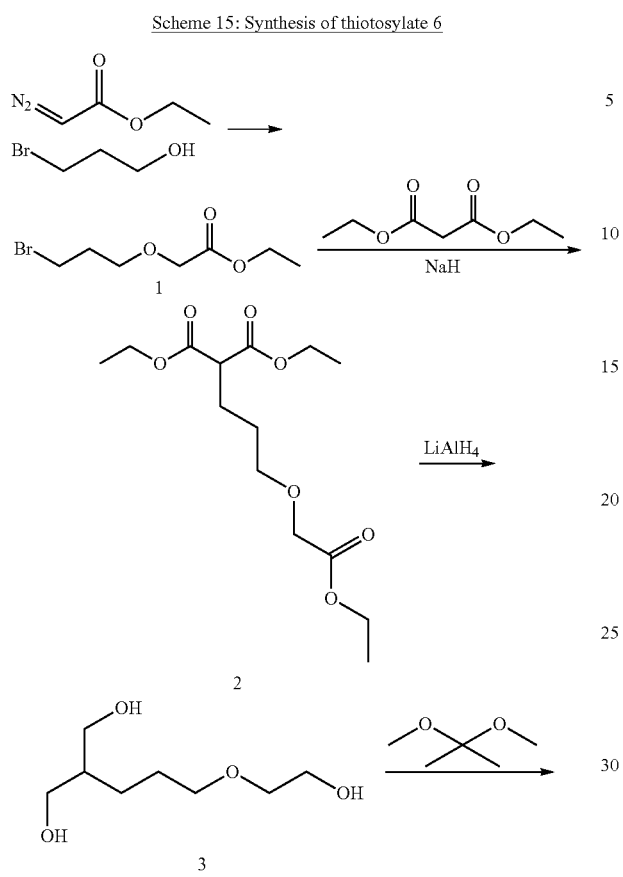

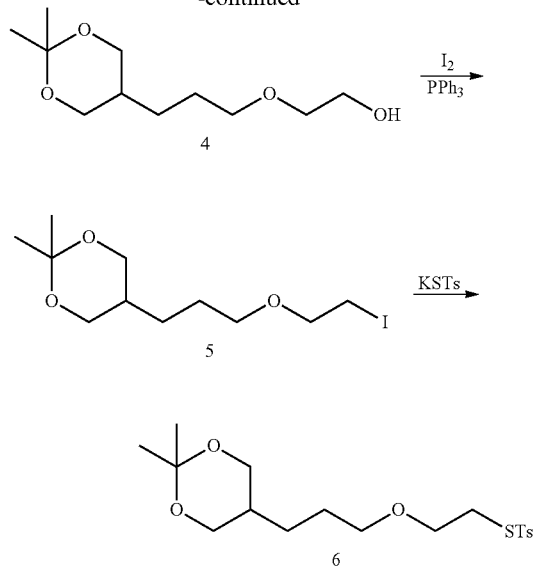

Integration of the Fragments into the Final Formula (VIII-F)-Precursor:

The assembly of Formula (VIII-F)-Precursor starts with the disulfide formation between building blocks K-93-F-4 and thiotosylate 6. Then, the acetonide moiety and the Boc-group are simultaneously removed by treatment with acid. The free secondary amine is then protected with the Fmoc group. Subsequent DMT attachment and phosphoramidite formation provide Formula (VIII-F)-Precursor (Scheme 16).

Scheme 16: Integration into the final Formula (VIII-F)-Precursor

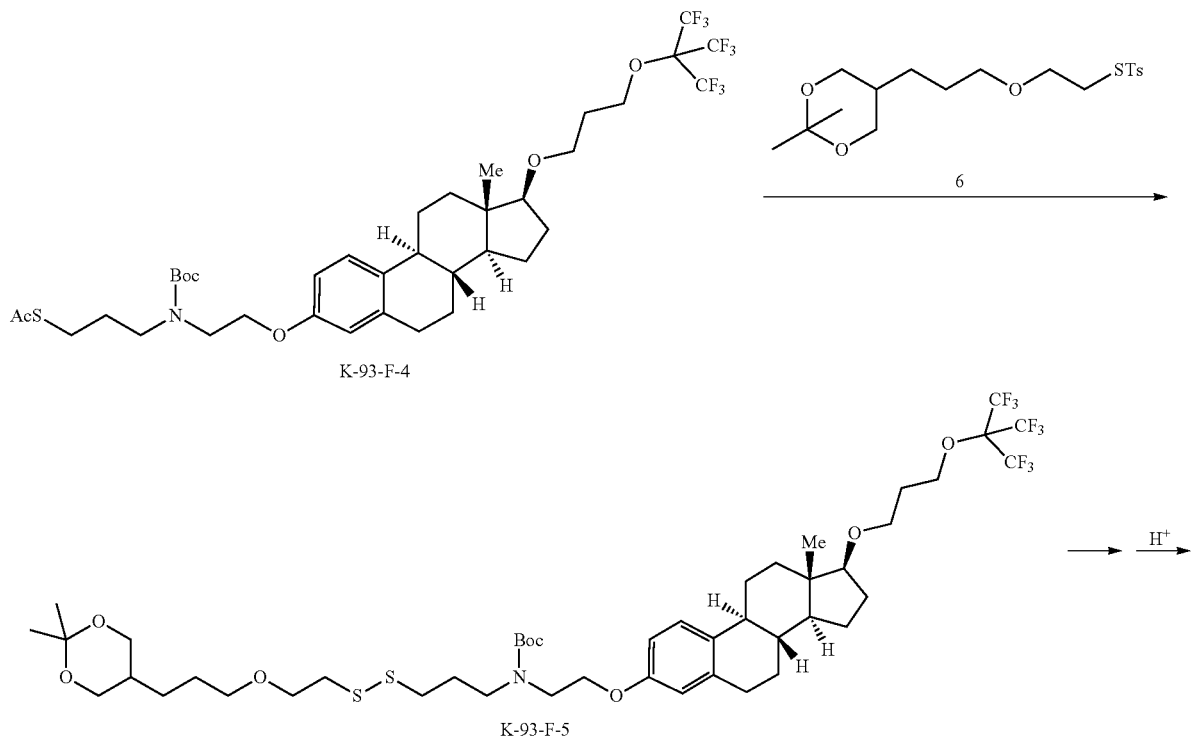

-continued
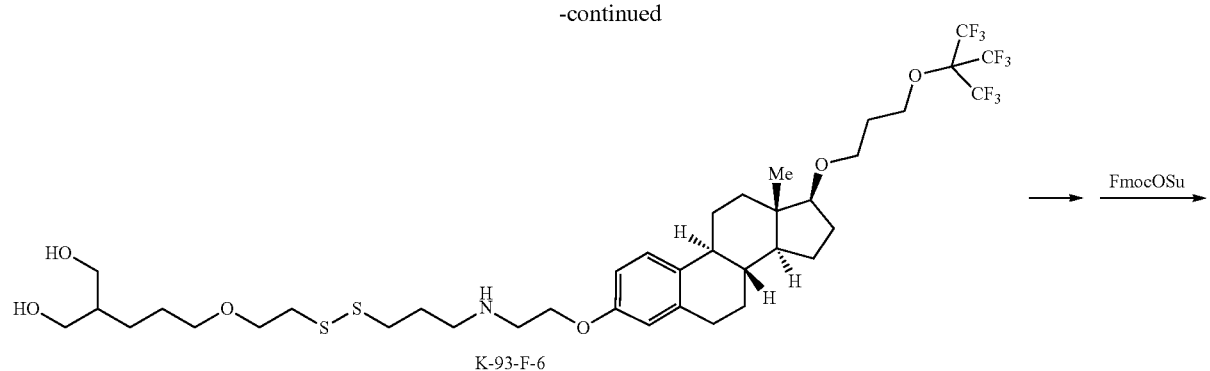
K-93-F-6
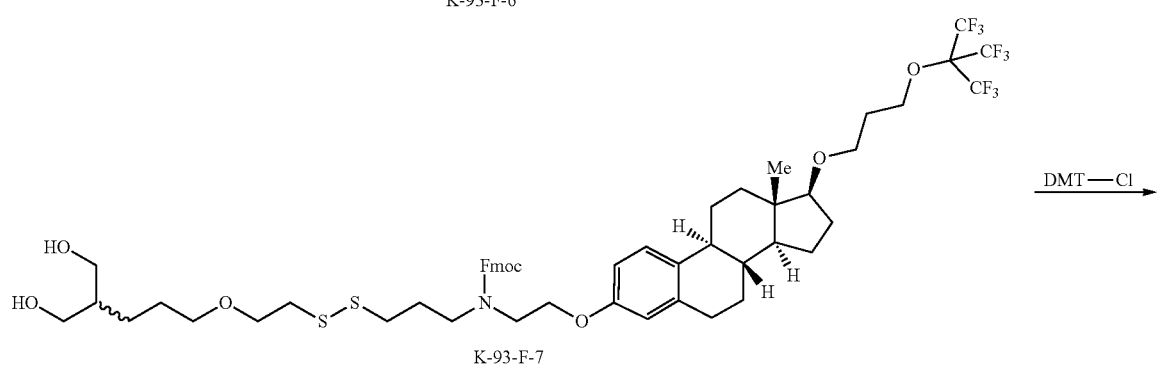
K-93-F-7
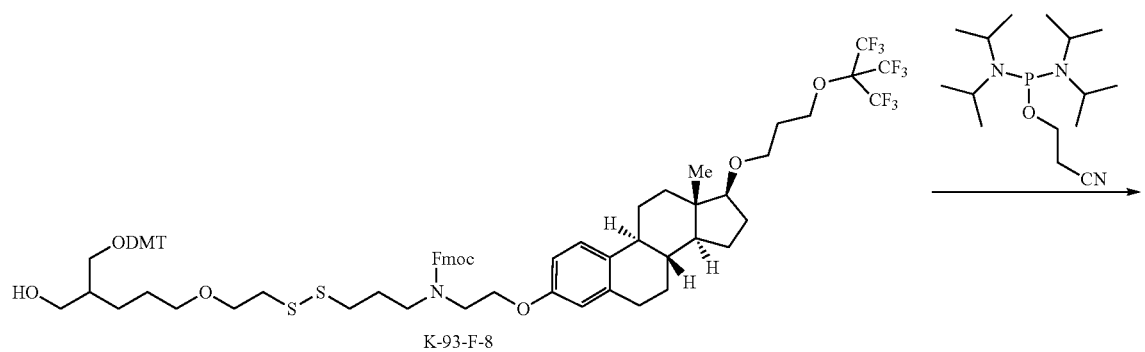
K-93-F-8
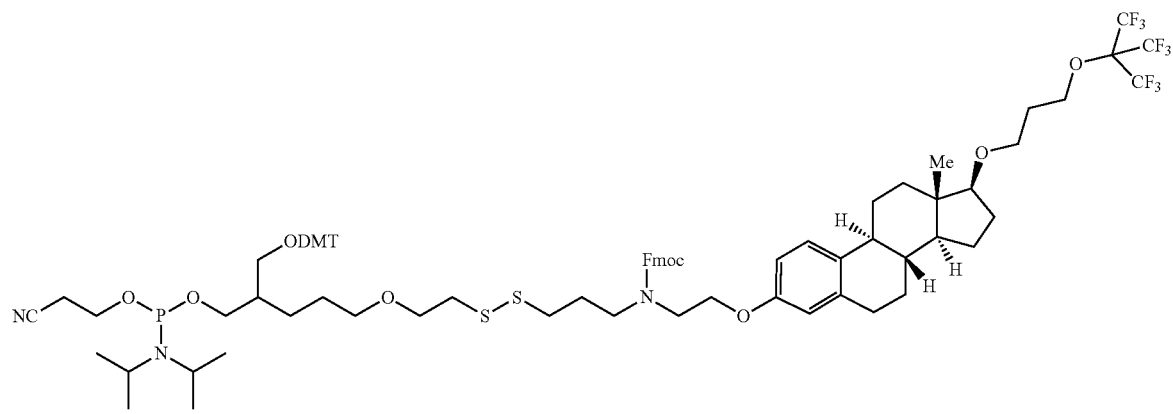
Formula (VIII-F)-Precursor Example 2h: A Method for Synthesis of Formula (XIIa)-Precursor

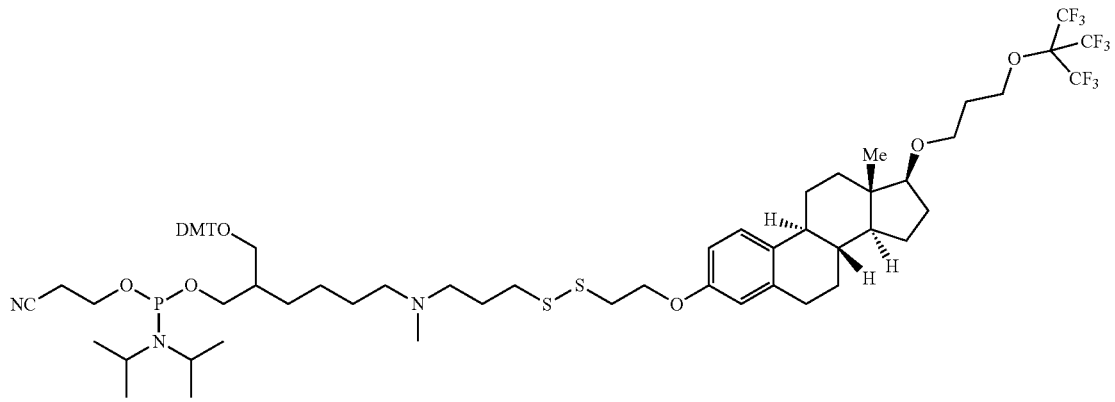

Formula (XIIa)-Precursor

The synthesis of is depicted in the schemes below. The synthesis converges both sides of the disulfide moiety, for which the left-part is functionalized as an thioacetate, and the steroid-containing right part as a thiotosylate. These are merged and require minor modifications to provide the final compound.

Synthesis of Thiotosylate 8:

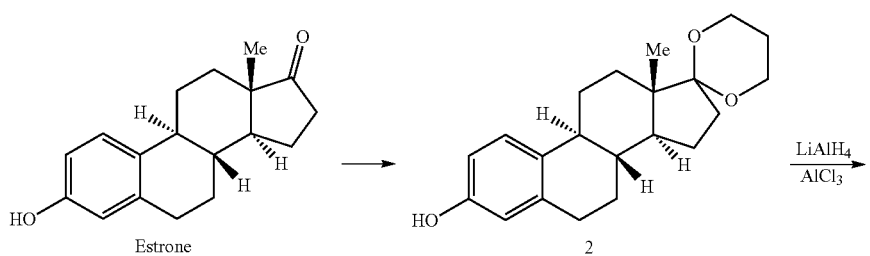

Scheme 17. Synthesis of thiotosylate 8

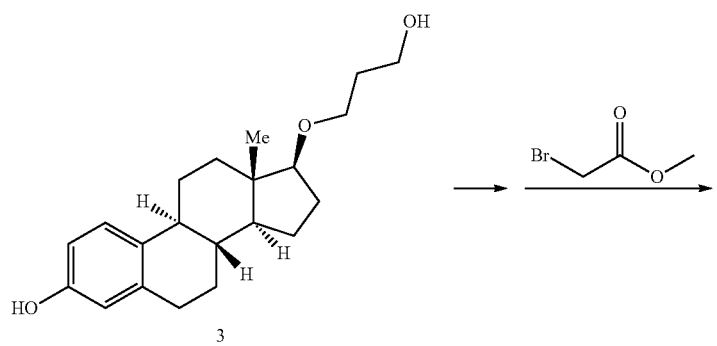

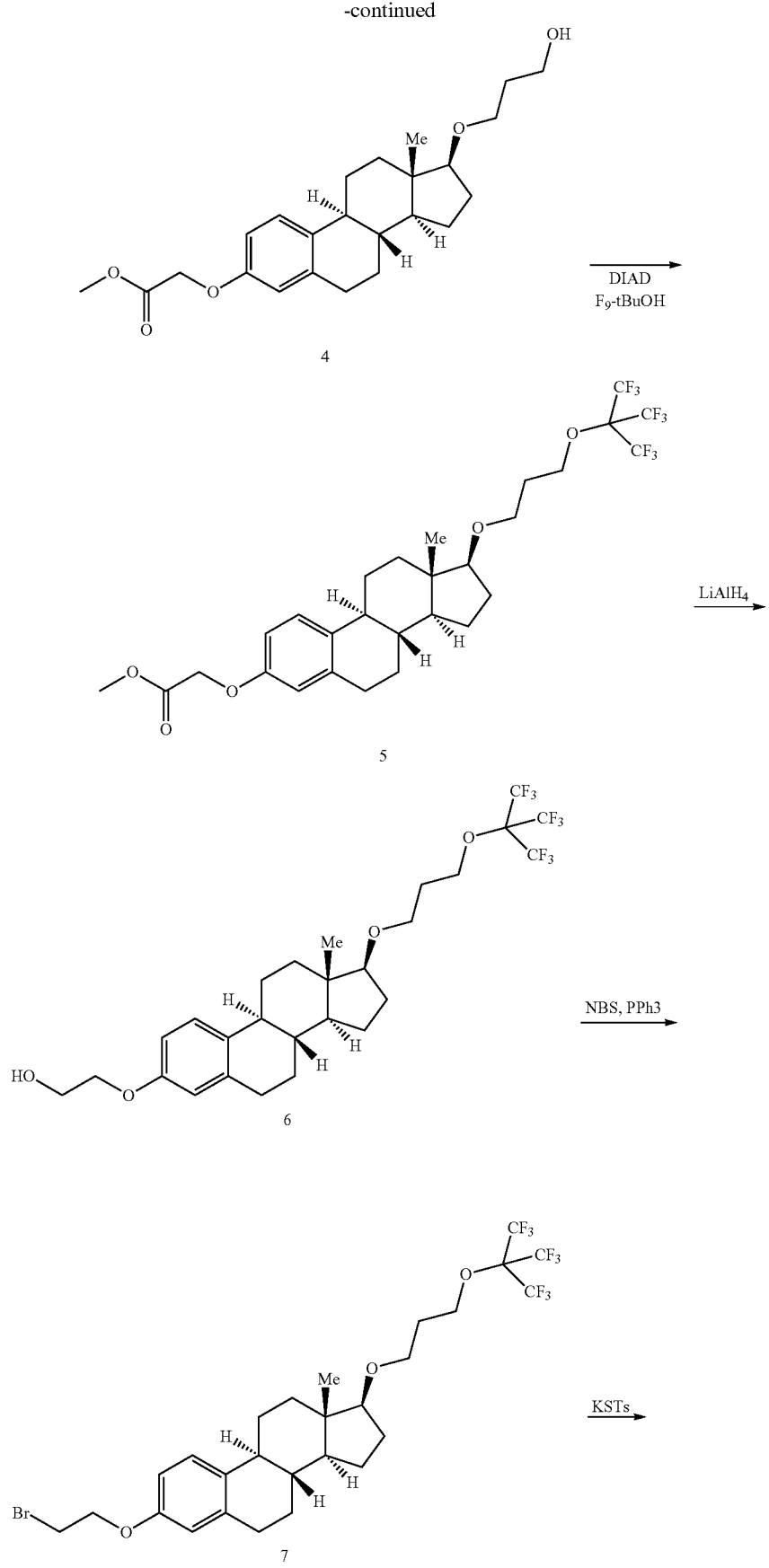

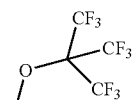
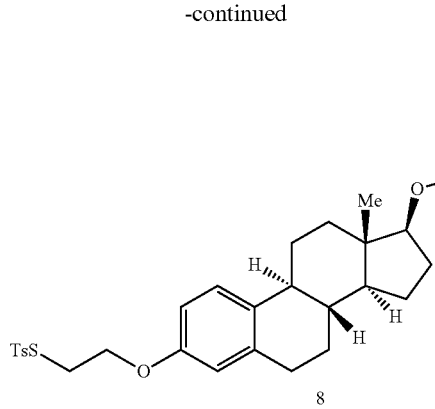

8

The synthesis commenced by protection of the ketone with 1,3-propanediol, to provide compound 2 in good purity. LiAlH$_4$ and AlCl$_3$-ring opening of the acetal gave a mixture of compound 3 and estradiol in a ratio of ca 85:15, the latter being less reactive and will be removed in the next-steps. The phenol was alkylated with methyl bromoacetate to provide methyl ester 4. The perfluorobutanol moiety was then introduced using Mitsunobu conditions and provided compound 5. The methyl ester was reduced by lithium aluminum hydride, and formed alcohol 6 was brominated to provide bromide 7. Treatment with potassium thiotosylate afforded the desired building block thiotosylate 8.

Synthesis of Thioacetate 16:

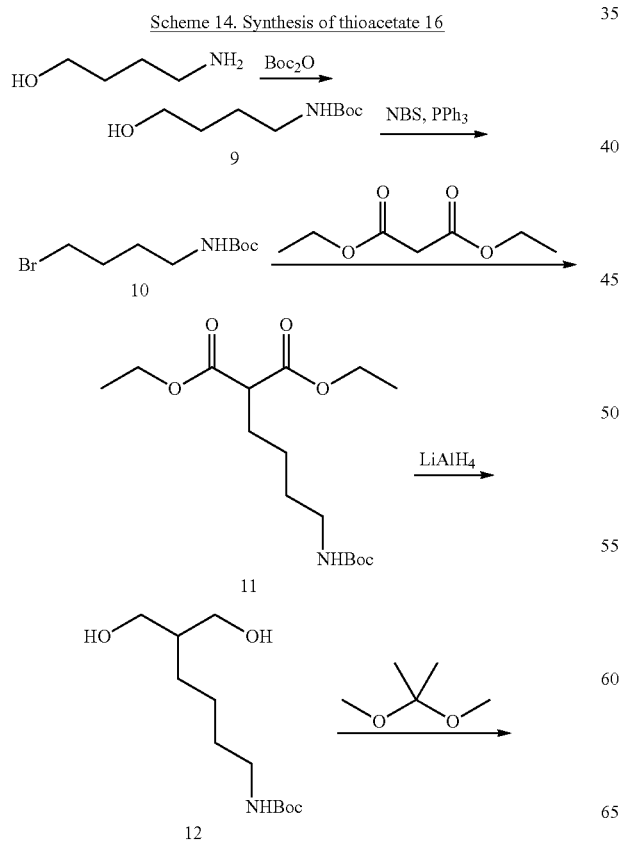

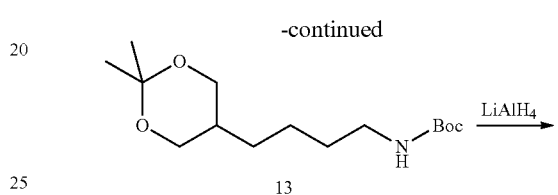

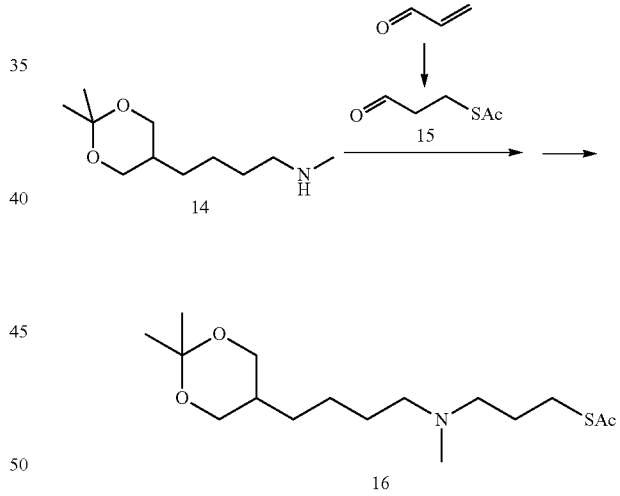

The synthesis of building block 16 started from 4-aminobutan-1-ol. The amine was protected with a Boc group. The alcohol was subsequently converted to the corresponding bromide (10), which could then be alkylated onto diethyl malonate to provide bis-ester 11. When compound 11 is treated with LiAlH$_4$ at room temperature, the esters are reduced but the Boc group is untouched. Diol 12 is subsequently protected by treatment with dimethoxypropane in the presence of a catalytic amount of acid to provide acetonide 13. Treatment with LiAlH$_4$ at elevated temperature reduced the Boc moiety to the desired methylamine (14). Finally, reductive amination with aldehyde 15 provided thioacetate 16. Aldehyde 15 was readily available through a one-step reaction, i.e. Michael addition of thioacetic acid on acrolein.

Integration of Formula (XIIa)-Precursor:
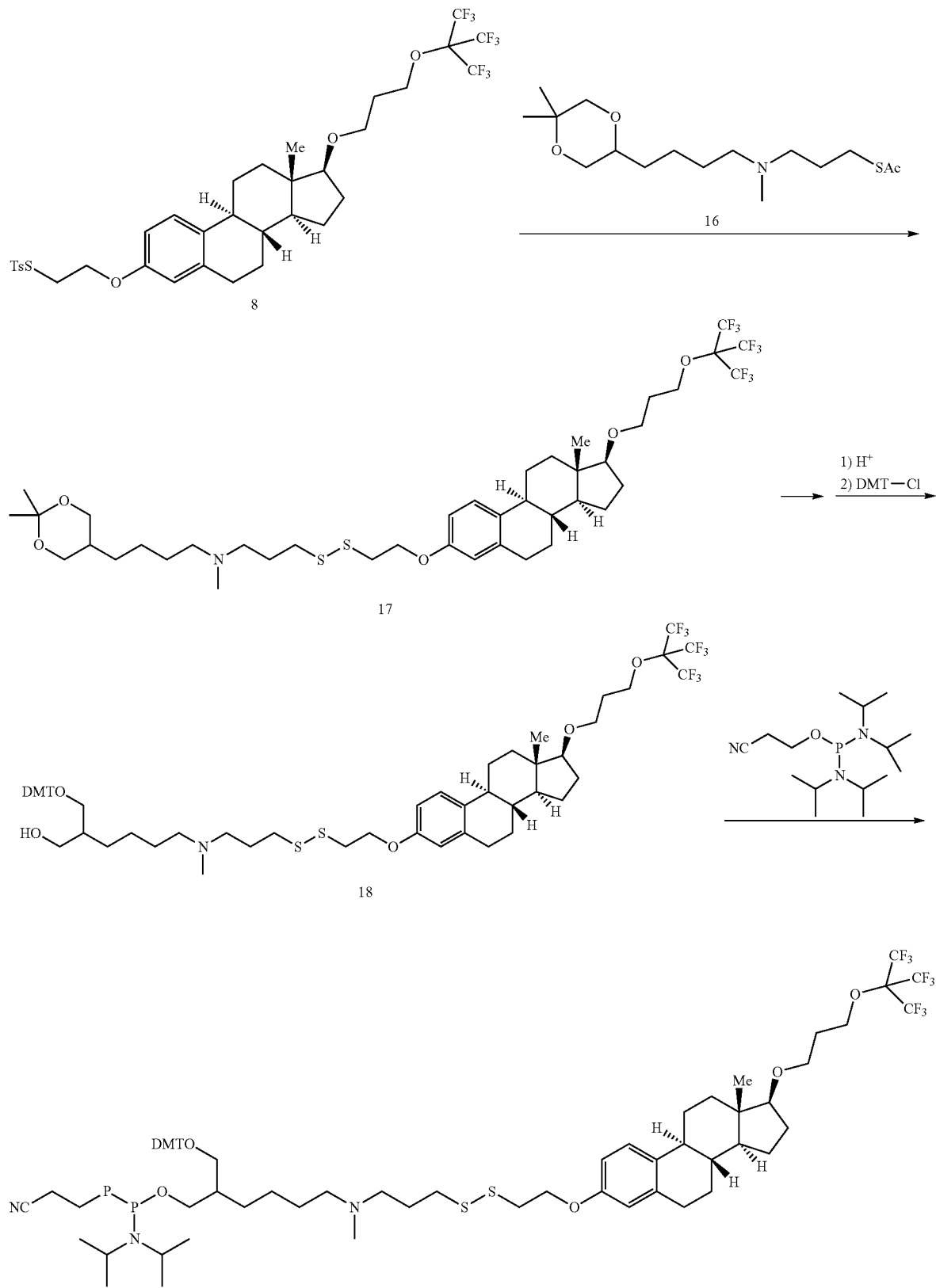

Disulfide formation between thiotosylate 8 and thioacetate 16 was performed in known reaction conditions, where the acetate is removed in situ by NaOMe and the resulting thiol attacks on the thiotosylate. Removal of the acetonide and subsequent attachment of the DMT-Cl provided 18. Final phosphoramidite formation afforded Formula (XIIa)-Precursor.

Experimental Section:
Synthesis of Thiotosylate 8:

(8R,9S,13S,14S)-13-Methyl-6,7,8,9,11,12,13,14,15,
16-decahydrospiro[cyclopenta[a]phenanthrene-17,2'-
[1,3]dioxan]-3-ol (2)

To a suspension of estrone (252 gram, 0.93 mol) in toluene (1.5 L) were added trimethoxymethane (297 g, 350 mL, 2.80 mol), propane-1,3-diol (213 g, 250 mL, 2.80 mol) and pTsOH (2 g, 10 mmol). Warmed to 60° C. and stirred for 16 h. Added triethylamine (6 mL) and water (600 mL) and continued stirring for 1 more hour. Separated phases and washed the organic layer with water (3×400 mL) and brine. Dried over $Na_2SO_4$ and partially concentrated to ca 1 L. Poured into heptane (4 L) and filtered the white solids off. Washed with heptane, dried in vacuo. Compound 2 (271 gram, 825 mmol) was isolated as a white solid in 88.5% yield.

(8R,9S,13S,14S,17S)-17-(3-Hydroxypropoxy)-13-
methyl-7,8,9,11,12,13,14,15,16,17-decahydro-6H-
cyclopenta[a]phenanthren-3-ol (3)

To a solution of (13S)-13-methyl-6,7,8,9,11,12,13,14,15, 16-decahydro spiro[cyclopenta[a]phenanthrene-17,2'-[1,3] dioxan]-3-ol (2, 60.7 g, 185 mmol) in THF at 0° C. was added carefully lithium aluminum hydride (8.42 g, 222 mmol) followed by portion wise addition of aluminum chloride (98.6 g, 739 mmol) (very exothermic!). Stirred 15 min at 0° C., then warmed to 50° C. Stirred 2 h at 50° C. (due to clogging on a rotary evaporator), then cooled to 0° C. and started quenching dropwise with $NH_4Cl$(aq) (500 mL). Stirred 1 h at room temperature. The phases were separated and the organic layer was washed with brine, concentrated. A white solid (65 gram) was obtained, contaminated with estradiol (ca 15%).

Methyl 2-(((8R,9S,13S,14S,17S)-17-(3-hydroxy-
propoxy)-13-methyl-7,8,9,11,12,13,14,15,16,17-
decahydro-6H-cyclopenta[a]phenanthren-3-yl)oxy)
acetate (4)

The crude material 3 (89.4 gram) was dissolved in acetone (1.25 L) and MeOH (0.2 L) and treated with potassium carbonate (60 gram, 435 mmol) and methyl bromoacetate (50 mL, 435 mmol). The suspension was warmed to 60° C. and stirring continued for 16 h. Based on TLC, all phenolic moieties had been alkylated. The mixture was cooled to room temperature and filtered. The filtrate was concentrated and further purified using flash chromatography (eluent 20% to 30% EtOAc in heptane, removing all impurities, 100% EtOAc to obtain the desired material). Compound 4 (56.7 gram, 140.3 mmol) was isolated as a yellow oil in 65% yield.

Methyl 2-(((8R,9S,13S,14S,17S)-17-(3-((1,1,1,3,3,
3-hexafluoro-2-(trifluoromethyl) propan-2-yl)oxy)
propoxy)-13-methyl-7,8,9,11,12,13,14,15,16,17-
decahydro-6H-cyclopenta[a]phenanthren-3-yl)oxy)
acetate (5)

To a solution of compound 4 (56.7 gram, 140.3 mmol) in THF (1 L) were added triphenylphosphine (55.4 gram, 211 mmol), nonafluoro-tert-butyl alcohol (30 mL) and di-tert-butyl azodicarboxylate (38.5 gram, 167 mmol). The mixture was stirred for 30 min when TLC showed full conversion. Heptane (500 mL) was added and the mixture was partially concentrated to ~500 mL. More heptane (1 L) was added and the mixture was stirred overnight at room temperature. Precipitates were filtered off, and the filtrate was concentrated, to provide compound 5 as yellow syrup.

2-(((13S,17S)-17-(3-((1,1,1,3,3,3-Hexafluoro-2-(trif-
luoromethyl)propan-2-yl)oxy)propoxy)-13-methyl-7,
8,9,11,12,13,14,15,16,17-decahydro-6H-cyclopenta
[a]phenanthren-3-yl)oxy)ethan-1-ol (6)

To an ice-cooled suspension of lithium aluminum hydride (2.0 g, 53 mmol) in THF (300 mL) was added slowly a solution of methyl ester 5 (17 g, 27 mmol) in THF (100 mL) and the resulting mixture was stirred at room temperature for 2 hours. KOH (8.5 mL, 20% aq. 160 mL/mol $LiAlH_4$) was added slowly at 0° C. and the resulting mixture was stirred for 30 minutes at room temperature. The mixture was filtered over celite, dried over $Na_2SO_4$, and concentrated to provide alcohol 6 (15 g, 94%) as a clear oil that slowly crystallized.

(13S,17S)-3-(2-Bromoethoxy)-17-(3-((1,1,1,3,3,3-
hexafluoro-2-(trifluoromethyl)propan-2-yl)oxy)
propoxy)-13-methyl-7,8,9,11,12,13,14,15,16,17-
decahydro-6H-cyclopenta[a]phenanthrene (7)

To a solution of compound 6 (15 g, 25 mmol) in DCM (300 mL) were added triphenylphosphine (9.8 g, 38 mmol) and NBS (5.3 g, 30 mmol) and the resulting mixture was stirred at room temperature for 16 hours. The mixture was washed with $NaHCO_3$, dried over $Na_2SO_4$, and concentrated. To the dark green residue was added heptane (500 mL) and the resulting mixture was stirred for 30 minutes. The solids were removed by filtration and the filtrate was concentrated. The mixture was taken up in heptane (250 mL) and stirred for 1 hour. The mixture was filtered and the filtrate was concentrated to provide bromide 7 (15.4 g, 94.1%) as a clear slightly yellow oil. To remove residual $PPh_3$, the material was dissolved in $Et_2O$ (300 mL) and was washed with an aqueous $KMnO_4$ solution, water, and brine. The organic layer was dried over $Na_2SO_4$ and concentrated. The $P(O)Ph_3$ was then removed by column chromatography (5% EtOAc in heptane) to provide the product as a clear oil.

S-(2-(((13S,17S)-17-(3-((1,1,1,3,3,3-Hexafluoro-2-
(trifluoromethyl)propan-2-yl)oxy)propoxy)-13-
methyl-7,8,9,11,12,13,14,15,16,17-decahydro-6H-
cyclopenta[a]phenanthren-3-yl)oxy)ethyl)4-
methylbenzenesulfonothioate (8)

To a solution of bromide 7 (2.9 g, 4.4 mmol) in DMF (150 mL) was added potassium 4-methylbenzenesulfonothioate (2.0 g, 8.8 mmol) and the resulting mixture was stirred at 50° C. for 16 hours and for 128 hours at room temperature. Water (500 mL) was added and the mixture was extracted with EtOAc/heptane (1/1, 2×250 mL). The combined organic layers were washed with brine, dried over $Na_2SO_4$, and concentrate to provide thiotosylate 8 (2.2 g, 65%).

Synthesis of Thioacetate 14:

tert-Butyl (4-hydroxybutyl)carbamate (9)

To a solution of 4-aminobutan-1-ol (25 g, 0.28 mol) in DCM (50 mL) was added slowly a solution of di-tert-butyl dicarbonate (61 g, 0.28 mol) in DCM (150 mL). The resulting mixture was stirred for 90 minutes, after which no gas development was observed anymore. The mixture was diluted with DCM (200 mL), washed with 1M HCl (400 mL), dried over $Na_2SO_4$, and concentrated to provide tert-butyl (4-hydroxybutyl)carbamate (43 g, 230 mmol, 82%) as a clear oil.

tert-Butyl (4-bromobutyl)carbamate (10)

tert-Butyl (4-hydroxybutyl)carbamate (7, 43 g, 230 mmol) was dissolved in DCM (500 mL) and triphenylphosphine (90 g, 340 mmol) and slowly NBS (45 g, 250 mmol) were added while cooling by water. The resulting mixture was stirred at room temperature for 90 minutes. NMR showed full conversion. The mixture was washed with aqueous saturated sodium bicarbonate (sat. 300 mL), dried over $Na_2SO_4$, and concentrated till one third of the volume. Heptane (500 mL) was added and the remaining DCM was removed in vacuo. Additional heptane (200 mL) was added and the mixture was stirred overnight at room temperature. The mixture was filtered and concentrated to provide crude tert-butyl (4-bromobutyl)carbamate (10, 75 g, 74%) as a yellow oil. NMR showed 43% $PPh_3$ and 57% correct product.

Diethyl 2-(4-((tert-butoxycarbonyl)amino)butyl) malonate (11)

To an ice cooled suspension of sodium hydride (6.8 g, 0.17 mol) in DMF (500 mL) was added diethyl malonate (27 g, 26 mL, 0.17 mol) slowly and the reaction mixture was stirred at room temperature for 1 h. The reaction mixture was cooled again at 0° C. and tert-butyl (4-bromobutyl)carbamate (10, 75 g, 0.17 mol) was added. Reaction mixture was allowed to reach room temperature and stirred for 18 hours. The reaction mixture was quenched with 1 N HCl (300 mL) and water (1.3 L). The mixture was extracted with Hept/EtOAc (1/1) (2×250 mL). The combined organic layers were washed brine (500 mL), dried over sodium sulfate, filtered and concentrate. The crude material was purified by column chromatography (20% EtOAc/heptane) to provide compound 11 (48 g, 85%) as a clear oil. NMR showed a little bit of diethyl malonate still present. The material was used as such for reduction.

tert-Butyl (6-hydroxy-5-(hydroxymethyl)hexyl)carbamate (12)

To an ice cooled solution of $LiAlH_4$ (25 g, 0.66 mol) in THF (750 mL) was added diethyl 2-(4-((tert-butoxycarbonyl)amino)butyl)malonate (11, 48 g, 0.14 mol) in THF (100 mL) dropwise. Reaction mixture stirred at 0° C. for 2.5 hours. The reaction was quenched by the addition of 20% KOH (106 mL) 0° C. slowly. The resulting mixture was stirred at room temperature for 1 hour, after which it was filtered over celite. The filtrate was dried over $Na_2SO_4$ and concentrated to provide tert-butyl (6-hydroxy-5-(hydroxymethyl)hexyl)carbamate (12, 22.3 g, 62%) as a clear oil.

tert-Butyl(4-(2,2-dimethyl-1,3-dioxan-5-yl)butyl) carbamate (13)

To a solution of tert-butyl (6-hydroxy-5-(hydroxymethyl) hexyl)carbamate (12, 22.3 g, 90.2 mmol) in THF (300 mL) was added 2,2-dimethoxypropane (28.2 g, 34 mL, 270 mmol) and 4-methylbenzenesulfonic acid hydrate (3.43 g, 18.0 mmol). Reaction mixture stirred at room temperature for 30 min, after which NMR showed full conversion. The mixture was diluted with EtOAc (300 mL) and washed with a saturated solution of sodium bicarbonate (300 mL). Aqueous layer extracted once more with EtOAc. Combined organic layers dried over $Na_2SO_4$, filtered, and concentrated to provide tert-butyl (4-(2,2-dimethyl-1,3-dioxan-5-yl) butyl)carbamate (13, 21.6 g, 83.4%) as a clear oil.

4-(2,2-Dimethyl-1,3-dioxan-5-yl)-N-methylbutan-1-amine (14)

To a suspension of $LiAlH_4$ (4.28 g, 113 mmol) in THF (300 mL) was added slowly a solution of tert-butyl (4-(2, 2-dimethyl-1,3-dioxan-5-yl)butyl)carbamate (13, 21.6 g, 75.2 mmol) in THF (100 mL). The resulting mixture was refluxed for 16 hour at 70° C. The mixture was cooled to 0° C., after which the reaction was quenched by the slow addition of KOH (20% aq, 18 mL). The resulting mixture was stirred at room temperature for 1 hour. The mixture was filtered over celite and the filtrate was dried over $Na_2SO_4$ before concentrating it in vacuo to provide compound 14 (13 g, 86%) as a slightly yellowish clear oil.

S-(3-Oxopropyl) ethanethioate (15)

To a solution of acrylaldehyde (15 g, 18 mL, 0.27 mol) in DCM (200 mL) were added triethylamine (6.8 g, 9.3 mL, 67 mmol) and slowly thioacetic acid (20 g, 19 mL, 0.27 mol). The resulting mixture was stirred at room temperature for 18 hours. The mixture was concentrated and the crude material was purified by column chromatography (15% EtOAc/heptane) to provide S-(3-oxopropyl) ethanethioate (15, 26.3 g, 74%) as a dark yellow/orange oil.

S-(3-((4-(2,2-Dimethyl-1,3-dioxan-5-yl)butyl) (methyl)amino)propyl) ethanethioate (16)

To a solution of 4-(2,2-dimethyl-1,3-dioxan-5-yl)-N-methylbutan-1-amine (14, 9.2 g, 46 mmol) in 1,2-Dichloroethane (400 mL) and acetic acid (11 g, 10 mL, 0.18 mol) was added S-(3-oxopropyl) ethanethioate (15 7.2 g, 55 mmol) and the resulting mixture was stirred for 5 minutes. Then, sodium triacetoxyborohydride (39 g, 180 mmol) was added and the resulting mixture was stirred for 90 minutes at room temperature. Aqueous saturated sodium bicarbonate (100 mL) was added to quench the reaction and the mixture was stirred for 15 min. The mixture was diluted with Aqueous saturated sodium bicarbonate (300 mL) and the phases were separated. The aqueous phase was extracted with dichloromethane and the combined organic phases were washed with brine, dried over $Na_2SO_4$ and concentrated. The crude material was purified using column chromatography (40-50% EtOAc in heptane+1% $NEt_3$) to provide S-(3-((4-(2,2-dimethyl-1,3-dioxan-5-yl)butyl)(methyl) amino)propyl) ethanethioate (16, 11.5 g, 79%) as an orange oil.

Synthesis of Formula (XIIa)-Precursor:

4-(2,2-dimethyl-1,3-dioxan-5-yl)-N-(3-((2-(((13S, 17S)-17-(3-((1,1,1,3,3,3-hexafluoro-2-(trifluoromethyl)propan-2-yl)oxy)propoxy)-13-methyl-7,8,9,11, 12,13,14,15,16,17-decahydro-6H-cyclopenta[a] phenanthren-3-yl)oxy)ethyl)disulfaneyl)propyl)-N-methylbutan-1-amine (17)

To a solution of thiotosylate 8 (3.3 g, 4.3 mmol) and thioacetate 16 (2.3 g, 7.4 mmol) in DCM (200 mL) and MeOH (20 mL) was added sodium methoxide (0.47 g, 1.6 mL, 8.7 mmol) in MeOH. The resulting mixture was stirred for 2 hours. NMR showed full consumption of the thiotosylate. The mixture was diluted with DCM (200 mL), washed with NaHCO$_3$, dried over Na$_2$SO$_4$, and concentrated. The crude material was purified by column chromatography (10% Acetone in heptane+1% NEt$_3$) to provide disulfide 17 (0.85 g, 22%) as a clear oil.

2-(4-((3-((2-((((13S,17S)-17-(3-((1,1,1,3,3,3-hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)ethyl)disulfaneyl)propyl)(methyl)amino)butyl)propane-1,3-diol To a solution of acetonide 17 (2.1 g, 2.3 mmol) in MeOH (100 mL) was added tosic acid (530 mg, 2.8 mmol), and the resulting mixture was stirred at room temperature for 1 hour, after which TLC showed full conversion. The volatiles were removed in vacuo. The crude material was dissolved in DCM (100 mL), washed with NaHCO$_3$, dried over Na$_2$SO$_4$, and concentrated to provide the product (1.7 g, 2.0 mmol, 87%) as a white solid.

2-((bis(4-methoxyphenyl)(phenyl)methoxy)methyl)-6-((3-((2-(((13S,17S)-17-(3-((1,1,1,3,3,3-hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)ethyl)disulfaneyl)propyl)(methyl)amino)hexan-1-ol (18)

To a solution of the diol (1.7 g, 2.0 mmol), triethylamine (0.25 g, 0.34 mL, 2.4 mmol), and DMAP (25 mg, 0.20 mmol) in DCM (100 mL) was added 4,4'-(chloro(phenyl)methylene)bis(methoxybenzene) (0.68 g, 2.0 mmol) and the resulting yellow mixture was stirred at room temperature for 16 hours. The mixture was washed with NaHCO$_3$ and brine, dried over Na$_2$SO$_4$, and concentrated. The crude material was purified by column chromatography (25% Acetone/heptane+1% NEt$_3$) to provide the product 18 (1.3 g, 1.1 mmol, 56%) as a clear oil.

2-((bis(4-methoxyphenyl)(phenyl)methoxy)methyl)-6-((3-((2-(((8R,9S,13S,14S,17S)-17-(3-((1,1,1,3,3,3-hexafluoro-2-(trifluoromethyl)propan-2-yl)oxy)propoxy)-13-methyl-7,8,9,11,12,13,14,15,16,17-decahydro-6H-cyclopenta[a]phenanthren-3-1)oxy)ethyl)disulfaneyl)propyl)(methyl)amino)hexyl (2-cyanoethyl) diisopropylphosphoramidite (Apo-Si—K-113)

To a solution of compound 18 (1.3 g, 1.1 mmol) in DCM (100 mL) was added a solution of N-methylmorpholine (0.15 g, 3.0 mL, 1.5 mmol) and TFA (84 mg, 3.0 mL, 0.74 mmol) in DCM (0.5 M NMM, 0.25 M TFA). Then, 3-((bis(diisopropylamino)phosphaneyl)oxy)propanenitrile (0.45 g, 0.47 mL, 1.5 mmol) was added and the resulting mixture was stirred at room temperature for 2 hours and the reaction was monitored by TLC. After full conversion, the mixture was washed with NaHCO$_3$, dried over Na$_2$SO$_4$, and concentrated. The crude material was purified using column chromatography (15% Acetone in heptane+1% NEt$_3$) to provide Apo-Si—K-113 (1.5 g, 1.1 mmol, 98%) as a clear oil.

Example 2i: A Method for Synthesis of Formula (XIIb)-Precursor

Formula (XIIb)-Precursor

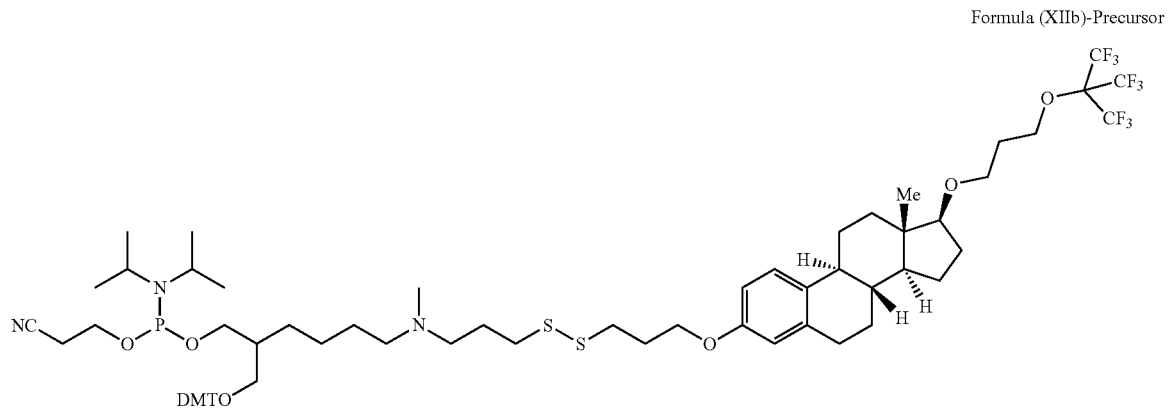

Synthesis of Formula (XIIb)-Precursor is performed according to the following synthetic scheme:
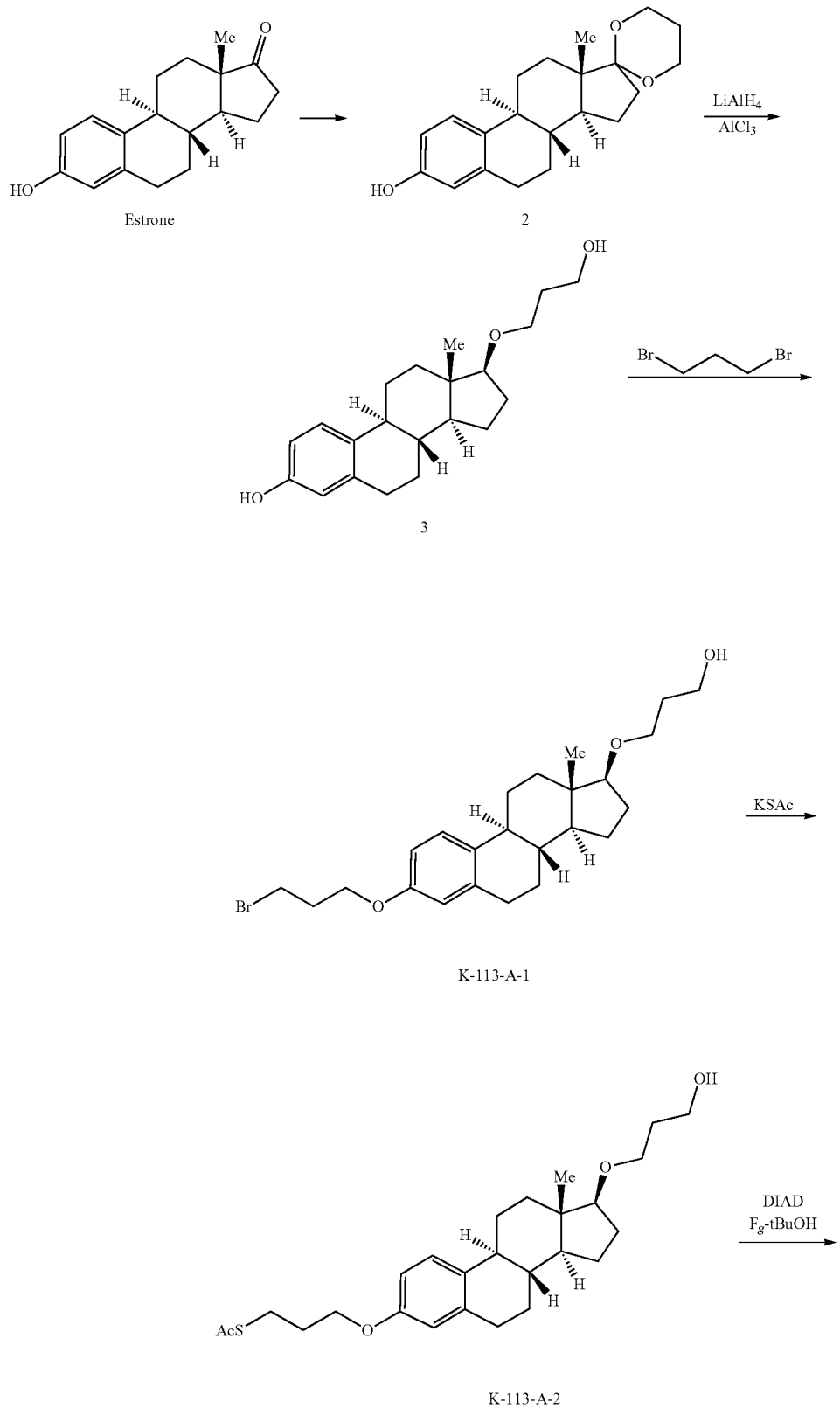

-continued
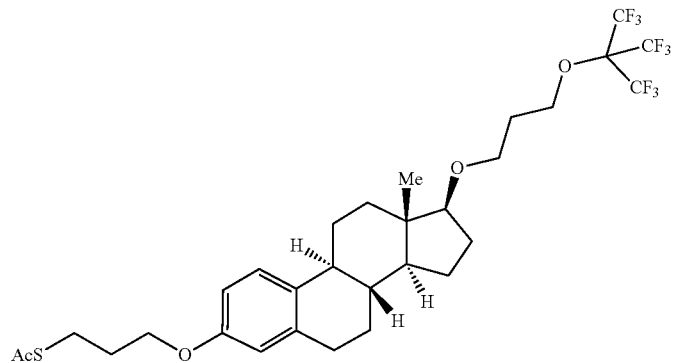
K-113-A-3
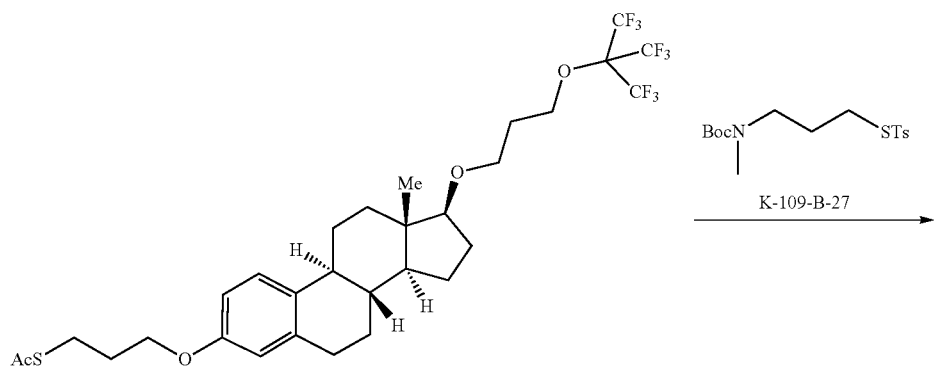
K-113-A-3
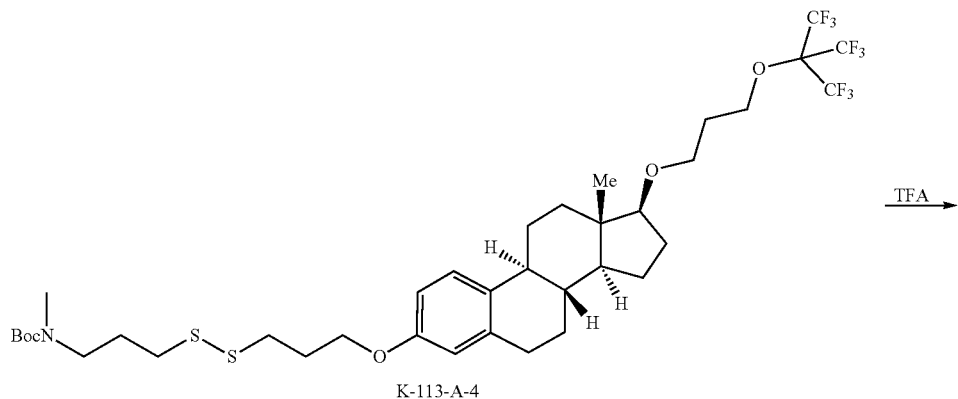
K-113-A-4
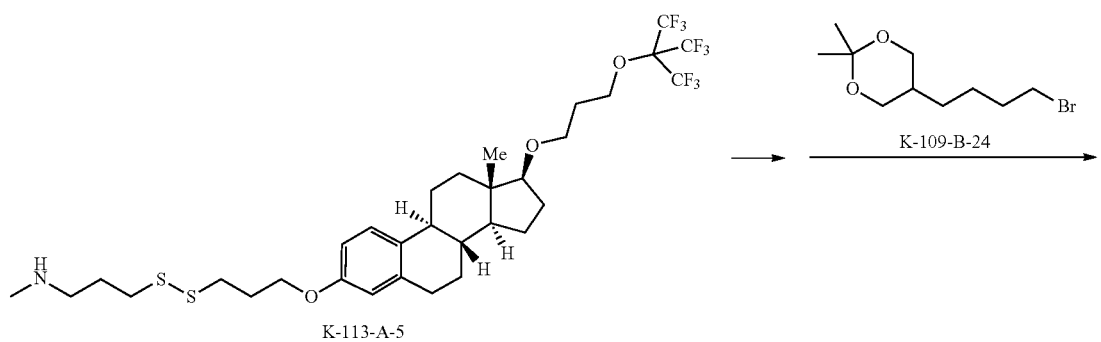
K-113-A-5

-continued
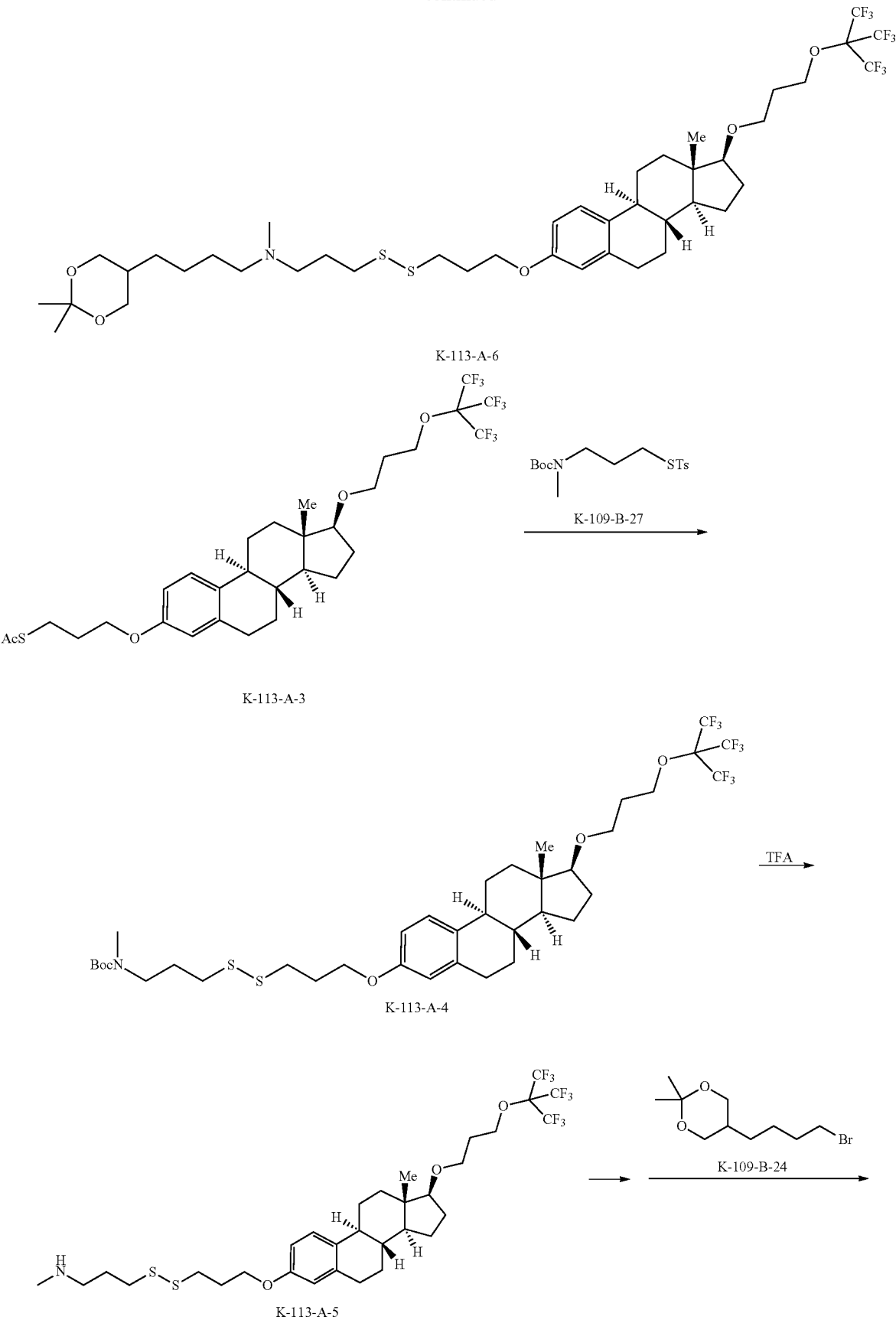

-continued
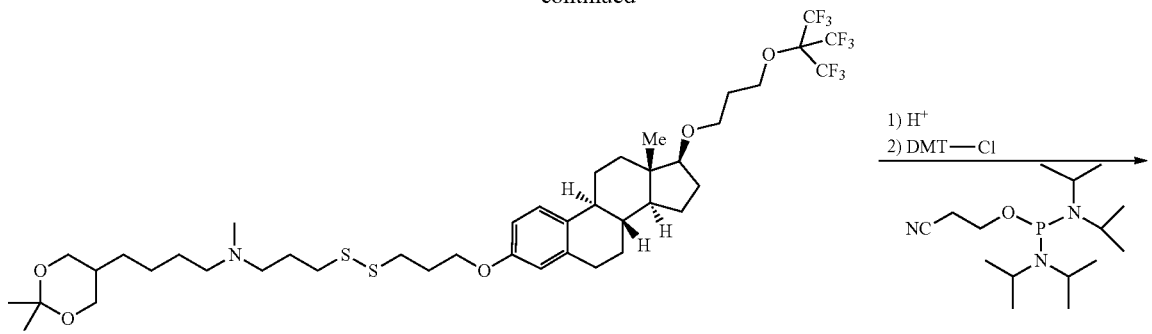
K-113-A-6
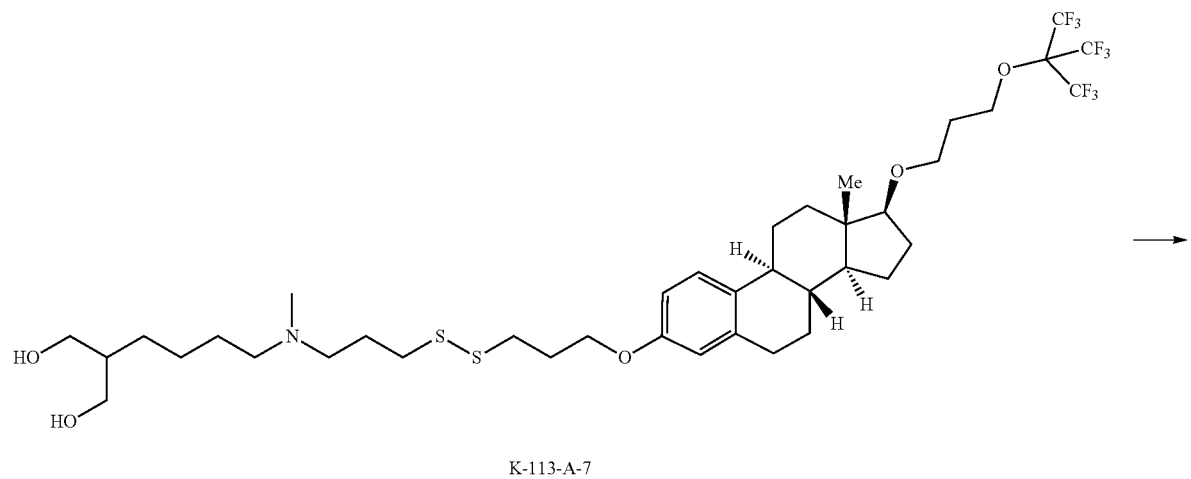
K-113-A-7
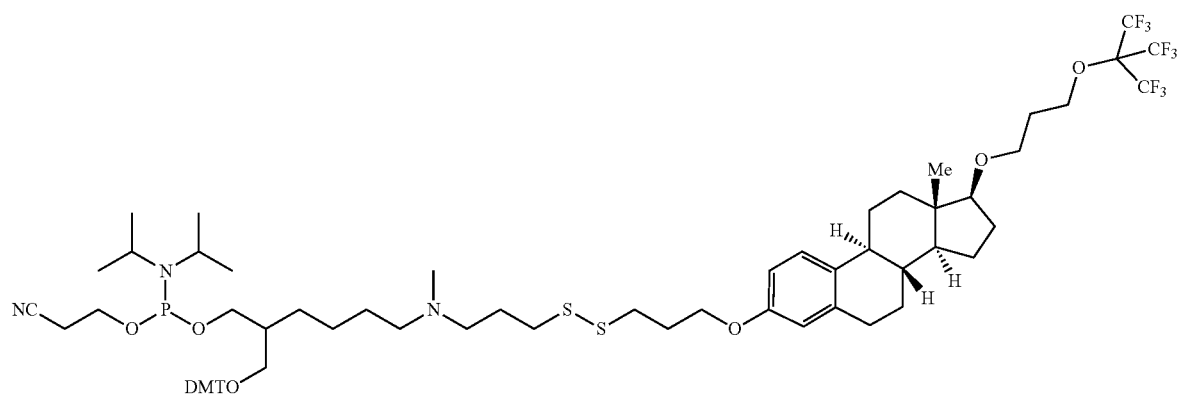

Example 2j: A Method for Synthesis of Formula (XIIIa)-Precursor
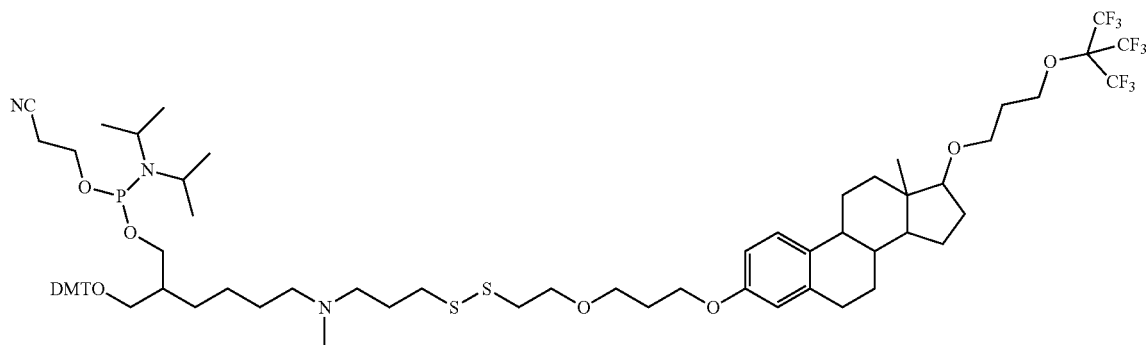
Formula (XIIIa)-Precursor
Synthesis of Formula (XIIIa)-Precursor is performed according to the following synthetic scheme:
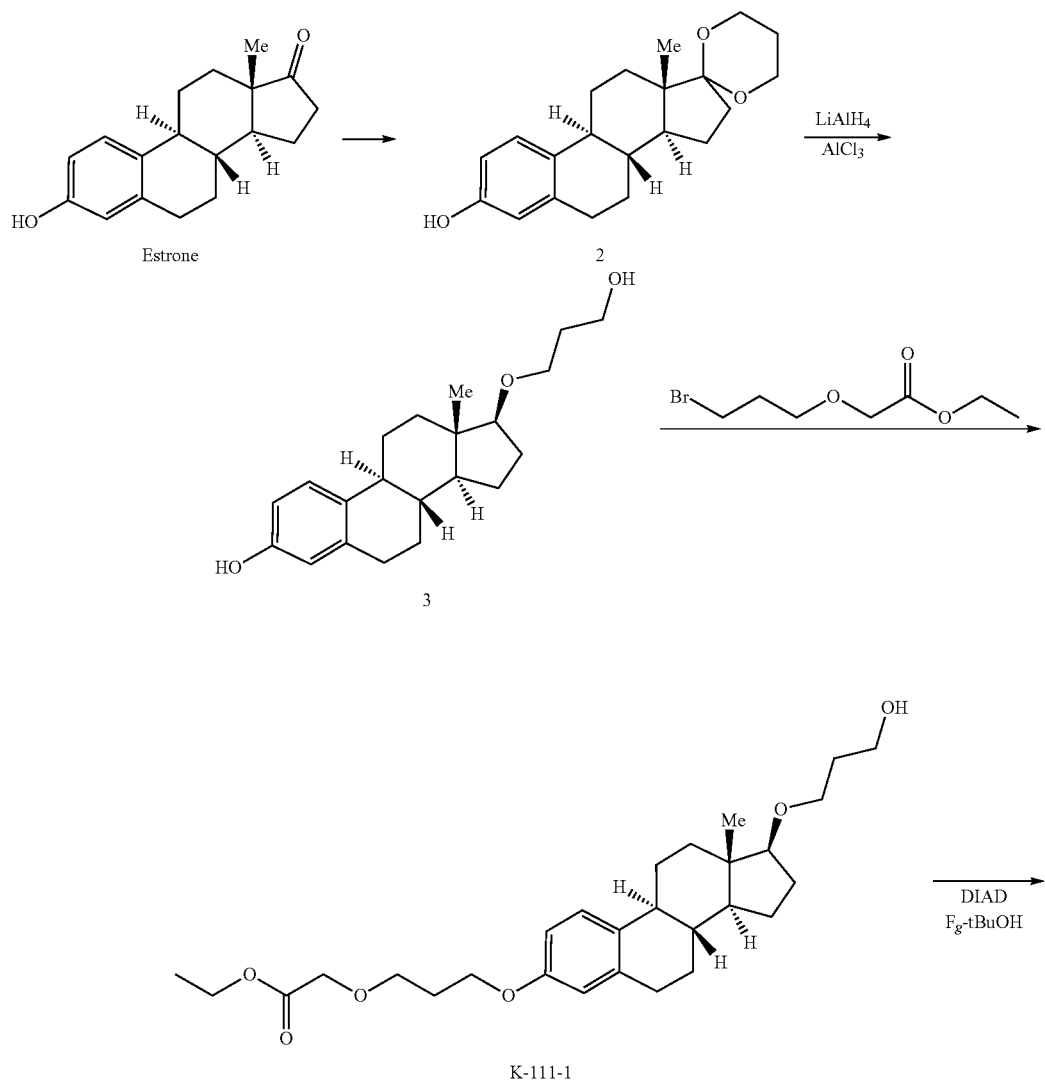
Scheme 16. Synthesis of Formula (XIIIa)-Precrssor

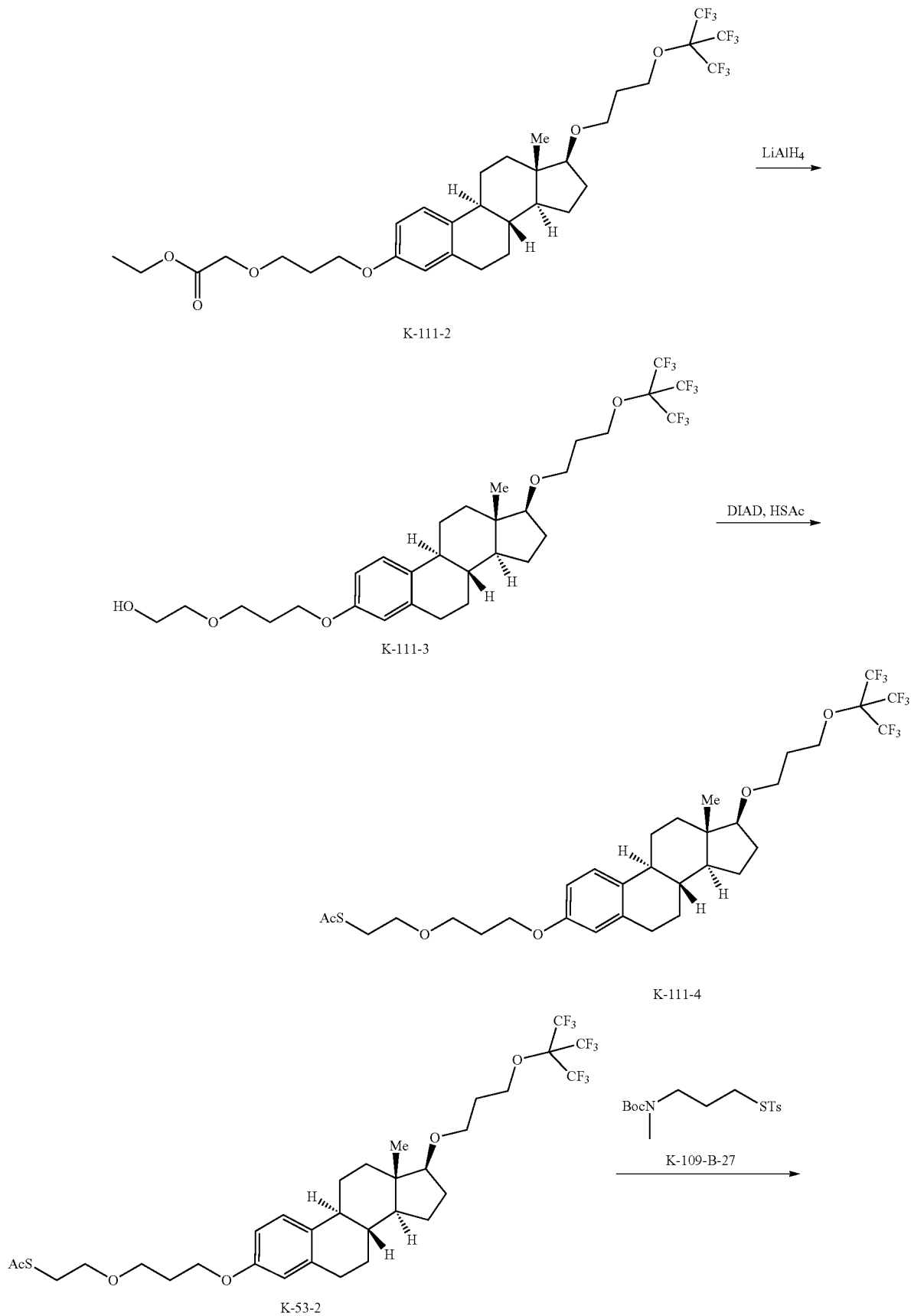

-continued
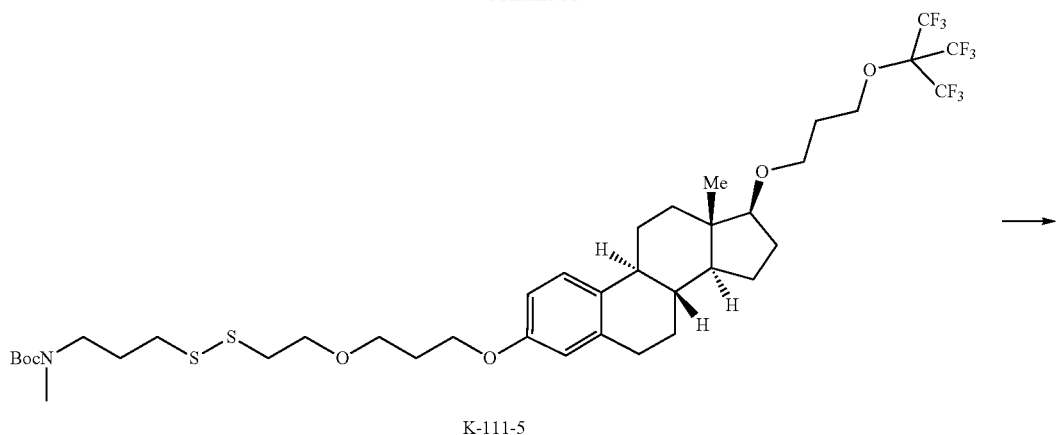
K-111-5
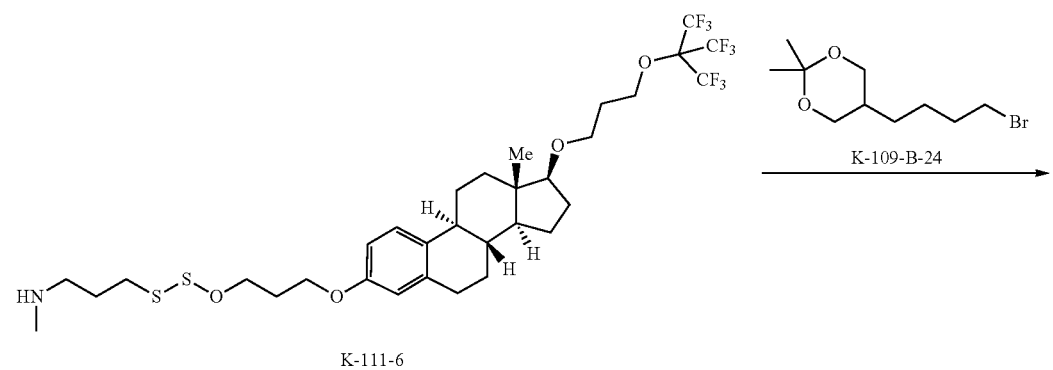
K-111-6
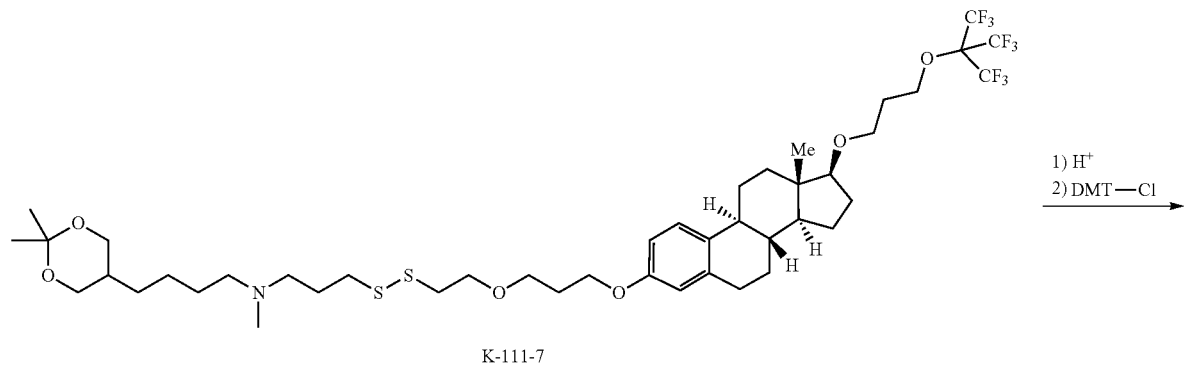
K-111-7
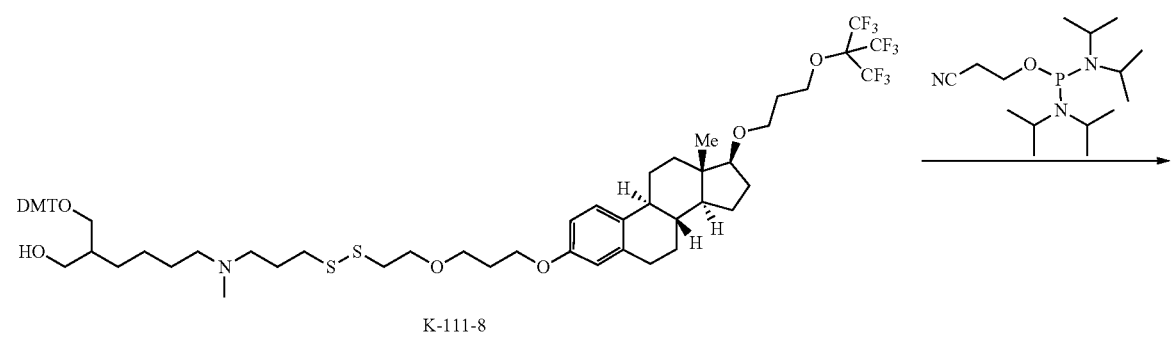
K-111-8

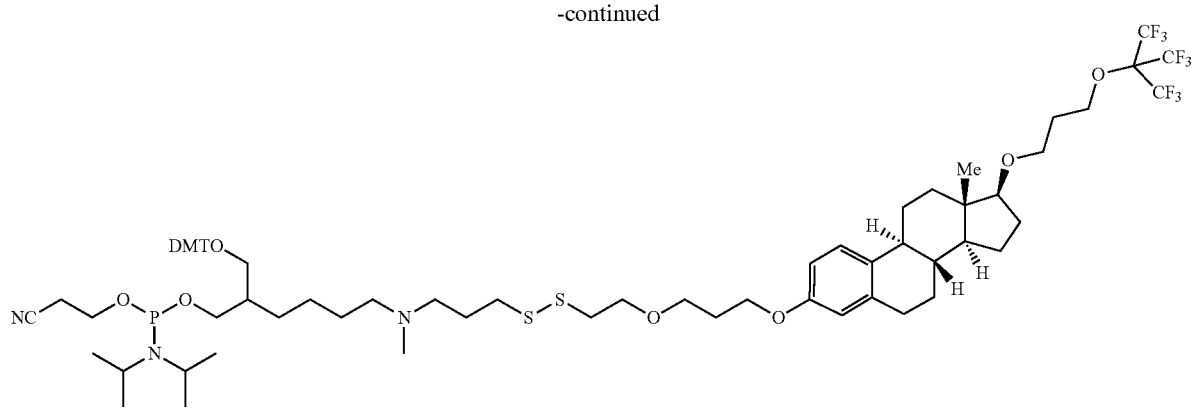
Example 2k: A method for Synthesis of Formula (XIIIb)-Precursor
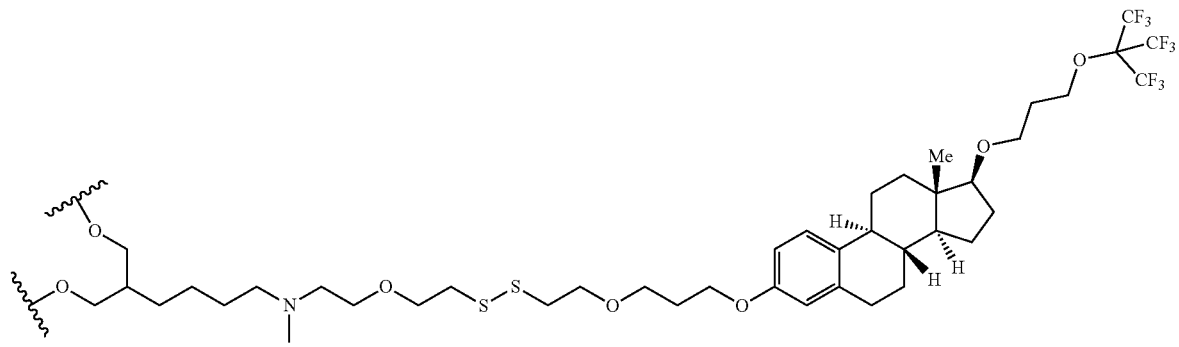
Formula (XIIIb)-Precursor
The key features of Formula (XIIIb)-Precursor are an ether group between the disulfide and the steroid part. On the other side of the disulfide, another ether as well as a tertiary amine are present.
Synthesis of Thiotosylate 10:
Scheme 17. Synthesis of thiotosylate 10.
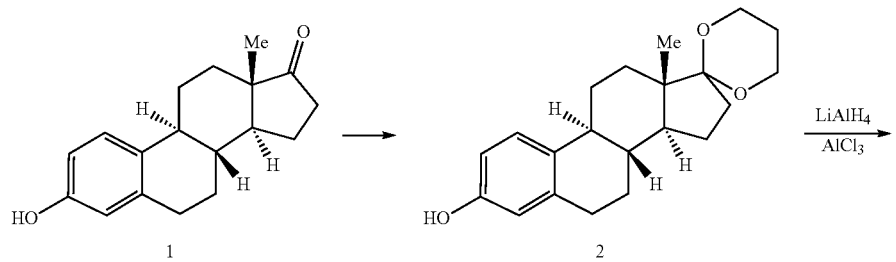

-continued
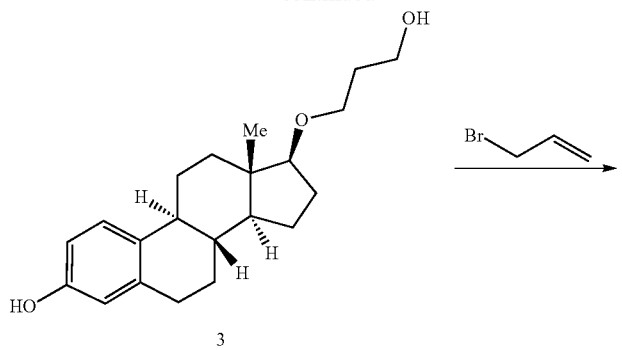
3
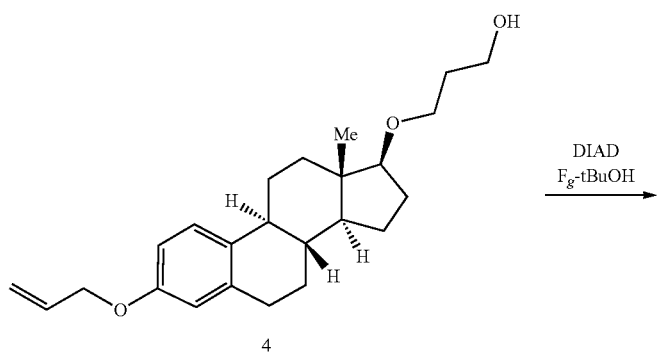
4
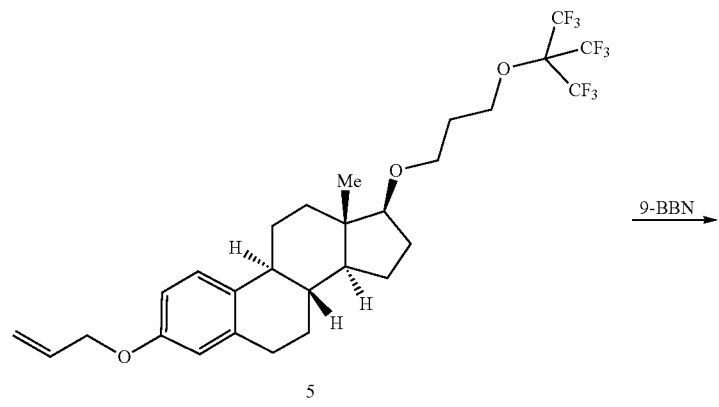
5
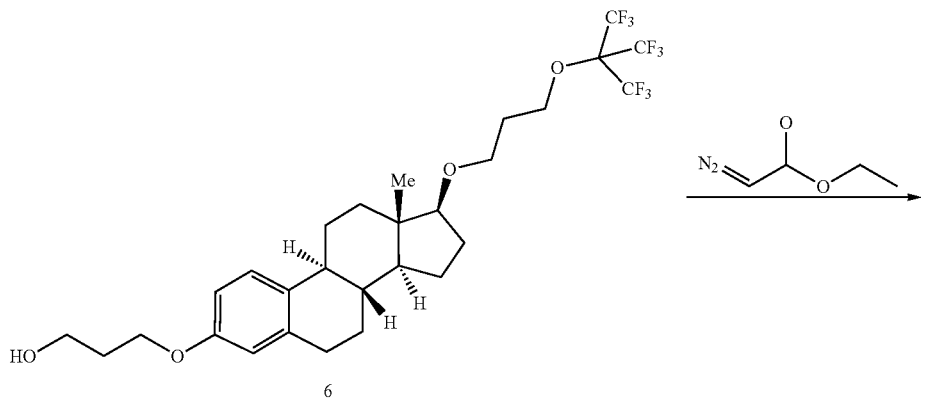
6

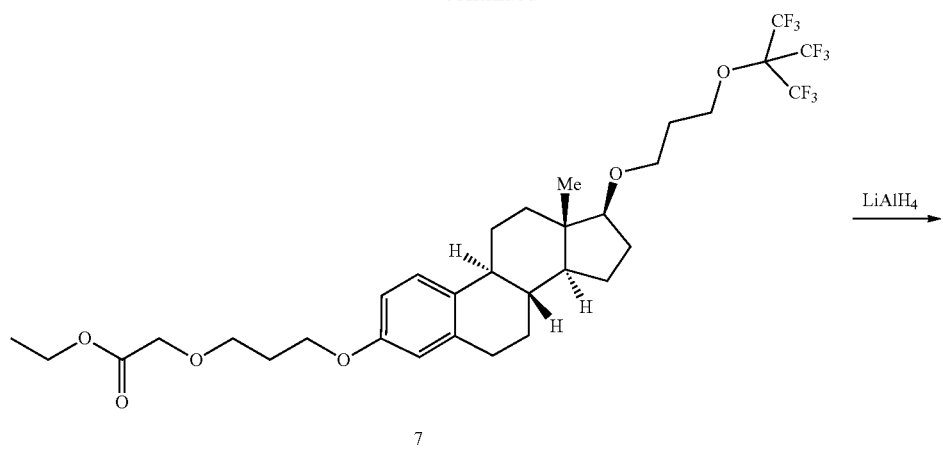
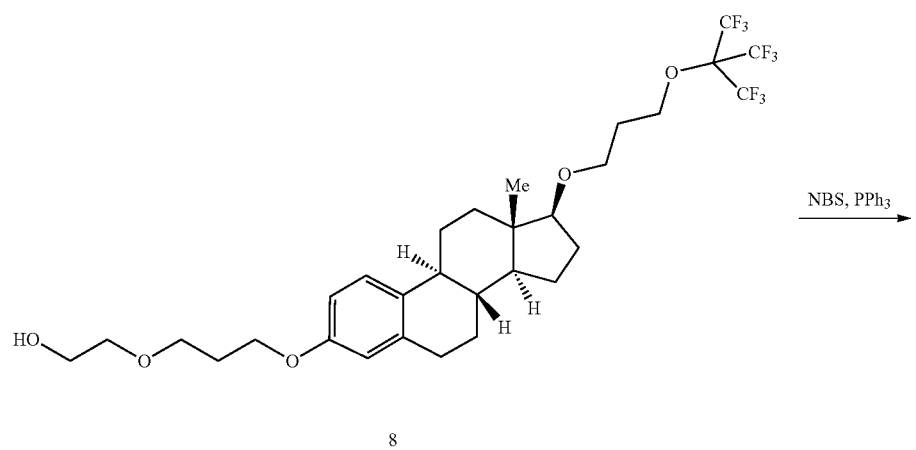
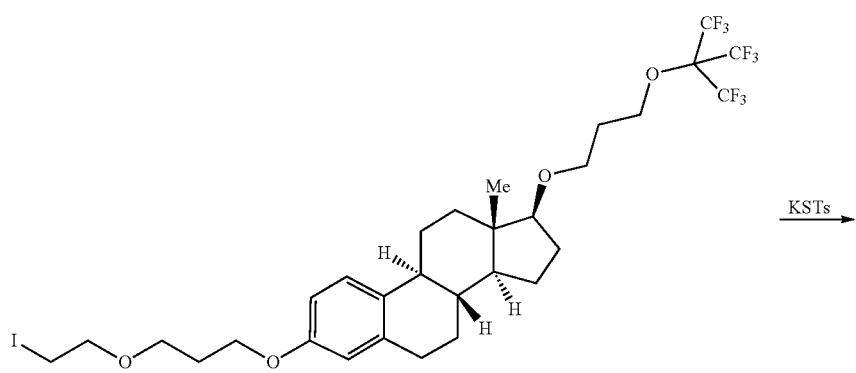

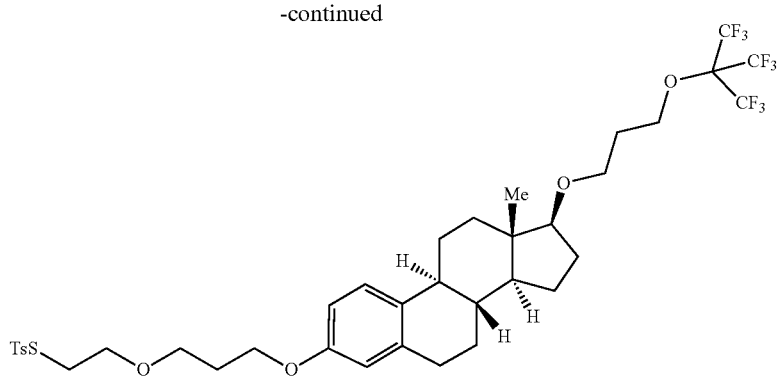

10

The synthesis commenced by protection of the ketone with 1,3-propanediol to provide compound 2 in good purity. LiAlH$_4$ and AlCl$_3$-ring opening of the acetal gave a mixture of compound 3 and estradiol in a ratio of ca 85:15, the latter being less reactive and will be removed in the next-steps. Allyl bromide was employed as a reactive electrophile. The selective alkylation on the phenol allowed for a subsequent attachment of per fluorinated tert-butanol on the aliphatic alcohol using Mitsunobu-conditions to provide compound 5. Further functionalization of the allyl by 9-BBN treatment and subsequent reduction provided alcohol 6. This alcohol could be elongated with ethyl diazoacetate to provide compound 7. The reduction to an alcohol, the conversion to the corresponding iodide and subsequent thiotosylation provided compound 10.

Synthesis of Thioacetate 18:

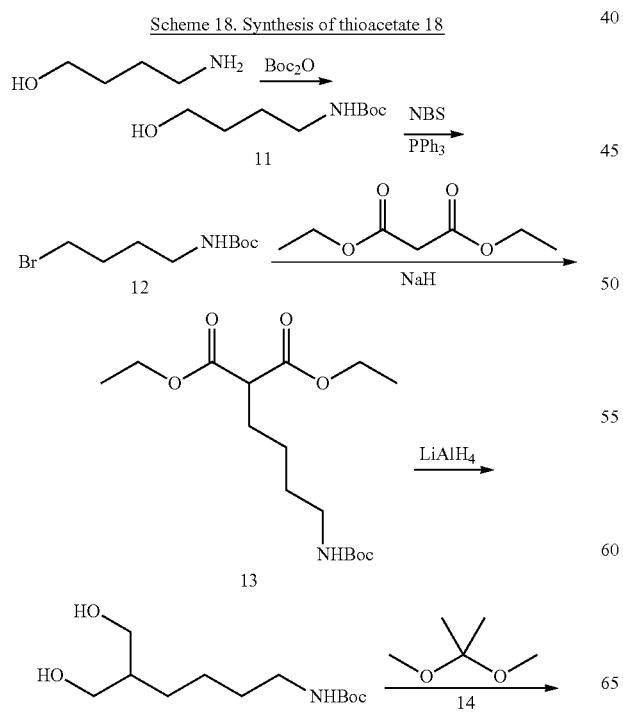

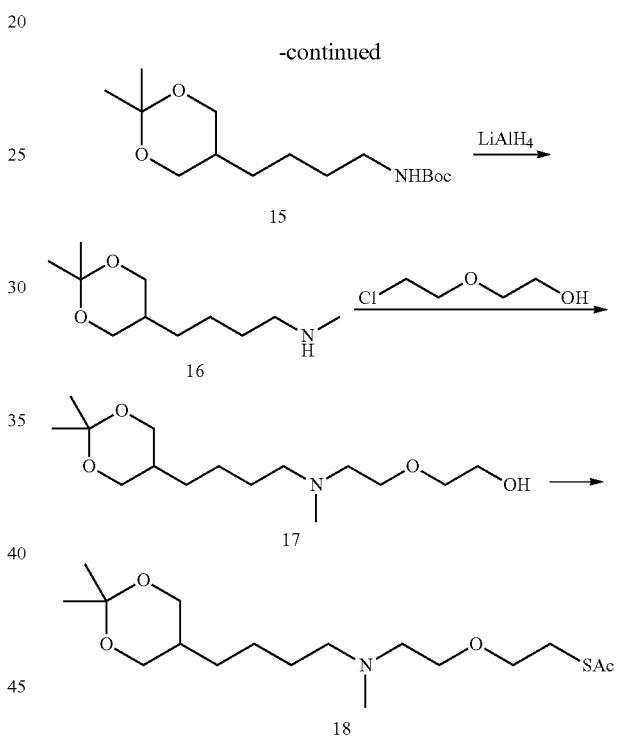

The first step in the synthesis of building block 18 was the protection of the amine of aminobutanol to provide alcohol 11. The alcohol was subsequently converted to bromide 12 by treatment with NBS and PPh$_3$. The bromide was then alkylated onto diethylmalonate to provide diester 13. Treatment with LiAlH$_4$ at room temperature reduces the esters but does not reduce the Boc-group, thus affording diol 14. The diol was then protected as the acetonide (15). The Boc-group was reduced by treatment with LiAlH$_4$ at elevated temperature to provide amine 16. Alkylation of the amine with the appropriate chloride provided compound 17. The hydroxy moiety was converted to a thioacetate using Mitsunobu conditions to provide building block 18.

Synthesis of Formula (XIIIb)-Precursor:
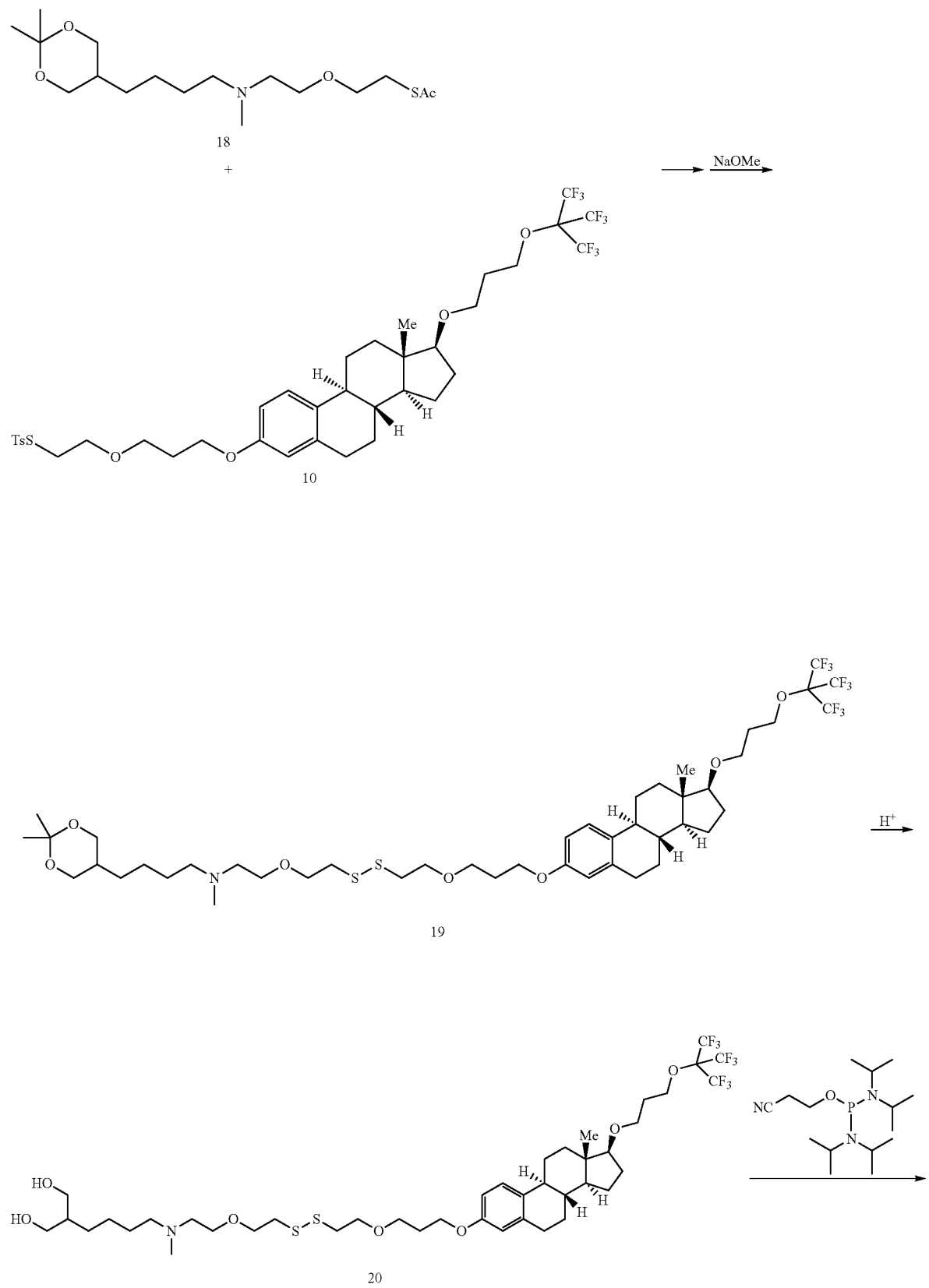

-continued

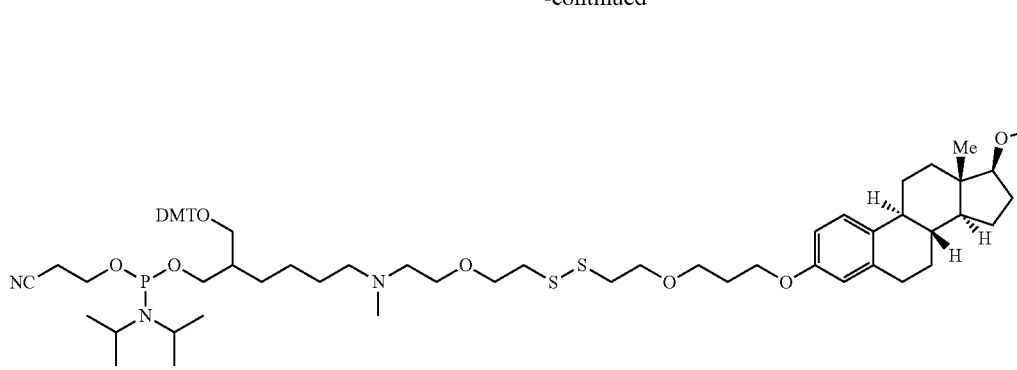

A mixture of thiotosylate 10 and thioacetate 18 was treated with NaOMe to provide disulfide 19. The acetonide group was removed by treatment with acid to provide diol 20. A DMT group was attached to one of the alcohols to afford compound 21. Finally, phosphoramidite formation provided Formula (XIIIb)-Precursor.

Experimental Section:
Synthesis of Thiotosylate 10:

(8R,9S,13S,14S)-13-Methyl-6,7,8,9,11,12,13,14,15, 16-decahydrospiro[cyclopenta[a]phenanthrene-17,2'-[1,3]dioxan]-3-ol (2)

To a suspension of estrone (252 gram, 0.93 mol) in toluene (1.5 L) were added trimethoxymethane (297 g, 350 mL, 2.80 mol), propane-1,3-diol (213 g, 250 mL, 2.80 mol) and pTsOH (2 g, 10 mmol). The mixture was warmed to 60° C. and stirred for 16 h. Added triethylamine (6 mL) and water (600 mL) and continued stirring for 1 additional hour. Phases were separated and the organic layer was washed with water (3×400 mL) and brine. The mixture was dried over Na$_2$SO$_4$ and partially concentrated to ca 1 L. The mixture was poured into heptane (4 L) and the white solids were filtered off, washed with heptane, and dried in vacuo. Compound 2 (271 gram, 825 mmol) was isolated as a white solid in 88.5% yield.

(8R,9S,13S,14S,17S)-17-(3-Hydroxypropoxy)-13-methyl-7,8,9,11,12,13,14,15,16,17-decahydro-6H-cyclopenta[a]phenanthren-3-ol (3)

To a solution of (13S)-13-methyl-6,7,8,9,11,12,13,14,15, 16-decahydro spiro[cyclopenta[a]phenanthrene-17,2'-[1,3] dioxan]-3-ol (2, 60.7 g, 185 mmol) in THF at 0° C. was added carefully lithium aluminum hydride (8.42 g, 222 mmol) followed by portion wise addition of aluminum chloride (98.6 g, 739 mmol) (very exothermic!). Stirred 15 min at 0° C., then warmed to 50° C. Stirred 2 h at 50° C. (due to clogging on a rotary evaporator), then cooled to 0° C. and started quenching dropwise with NH$_4$Cl(aq) (500 mL). Stirred 1 h at room temperature. The phases were separated and the organic layer was washed with brine, concentrated. A white solid (65 gram) was obtained, which was contaminated with estradiol (ca 15%).

3-(((8R,9S,13S,14S,17S)-3-(Allyloxy)-13-methyl-7, 8,9,11,12,13,14,15,16,17-decahydro-6H-cyclopenta [a]phenanthren-17-yl)oxy)propan-1-ol (4)

A suspension of compound 3 (10.1 g, 30.6 mmol) and potassium carbonate (8.45 g, 61.1 mmol) in MeOH/acetone was treated with allyl bromide (7.39 g, 5.28 mL, 61.1 mmol). Heated to reflux for 4 h, then full conversion was observed. Cooled to room temperature, filtered and concentrated. Added dichloromethane (250 mL) and washed with brine, dried over Na$_2$SO$_4$ and concentrated.

The crude material (12.8 gram, 34.5 mmol) was used as such in follow-up chemistry:

(8R,9S,13S,14S,17S)-3-(Allyloxy)-17-(3-((1,1,1,3,3, 3-hexafluoro-2-(trifluoromethyl)propan-2-yl)oxy) propoxy)-13-methyl-7,8,9,11,12,13,14,15,16,17-decahydro-6H-cyclopenta[a]phenanthrene (5)

To a solution of compound 4 (12.78 g, 34.49 mmol) and triphenylphosphine (13.57 g, 51.74 mmol) in THF (300 mL) were added 1,1,1,3,3,3-hexafluoro-2-(trifluoromethyl)propan-2-ol (12.21 g, 7.23 mL, 51.74 mmol) and di-tert-butyl (E)-diazene-1,2-dicarboxylate (10.32 g, 44.84 mmol). The mixture was stirred 16 h at room temperature, and was then concentrated.

After purification using flash chromatography (gradient 5% to 10% EtOAc in heptane), compound 5 (16.7 gram, 28.4 mmol) was isolated as yellowish oil in 82% yield.

3-(((8R,9S,13S,14S,17S)-17-(3-((1,1,1,3,3,3-Hexafluoro-2-(trifluoromethyl)propan-2-yl)oxy) propoxy)-13-methyl-7,8,9,11,12,13,14,15,16,17-decahydro-6H-cyclopenta[a]phenanthren-3-yl)oxy) propan-1-ol (6)

9-BBN (5.54 g, 90 mL, 45.4 mmol) was added dropwise to a solution of the crude compound 5 (16.7 g, 28.4 mmol) in THF (250 mL) at 0° C. and upon complete addition the mixture was stirred at room temperature overnight. The solution was cooled to 0° C. and slowly sodium hydroxide (20 g, 16 mL, 148 mmol) and hydrogen peroxide (14 g, 13 mL, 148 mmol) were added dropwise simultaneously and the resulting heterogeneous mixture was vigorously stirred at room temperature for ca. 1 h. The reaction mixture was decanted and partitioned between EtOAc (700 mL) and brine (100 mL). The organic phase was washed with an additional amount of brine (100 mL), dried over Na$_2$SO$_4$ and concentrated in vacuo. Further purification of the concentrate by flash chromatography (silica gel, gradient 25% to 35% EtOAc in heptanes) afforded compound 6 (13.6 g, 22.4 mmol) in 79.0% yield.

Ethyl 2-(3-(((8R,9S,13S,14S,17S)17-(3-((1,1,1,3,3, 3-hexafluoro-2-(trifluoromethyl) propan-2-yl)oxy) propoxy)-13-methyl-7,8,9,11,12,13,14,15,16,17- decahydro-6H-cyclopenta[a]phenanthren-3-yl)oxy) propoxy)acetate (7)

Compound 6 (13.6 g, 22.4 mmol) and ethyl 2-diazoacetate (3.0 g, 2.8 mL, 22.4 mmol) were dissolved in DCM (250 mL) and at 0° C. BF$_3$·OEt$_2$ (31.8 mg, 28.4 µL, 224 µmol) was added. The reaction was stirred at 0° C. for 15 min and at room temperature for 3 hours until no more gas development was observed. Based on TLC, no full conversion was observed. Added more ethyl 2-diazoacetate (5 mL) and BF$_3$·OEt$_2$ and continued stirring for 2 h. The mixture was diluted with DCM (200 mL), triethylamine (1 mL) was added and the mixture was washed with water (100 mL) and brine (50 mL) and dried over Na$_2$SO$_4$. The solvents were removed in vacuo and further purification using flash chromatography (gradient 5% to 10% EtOAc in heptane) provided compound 7 (5.5 gram, 7.9 mmol) as a clear yellowish oil in 35% yield.

2-(3-(((8R,9S,13S,14S,17S))-17-(3-((1,1,1,3,3,3- Hexafluoro-2-(trifluoromethyl)propan-2-yl)oxy) propoxy)-13-methyl-7,8,9,11,12,13,14,15,16,17- decahydro-6H-cyclopenta[a]phenanthren-3-yl)oxy) propoxy)ethan-1-ol (8)

To a suspension of LiAlH$_4$ (0.36 g, 9.5 mmol) in THF (100 mL) at 0° C. was added dropwise a solution of compound 7 (5.5 g, 7.9 mmol). The mixture was stirred for 2 h at room temperature, then quenched by addition of 20% KOH in water (1.7 mL). The suspension was stirred for 1 h more, then filtered over a short path of celite. Concentrated. Compound 8 (4.81 gram, 7.4 mmol) was isolated in 93% yield and used as such in follow-up chemistry.

(8R,9S,13S,14S,17S)-3-(3-(2-Bromoethoxy) propoxy)-17-(3-((1,1,1,3,3,3-hexafluoro-2-(trifluoromethyl)propan-2-yl)oxy)propoxy)-13-methyl-7,8, 9,11,12,13,14,15,16,17-decahydro-6H-cyclopenta[a] phenanthrene (9)

To a solution of compound 8 (4.81 g, 7.39 mmol), imidazole (604 mg, 8.87 mmol) and triphenylphosphine (2.33 g, 8.87 mmol) in dichloromethane (250 mL) was added at 0° C. iodine (2.06 g, 8.13 mmol). The mixture was stirred for 16 h, then aqueous saturated sodium thiosulfate was added and the phases were separated. The organic layer was washed with brine, dried over sodium sulfate and concentrated. The residue was dissolved in heptane, left standing for precipitation and the solids were filtered off. Concentrated.

Further purification using flash chromatography (5% EtOAc in heptane) gave compound 9 (3.90 g, 5.13 mmol) as a clear oil in 69% yield.

S-(2-(3-(((8R,9S,13S,14S,17S)17-(3-((1,1,1,3,3,3- Hexafluoro-2-(trifluoromethyl)propan-2-yl)oxy) propoxy)-13-methyl-7,8,9,11,12,13,14,15,16,17- decahydro-6H-cyclopenta[a]phenanthren-3-yl)oxy) propoxy)ethyl) 4-methylbenzenesulfonothioate (10)

Compound 9 (3.90 g, 5.13 mmol) was dissolved in DMF and potassium 4-methylbenzenesulfonothioate (1.72 g, 7.6 mmol) was added. The suspension was stirred at room temperature for 16 h. TLC showed only partial conversion. The mixture was warmed to 50° C. for 4 h, and was then cooled to room temperature. EtOAc (50 mL) was added followed by heptane (100 mL) and washed 3× with water, then once with brine, dried over sodium sulfate and concentrated. Further purification using flash chromatography (5% to 15% EtOAc in heptane). Compound 10 (3.45 g, 4.2 mmol) was isolated as clean oil in 83% yield.

Synthesis of Thioacetate 18:

tert-Butyl (4-hydroxybutyl)carbamate (11)

To a solution of 4-aminobutan-1-ol (25 g, 0.28 mol) in DCM (50 mL) was added slowly a solution of di-tert-butyl dicarbonate (61 g, 0.28 mol) in DCM (150 mL). The resulting mixture was stirred for 90 minutes after which no gas development was observed anymore. The mixture was diluted with DCM (200 mL), washed with 1M HCl (400 mL), dried over Na$_2$SO$_4$, and concentrated to provide tert-butyl (4-hydroxybutyl)carbamate (11, 43 g, 82%) as a clear oil.

tert-Butyl (4-bromobutyl)carbamate (12)

To a solution of tert-butyl (4-hydroxybutyl)carbamate (11, 23 g, 120 mmol) in DCM (500 mL) were added triphenylphosphine (44 g, 170 mmol) and slowly NBS (25 g, 143 mmol). The resulting mixture was stirred for 2 hours at room temperature. The mixture was washed with NaHCO$_3$, dried over Na$_2$SO$_4$, and concentrated. Heptane (500 mL) was added and the mixture was stirred at room temperature for 1 hour. The formed solids were removed by filtration and the filtrate was concentrated to provide tert-butyl (4-bromobutyl)carbamate (12, 32.8 g, 130 mmol, quant.) as a clear oil.

Diethyl 2-(4-((tert-butoxycarbonyl)amino)butyl) malonate (13)

To an ice cooled suspension of sodium hydride (6.8 g, 0.17 mol) in DMF (500 mL) was added diethyl malonate (27 g, 26 mL, 0.17 mol) slowly and the reaction mixture was stirred at room temperature for 1 h. The reaction mixture was cooled again to 0° C. and tert-butyl (4-bromobutyl)carbamate (12, 75 g, 0.17 mol) was added. The reaction mixture was allowed to reach room temperature and stirred for 18 hours. The reaction mixture was quenched with 1 N HCl (300 mL) and water (1.3 L). The mixture was extracted with Heptane/EtOAc (1/1, 2×250 mL). Combined organic layers were washed with brine (500 mL), dried over sodium sulfate, filtered and concentrated. The crude material was purified by column chromatography (20% EtOAc/heptane) to provide diester 13 (48 g, 0.14 mol, 85%) as a clear oil.

tert-Butyl (6-hydroxy-5-(hydroxymethyl)hexyl)carbamate (14)

To an ice cooled solution of LiAlH$_4$ (8.7 g, 0.23 mol) in THF (750 mL) was added diester 13 (19 g, 57 mmol) in THF (100 mL) dropwise. The reaction mixture was stirred at room temperature for 3 hours. The reaction was quenched by the slow addition of 20% KOH (aqueous. 37 mL) at 0° C. The resulting mixture was stirred at room temperature for 1 hour, after which it was filtered over Celite. The filtrate was dried over Na$_2$SO$_4$ and concentrated to provide diol 14 (12 g, 50 mmol, 86%) as a clear oil.

tert-Butyl (4-(2,2-dimethyl-1,3-dioxan-5-yl)butyl) carbamate (15)

To a solution of diol 14 (22 g, 90 mmol) in THF (300 mL) was added 2,2-dimethoxypropane (28 g, 34 mL, 270 mmol) and 4-methylbenzenesulfonic acid hydrate (3.4 g, 18 mmol). The reaction mixture was stirred at room temperature for 30 min. The mixture was diluted with EtOAc (300 mL) and washed with a saturated solution of sodium bicarbonate (300 mL). The aqueous layer was extracted once more with EtOAc. The combined organic layers were dried over $Na_2SO_4$, filtered, and concentrated to provide acetonide 15 (21.6 g, 83.4%) as a clear oil.

4-(2,2-Dimethyl-1,3-dioxan-5-yl)-N-methylbutan-1-amine (16)

To a suspension of $LiAlH_4$ (2.2 g, 58 mmol) in THF (300 mL) was added acetonide 15 (11 g, 39 mmol) and the resulting mixture was stirred at 70° C. for 16 h. The mixture was allowed to cool to room temperature. Then, the mixture was cooled to 0° C. and the reaction was quenched by the addition of KOH (20%, 9.3 mL) slowly at 0° C. The resulting mixture was stirred for 1 hour at room temperature. The mixture was filtered over Celite, dried over $Na_2SO_4$, and concentrated to provide methylamine 16 (7.8 g, 39 mmol, quant.) as a clear oil.

2-(2-((4-(2,2-Dimethyl-1,3-dioxan-5-yl)butyl)(methyl)amino)ethoxy)ethan-1-ol (17)

To a solution of amine 16 (4.1 g, 20 mmol) in MeCN (150 mL) were added 2-(2-chloroethoxy)ethan-1-ol (2.5 g, 2.1 mL, 20 mmol), potassium iodide (0.34 g, 2.0 mmol), and potassium carbonate (5.6 g, 41 mmol) and the resulting mixture was stirred for 40 hours at 80° C. The mixture was diluted with water (100 mL) and $NaHCO_3$ (100 mL) and extracted with DCM (2×200 mL). The combined organic layers were washed with brine, dried over $Na_2SO_4$, and concentrated. The crude material was purified using column chromatography (3% 7M $NH_3$ in MeOH: 97% DCM) to provide alcohol 17 (2.9 g, 10 mmol, 49%) as a yellowish oil.

S-(2-(2-((4-(2,2-dimethyl-1,3-dioxan-5-yl)butyl)(methyl)amino)ethoxy)ethyl) ethanethioate (18)

To a solution of alcohol 17 (2.9 g, 10 mmol) in THF (100 mL) were added triphenylphosphine (4.2 g, 16 mmol) and di-tert-butyl (E)-diazene-1,2-dicarboxylate (3.0 g, 13 mmol) and the resulting mixture was stirred for 5 minutes. Then, thioacetic acid (0.99 g, 0.94 mL, 13 mmol) was added and the mixture decolorized for the most part. The resulting mixture was stirred for 16 hours at room temperature. The reaction mixture was concentrated and the crude material was purified by column chromatography (20% Acetone in heptane+1% $NEt_3$) to provide thioacetate 18 (3.5 g, 10 mmol, quant.) as a yellow oil.

Integration of Formula (XIIIb)-Precursor:

4-(2,2-dimethyl-1,3-dioxan-5-yl)-N-(2-(2-((2-(3-(((13S,17S)-17-(3-((1,1,1,3,3,3-hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)propoxy)ethyl)disulfaneyl)ethoxy)ethyl)-N-methylbutan-1-amine (19)

To a solution of thiotosylate 10 (1.1 g, 1.3 mmol) and thioacetate 18 (0.70 g, 2.0 mmol) in DCM (100 mL) and MeOH (10 mL) was added a solution of sodium methoxide (5.4 M, 0.50 mL, 2.7 mmol). The resulting mixture was stirred for 1 hour. The mixture was diluted with DCM (100 mL), washed with $NaHCO_3$ and brine, dried over $Na_2SO_4$, and concentrated. The crude material was purified by column chromatography (10-20% Acetone/heptane+1% $NEt_3$) to provide disulfide 19 (0.58 g, 0.6 mmol, 45%) as a clear oil.

2-(1-(((13S,17S)-17-(3-((1,1,1,3,3,3-hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)-14-methyl-4,11-dioxa-7,8-dithia-14-azaoctadecan-18-yl)propane-1,3-diol (20)

To a solution of disulfide 20 (0.58 g, 0.60 mmol) in MeOH (50 mL) (extra DCM was added for solubility) was added p-toluene sulfonic acid (0.14 g, 0.72 mmol) and the resulting mixture was stirred at room temperature for 1 hour. The mixture was concentrated and the residue dissolved in DCM (100 mL). The mixture was washed with $NaHCO_3$ and brine, dried over $Na_2SO_4$, and concentrated to provide diol 20 (0.53 g, 0.57 mmol, 95%) as a clear oil.

19-((bis(4-methoxyphenyl)(phenyl)methoxy)methyl)-1-(((13S,17S)-17-(3-((1,1,1,3,3,3-hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)-14-methyl-4,11-dioxa-7,8-dithia-14-azaicosan-20-ol (21)

To a solution of diol 20 (1.0 g, 1.1 mmol) in DCM (50 mL) were added triethylamine (0.22 g, 0.30 mL, 2.2 mmol), DMAP (13 mg, 0.11 mmol) and finally 4,4'-(chloro(phenyl)methylene)bis(methoxybenzene) (0.36 g, 1.1 mmol) and the resulting mixture was stirred 16 hours at room temperature. The mixture was washed with $NaHCO_3$ and brine, dried over $Na_2SO_4$, and concentrated. The crude material was purified by column chromatography (20-25% Acetone in heptane+1% $NEt_3$, using silica pretreated with $NEt_3$) to provide compound 21 (0.96 g, 0.78 mmol, 72%) as a clear yellowish oil.

19-((bis(4-methoxyphenyl)(phenyl)methoxy)methyl)-1-(((13S,17S)-17-(3-((1,1,1,3,3,3-hexafluoro-2-(trifluoromethyl)propan-2-yl)oxy)propoxy)-13-methyl-7,8,9,11,12,13,14,15,16,17-decahydro-6H-cyclopenta[a]phenanthren-3-yl)oxy)-14-methyl-4,11-dioxa-7,8-dithia-14-azaicosan-20-yl (2-cyanoethyl) diisopropyl phosphoramidite [Formula (XIIIb)-Precursor]

To a solution of alcohol 21 (0.96 g, 0.78 mmol) in DCM (50 mL) were added 3-((bis(diisopropylamino)phosphaneyl)oxy)propanenitrile (0.31 g, 0.32 mL, 1.0 mmol) and a solution of NMM and TFA (2.0 mL, 0.5 M NMM and 0.25 M TFA, 1.3 eq. NMM) in DCM. The resulting mixture was stirred at room temperature for 2 hours after which TLC showed partial conversion. Additional phosphaneyl (0.5 eq.) and NMM/TFA solution (0.5 eq. NMM) were added and the mixture was stirred for 1 hour. TLC showed full conversion. The mixture was washed with $NaHCO_3$ and brine, dried over $Na_2SO_4$, and concentrated. The crude material was purified using column chromatography (20% acetone in heptane+1% $NEt_3$, using silica pretreated with $NEt_3$) to provide Formula (XIIIb)-Precursor (0.96 g, 0.67 mmol, 86%) as a clear oil.

Example 2L: Synthesis of Formula (XIV-F) Precursor

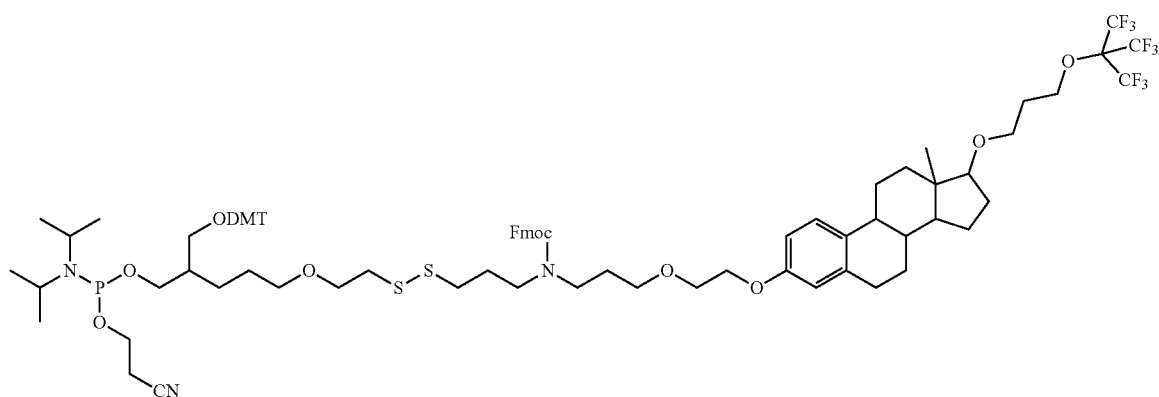

Formula (XIV-F) Precursor

Starting from compound 3 the phenol can be alkylated using bromide K-105-F-1 (see below). The perfluoro-moiety can then be introduced using Mitsunobu conditions (K-150-F-3). The amide and ester will be reduced simultaneously and the formed secondary amine can then be protected with a Boc-group. Final introduction of the thioacetate group using Mitsunobu conditions will provide building block K-150-F-6.

Scheme 20. Synthesis of thioacetate K-150-F-6

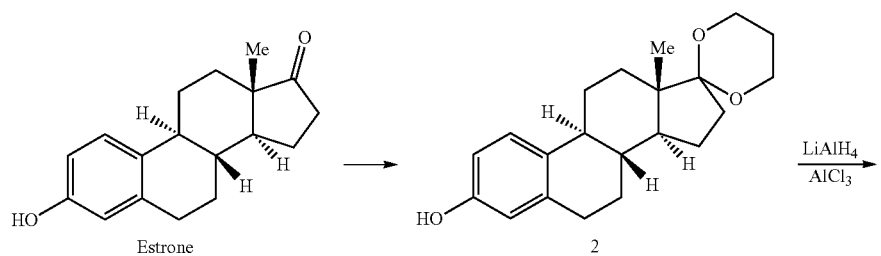

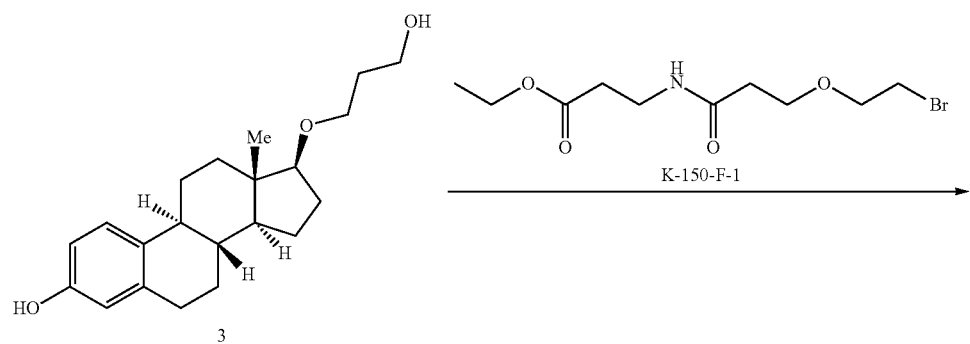

-continued
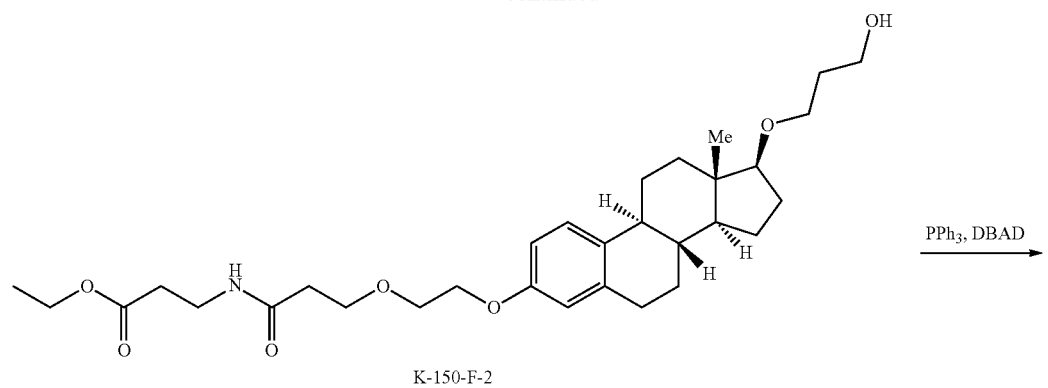
K-150-F-2
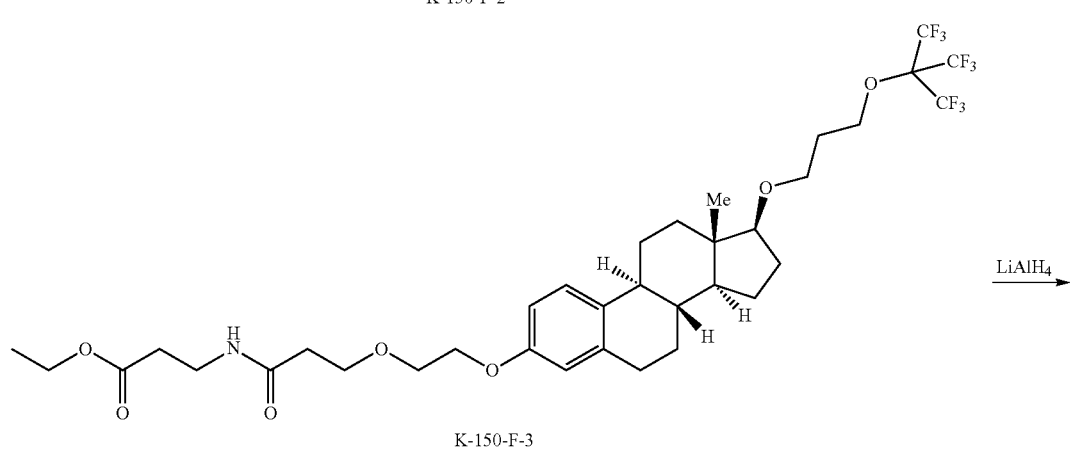
K-150-F-3
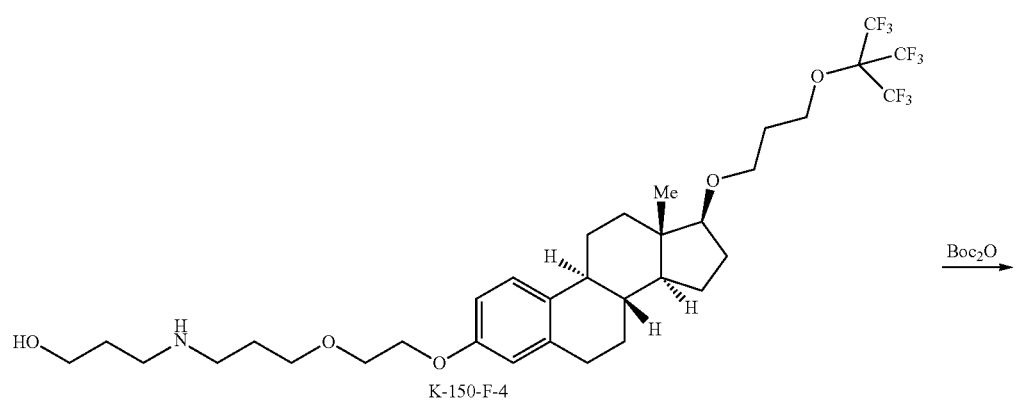
K-150-F-4
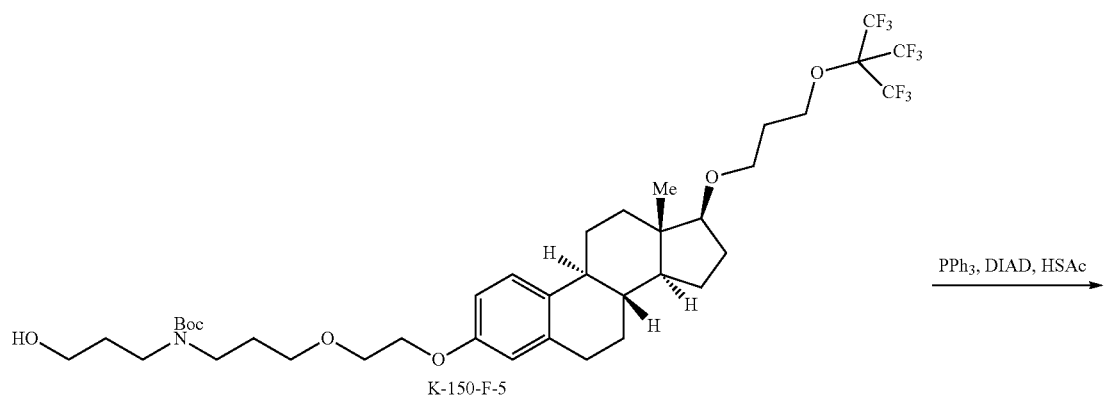
K-150-F-5

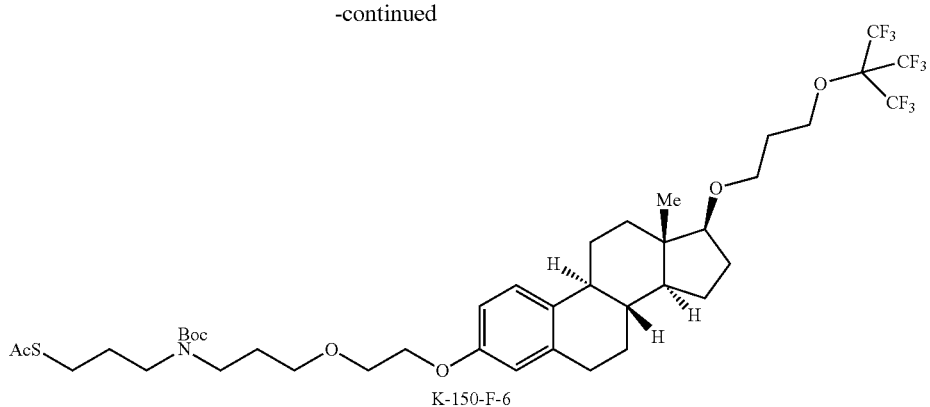

K-150-F-6

The quickest route towards desired building block K-150-F is the ring-opening of 1,5-dioxepan-2-one with beta-alanine. Ring-opening with beta-alanine provides amide K-150-F-7. Esterification with EtOH protects the carboxylic acid. Subsequent conversion of the alcohol to the bromide m to provide building block K-105-F-1, which is then alkylated onto the phenol.

Scheme 21. Synthesis of bromide K-150-F-1

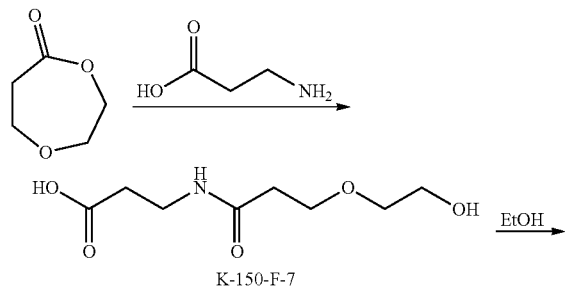

K-150-F-7

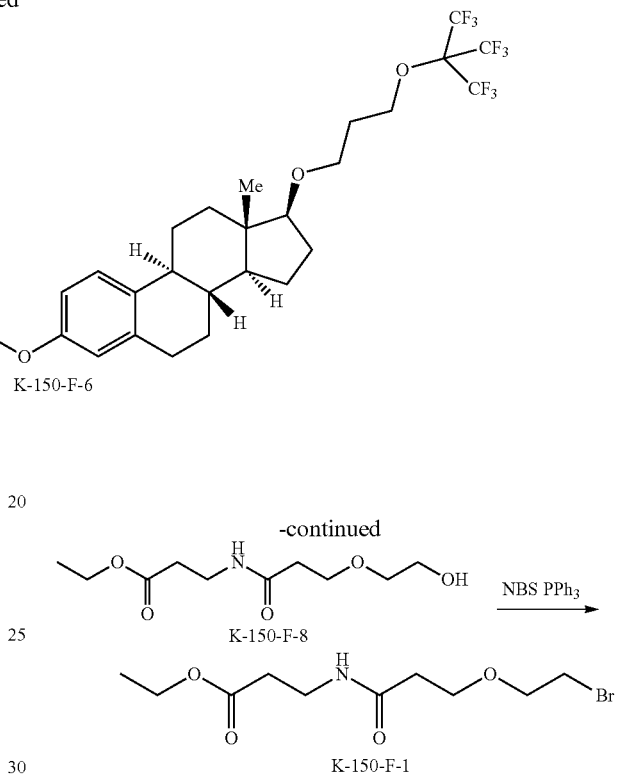

K-150-F-8

K-150-F-1

Integration of Formula (XIV-F) Precursor

The assembly starts with the disulfide formation between building blocks K-150-F-6 and thiotosylate 6. Then, the acetonide moiety and the Boc-group will be simultaneously removed by treatment with acid. The free secondary amine can then be protected with the Fmoc group. Subsequent DMT attachment and phosphoramidite formation will provide Formula (XIV-F) Precursor.

Example 2m: Synthesis of Formula (XV-F) Precursor

Formula (XV-F)-Precursor

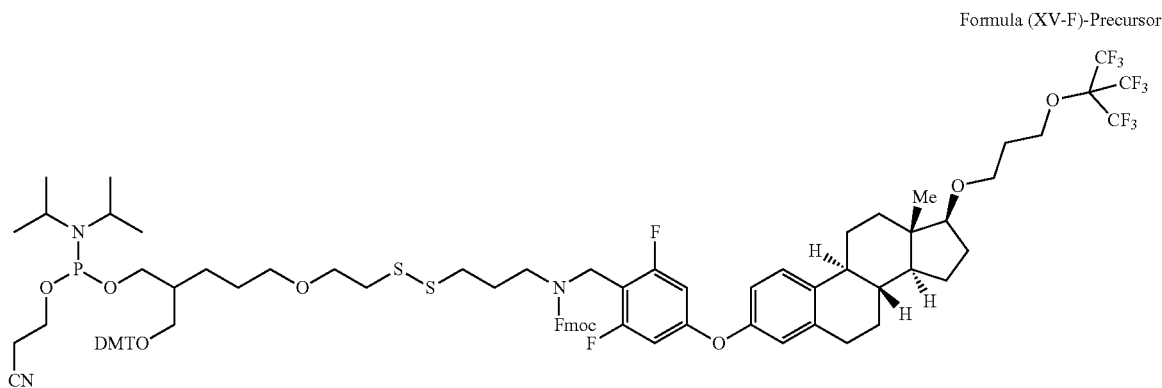

Formula (XV-F) Precursor will be prepared from thiotosylate 13 (Scheme 22) and building block 7 (Scheme 23):
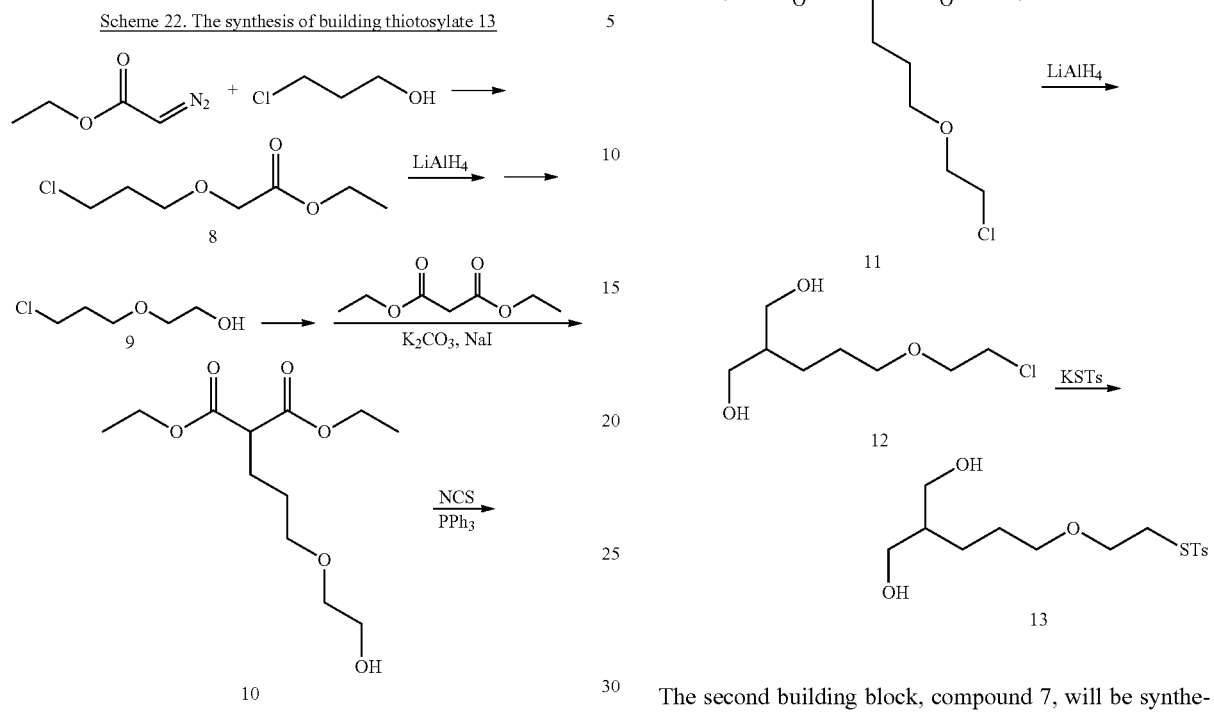
The second building block, compound 7, will be synthesized as shown in Scheme 23:
Scheme 23. The synthesis of building block 7
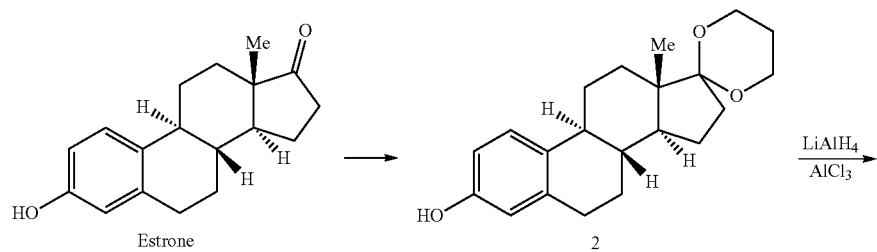
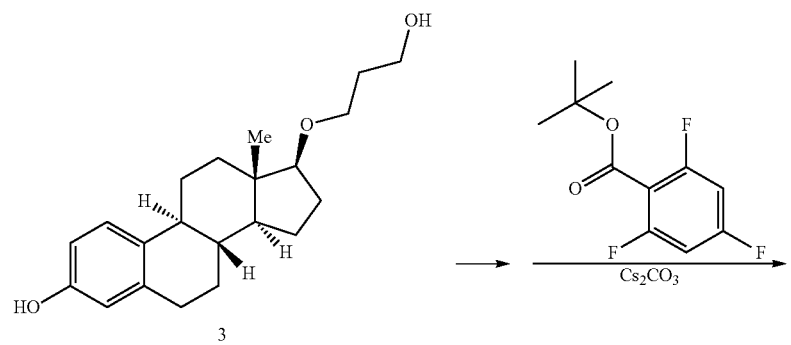

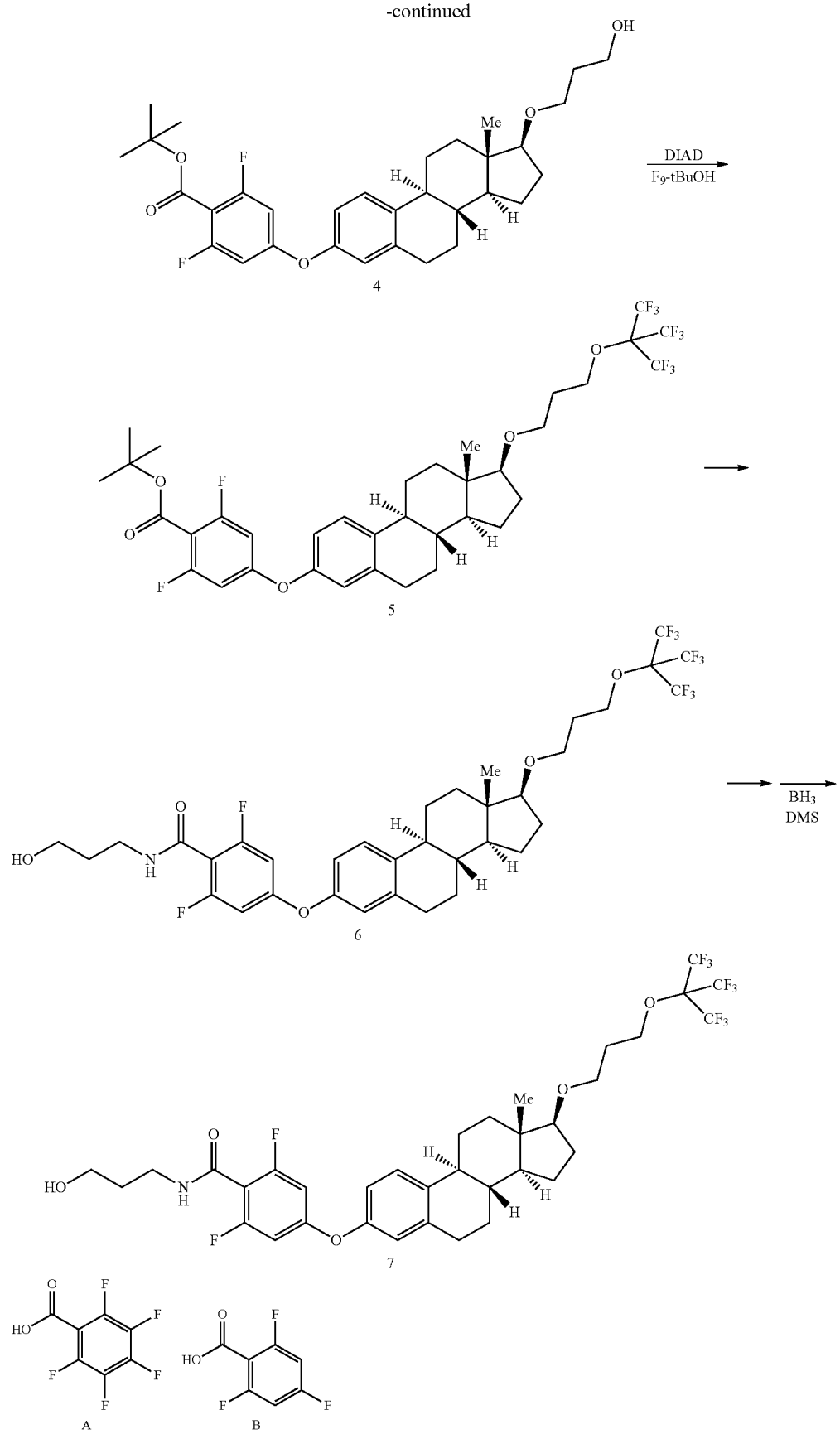

Integration and Completion of the Synthesis of Formula (XV-F)-Precursor:
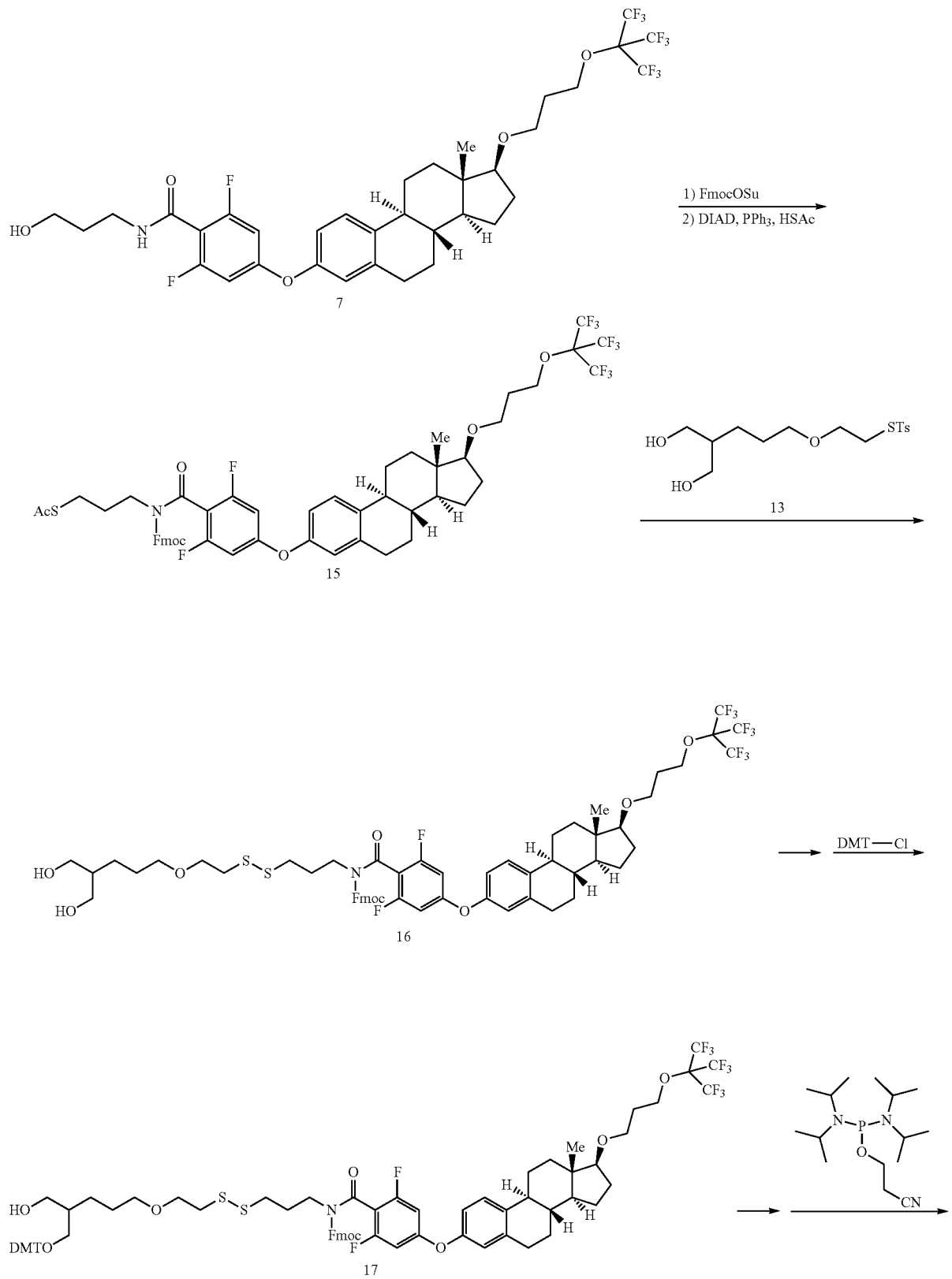
Scheme 24. Synthetic strategy towards Formula (XV-F)-Precursor

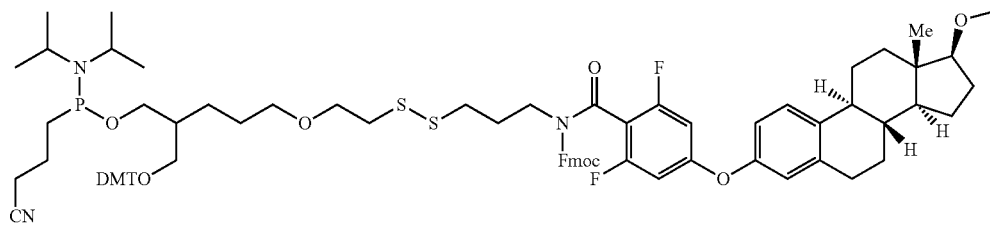
Formula (XV-F)-Precursor
Example 2n: A Method for Synthesis of Formula (VIII-F) Precursor
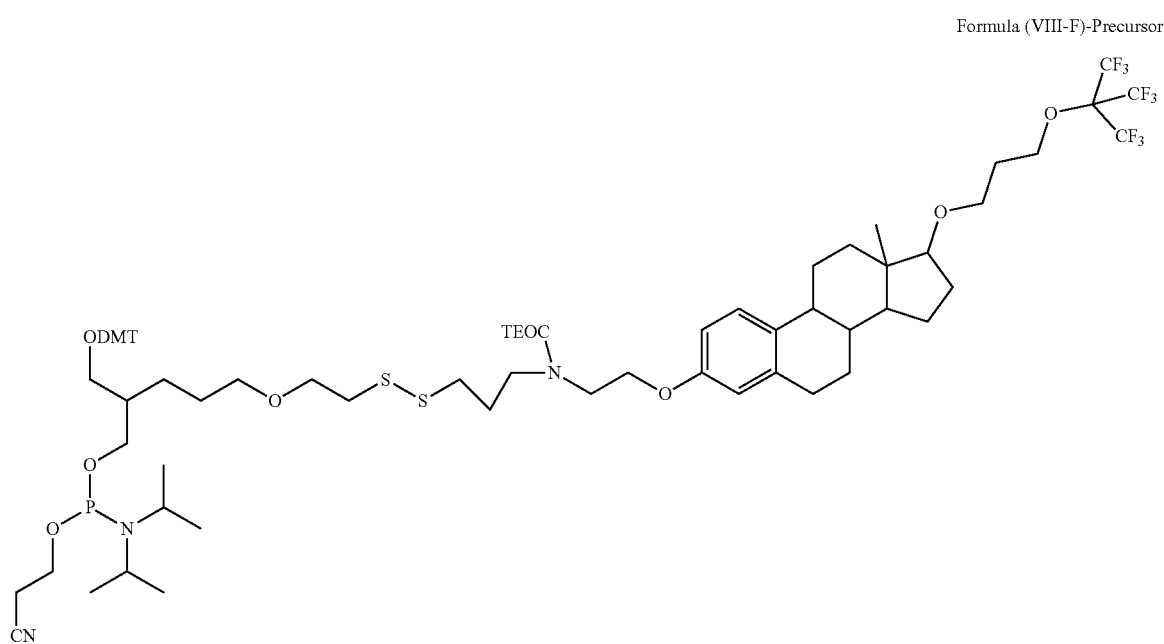
Formula (VIII-F)-Precursor Synthesis starts by the synthesis of the key building block thiotosylate 16, which is performed according to the following Scheme 25:
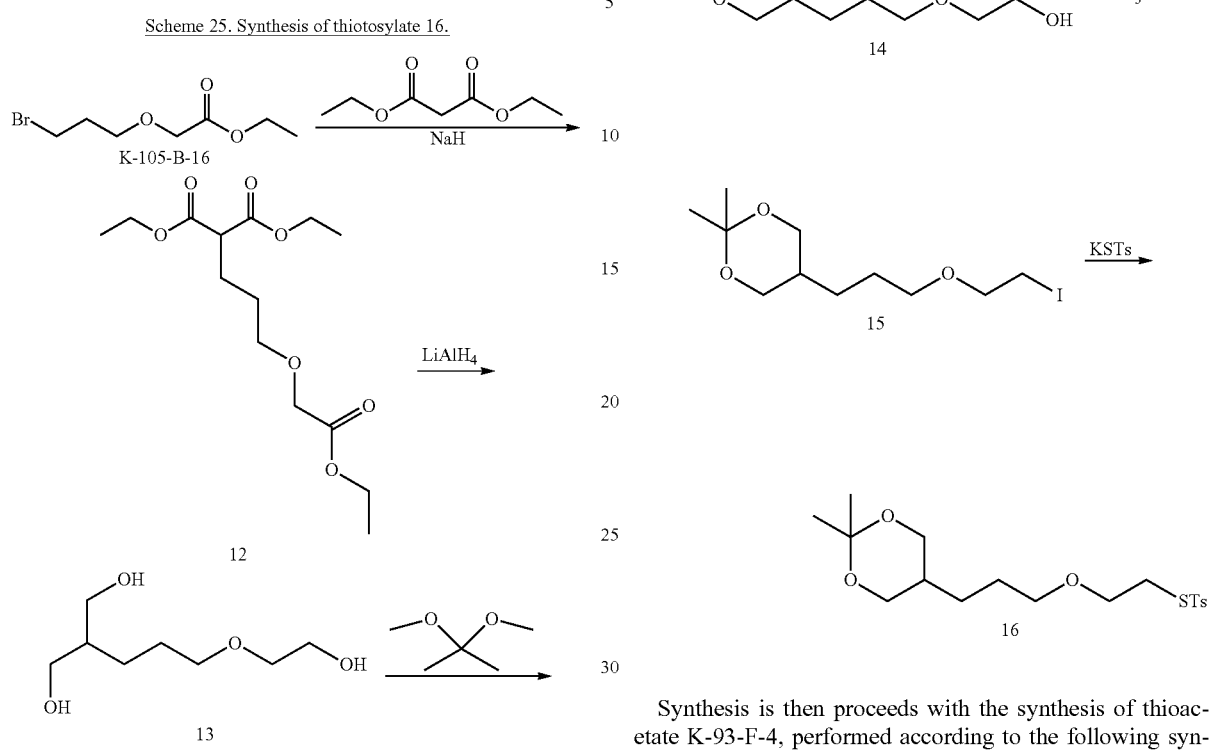
Scheme 25. Synthesis of thiotosylate 16.
Synthesis is then proceeds with the synthesis of thioacetate K-93-F-4, performed according to the following synthetic scheme 26:
Scheme 26. Synthesis of thioacetate K-93-F-4
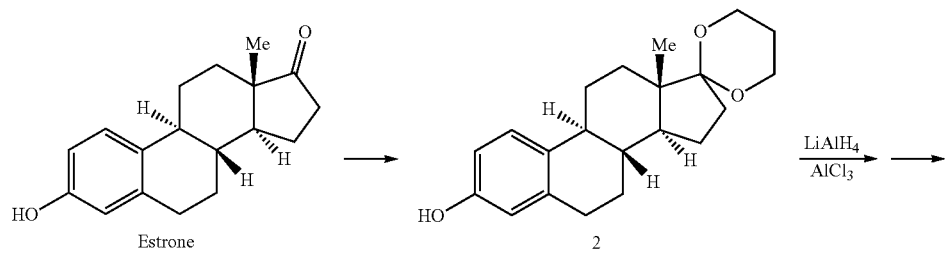
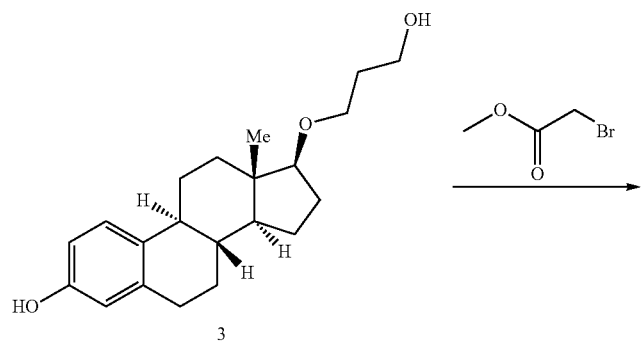

-continued
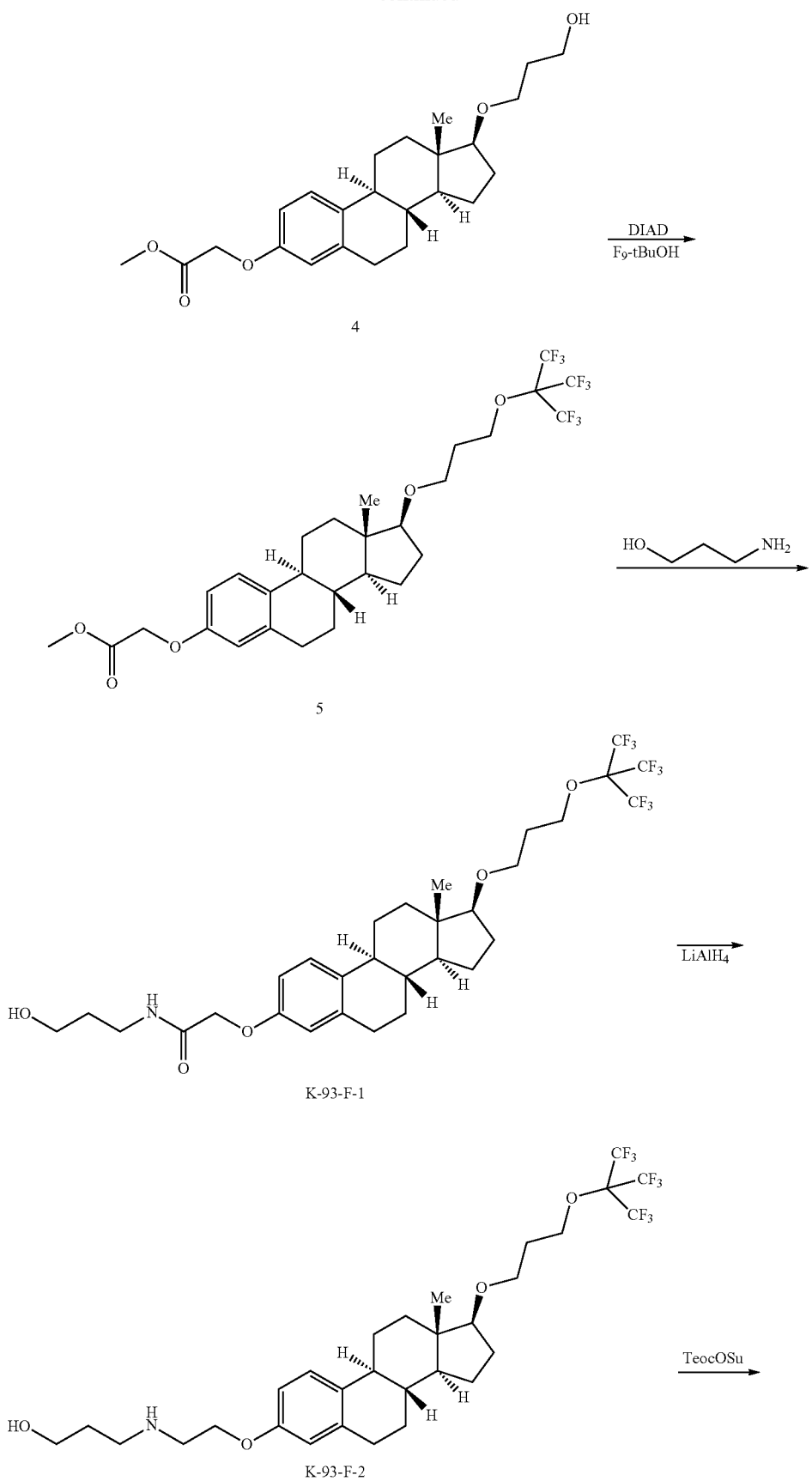

-continued
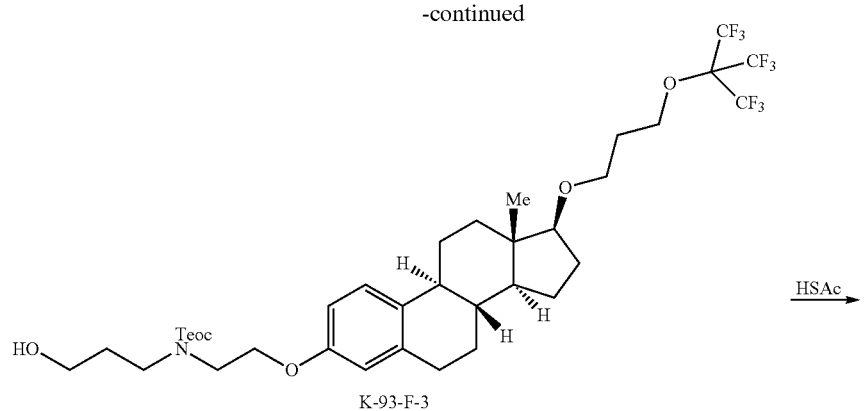
K-93-F-3
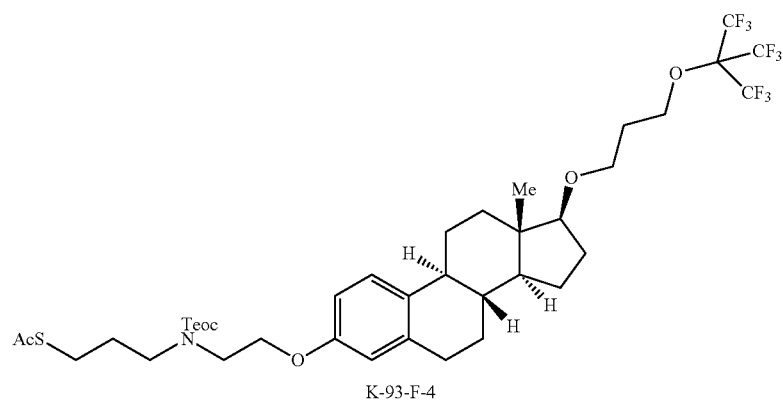
K-93-F-4
Compound F-2 was Teoc-protected to provide compound F-3 in 95% yield. The synthesis of the thioacetate F-4 was performed in ca 60% yield. 1.76 grams were isolated.
Having the key fragments thiotosylate 16 and thioacetate K-93-F-4, synthesis then proceeded according to the following Scheme 27:
Scheme 27: Completion of synthesis of Formula (VIII-F)-Precursor
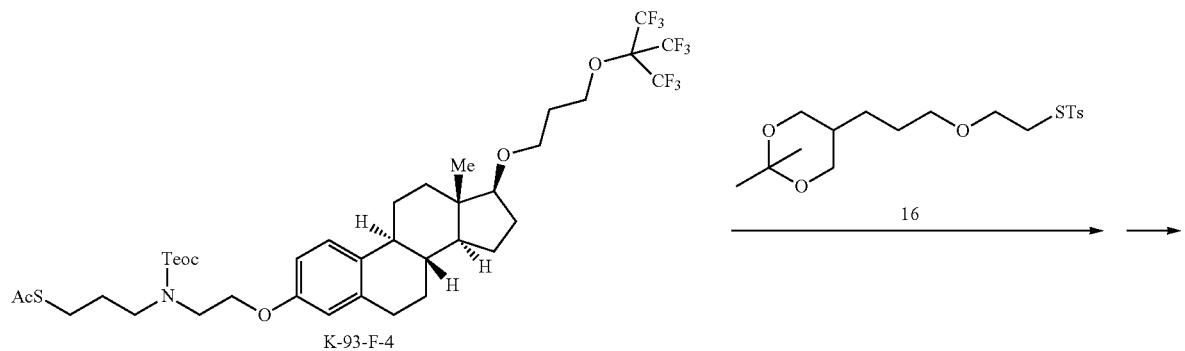

-continued
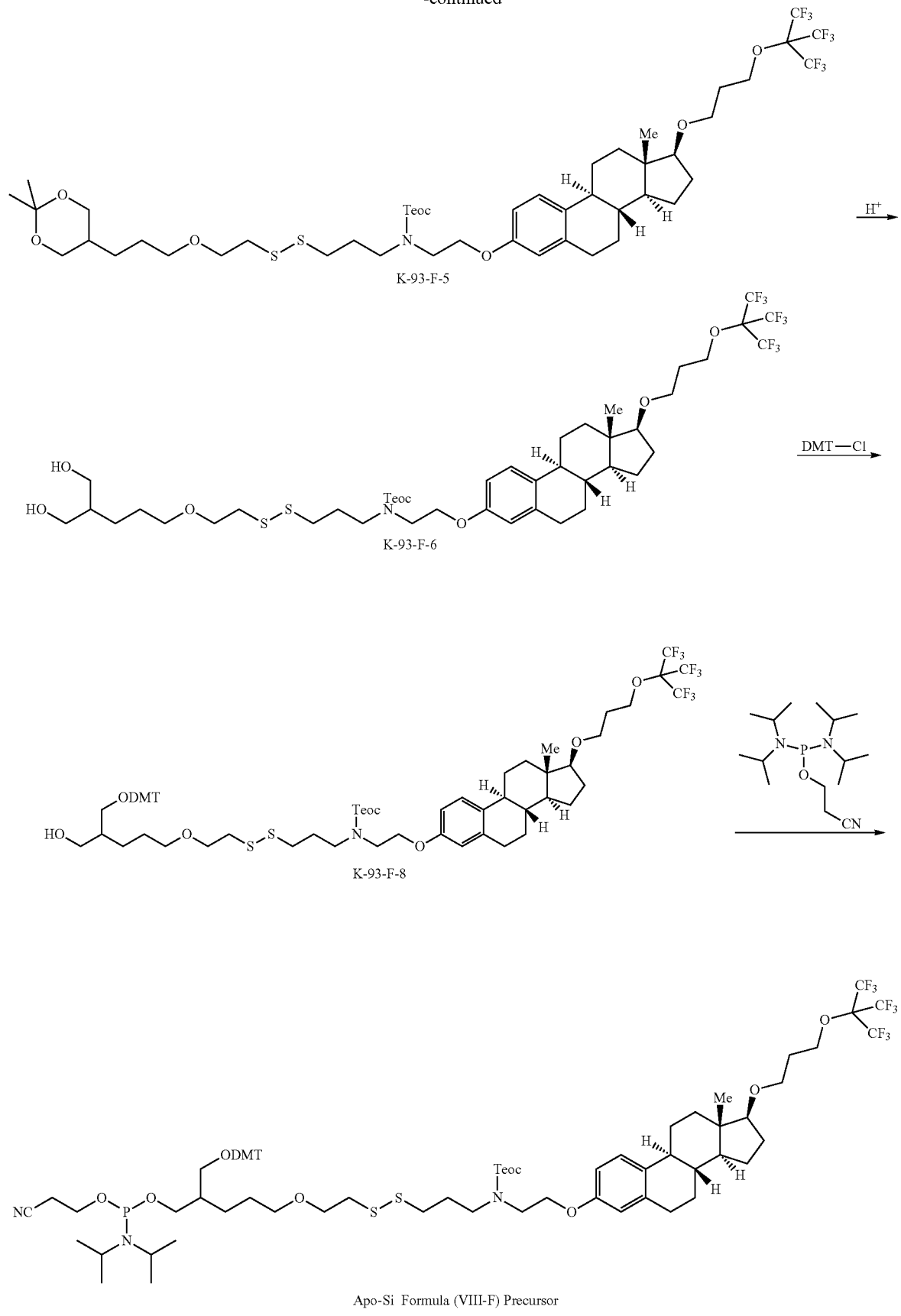

Initially, fragments thiotosylate 16 and thioacetate K-93-F-4 were coupled with generation of a disulfide bond, to provide intermediate K-95-F-5. F-5 was treated with pTsOH in MeOH to liberate the diol, thus generating F-6 (93% yield; 1.3 grams). F-6 was then monoprotected with DMT-Cl to provide compound F-8. Phosphoramidite was then attached, compound according to Formula (VIII-F)-Precursor (Teoc), was isolated in 1.004 gram, and stored in vials for shipment. It is noteworthy, that Teoc as a protecting group is relatively stable towards acids, bases, as well as towards reducing and oxidizing agents, but can be easily removed by addition of fluorides, thus rendering it useful as a protecting group for amines, during the synthesis of oligonucleotides. In the synthesis of E moieties of the Invention, this protecting group can therefore have a role in the generation of secondary amines, as installed in the compounds according to Formulae (VIII-H), (XIV-H) and (XV-H).

Example 2p: A Method for Synthesis of Formula (XVI-F) Precursor

Formula (XVI-F)-Precursor

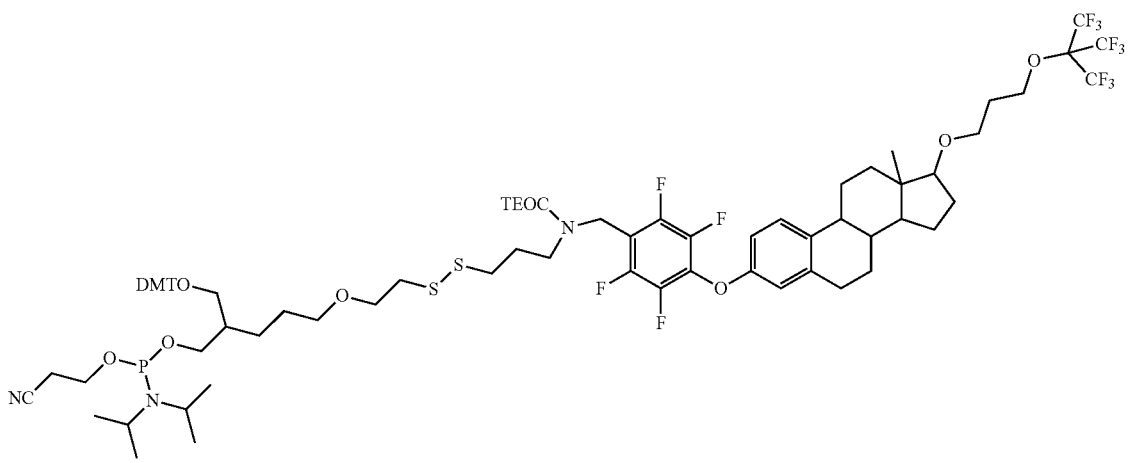

Synthesis is identical to the synthesis of Formula (XV-F) Precursor, as described in Example 2m; with two exceptions: (i). The starting material for the L moiety is pentafluoro-benzoate (A), and not difluorobenzoate (B). (ii), The protecting group for the amine is TEOC, installed as described in Example 2n;

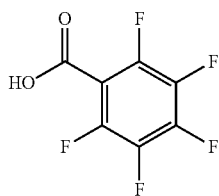

A

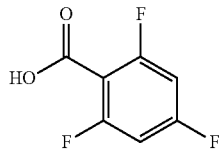

B

Example 3: A Potential Mechanism of Action (MOA) of a Conjugate of the Invention, being a Dicer Substrates, in Trans-Membrane Delivery A potential Mechanism of Action of the Conjugates of the Invention comprising OD is described herein in a non-limiting manner. Said MOA comprises four steps:
1. Interaction of the Conjugate with the Outer Membrane Leaflet:
When the Conjugate of the Invention is siRNA or dsiRNA, linked to 2-3 E moieties, the Conjugate approaches the outer leaflet of the membrane in a position wherein the cylindrical RNA Duplex is parallel to the membrane surface, and the E, E' or E" moieties are oriented towards the membrane core, perpendicular to the membrane surface. This approach acts to anchor the OD to the membrane surface. The resultant forced proximity of the highly negatively-charged RNA to the outer membrane leaflet, results in energetically-unfavorable focal membrane strain, extension of the surface area of the outer phospholipid leaflet and disturbance of the hydration shell of the phospholipid head-groups, which all lead to focal bending of the membrane.
2. Relaxation of the Bending Energy:
Relaxation of the unfavorable membrane bending can take place either through endocytosis, flip-flop or both. Both processes are supportive of initiation and/or propagation of trans-membrane delivery of a conjugate of the Invention, comprising the macromolecular drug into the cytoplasm, either directly, or through the endosomal compartment.
3. Detachment of the E, E' or E" Moieties within the Cytoplasm in a Red-Ox-Mediated Process, with Release of the Cargo Drug.
While one or more E, E' or E" moiety, as described above, is required for the trans-membrane passage of siRNA or dsiRNA Conjugates, it is desirable to remove these delivery moieties, once the Conjugate reaches the cytoplasm, and excrete them from the body, thus liberating the cargo drug to approach its cytoplasmatic sites of action. In the case that the cargo drug is siRNA or dsiRNA, this cleavage enables to avoid steric hindrance in the interaction of the siRNA or dsiRNA with the gene silencing protein complexes (Dicer and RISC). In addition, such detachment of the cargo drug from the E moieties would minimize burden of Conjugates on cellular phospholipid membranes, a measure that would be advantageous from the safety perspective. For this purpose, the E moieties of the Invention comprise a disulfide moiety. Under oxidative conditions, such as those that prevail in the extracellular milieu, the disulfide manifests high stability, and therefore enables the Conjugate of the Invention, upon its systemic administration in vivo, to distribute widely in the body, and contact the huge cell membrane pool.

By contrast, the cytoplasm is a highly reductive environment, mainly due to its high concentrations of reduced glutathione (GSH), being continuously generated within the cytoplasm of any living cell, being about three to four-orders of magnitude higher in the cytoplasm, in comparison with the extracellular space: 1-5 mM versus 3-5 µM.

Due to these remarkable reductive conditions within the cytoplasm, disulfide groups of E moieties undergo robust reduction in the cytoplasmatic milieu. Consequently, there is release of the Cargo drug (e.g., dsiRNA), to exert its pharmacological actions at its target sites in the cytoplasm (e.g., at the Dicer and/or RISC protein complexes for gene silencing). Following the disulfide cleavage, the E moieties of the Invention are excreted from the body via the bile and/or the urine, similar to other sterol-based molecules (e.g., estrogens), either directly, or following metabolism (e.g., cytochrome-P-450-mediated hydroxylation or glucuronidation in the liver).

Figure 2E:
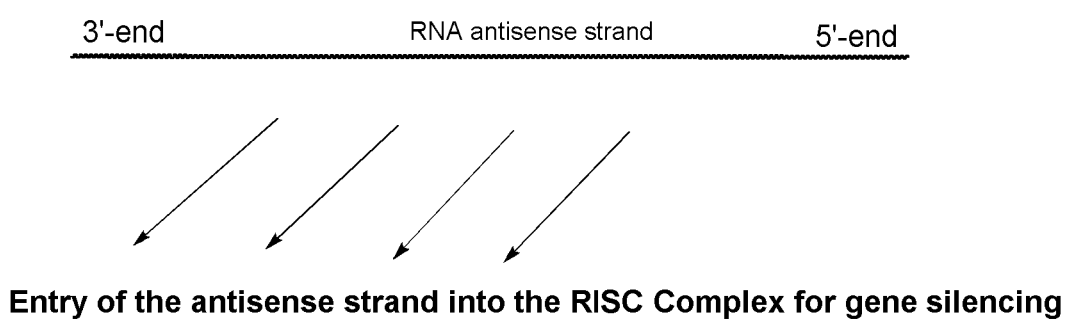

4. Interaction of the Liberated OD with the Cytoplasmatic Sites for Gene Silencing, The above MOA of a Conjugate of the Invention is exemplified, without limitation, in FIGS. 2A, 2B, 2C, 2D and 2E. Exemplified is a Conjugate according to [Cn-1-(III)], with E, and E', each having the structure according to Formulae (III). W is according to Formula (II$^1$). The exemplified RNA Duplex is a Dicer substrate of 25/27-nucleotide long, with a phosphate group linked to the 5'-end of each strand. Following the trans-membrane delivery, upon reaching the cytoplasm, due to the markedly reductive ambient conditions, cleavage and removal of the E, E' and E'' moieties take place, leaving a short stump per each E moiety, still linked to the RNA Duplex, comprising a thiol group, linked to a short hydrocarbon chain (FIG. 2B). The RNA Duplex then interacts with the Dicer endonuclease. This interaction is initiated by binding of the 3'-end of the Guide (Antisense) strand Duplex, which has a 2-nucleotide overhang, to a hydrophobic pocket of the Dicer protein; and interaction of the phosphate group of the Passenger (Sense) strand, with a respective positively-charged pocket on the protein surface. This anchoring positions the RNA Duplex on the protein surface, and enables the enzyme to perform an accurate double-strand break of the RNA Duplex, leaving a 21/21-nucleotide double-helix, with two E stumps remaining on the Passenger (Sense) strand (FIG. 2C). FIG. 2D demonstrates the subsequent removal of the sense strand by the enzyme helicase (a cytoplasmatic enzyme, capable of separating RNA strands). This action removes the residual stumps of the E moieties, thus releasing an intact antisense strand, to enter the RNA-induced silencing complex (RISC), in order to induce the desired gene silencing (FIG. 2E).

Example 4: Biological Performance of a Conjugate of the Invention in Induction of Gene Silencing, Following Intravenous Administration, in a Murine Model, in Vivo Objective:

Demonstration of the capability of a Conjugate of the Invention, comprising dsiRNA, linked to two E moieties of the Invention, to induce gene silencing upon intravenous administration.

Methods:

1). dsi-RNA Duplex, Conjugated to the E Moieties of the Invention:

A 25/27-nucleotide long dsiRNA Duplex was utilized, designed to silence the APOC3 gene. This RNA Duplex was linked at the 5'-end of each strand to an E moiety of the invention, according to Formula (IX), having the structure as described below. The APOC3 gene encodes for the APOC3 protein, a protein that is synthesized by the liver, and which has a pivotal role in the distribution and metabolism of triglycerides. Expression of APOC3 is mainly limited to the liver and the kidney.

The E moiety utilized for the experiment was according to Formula (IX). It was synthesized by Syncom BV (the Netherlands) as a precursor molecule, having DMT and phosphoramidite as protecting groups. The Apo-Si-APOC3-dsiRNA Conjugate was synthesized by Integrated DNA Technologies (IDT, Leuven, Belgium), as described in Example 1 above. It was a [Cn-1-(IX)]-APOC3-dsiRNA Conjugate, namely, it comprised two E moieties, each having the structure as set forth in Formula (IX), conjugated to dsiRNA, for silencing the APOC3gene. Therefore, the Conjugate had the following structure:

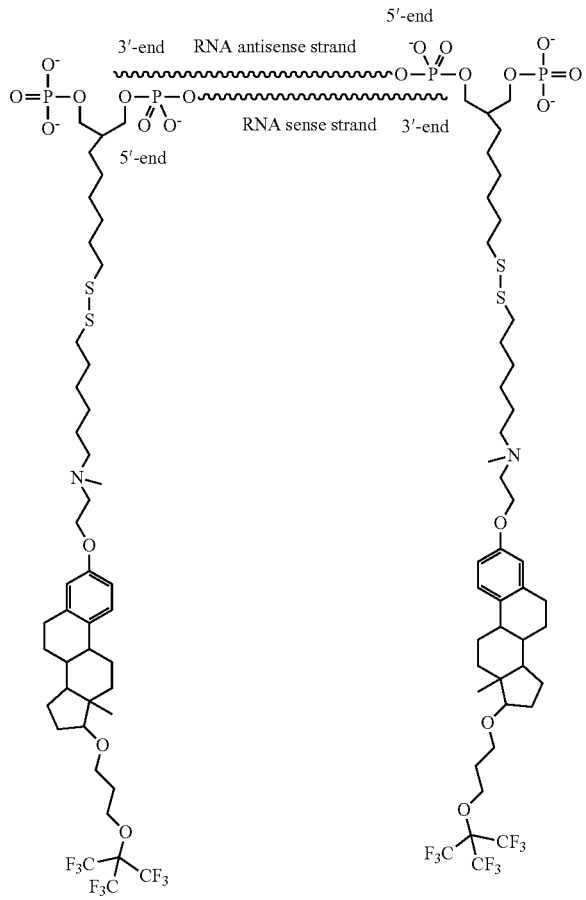

[Cn-1-(IX)]-APOC3-dsiRNA Conjugate

The genetic sequences used in this study were:
The target ApoC3-dsiRNA-Conjugate:
The sequence of the sense strand: /5'-(IX)/mGmGrAmUrGmGrArCrArArUmCrAmCrUmUrCmArGrArUrCr CCT;
The sequence of the anti-sense strand: /5'(IX)/rArGmGrGrArUrCrUmGrAmArGmUrGrArUrUrGrUrCrCrAmUrCmCmA mG;
wherein m means methylated, and r means a ribonucleotide.
Control #1: Naked APoC3-dsiRNA Conjugate (RNA Duplex, with sequence that is specific for silencing the ApoC3 gene, but devoid of Apo-Si Molecular Nanomotor delivery system).
The sequence of the sense strand:
mGmGrAmUrGmGrArCrA rArUmCrAmCrUmUrCmA rGrArU rCrCCT;
The sequence of the anti-sense strand:
rArGmG rGrArU rCrUmG rAmArG mUrGrA rUrUrG rUrCrCrAmUrCmCmAmG.
Control #2: [Cn-1-(IX)]-KRAS-dsiRNA Conjugate; (non-related RNA sequence, conjugated to the Apo-Si Molecular Nanomotor delivery system).
The sequence of the sense strand: /5'-(IX)/mAmArGmGrUmGrUrArCrArGmUrUmArU mGrUmGrArArUrArCTT;
The sequence of the anti-sense strand: /5'-(IX)/rArAmGrUrArUrUrCmArCmArUmArArCrUrGrUrArCrArCmCrUmU mGmU.
Control #3: Vehicle; 5% glucose solution, in water for injection.

2). Formulation:
All Test and Control Article(s) were dissolved in sterile water for injection, RNase free, that contained 5% glucose. A stock solution of 5 mg/ml was freshly prepared before administration.

3). Animal Care and Housing:
BALB/c mice (Male, 22-29 gr) were obtained from Envigo (Israel Ltd.). Mice were kept in 12-hour day/night cycle conditions, fed ad libitum diet, and allowed to acclimate for at least 3 days before the performance of the experiments. Each experimental group comprised 7 animals.

4). Study Design:
Study included 4 treatment groups as follows: (i). Vehicle: 5% glucose in water for injection; (ii). "Naked" dsiRNA for ApoC3 (without attachment of Molecular Nanomotor moieties); (iii). [Cn-1-(IX)]-KRAS-dsiRNA Conjugate (non-related RNA sequence, conjugated to the Apo-Si Molecular Nanomotor delivery system); (iv). The target [Cn-1-(IX)]-ApoC3 dsiRNA Conjugate.
Each of the study groups comprised 5-7 mice. Mice were injected intravenously (i.v.) 3 consecutive daily doses, each dose being of 50 mg/Kg, injected through the tail vein, in a dose volume of 10 ml/Kg. The protocol was adopted, without modification, from Wolfram, C, et al., (*Nat Biotechnol.* 25:1149-57, 2007). On day #4, 24 hours after the last dose, mice were weighted, sacrificed using $CO_2$ narcosis, livers were harvested and subjected immediately to RNA extraction.

5). RNA Extraction and qRT-PCR:
Liver samples of 10-100 mg were extracted and soaked in TRIzol reagent. Tissues were then homogenized by the bullet blender homogenizer (Next Advance) in the presence of stainless steel beads (0.9-2.0 mm). Mixtures were briefly centrifuged to remove debris and bullets. Total RNA was extracted using the PureLink RNA mini kit (Invitrogen) according to the manufacturer instructions. RNA was quantified with the infinite M200-Pro Multimode Reader (Tecan). RNA was reversed transcribed with the High-Capacity cDNA Reverse Transcription Kit (ABI), and ApoC3 mRNA expression was measured with the Taqman qRT-PCR procedure, with normalization to beta-Actin (Step-one-Plus, ABI).

6). Data Analysis
Data analysis was performed using the Microsoft Excel software. Statistical significance of inter-group was evaluated using unpaired Student t-test (two-tailed), with significance determined as $p<0.05$. Data are presented as mean±SD.

Results:
As shown in FIG. 3A, [Cn-1-(IX)]-ApoC3 dsiRNA Conjugate induced marked knock-down of the expression of the ApoC3 gene (40%). This reduction in gene expression was highly statistically-significant, in comparison to all other experimental groups.
As shown in FIG. 3B, a statistically-significant knock-down of the expression of the ApoC3 gene was also observed in the kidneys (21%). Importantly, also in the kidneys, this difference was statistically-significant in comparison to all three control groups.

Conclusion:
A Conjugate of the Invention, comprising two E moieties, linked to dsiRNA designed to silence the expression of the ApoC3 gene, manifested significant activity upon systemic intravenous administration in vivo, in induction of selective knock-down of the expression of the target gene, in both liver and kidney. These results support the notion, that the Apo-si drug delivery system has a systemic mode of activity: upon intravenous administration, the Apo-Si system, conjugated to dsiRNA, enables systemic distribution of the genetic drug, and respective multi-organ and specific gene silencing.

Example 5: Biological Performance of a Conjugate of the Invention, Wherein E and E' are Each According to Formula (IV), in Gene Silencing In Vitro Study Objective:
Assessment of the performance of a Conjugate of the Invention, [Cn-1-(IV)]-EGFP-dsiRNA, comprising E and E' moieties, each having the structure as set forth in Formula (IV), and linked to EGFP-specific dsiRNA, in silencing the expression of the EGFP gene, in vitro.

Methods:
The dsiRNA Duplex:
The siRNA Duplex was a Dicer's substrate, designed to silence the EGFP gene. An E moiety of the structure as set forth in Formula (IV) was attached to each RNA strand, at its 5'-end. Therefore, the Conjugate utilized in this study was [Cn-1-(IV)]-EGFP-dsiRNA, having the following structure:

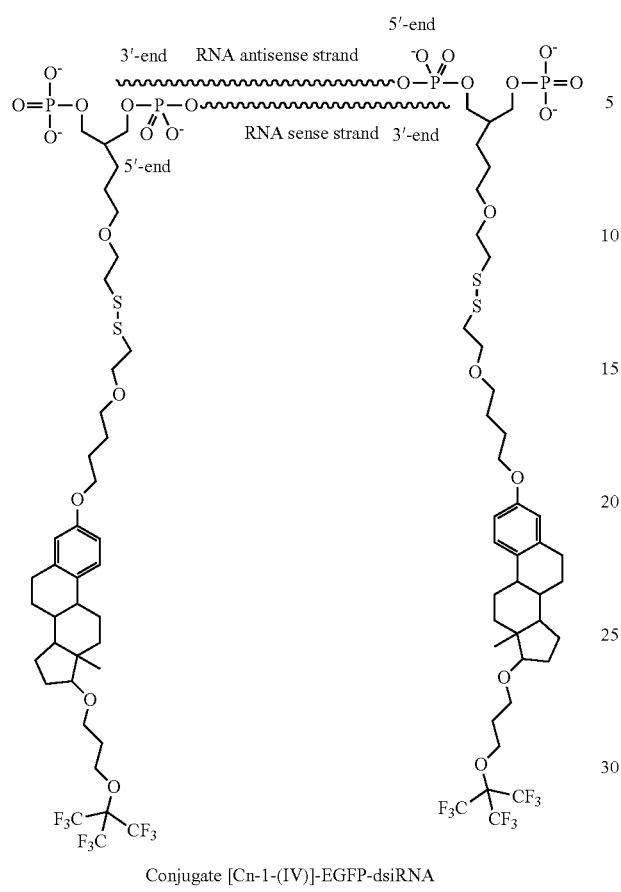

Conjugate [Cn-1-(IV)]-EGFP-dsiRNA

The nucleotide sequences were as follows:
Sense: 5'-pho s/iApo-Si-K103A/mAmCrCmCrUmGrA-rArGrUrUmCrAmUrCmUrG mC rArCr-CrArCmCGrUrCrA
Anti-sense: 5'-phos/iApo-Si-K103A/rCrGmGrUrGrGrU-rGmCrAmGrAmUrGrArA rCrUrGmGrGmUmCmA
Studies in vitro: Hela-GFP cell lines were obtained from Cell Biolabs. Cells were grown in Dulbecco's modified Eagle's medium (Gibco) supplemented with 10% FBS (Gibco), 100 U/ml penicillin 100 mg/ml streptomycin (Biological Industries, Israel) and blasticidin 10 µg/ml. Cells were maintained in a 37° C. incubator, with 5% CO2 humidified air. One day before transfection, cells were plated (40,000 cells/well) on 24-well black glass bottom plates. The following day, cells were exposed to Conjugate [Cn-1-(IV)]-EGFP-dsiRNA in the presence of 10% serum. For serum-free transfections, medium was aspirated, cells were washed with Hank's Balanced Salt Solution (HBSS), and medium was then replaced with serum free Opti-MEM (Thermo Fisher Scientific) for 24 hours, followed by addition of serum for incubation for additional 48 hours. Down-regulation of protein expression was measured at 72 hours post transfection. For this purpose, medium was aspirated, and cells were washed with HBSS. EGFP fluorescence intensity was quantified by the Infinite M200-Pro Multimode Reader (Tecan), excitation wavelength 488 nm, emission wavelength 535 nm. Untreated cells were used as Controls. Experiments were performed in triplicates, results were presented as mean±SD, inter-group differences were evaluated by two-tail t-Test, and statistical significance was defined as $p<0.05$.

Results:

The [Cn-1-(IV)]-EGFP-dsiRNA Conjugate induced efficacious knockdown of expression of EGFP, as follows:

In the presence of serum, 600 nM of the Conjugate reduced EGFP expression to 73.7%±1.3 (mean±SD) of Control. In serum-free conditions, a robust EGFP knockdown was induced by the Conjugate, in a dose-dependent manner, with the EGFP expression being reduced to 55.0%±2.6%, 29.9%±0.5% and 7.4%±0.6% of Control, when cells were treated by 10, 40 and 150 nM of the Conjugate, respectively ($p<0.001$ in all intergroup comparisons).

Conclusions:

The Conjugate of the Invention [Cn-1-(IV)]-EGFP-dsiRNA is a potent moiety for delivery of a macromolecular dsiRNA Construct across phospholipid membranes into cells, and for respective induction of significant gene silencing.

Example 6: Biological Performance of a Conjugate of the Invention, Comprising E, E' and E', that are Each According to Formula (VIII-M), in Gene Silencing in Vitro; a Dose/Response Study Study Objective:

Assessment of the biological performance in vitro, of the Conjugate of the Invention [Cn-2-(VIII-M)], namely, dsiRNA, harboring E, E', and E" moieties, each being according to Formula (VIII-M), and linked to 25/27 nucleotide Dicer's substrate Duplex, designed to silence the EGFP gene.

Methods:

The structure of the Conjugate [Cn-2-(VIII-M)] is as follows:

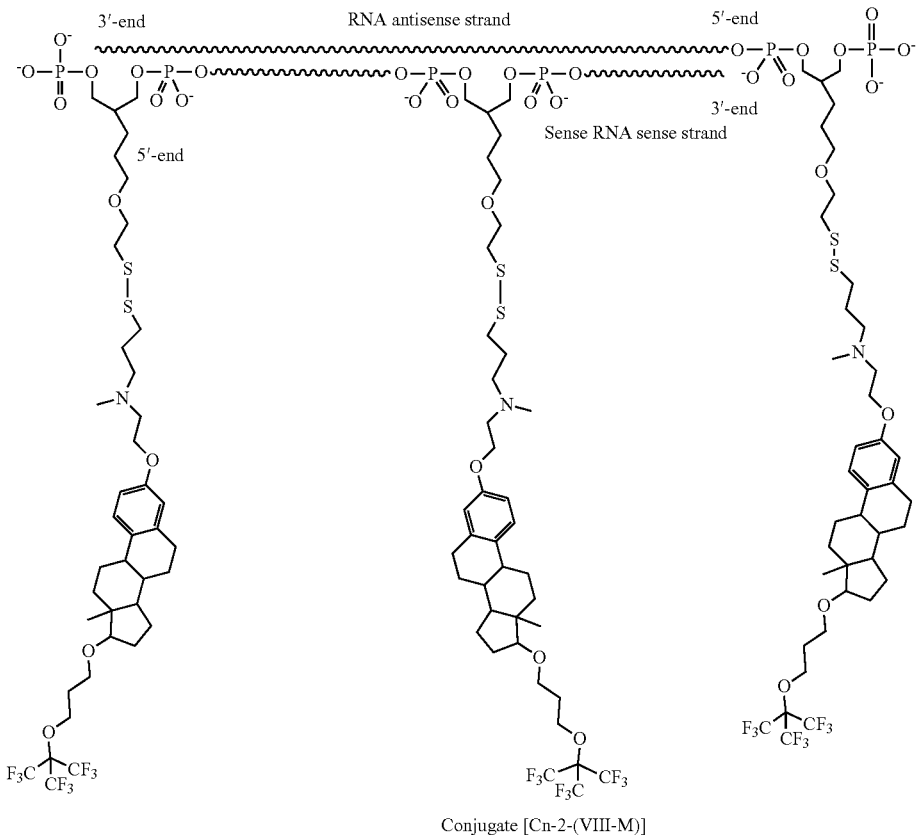

Conjugate [Cn-2-(VIII-M)]

Cell Culture:

Hela-GFP and 3T3 cell lines were obtained from Cell Biolabs. Cells of each cell type were grown in Dulbecco's modified Eagle's medium (Gibco), supplemented with 10% FBS (Gibco), 100 U/ml penicillin 100 mg/ml streptomycin (Biological Industries, Israel) and blasticidin 10 μg/ml. Cells were maintained in a 37° C. incubator with 5% CO2 humidified air. The day before transfection, cells were plated (40,000 cells/well) on 24-well black-plate glass bottom. The following day, cells started incubation for 72 hours with Conjugate [Cn-2-(VIII-M)], at concentrations of 2 nM, 10 nM, 20 nM, 40 nM, 80 nM, 150 nM and 300 nM, of which the first 24 hours were in serum-free Opti-MEM medium (Thermo Fisher Scientific), followed by incubation in medium that comprises 10% serum for additional 48 hours. Down-regulation of protein expression was measured at 72 hours post transfection. For this purpose medium was aspirated, and cells were washed with HBSS. EGFP fluorescence intensity was quantified by the Infinite M200-Pro Multimode Reader (Tecan), excitation wavelength 488 nm, emission wavelength 535 nm. Untreated cells were used as Controls. Experiments were performed in triplicates, results were presented as mean±SD. Curves of gene expression vs. Conjugate concentrations were drawn for and curve fit was calculated utiliging GraphPad, Prism-5 software.

Results:

As shown in FIGS. 4A and 4B, for both Hela cells and 3T3 cells, a clear dose/response was observed, with a highly-significant logarithmic decay, with curve fit of $R^2 \approx 0.95$ for both cell lines. For the Hela cells, $IC_{50}$ was found to be 13.54 nM, similar to the 3T3 cells, which manifested $IC_{50}$ of 19.25 nM.

Conclusions:

As examined in two cell lines in vitro, Conjugate [Cn-2-(VIII-M)]-EGFP, manifests robust delivery into cells in culture, and potent induction of gene silencing, as evaluated through assessment of protein levels. The observed low nanomolar $EC_{50}$ values support the notion, that the design of the Conjugate, with attachment of three E moieties per Duplex, is useful in enabling efficacious biological performance in gene silencing.

Example 7: Biological Performance of a Conjugate of the Invention, Comprising E and E', Moieties, that are Each According to Formula (X), in Gene Silencing in Vitro Study Objective:

Assessment of the biological performance in vitro of the Conjugate of the Invention [Cn-1-(X)], namely, dsiRNA, harboring E, and E' moieties, each being according to Formula (X), and linked to 25/27 nucleotide Dicer's substrate Duplex, designed to silence the EGFP gene.

Methods:

The structure of the Conjugate [Cn-1-(X)]-EGFP-dsiRNA is as follows:

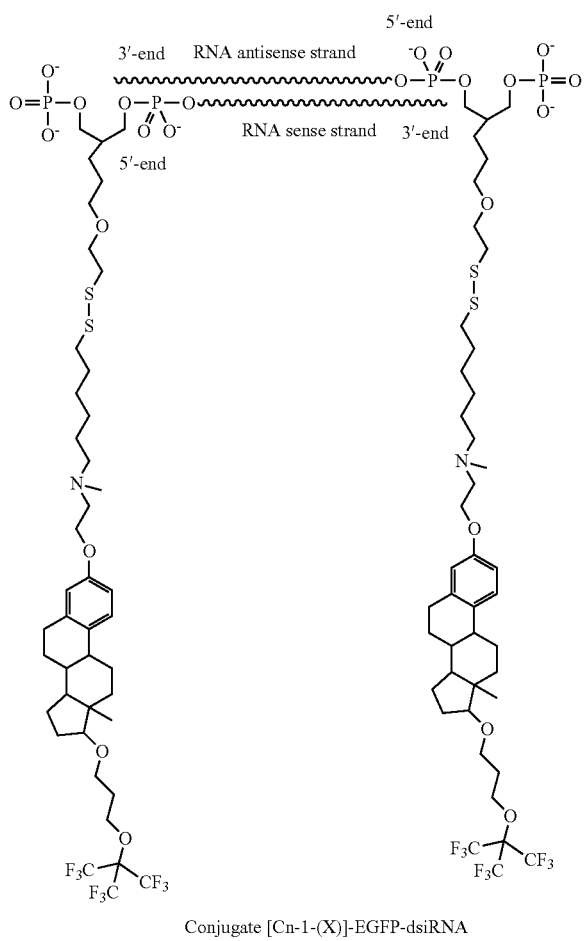

Conjugate [Cn-1-(X)]-EGFP-dsiRNA

The sequence of the EGFP-dsiRNA, the cell cultures of both Hela and 3T3 cells, and treatment protocols were all as described in Example 5. Quantification of the EGFP fluorescence intensity was performed using the Infinite M200-Pro Multimode Reader (Tecan), excitation wavelength 488 nm, emission wavelength 535 nm. Untreated cells were used as Controls. Experiments were performed in triplicates, results were presented as mean±SD, inter-group differences were evaluated by two-tail t-Test, and statistical significance was defined as $p<0.05$.

Results:

The [Cn-1-(X)]-EGFP-dsiRNA Conjugate induced efficacious knockdown of expression of EGFP, as follows:

In Hela cells: In the presence of serum, 600 nM of the Conjugate reduced EGFP expression to 76%±2 (mean±SD) of Control. In serum-free conditions, a robust knockdown of EGFP expression was induced by the Conjugate, in a dose-dependent manner, with the EGFP expression being reduced to 57.4%±4.8%; 32.1%±5.0%; and 15.9%±4.2% of Control, when cells were treated by 10, 40 and 150 nM of the Conjugate, respectively ($p<0.001$ in all intergroup comparisons).

In 3T3 cells: In serum-free conditions, a marked knockdown of EGFP expression was induced by the Conjugate, in a dose-dependent manner, with the EGFP expression being reduced to 91%±2.0%; 50.0%±5.0%; and 27%±4.0% of Control, when cells were treated by 10, 40 and 150 nM of the Conjugate, respectively ($p<0.001$ in all intergroup comparisons).

Conclusions:

The Conjugate of the Invention [Cn-1-(X)]-EGFP-dsiRNA is a potent moiety for delivery of a macromolecular dsiRNA Construct across phospholipid membranes into cells, and for the consequent respective induction of significant gene silencing.

Example 8: Biological Performance of a Conjugate of the Invention, Comprising E and E', Moieties, that are Each According to Formula (XI), in Gene Silencing in Vitro Study Objective:

Assessment of the biological performance in vitro of the Conjugate of the Invention [Cn-1-(XI)], namely, dsiRNA, harboring E, and E' moieties, each being according to Formula (XI), and linked to 25/27 nucleotide Dicer's substrate Duplex, designed to silence the EGFP gene.

Methods:

The structure of the Conjugate [Cn-1-(XI)]-EGFP-dsiRNA is as follows:

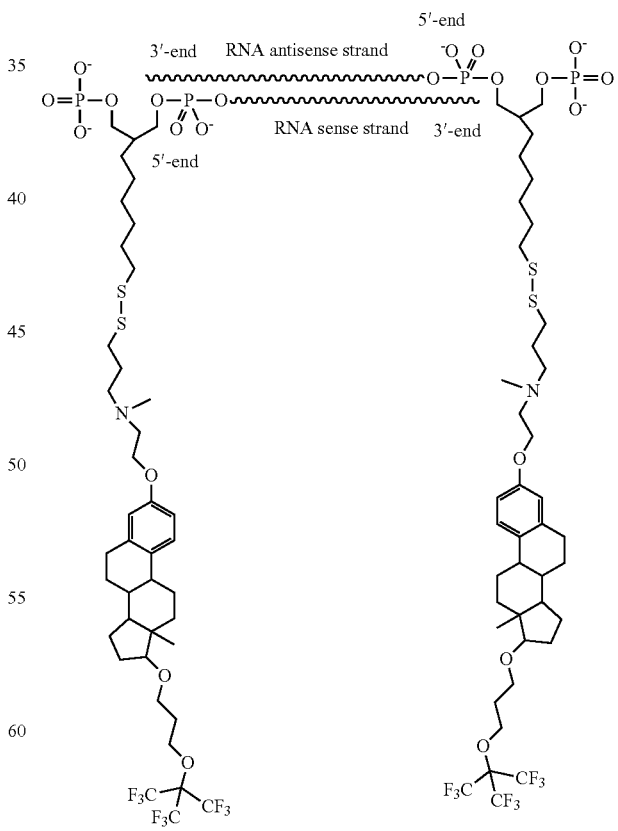

Conjugate [Cn-1-(XI)]-EGFP-dsiRNA

Study was performed in Hela cells. The sequence of the EGFP-dsRNA, the cell culture, and treatment protocols were all as described in Example 5. Quantification of the EGFP fluorescence intensity was performed using the Infinite M200-Pro Multimode Reader (Tecan), excitation wavelength 488 nm, emission wavelength 535 nm. Untreated cells were used as Controls. Experiments were performed in triplicates, results were presented as mean±SD, inter-group differences were evaluated by two-tail t-Test, and statistical significance was defined as p<0.05.

Results:

The [Cn-1-(XI)]-EGFP-dsiRNA Conjugate induced efficacious knockdown of expression of EGFP, as follows: In the presence of serum, 600 nM of the Conjugate reduced EGFP expression to 83%±4 (mean±SD) of Control. In serum-free conditions, a marked knockdown of EGFP expression was induced by the Conjugate, in a dose-dependent manner, with the EGFP expression being reduced to 55.2%±10%; 34.5%±8%; and 15.9%±4.2% of Control, when cells were treated by 10, 40 and 150 nM of the Conjugate, respectively (p<0.01 in all intergroup comparisons).

Conclusions:

The Conjugate of the Invention [Cn-1-(XI)]-EGFP-dsiRNA is a potent moiety for delivery of a macromolecular dsiRNA Construct across phospholipid membranes into cells, and for the consequent respective induction of significant gene silencing.

Example 9: Biological Performance of (Cn-1) and (Cn-2) Conjugates of the Invention, Harboring Various E, E', and E" Moieties, in Silencing the Expression of the EGFP Gene In Vitro Study Objective:

Assessment of gene silencing exerted in vitro by various Conjugates of the Invention, having various E, E' or E" moieties, that all relate to General Formulae (I) and (II), thus exemplifying Formulae (I) and (II) as general unified structural motifs, that enable trans-membrane delivery of dsiRNA across phospholipid membranes into cells, with consequent exertion of biological activity.

Methods:

Study was performed on cultured 3T3 cells, and silencing of the EFGP gene was evaluated following incubation with various Conjugates of the Invention. Study's methodology was as described in Examples 5-8 above. Incubation was performed for 72 hours, of which incubation during the first 24 hours was without serum, with addition of 10% serum thereafter. In all assessments, the concentrations of the Conjugate were either 40 nM or 150 nM. EGFP expression was evaluated by measuring the protein's fluorescence via ELISA, as described in the Examples above. EGFP expression was also measured in untreated cells, which served as Controls. The E moieties of the Invention that were evaluated were (II), (III), (IV), (V), (VI), (VII), (VIII-M), (IX). As specified above, all these moieties relate to general Formula (II). In addition, 6 Control E moieties were synthesized and conjugated to dsiRNA for silencing of the EGFP gene. The structural features of the Control moieties (Table 3) were similar to the E moieties constructed according to General Formula (II). However, they lacked full alignment with the key structure Formula (II).

Results:

Results are presented in Tables 1, 2, and 3 below.

TABLE 1

Conjugate concentration 40 nM:

| Formula Name | Formula of the Conjugate bakbone | Formula of The E moieties | Number of E moieties per conjugate | EGFP Expression (% of Control) | % silencing of the EGFP gene |
|---|---|---|---|---|---|
| [Cn-1-(VIII-M)] | (Cn-1) | (VIII-M) | 2 | 31.8 | 68.2 |
| [Cn-2-(VIII-M)] | (Cn-2) | (VIII-M) | 3 | 13.4 | 86.6 |
| [Cn-1-(III)] | (Cn-1) | (III) | 2 | 55 | 45.0 |
| [Cn-2-(III)] | (Cn-2) | (III) | 3 | 18.3 | 81.7 |
| [Cn-1-(IV)] | (Cn-1) | (IV) | 2 | 34.4 | 65.6 |
| [Cn-1-(V)] | (Cn-1) | (V) | 2 | 24.8 | 75.2 |
| [Cn-1-(VI)] | (Cn-1) | (VI) | 2 | 23.8 | 76.2 |
| [Cn-1-(VII)] | (Cn-1) | (VII) | 2 | 23.2 | 78.8 |

TABLE 2

Conjugate concentration 150 nM:

| Formula Name | Formula of the Conjugate backbone | Formula of The E moieties | Number of E moieties per conjugate | EGFP Expression (% of Control) | % silencing of the EGFP gene |
|---|---|---|---|---|---|
| [Cn-1-(IX)] | (Cn-1) | (IX) | 2 | 21.9 | 78.1 |
| [Cn-1-(VIII-M)] | (Cn-1) | (VIII-M) | 2 | 15.5 | 84.5 |
| [Cn-1-(III)] | (Cn-1) | (III) | 2 | 34.2 | 63.8 |
| [Cn-1-(IV)] | (Cn-1) | (IV) | 2 | 18.5 | 81.5 |
| [Cn-1-(VI)] | (Cn-1) | (VI) | 2 | 12.1 | 87.9 |

TABLE 3
Conjugates with Control E moieties; examined in Conjugate concentrations of up to 400 nM:
| # | Formula of the Conjugate backbone | Number of E moieties per conjugate | Structure of the Control E Moiety | % silencing of the EGFP gene |
|---|---|---|---|---|
| Control 1 | (Cn-1) | 2 | 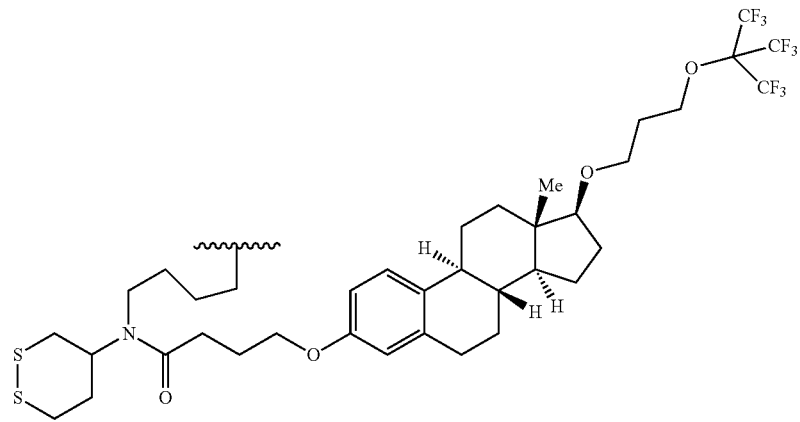 [SMILES: *CCCCN(C(=O)CCCOc1ccc2c(c1)CC[C@@H]1[C@@H]2CC[C@]2(C)[C@@H](OCCCOC(C(F)(F)F)(C(F)(F)F)C(F)(F)F)CC[C@@H]12)C1CCSSC1] | 0% |
| Control 2 | (Cn-1) | 2 | 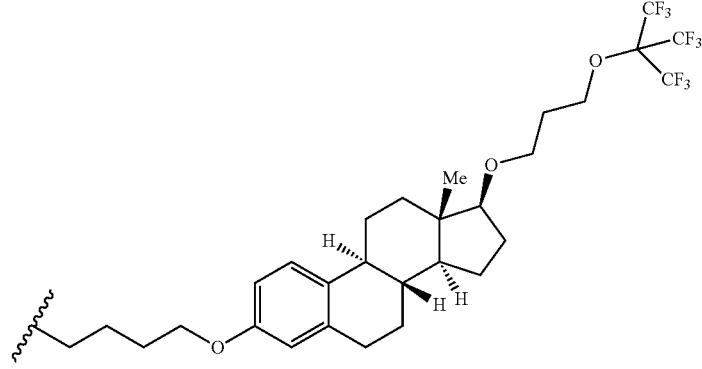 [SMILES: *CCCCOc1ccc2c(c1)CC[C@@H]1[C@@H]2CC[C@]2(C)[C@@H](OCCCOC(C(F)(F)F)(C(F)(F)F)C(F)(F)F)CC[C@@H]12] | 0% |
| Control 3 | (Cn-1) | 2 | 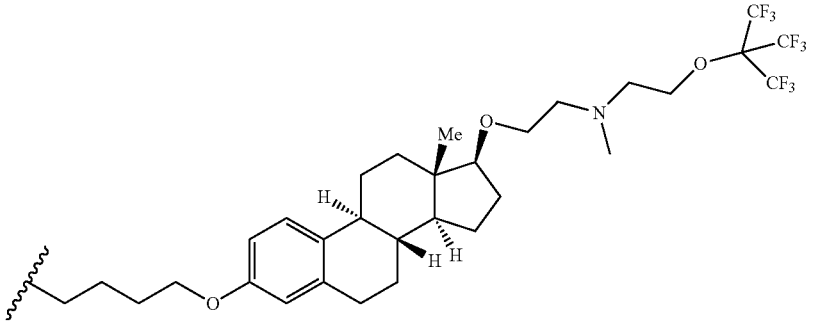 [SMILES: *CCCCOc1ccc2c(c1)CC[C@@H]1[C@@H]2CC[C@]2(C)[C@@H](OCCN(C)CCOC(C(F)(F)F)(C(F)(F)F)C(F)(F)F)CC[C@@H]12] | 0% |

TABLE 3-continued

Conjugates with Control E moieties; examined in Conjugate concentrations of up to 400 nM:

| # | Formula of the Conjugate backbone | Number of E moieties per conjugate | Structure of the Control E Moiety | % silencing of the EGFP gene |
|---|---|---|---|---|
| Control 4 | (Cn-1) | 2 | | 0% |
| Control 5 | (Cn-1) | 2 | | 0% |
| Control 6 | (Cn-1) | 2 | | 0% |

Summary of the Results:

As presented in Table 1 and Table 2, all Conjugates, which structure conforms to general Formulae (I) and (II), albeit having various Conjugate backbones and E moieties manifested robust silencing of the examined gene EGFP, at the examined nanomolar concentrations (40 and 150 nM).). By contrast, all the Control Conjugates (Table 3) did not manifest gene silencing, even when tested in relatively high concentrations (up to 400 nM).

Conclusions:

This performance profile thus supports the notion, that Conjugates according to Formulae (I) and (II), have general and characteristic structural motifs, that enable a useful delivery of macromolecular ODs across phospholipid membranes into cells, with consequent useful biological performance (in this case, gene silencing).

Example 10: Biological Performance of a Conjugate of the Invention, Comprising E Moieties that are Each According to Formula (VIII-M), in Gene Silencing in Vitro; a Dose/Response Study, and Comparative Analysis of (Cn-1) and (Cn-2)

Conjugates

Study Objective:

Assessment of the biological performance in vitro, of the Conjugates of the Invention [Cn-1-(VIII-M)] and [Cn-2-(VIII-M)], namely, dsiRNA, harboring either 2 or 3 E moieties, respectively, each E moiety being according to Formula (VIII-M), and linked to 25/27 nucleotide Dicer's substrate Duplex, designed to silence the EGFP gene.

Methods:

Cell Culture:

3T3 cell lines were obtained from Cell Biolabs. Cells of each cell type were grown in Dulbecco's modified Eagle's medium (Gibco), supplemented with 10% FBS (Gibco), 100

U/ml penicillin 100 mg/ml streptomycin (Biological Industries, Israel) and blasticidin 10 μg/ml. Cells were maintained in a 37° C. incubator with 5% CO2 humidified air. The day before transfection, cells were plated (40,000 cells/well) on 24-well black-plate glass bottom. The following day, cells started incubation for 48 hours with Conjugate [Cn-1-(VIII-M)], or Conjugate [Cn-2-(VIII-M)], at concentrations of 1 nM, 2 nM, 5 nM, 10 nM, and 40 nM, of which the first 24 hours were in serum-free Opti-MEM medium (Thermo Fisher Scientific), followed by incubation in medium that comprises 10% serum for additional 24 hours. Down-regulation of protein expression was measured at 48 hours post-transfection. For this purpose medium was aspirated, and cells were washed with HBSS.

RNA Extraction and qRT-PCR:

Total RNA was extracted using the PureLink RNA mini kit (Invitrogen) according to the manufacturer instructions. RNA was quantified with the infinite M200-Pro Multimode Reader (Tecan). RNA was reversed transcribed with the High-Capacity cDNA Reverse Transcription Kit (ABI), and ApoC3 mRNA expression was measured with the Syber qRT-PCR procedure, with normalization to beta-Actin (Step-one-Plus, ABI).

Results:

As shown in FIG. 5, both Conjugate [Cn-1-(VIII-M)] and Conjugate [Cn-2-(VIII-M)] induced robust silencing of the expression of the EGFP gene, as evaluated for 3T3 cells in vitro. A clear dose/response was observed, with a highly-significant logarithmic decay, with a curve fit of $R^2 \approx 0.97$ for both cell lines. For Conjugate [Cn-1-(VIII-M)] (dotted line), having 2 E moieties, $IC_{50}$ was found to be 2.2 nM, while for Conjugate [Cn-2-(VIII-M)] (solid line), having 3 E moieties, $IC_{50}$ was found to be 0.8 nM (FIG. 5).

Conclusions:

As examined for two Conjugates: Conjugate [Cn-1-(VIII)]-EGFP, and Conjugate [Cn-2-(VIII-M)], the Conjugates of the Invention exert robust gene silencing, as evaluated via measurement of RNA levels, with very low $IC_{50}$ values. Interestingly, the Conjugate that comprises three E moieties [Cn-2-(VIII-M)] manifested higher potency in gene silencing, as compared to the Conjugate that comprises two E moieties, reflected by lower $IC_{50}$ values (0.8 vs. 2.2 nM). This observation supports the notion, that the delivery system of the Invention manifests a positive co-operativity effect, wherein each E moiety contributes and augments the overall performance of the Conjugate in gene silencing.

The invention claimed is:

1. A Conjugate, having the structure as set forth in Formula (I):

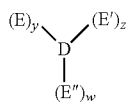

Formula (I)

including pharmaceutically acceptable salts, hydrates, solvates of the compound represented by the structure as set forth in Formula (I), and solvates and hydrates of the salts, wherein:

D is an oligonucleotide (OD);

y, z and w are each an integer, independently selected from 0, 1, 2, 3 or 4, wherein if any of y, z or w is 0, it means that the respective E moiety (or moieties) is (are) null; at least one of y, z or w is different from 0;

E, E', or E" can be the same or different, each having independently a structure as set forth in general Formula (II):

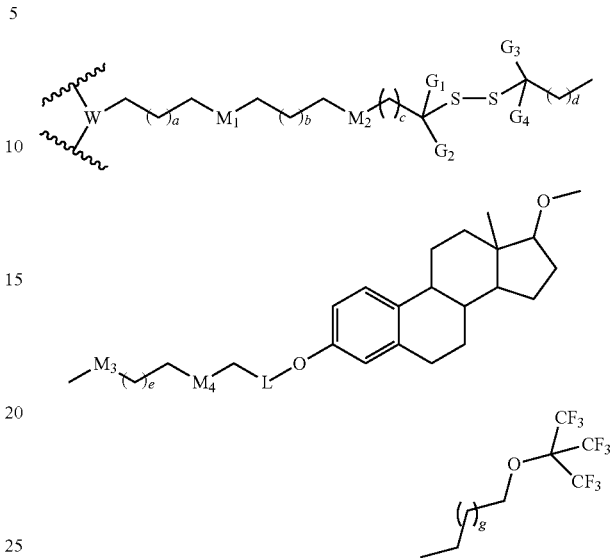

including pharmaceutically acceptable salts, hydrates, solvates and metal chelates of the compound represented by the structure as set forth in Formula (II), and solvates and hydrates of the salts, wherein:

$M_1$, $M_2$, $M_3$, $M_4$ are each individually selected from the group consisting of N', N'', null, ether, amide, ester, thioether and thioester; wherein N' and N'' are each selected independently from the group consisting of —N(CH$_3$)—, —NH—, and —N(X)—; wherein X is a protecting group for amine; $M_1$, $M_2$, $M_3$, $M_4$ can be the same or different; N', N'' can be the same or different;

L is selected from $C_5$ heteroaryl, $C_6$ aryl, $C_6$ heteroaryl and a combination of $C_1$-$C_2$ alkylene and $C_5$ heteroaryl, $C_6$ aryl or $C_6$ heteroaryl; wherein each of $C_5$ heteroaryl, $C_6$ aryl and $C_6$ heteroaryl is optionally substituted by fluorine atom(s), or hydroxyl group(s), $G_1$, $G_2$, $G_3$, $G_4$, each stands independently for a hydrogen atom or a methyl group; G groups can be the same or different; at least two of $G_1$, $G_2$, $G_3$ or $G_4$ groups are hydrogen atoms;

a, b, c, d, e are integers, each independently selected from the group consisting of 0, 1, 2, 3, 4, 5, or 6, wherein 0=null; a, b, c, d, e can be the same or different;

g stands for an integer, selected from 0, 1, 2, 3, 4 or 5;

W is selected from the group consisting of null and any of the structures as set forth in Formulae (II$^1$) and (II$^3$), and combinations thereof:

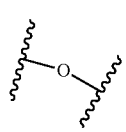

Formula (II$^3$)

-continued

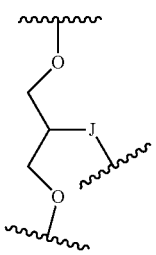

Formula (II¹)

wherein J is selected from the group consisting of null, —CH₂—, and oxygen;

at least two of E, E', and E" are linked to said D.

2. A Conjugate according to claim 1, wherein g is an integer of 0, 1, or 2.

3. A Conjugate according to claim 1, wherein $M_1$, $M_2$, $M_3$, $M_4$ are each individually selected from the group consisting of N', null and ether; wherein N' is —N(CH₃)— or —NH—.

4. A Conjugate according to claim 1, wherein L is difluorobenzylamine.

5. A Conjugate according to claim 1, wherein $G_1$, $G_2$, $G_3$, $G_4$ are all hydrogen atoms.

6. A Conjugate according to claim 1, wherein the protecting group for amine is selected from the group consisting of Carbobenzyloxy (Cbz) group; p-Methoxybenzyl carbonyl (Moz or MeOZ) group; tert-Butyloxycarbonyl (BOC) group; 9-Fluorenylmethyloxycarbonyl (FMOC) group; Phenoxyacetyl (PAC) group; 4-tertbutylphenoxyacetyl (t-PAC) group; Acetyl (Ac) group; Benzoyl (Bz) group, Benzyl (Bn) group; Carbamate group; p-Methoxybenzyl (PMB); 3,4-Dimethoxybenzyl (DMPM); p-methoxyphenyl (PMP) group; Tosyl (Ts) group; Troc (trichloroethyl chloroformate) group, and 2-(trimethylsilyl) ethyl carbamate (TEOC).

7. A Conjugate according to claim 1, wherein the E, E', or E" have the structure as set forth in Formula (XV):

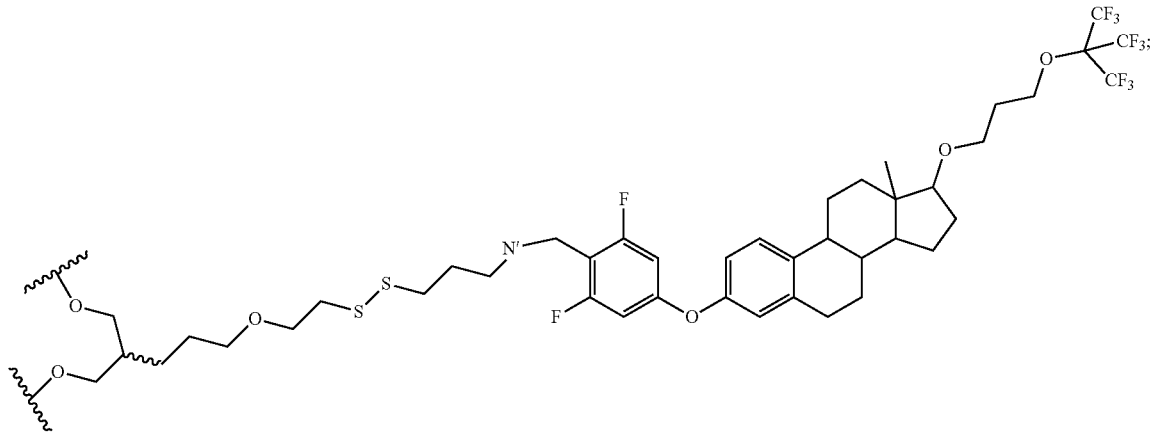

Formula (XV)

or wherein the E, E', or E" have the structure as set forth in Formula (XVI):

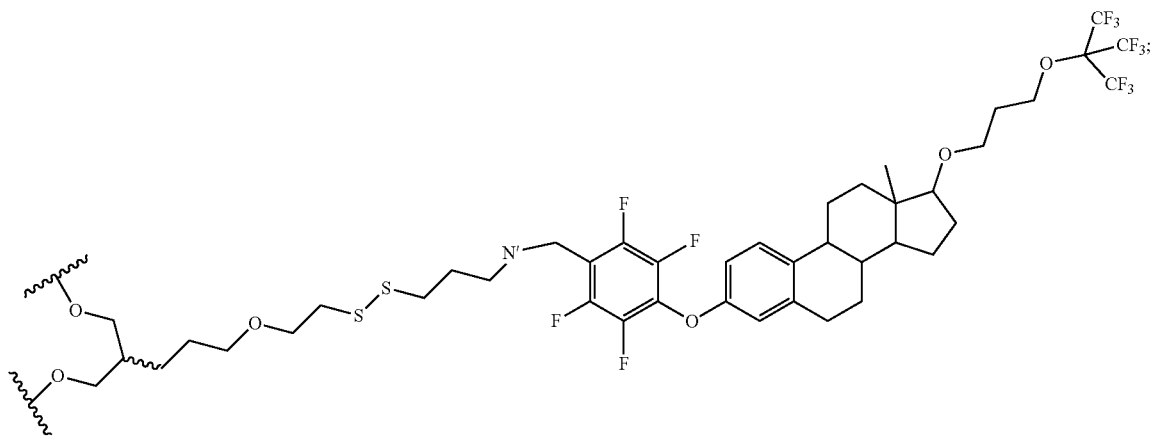

Formula (XVI)

or
wherein the E, E', or E" have the structure as set forth in Formula (XV-H):

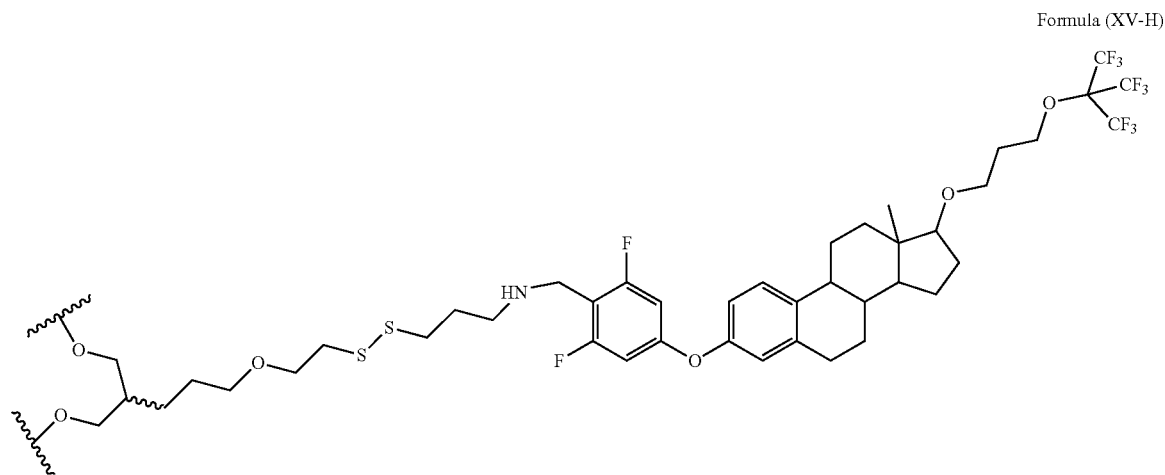 [SMILES: *OCC(CCCOCCSSCCCNCc1c(F)cc(Oc2ccc3c(c2)CCC2C3CCC3(C)C(OCCCOC(C(F)(F)F)(C(F)(F)F)C(F)(F)F)CCC23)cc1F)CO*]

Formula (XV-H)

including pharmaceutically acceptable salts, hydrates, solvates of the compound represented by the structure as set forth in Formula (XV-H), and solvates and hydrates of the salts; or wherein the E, E', or E" have the structure as set forth in Formula (XV-M):

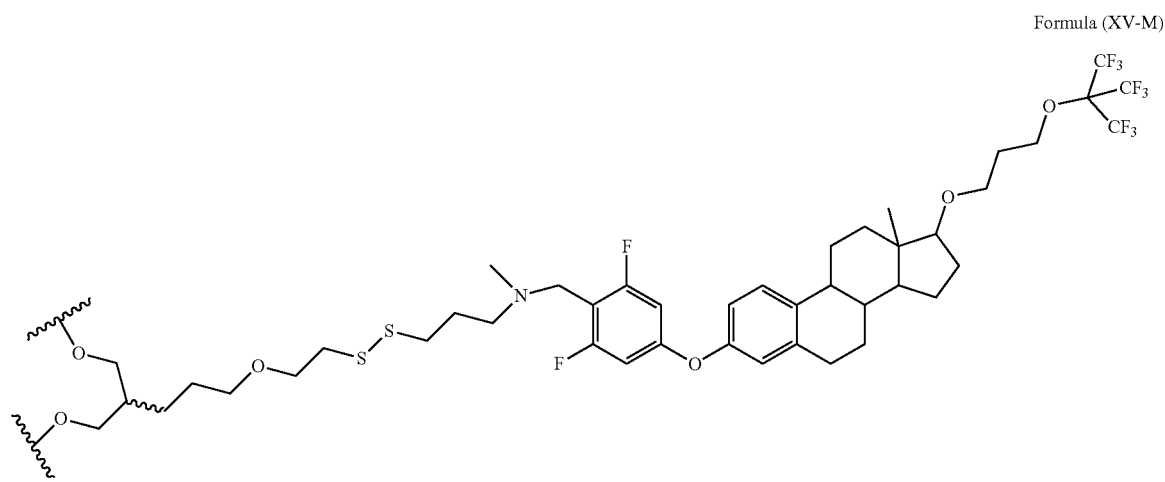 [SMILES: *OCC(CCCOCCSSCCCN(C)Cc1c(F)cc(Oc2ccc3c(c2)CCC2C3CCC3(C)C(OCCCOC(C(F)(F)F)(C(F)(F)F)C(F)(F)F)CCC23)cc1F)CO*]

Formula (XV-M)

including pharmaceutically acceptable salts, hydrates, solvates of the compound represented by the structure as set forth in Formula (XV-M), and solvates and hydrates of the salts; or wherein the E, E', or E" have the structure as set forth in Formula (XV-F):

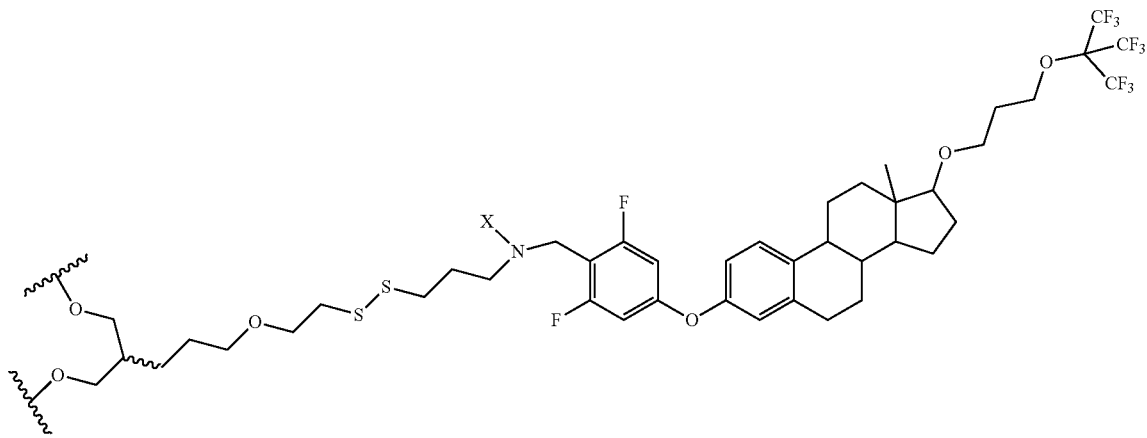

Formula (XV-F)

including pharmaceutically acceptable salts, hydrates, solvates of the compound represented by the structure as set forth in Formula (XV-F), and solvates and hydrates of the salts; or wherein the L moiety is tetra-fluorobenzylamine; and therefore E, E', or E" have the structure as set forth in Formula (XVI-H):

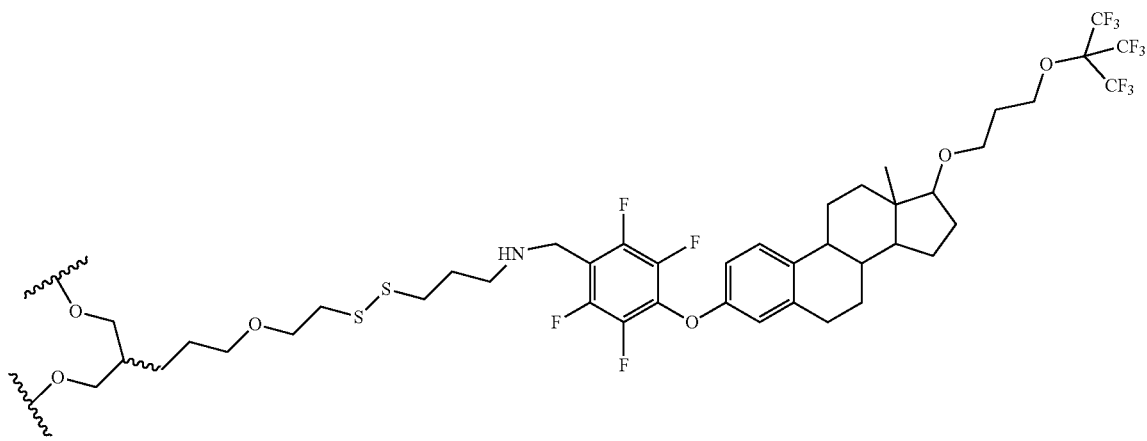

Formula (XVI-H)

including pharmaceutically acceptable salts, hydrates, solvates of the compound represented by the structure as set forth in Formula (XVI-H), and solvates and hydrates of the salts; or
wherein the E, E', or E" have the structure as set forth in Formula (XVI-M):

Formula (XVI-M)

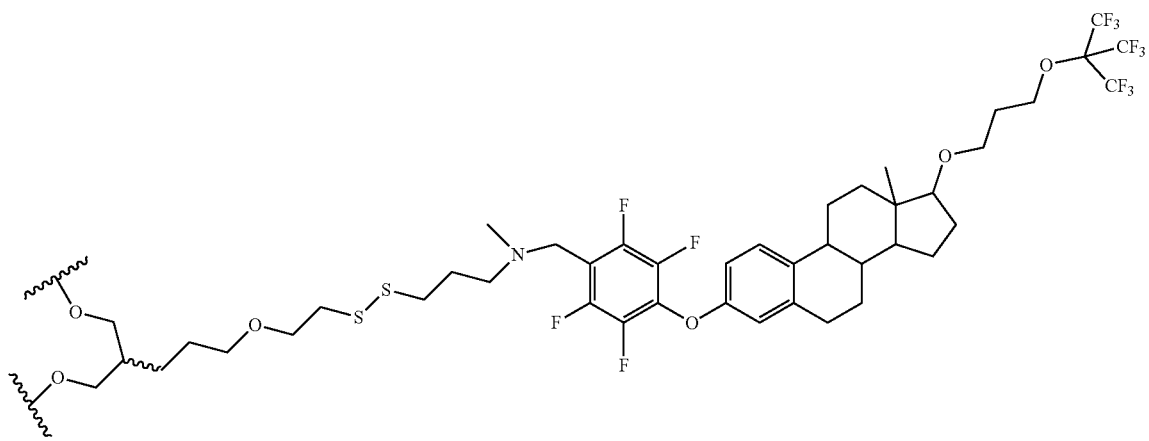

including pharmaceutically acceptable salts, hydrates, solvates of the compound represented by the structure as set forth in Formula (XVI-M), and solvates and hydrates of the salts; or wherein the E, E', or E" have the structure as set forth in Formula (XVI-F):

nucleotides, an RNA Duplex of 25 and 27 nucleotides, or an RNA Duplex of 27 and 27 nucleotides.

12. A Conjugate according to claim 7, wherein y and z are 1, and w is null; and wherein E and E' are each represented by Formula XV-M.

Formula (XVI-F)

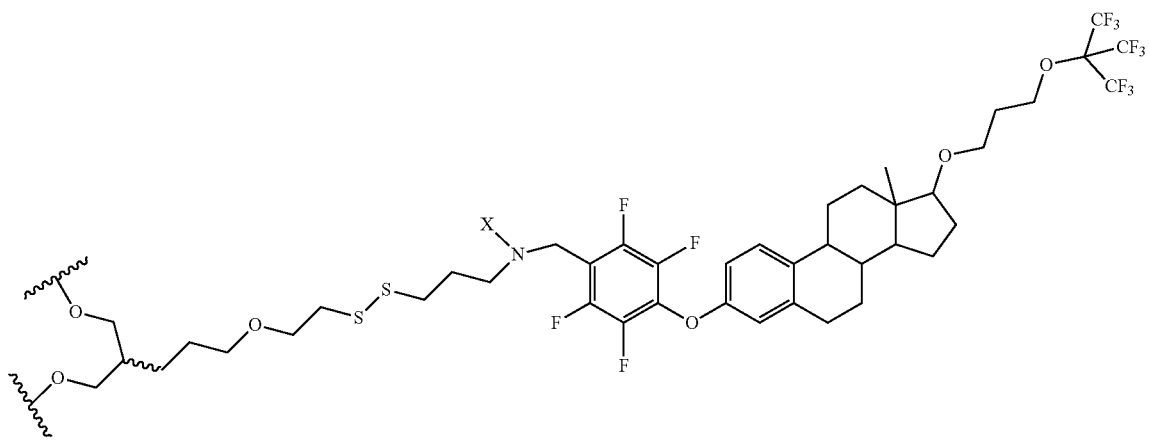

including pharmaceutically acceptable salts, solvates of the compound represented by the structure as set forth in Formula (XVI-F), and solvates and hydrates of the salts; wherein X is the protecting group for amine and wherein the protecting group for amine is selected from a carbamate-based protecting group, benzyl-based protecting group and sulfonamide-based protecting group.

8. A Conjugate according to claim 7, comprising E, E', or E" moieties according to any of Formulae (XV), (XV-H), (XV-M), (XVI), (XVI-H), or (XVI-M).

9. A pharmaceutical composition, comprising a Conjugate according to claim 1, and a pharmaceutically-acceptable salt or carrier.

10. A Conjugate according to claim 1, wherein said OD is RNA.

11. A Conjugate according to claim 1, wherein the OD is a Dicer substrate, being an RNA Duplex of 24 and 27

13. A Conjugate according to claim 1, wherein the OD is siRNA or dsiRNA, that comprises at least one E moiety at an internal position along the oligonucleotide chain; said internal position being position #12 or position #14 of the oligonucleotide chain, either replacing the respective nucleotide, or being added to the nucleotide sequence.

14. A Conjugate, having the structure as set forth in Formula (I):

Formula (I)

$$(E)_y \diagdown_{D} \diagup (E')_z$$
$$\mid$$
$$(E'')_w$$

including pharmaceutically acceptable salts, hydrates, solvates of the compound represented by the structure as set forth in Formula (I), and solvates and hydrates of the salts, wherein:

D is an oligonucleotide (OD);

y, z and w are each an integer, independently selected from 0, 1, 2, 3 or 4, wherein if any of y, z or w is 0, it means that the respective E moiety (or moieties) is (are) null; at least one of y, z or w is different from 0;

E, E', or E" can be the same or different, each having independently a structure as set forth in general Formula (II):

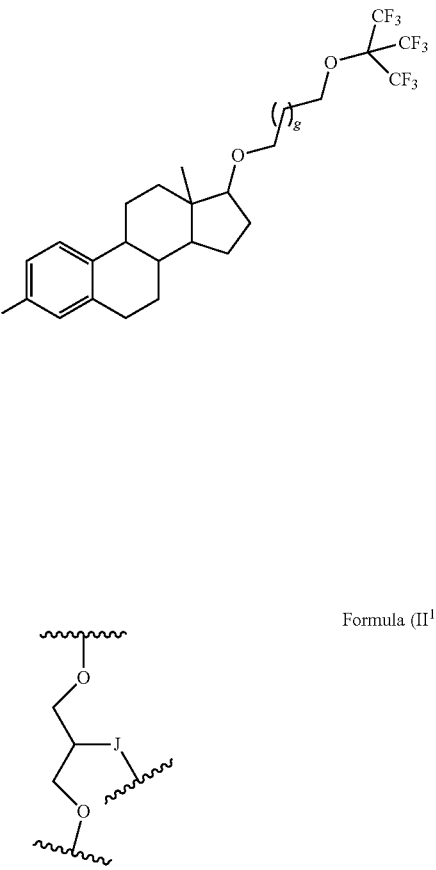

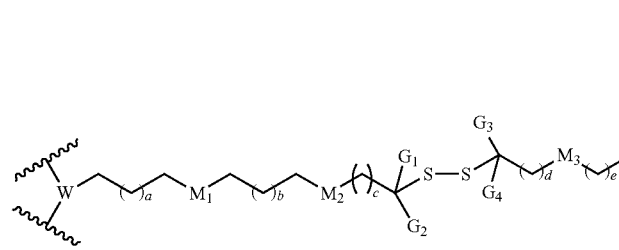

including pharmaceutically acceptable salt of the compound represented by the structure as set forth in Formula (II), wherein:

$M_1$, $M_2$, $M_3$, $M_4$ are each individually selected from the group consisting of N', N", null, and ether; wherein N' and N" are each selected independently from the group consisting of —N(CH$_3$)—, —NH—, and —N(X)—; wherein X is a protecting group for amine; $M_1$, $M_2$, $M_3$, $M_4$ can be the same or different; N', N" can be the same or different;

wherein the protecting group for amine is selected from the group consisting of Carbobenzyloxy (Cbz) group; p-Methoxybenzyl carbonyl (Moz or MeOZ) group; tert-Butyloxycarbonyl (BOC) group; 9-Fluorenylmethyloxycarbonyl (FMOC) group; Phenoxyacetyl (PAC) group; 4-tertbutylphenoxyacetyl (t-PAC) group; Acetyl (Ac) group; Benzoyl (Bz) group, Benzyl (Bn) group; Carbamate group; p-Methoxybenzyl (PMB); 3,4-Dimethoxybenzyl (DMPM); p-methoxyphenyl (PMP) group; Tosyl (Ts) group; Troc (trichloroethyl chloroformate) group, and 2-(trimethylsilyl) ethyl carbamate (TEOC);

L is selected from $C_5$ heteroaryl, $C_6$ aryl, $C_6$ heteroaryl and a combination of $C_1$-$C_2$ alkylene and $C_5$ heteroaryl, $C_6$ aryl or $C_6$ heteroaryl; wherein each of $C_5$ heteroaryl, $C_6$ aryl and $C_6$ heteroaryl is optionally substituted by fluorine atom(s), or hydroxyl group(s), $G_1$, $G_2$, $G_3$, $G_4$, each stands independently for a hydrogen atom or a methyl group; G groups can be the same or different; at least two of $G_1$, $G_2$, $G_3$ or $G_4$ groups are hydrogen atoms;

a, b, c, d, e are integers, each independently selected from the group consisting of 0, 1, 2, 3, 4, 5, or 6, wherein 0=null; a, b, c, d, e can be the same or different;

g stands for an integer, selected from 0, 1, 2, 3, 4 or 5;

W is null or a structure as set forth in Formulae (II$^1$) and (II$^3$):

Formula (II$^1$)

Formula (II$^3$)

wherein J is selected from the group consisting of null, —CH$_2$— and oxygen; and wherein at least two of E, E', and E" are linked to said D.

* * * * *